(12) United States Patent
Wittman et al.

(10) Patent No.: US 8,592,579 B2
(45) Date of Patent: *Nov. 26, 2013

(54) PYRROLOTRIAZINE KINASE INHIBITORS

(75) Inventors: Mark D. Wittman, Wallingford, CT (US); Harold Mastalerz, Guilford, CT (US); Kurt Zimmermann, Durham, CT (US); Mark G. Saulnier, Higganum, CT (US); Upender Velaparthi, Cheshire, CT (US); Dolatrai M. Vyas, Madison, CT (US); Guifen Zhang, Wallingford, CT (US); Walter Lewis Johnson, Waterbury, CT (US); David B. Frennesson, Naugatuck, CT (US); Xiaopeng Sang, Glastonbury, CT (US); Peiying Liu, Madison, CT (US); David R. Langley, Meriden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/568,750

(22) Filed: Aug. 7, 2012

(65) Prior Publication Data

US 2012/0302747 A1     Nov. 29, 2012

Related U.S. Application Data

(63) Continuation of application No. 13/015,687, filed on Jan. 28, 2011, now Pat. No. 8,263,765, which is a continuation of application No. 12/411,724, filed on Mar. 26, 2009, now Pat. No. 7,879,855, which is a continuation of application No. 11/773,466, filed on Jul. 5, 2007, now Pat. No. 7,534,792.

(60) Provisional application No. 60/819,171, filed on Jul. 7, 2006.

(51) Int. Cl.
| C07D 487/04 | (2006.01) |
| C07D 401/14 | (2006.01) |
| A61K 31/53 | (2006.01) |
| A61P 35/00 | (2006.01) |

(52) U.S. Cl.
USPC .......................................... 544/183; 514/243

(58) Field of Classification Search
USPC .......................................... 544/183; 514/243
See application file for complete search history.

(56) References Cited

U.S. PATENT DOCUMENTS

| 6,670,357 B2 | 12/2003 | Leftheris et al. | |
| 6,869,952 B2 | 3/2005 | Bhide et al. | |
| 6,982,265 B1 | 1/2006 | Hunt et al. | |
| 7,531,539 B2* | 5/2009 | Fink et al. | 514/243 |
| 7,534,792 B2* | 5/2009 | Wittman et al. | 514/243 |
| 7,605,160 B2 | 10/2009 | Fink et al. | |
| 7,713,973 B2 | 5/2010 | Dong et al. | |
| 7,879,855 B2* | 2/2011 | Wittman et al. | 514/243 |
| 8,263,765 B2* | 9/2012 | Wittman et al. | 544/183 |
| 2006/0084650 A1 | 4/2006 | Dong et al. | |
| 2010/0081662 A1 | 4/2010 | Fink et al. | |

FOREIGN PATENT DOCUMENTS

| WO | WO 00/71129 | 11/2000 |
| WO | WO 2004/009601 | 1/2004 |
| WO | WO 2004/013145 | 2/2004 |

OTHER PUBLICATIONS

Cecil Textbook of Medicine, 20th Edition, vol. 1, pp. 1004-1010 (1996).
Malumbres et al., Trends in Biochemical Sciences, vol. 30(11), pp. 630-641 (2005).
Lolli et al., Cell Cycle, vol. 4(4), pp. 572-577 (2005).
Sherr et al., Genes & Developement, vol. 18, pp. 2699-2711 (2004).
Fischer, Cell Cycle, vol. 3(6), pp. 742-746 (2004).
Blain et al., The Journal of Biological Chemistry, vol. 272(41), pp. 25863-25872 (1997).
LuValle et al., Frontiers in Bioscience, vol. 5, d493-503 (2000).
Patel et al., Biochem. Soc. Trans., vol. 32(5), pp. 803-808 (2004).
Jope et al., Trends in Biochemical Sciences, vol. 29(2), pp. 95-102 (2004).
Mass, R. D., Int. Radiation Oncology Bio. Phys., vol. 58(3), pp. 932-940 (2001).
Fabbro et al., Pharmacology & Therapeutics, vol. 93, pp. 79-98 (2002).
Search of: BMS-754807—List Results; www.ClinicalTrials.gov (Aug. 18, 2010) 1 page.
Freshney, et al., Culture of Animal Cells, A Manual of Basic Technique; Liss, Inc., New York, Jan. 7, 1983.
Dermer et al., Bio/Technology, 1994, 12:320.
Cohen, et al., Current Opinion in Chemical Biology, vol. 3, pp. 459-465, 1999.
Golub et al., Science, vol. 286, pp. 531-537, 1999.
Dayam, R. et al., Expert Opinion on Therapeutic Patents 2007, United Kingdom, vol. 17, No. 1, pp. 83-102.

* cited by examiner (Continued)

*Primary Examiner* — Venkataraman Balasubramanian
(74) *Attorney, Agent, or Firm* — Elliott Korsen

(57) ABSTRACT

The invention provides compounds of formula I

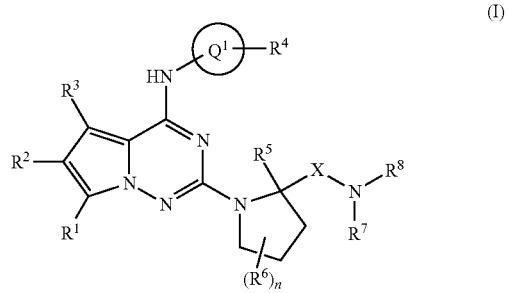

and pharmaceutically acceptable salts thereof.
The formula I compounds inhibit tyrosine kinase activity thereby making them useful as anticancer agents and for the treatment of Alzheimer's Disease.

1 Claim, No Drawings

PYRROLOTRIAZINE KINASE INHIBITORS

RELATED APPLICATION

This application is a continuation of U.S. Non-Provisional application Ser. No. 13/015,687 filed Jan. 28, 2011, issuing as U.S. Pat. No. 8,263,765 on Sep. 11, 2012, which is a continuation of U.S. Non-Provisional application Ser. No. 12/411,724, filed Mar. 26, 2009, issuing as U.S. Pat. No. 7,879,855 on Feb. 1, 2011, which is a continuation of U.S. Non-Provisional application Ser. No. 11/773,466, filed on Jul. 5, 2007 issuing as U.S. Pat. No. 7,534,792 on May 19, 2009, which claims the benefit of U.S. Provisional Application No. 60/819,171, filed Jul. 7, 2006, incorporated herein by reference in its entirety.

FIELD OF THE INVENTION

The invention relates to novel pyrrolotriazine compounds that are useful as anti-cancer agents. This invention also relates to a method of using the compounds in the treatment of proliferative and other diseases and to pharmaceutical compositions containing the compounds.

BACKGROUND

The invention relates to compounds which inhibit tyrosine kinase enzymes, compositions which contain tyrosine kinase inhibiting compounds and methods of using inhibitors of tyrosine kinase enzymes to treat diseases which are characterized by an overexpression or upregulation of tyrosine kinase activity such as cancer, diabetes, restenosis, arteriosclerosis, psoriasis, Alzheimer's disease, angiogenic diseases and immunologic disorders (Powis, G.; Workman P. Signaling Targets For The Development of Cancer Drugs. *Anti-Cancer Drug Design* (1994), 9: 263-277; Merenmies, J.; Parada, L. F.; Henkemeyer, M. Receptor Tyrosine Kinase Signaling in Vascular Development. *Cell Growth Differ* (1997) δ: 3-10; Shawver, L. K.; Lipsosn, K. E.; Fong, T. A. T.; McMahon, G.; Plowman, G. D.; Strawn, L. M. Receptor Tyrosine Kinases As Targets For Inhibition of Angiogenesis. *Drug Discovery Today* (1997) 2: 50-63; all herein incorporated by reference).

Tyrosine kinases play a critical role in signal transduction for several cellular functions including cell proliferation, carcinogenesis, apoptosis, and cell differentiation. Inhibitors of these enzymes are useful for the treatment or prevention of proliferative diseases which are dependent on these enzymes. Strong epidemiologic evidence suggests that the overexpression or activation of receptor protein tyrosine kinases leading to constitutive mitogenic signaling is an important factor in a growing number of human malignancies. Tyrosine kinases that have been implicated in these processes include Abl, CDKs, EGF, EMT, FGF, FAK, Flk-1/KDR, Flt-3, GSK-3, GSKbeta-3, HER-2, IGF-1R, IR, Jak2, LCK, MET, PDGF, Src, Tie-2, TrkA, TrkB and VEGF. Hence, there is an ongoing need to investigate novel compounds that can be used to regulate or inhibit tyrosine kinase enzymes.

SUMMARY OF THE INVENTION

The invention is directed to compounds having Formula I that inhibit tyrosine kinase enzymes for the treatment of cancer.

Furthermore, the invention is directed to methods for treating a condition associated with one or more tyrosine kinase inhibitor comprising administering to a mammal in need of such treatment a therapeutically effective amount of a compound of formula I and optionally one or more other anticancer agent.

The invention also provides methods for treating cancer using the compounds of the invention either alone or together with one or more other anticancer agent.

DETAILED DESCRIPTION OF THE INVENTION

The invention provides for compounds of formula I, pharmaceutical compositions employing such compounds and for methods of using such compounds.

In accordance with the invention, there are disclosed compounds of formula I

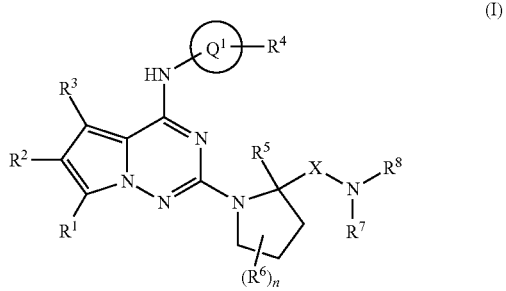

wherein:

$Q^1$ is aryl, substituted aryl, heteroaryl or substituted heteroaryl;

X is C=O, C=S, C=NR$^9$ or CH$_2$;

$R^1$, $R^2$, and $R^3$ are independently hydrogen, alkyl, substituted alkyl, cycloalkyl, substituted cycloalkyl, hydroxy, alkoxy, substituted alkoxy, halogen, haloalkyl, haloalkoxy, alkanoyl, substituted alkanoyl, amino, substituted amino, aminoalkyl, substituted aminoalkyl, alkylamino, substituted alkylamino, amide, substituted amide, carbamate, ureido, cyano, sulfonamido, substituted sulfonamido, alkylsulfone, nitro, thio, thioalkyl, alkylthio, disubstituted amino, alkylsulfonyl, alkylsulfinyl, carboxy, alkoxycarbonyl, alkylcarbonyloxy, carbamoyl, substituted carbamoyl, alkenyl, substituted alkenyl, alkynyl, substituted alkynyl, or alkylcarbonyl;

$R^4$ is hydrogen, alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, substituted amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocycle, substituted heterocycle, alkylcarbonyl, substituted heteroalkyl, heteroalkenyl, substituted heterolakenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl;

R⁵ is hydrogen, halogen, cyano, alkyl or substituted alkyl;

R⁶ is independently hydrogen, alkyl, substituted alkyl, alkylidene, substituted alkylidene, hydroxy, alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocycle, substituted heterocycle, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl;

n is 0, 1, 2, 3, 4, 5 or 6; or when n=2 and R⁶ are geminal substituents they may together form an optionally substituted 3-6 membered saturated or unsaturated carbocyclic or heterocyclic ring; or when n=2 and R⁶ are 1,2-cis substituents, they may together form an optionally substituted 3-6 membered fused saturated carbocyclic or heterocyclic ring; or when n=2, and R⁶ are 1,3-cis substituents they may together form an optionally substituted 1-4 membered alkyl or heteroalkyl bridge; or when there are two R⁶ on the same carbon, they may together form a carbonyl (C=O) or alkylidene group (C=CHR⁹);

R⁷ and R⁸ are independently hydrogen, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl, or substituted heteroalkynyl or R⁷ and R⁸ may be taken together to form an optionally substituted monocyclic 4-8 membered saturated or unsaturated carbocyclic or heterocyclic ring, or an optionally substituted bicyclic 7-12 membered saturated or unsaturated carbocyclic or heterocyclic ring;

R⁹ is hydrogen or lower alkyl;

or a pharmaceutically acceptable salt, tautomer or stereoisomer thereof.

Non-limiting examples of structures contemplated for R⁶ when n=2 (as defined above), include the following:

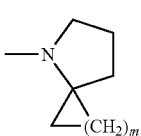 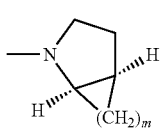 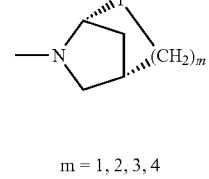

m = 1, 2, 3, 4    m = 1, 2, 3, 4    m = 1, 2, 3, 4
                                     Y = C, O, N (heterobridge)

In another aspect of the invention, there are disclosed compounds of formula I

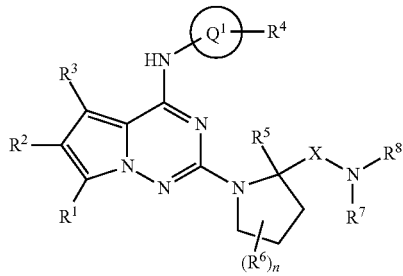

wherein:

Q¹ is heteroaryl or substituted heteroaryl;

X is C=O, C=S, C=NR⁹ or CH₂;

R¹ and R² are independently hydrogen, alkyl, substituted alkyl, hydroxy, alkoxy, substituted alkoxy, halogen, haloalkyl, haloalkoxy, alkanoyl, substituted alkanoyl, amino, aminoalkyl, substituted aminoalkyl, alkylamino, substituted alkylamino, amide, substituted amide, carbamate, ureido, cyano, sulfonamido, substituted sulfonamido, alkylsulfone, cycloalkyl, substituted cycloalkyl, nitro, thio, thioalkyl, alkylthio, disubstituted amino, alkylsulfonyl, alkylsulfinyl, carboxy, alkoxycarbonyl, alkylcarbonyloxy, carbamoyl, substituted carbamoyl, alkenyl, substituted alkenyl, alkynyl, substituted alkynyl, or alkylcarbonyl;

R³ is hydrogen, alkyl, substituted alkyl or halogen;

R⁴ is hydrogen, alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocycle, substituted heterocycle, alkylcarbonyl, substituted heteroalkyl, heteroalkenyl, substituted heterolakenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino or alkylaminocarbonyl;

R⁵ is hydrogen, halogen, cyano, alkyl or substituted alkyl;

R⁶ is independently hydrogen, alkyl, substituted alkyl, alkylidene, substituted alkylidene, hydroxy, alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocycle, substituted heterocycle, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl;

n is 0, 1, 2, 3, 4, 5 or 6; or when n=2 and $R^6$ are geminal substituents they may together form an optionally substituted 3-6 membered saturated or unsaturated carbocyclic or heterocyclic ring; or when n=2 and $R^6$ are 1,2-cis substituents, they may together form an optionally substituted 3-6 membered fused saturated carbocyclic or heterocyclic ring; or when n=2, and $R^6$ are 1,3-cis substituents they may together form an optionally substituted 1-4 membered alkyl or heteroalkyl bridge; or when there are two $R^6$ on the same carbon, they may together form a carbonyl (C=O) or alkylidene group (C=CHR$^9$);

$R^7$ and $R^8$ are independently hydrogen, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl, or substituted heteroalkynyl or $R^7$ and $R^8$ taken together may form an optionally substituted monocyclic 4-8 membered saturated or unsaturated carbocyclic or heterocyclic ring, or an optionally substituted bicyclic 7-12 membered saturated or unsaturated carbocyclic or heterocyclic ring;

$R^9$ is hydrogen or lower alkyl;

or a pharmaceutically acceptable salt, tautomer or stereoisomer thereof.

In a further aspect of the invention, there are disclosed compounds of formula I

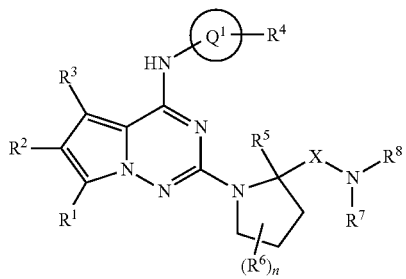

(I)

wherein:

$Q^1$ is pyrazole or imidazole;

$R^1$ and $R^2$ are independently hydrogen, alkyl, substituted alkyl, hydroxy, alkoxy, substituted alkoxy, halogen, haloalkyl, haloalkoxy, alkanoyl, substituted alkanoyl, amino, aminoalkyl, substituted aminoalkyl, alkylamino, substituted alkylamino, amide, substituted amide, carbamate, ureido, cyano, sulfonamido, substituted sulfonamido, alkylsulfone, cycloalkyl, substituted cycloalkyl, nitro, thio, thioalkyl, alkylthio, disubstituted amino, alkylsulfonyl, alkylsulfinyl, carboxy, alkoxycarbonyl, alkylcarbonyloxy, carbamoyl, substituted carbamoyl, alkenyl, substituted alkenyl, alkynyl, substituted alkynyl, or alkylcarbonyl;

$R^3$ is hydrogen, alkyl, substituted alkyl or halogen;

$R^4$ is hydrogen, alkyl, substituted alkyl, amide, substituted amide, cycloalkyl or substituted cycloalkyl;

$R^5$ is hydrogen, lower alkyl or substituted lower alkyl;

$R^6$ is independently hydrogen, alkyl, substituted alkyl, alkylidene, substituted alkylidene, hydroxy, alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocycle, substituted heterocycle, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl;

n is 0, 1, 2, 3 or 4; or when n=2 and $R^6$ are geminal substituents they may together form an optionally substituted 3-6 membered saturated or unsaturated carbocyclic or heterocyclic ring; or when n=2 and $R^6$ are 1,2-cis substituents, they may together form an optionally substituted 3-6 membered fused saturated carbocyclic or heterocyclic ring; or when n=2, and $R^6$ are 1,3-cis substituents they may together form an optionally substituted 1-4 membered alkyl or heteroalkyl bridge; or when there are two $R^6$ on the same carbon, they may together form a carbonyl (C=O) or alkylidene group (C=CHR$^9$);

$R^7$ and $R^8$ are independently hydrogen, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl, or substituted heteroalkynyl or $R^7$ and $R^8$ taken together may form an optionally substituted monocyclic 4-8 membered saturated or unsaturated carbocyclic or heterocyclic ring, or an optionally substituted bicyclic 7-12 membered saturated or unsaturated carbocyclic or heterocyclic ring;

or a pharmaceutically acceptable salt, tautomer or stereoisomer thereof.

In another aspect of the invention, there are disclosed compounds of formula II

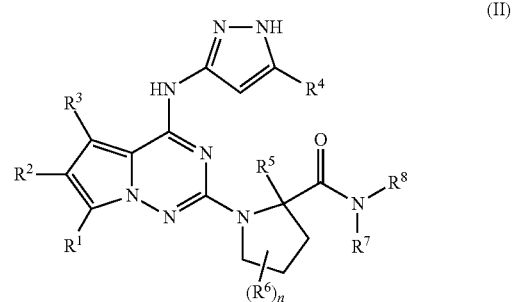

(II)

wherein:

$R^1$ and $R^2$ are independently hydrogen, alkyl, substituted alkyl, hydroxy, alkoxy, substituted alkoxy, halogen, amino, substituted amino, aminoalkyl, substituted aminoalkyl, alkylamino, substituted alkylamino, amide, substituted amide, carbamate, ureido or cyano;

$R^3$ is hydrogen, alkyl, substituted alkyl or halogen;

$R^4$ is hydrogen, alkyl, substituted alkyl, amide, substituted amide, cycloalkyl or substituted cycloalkyl;

$R^5$ is hydrogen, lower alkyl or substituted lower alkyl;

$R^6$ is independently hydrogen, alkyl, substituted alkyl, hydroxy, alkoxy, substituted alkoxy, halogen, haloalkyl, haloalkoxy, oxo, cyano, cycloalkyl, substituted cycloalkyl or carbonyl;

n is 0, 1, 2, 3 or 4; or when n=2 and $R^6$ are geminal substituents they may together form an optionally substituted 3-6 membered saturated or unsaturated carbocyclic or heterocyclic ring; or when n=2 and $R^6$ are 1,2-cis substituents, they may together form an optionally substituted 3-6 membered fused saturated carbocyclic or heterocyclic ring; or when n=2, and $R^6$ are 1,3-cis substituents they may together form an optionally substituted 1-4 membered alkyl or heteroalkyl bridge; or when there are two $R^6$ on the same carbon, they may together form a carbonyl (C=O);

$R^7$ and $R^8$ are independently hydrogen, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, or $R^7$ and $R^8$ taken together may form an optionally substituted monocyclic 4-8 membered saturated or unsaturated carbocyclic or heterocyclic ring, or an optionally substituted bicyclic 7-12 membered saturated or unsaturated carbocyclic or heterocyclic ring;

or a pharmaceutically acceptable salt, tautomer or stereoisomer thereof.

In yet another aspect of the invention, there are disclosed compounds of formula III

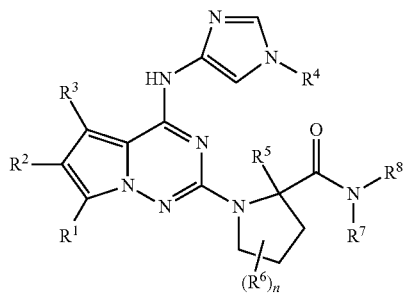

(III)

wherein:

$R^1$ and $R^2$ are independently hydrogen, alkyl, substituted alkyl, hydroxy, alkoxy, substituted alkoxy, halogen, amino, substituted amino, aminoalkyl, substituted aminoalkyl, alkylamino, substituted alkylamino, amide, substituted amide, carbamate, ureido or cyano;

$R^3$ is hydrogen, alkyl, substituted alkyl or halogen;

$R^4$ is hydrogen, alkyl, substituted alkyl, amide, substituted amide, cycloalkyl or substituted cycloalkyl;

$R^5$ is hydrogen, lower alkyl, or substituted lower alkyl;

$R^6$ is independently hydrogen, alkyl, substituted alkyl, hydroxy, alkoxy, substituted alkoxy, halogen, haloalkyl, haloalkoxy, oxo, cyano, cycloalkyl, substituted cycloalkyl or carbonyl;

n is 0, 1, 2, 3 or 4; or when n=2 and $R^6$ are geminal substituents they may together form an optionally substituted 3-6 membered saturated or unsaturated carbocyclic or heterocyclic ring; or when n=2 and $R^6$ are 1,2-cis substituents, they may together form an optionally substituted 3-6 membered fused saturated carbocyclic or heterocyclic ring; or when n=2, and $R^6$ are 1,3-cis substituents they may together form an optionally substituted 1-4 membered alkyl or heteroalkyl bridge; or when there are two $R^6$ on the same carbon, they may together form a carbonyl (C=O);

$R^7$ and $R^8$ are independently hydrogen, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, or $R^7$ and $R^8$ taken together may form an optionally substituted monocyclic 4-8 membered saturated or unsaturated carbocyclic or heterocyclic ring, or an optionally substituted bicyclic 7-12 membered saturated or unsaturated carbocyclic or heterocyclic ring;

or a pharmaceutically acceptable salt, tautomer or stereoisomer thereof.

Compounds of the invention include the following:

(S)-1-(4-(5-cyclopropyl-1H-pyrazol-3-ylamino)pyrrolo[1,2-f][1,2,4]triazin-2-yl)-N-methylpyrrolidine-2-carboxamide, (S)-1-(4-(5-cyclopropyl-1H-pyrazol-3-ylamino)pyrrolo[1,2-f][1,2,4]triazin-2-yl)-N-(thiazol-2-yl)pyrrolidine-2-carboxamide, (S)-1-(4-(5-cyclopropyl-1H-pyrazol-3-ylamino)pyrrolo[1,2-f][1,2,4]triazin-2-yl)-N-(5-methylthiazol-2-yl)pyrrolidine-2-carboxamide, (S)-1-(4-(5-cyclopropyl-1H-pyrazol-3-ylamino)pyrrolo[1,2-f][1,2,4]triazin-2-yl)-N-(pyridin-3-yl)pyrrolidine-2-carboxamide, (S)-1-(4-(5-cyclopropyl-1H-pyrazol-3-ylamino)pyrrolo[1,2-f][1,2,4]triazin-2-yl)-N-(6-fluoropyridin-3-yl)pyrrolidine-2-carboxamide, (S)-1-(4-(5-cyclopropyl-1H-pyrazol-3-ylamino)pyrrolo[1,2-f][1,2,4]triazin-2-yl)-N-((R)-1-cyclopropylpiperidin-3-yl)pyrrolidine-2-carboxamide, (S)-1-(4-(5-cyclopropyl-1H-pyrazol-3-ylamino)pyrrolo[1,2-f][1,2,4]triazin-2-yl)-N-((R)-1-(2-methoxyethyl)piperidin-3-yl)pyrrolidine-2-carboxamide, (S)-1-(4-(5-cyclopropyl-1H-pyrazol-3-ylamino)pyrrolo[1,2-f][1,2,4]triazin-2-yl)-N-(6-fluoropyridin-3-yl)-2-methylpyrrolidine-2-carboxamide, (S)-1-(4-(5-cyclopropyl-1H-pyrazol-3-ylamino)pyrrolo[1,2-f][1,2,4]triazin-2-yl)-2-methyl-N-(thiazol-2-yl)pyrrolidine-2-carboxamide, (S)-1-(4-(5-cyclopropyl-1H-pyrazol-3-ylamino)pyrrolo[1,2-f][1,2,4]triazin-2-yl)-2-methyl-N-(5-methylthiazol-2-yl)pyrrolidine-2-carboxamide, (S)-N-(5-chlorothiazol-2-yl)-1-(4-(5-cyclopropyl-1H-pyrazol-3-ylamino)pyrrolo[1,2-f][1,2,4]triazin-2-yl)-2-methylpyrrolidine-2-carboxamide, (S)-1-(4-(5-cyclopropyl-1H-pyrazol-3-ylamino)pyrrolo[1,2-f][1,2,4]triazin-2-yl)-2-methyl-N-(3-methylisothiazol-5-yl)pyrrolidine-2-carboxamide, (S)-N-(4-chloropyridin-3-yl)-1-(4-(5-cyclopropyl-1H-pyrazol-3-ylamino)pyrrolo[1,2-f][1,2,4]triazin-2-yl)-2-methylpyrrolidine-2-carboxamide, (S)-1-(4-(5-cyclopropyl-1H-pyrazol-3-ylamino)pyrrolo[1,2-f][1,2,4]triazin-2-yl)-2-methyl-N-(pyrazin-2-yl)pyrrolidine-2-carboxamide, (S)-1-(4-(5-cyclopropyl-1H-pyrazol-3-ylamino)pyrrolo[1,2-f][1,2,4]triazin-2-yl)-2-methyl-N-(5-methyl-1H-pyrazol-3-yl)pyrrolidine-2-carboxamide, (S)-1-(4-(3-cyclopropyl-1H-pyrazol-5-ylamino)pyrrolo[1,2-f][1,2,4]triazin-2-yl)-2-methyl-N-(1,2,4-thiadiazol-5-yl)pyrrolidine-2-carboxamide, (S)-1-(4-(3-Cyclopropyl-1H-pyrazol-5-ylamino)pyrrolo[1,2-f][1,2,4]triazin-2-yl)-N-(6-fluoropyridin-3-yl)-2,4,4-trimethylpyrrolidine-2-carboxamide, (S)-3-(2-(2-methyl-2-(thiazol-2-ylcarbamoyl)pyrrolidin-1-yl)pyrrolo[1,2-f][1,2,4]triazin-4-ylamino)-1H-pyrazole-5-carboxamide, (S)-1-(4-(5-(1-methylcyclopropyl)-1H-pyrazol-3-ylamino)pyrrolo[1,2-f][1,2,4]triazin-2-yl)-N-((R)-piperidin-3-yl)pyrrolidine-2-carboxamide, (2S,4R)-1-(4-(5-cyclopropyl-1H-pyrazol-3-ylamino)pyrrolo[1,2-f][1,2,4]triazin-2-yl)-4-fluoro-N-(thiazol-2-yl)pyrrolidine-2-carboxamide, (2S,4R)-1-(4-(5-cyclopropyl-1H-pyrazol-3-ylamino)pyrrolo[1,2-f][1,2,4]triazin-2-yl)-N-((R)-1-(cyclopropylmethyl)piperidin-3-yl)-4-fluoropyrrolidine-2-carboxamide, (2S,4R)-1-(4-(5-cyclopropyl-1H-pyrazol-3-ylamino)pyrrolo[1,2-f][1,2,4]triazin-2-yl)-4-fluoro-N-(6-fluoropyridin-3-yl)pyrrolidine-2-carboxamide, (2S,4R)-N-(4-chloropyridin-3-yl)-1-(4-(5-cyclopropyl-1H-pyrazol-3-ylamino)pyrrolo[1,2-f][1,2,4]triazin-2-yl)-4-fluoropyrrolidine-2-carboxamide, (2S,4R)-1-(4-(5-cyclopropyl-1H-pyrazol-3-ylamino)pyrrolo[1,2-f][1,2,4]triazin-2-yl)-4-fluoro-N-(pyridin-3-yl)pyrrolidine-2-carboxamide, (2S,4R)-1-(4-(5-cyclopropyl-1H-pyrazol-3-ylamino)pyrrolo[1,2-f][1,2,4]triazin-2-yl)-4-fluoro-N-(3-methylisothiazol-5-yl)pyrrolidine-2-carboxamide, (2S,4R)-1-(4-(5-cyclopropyl-1H-pyrazol-3-ylamino)pyrrolo[1,2-f][1,2,4]triazin-2-yl)-4-fluoro-N-(pyrazin-2-yl)pyrrolidine-2-carboxamide, (2S,4S)-1-(4-(5-cyclopropyl-1H-pyrazol-3-ylamino)pyrrolo[1,2-f][1,2,4]triazin-2-yl)-4-hydroxy-N-(pyrazin-2-yl)pyrrolidine-2-carboxamide, (2S,4S)-N-(4-chloropyridin-3-yl)-1-(4-(5-cyclopropyl-1H-pyrazol-3-ylamino)pyrrolo[1,2-f][1,2,4]triazin-2-yl)-4-hydroxypyrrolidine-2-carboxamide, (2S,4 S)-1-(4-(5-cyclopropyl-1H-pyrazol-3-ylamino)pyrrolo[1,2-f][1,2,4]triazin-2-yl)-4-hydroxy-N-(pyridin-3-yl)pyrrolidine-2-carboxamide, (2S,4 S)-1-(4-(5-cyclopropyl-1H-pyrazol-3-ylamino)pyrrolo[1,2-f][1,2,4]triazin-2-yl)-4-hydroxy-N-(3-methylisothiazol-5-yl)pyrrolidine-2-carboxamide, (2S,4 S)-1-(4-(5-cylopropyl-1H-pyrazol-3-ylamino)pyrrolo[1,2-f][1,2,4]triazin-2-yl)-4-hydroxy-N-(thiazol-2-yl)pyrrolidine-2-carboxamide, and (2S,4 S)-N-(5-chlorothiazol-2-yl)-1-(4-(5-cylopropyl-1H-pyrazol-3-ylamino)pyrrolo[1,2-f][1,2,4]triazin-2-yl)-4-hydroxypyrrolidine-2-carboxamide, or a pharmaceutically acceptable salt, tautomer or stereoisomer thereof.

In further aspects of the invention, there are disclosed a method of modulating protein kinase activity which comprises administering to a mammal in need thereof, a therapeutically effective amount of one or more compounds of formula I.

Another aspect of the invention is that said protein kinase comprises one or more protein serine/threonine kinase or one or more protein tyrosine kinase.

Additionally, it is an aspect of the invention that said protein tyrosine kinase is selected from the group consisting of one or more CDK2/cyclin E; Flt-3; Fak; GSK-3β; IGF-1R; IR; JAK2; Kit; Lck; Met; PDGFRβ; PKCα; Src, TrkA; TrkB; VEGFR-1;VEGFR-2; VEGFR-3.

Another aspect of the invention is that said protein tyrosine kinase is IGF-1R.

In another aspect, the invention relates to a method of treating or preventing a protein kinase (PK) related disorder in a mammal in need thereof comprising administering to said mammal a therapeutically effective amount of one or more compounds described herein.

In yet another aspect of the invention, the PK related disorder is an IGF-1R related disorder selected from the group consisting of cancer, diabetes, an autoimmune disease, a hyperproliferation disorder, aging, acromegaly and Crohn's disease.

Methods of treating or preventing cancers selected from the group consisting of carcinoma of the prostate, pancreatic ductal adreno-carcinoma, breast, colon, lung, ovary, pancreas and thyroid, neuroblastoma, glioblastoma, medulloblastoma and melanoma, multiple myeloma, and acute myelogenous leukemia (AML) are also part of the invention.

Definitions

The following are definitions of terms that may be used in the specification. The initial definition provided for a group or term herein applies to that group or term throughout the specification individually or as part of another group, unless otherwise indicated.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or arylalkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively.

The term "arylsulfonylaminocarbonyl" refers to an arylsulfonyl bonded to an aminocarbonyl.

The terms "aryloxyalkyl", "aryloxycarbonyl" or "aryloxyaryl" refer to an aryloxy bonded to an alkyl or substituted alkyl; a carbonyl; or an aryl or substituted aryl, respectively.

The term "arylalkyl" refers to an alkyl or substituted alkyl in which at least one of the hydrogen atoms bonded to at least one of the carbon atoms is replaced with an aryl or substituted aryl. Typical arylalkyls include, but are not limited to, for example, benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl.

The term "arylalkyloxy" refers to an arylalkyl bonded through an oxygen linkage (—O-arylalkyl).

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

An "alkylidene" group refers to an alkylene group consisting of at least two carbon atoms and at least one carbon-carbon double bond. Substituents on this group include those in the definition of "substituted alkyl". The following further illustrates the difference between "alkylidene" and "alkylene":

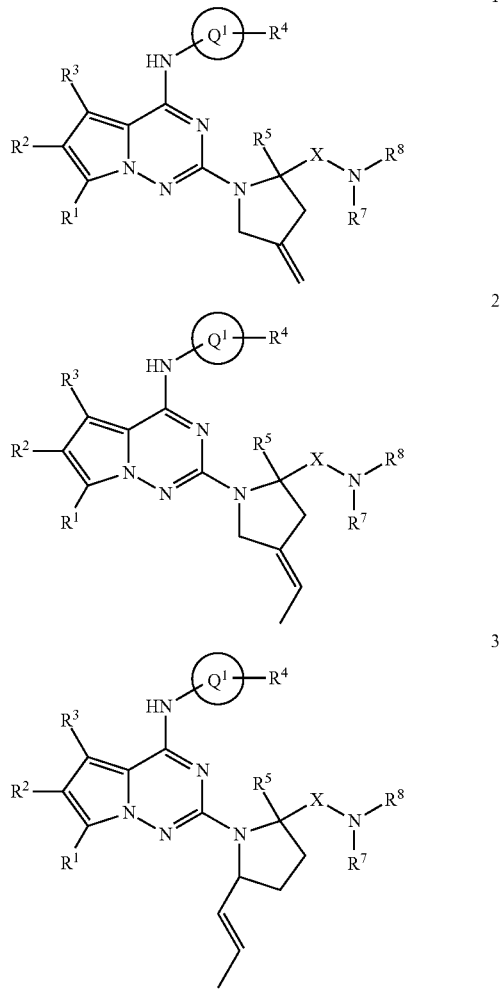

The first two structures illustrate an alkylidene while the third one illustrates an alkylene.

The term "cycloalkyl" refers to an optionally substituted, saturated cyclic hydrocarbon ring systems, preferably containing 1 to 3 rings and 3 to 7 carbons per ring which may be further fused with an unsaturated $C_3$-$C_7$ carbocylic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclyl" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, thienothienyl, and the like.

Exemplary substituents include one or more alkyl or arylalkyl groups as described above or one or more groups described above as alkyl substituents.

Also included are smaller heterocyclyls, such as, epoxides and aziridines.

The term "carbocyclic ring" or "carbocyclyl" refers to stable, saturated, partially saturated or unsaturated, mono or bicyclic hydrocarbon rings that contain 3-12 atoms. Particularly, this includes a monocyclic ring containing 5 or 6 atoms or a bicyclic ring containing 9 or 10 atoms. Suitable values include cyclopropyl, cyclobutyl, cyclopentyl, cyclohexyl, cycloheptyl, dihydroindenyl and tetrahydronaphthyl. The term "optionally substituted" as it refers to "carbocyclic ring" or "carbocyclyl" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The term "alkylsulfone" refers to —$R^kS(\!=\!O)_2R^k$, wherein $R^k$ is an alkyl or substituted alkyl.

The term "oxo" refers to the divalent radical $=O$.

The term "carbamate" refers to the group —$OC(\!=\!O)NH_2$.

The term "amide" refers to the group —$C(\!=\!O)NH_2$.

The term "sulfonamide" refers to the group —$SO_2NH_2$.

The terms "substituted amide", "substituted sulfonamide", or "substituted carbamate" refer to an amide, sulfonamide, or carbamate, respectively, having at least one hydrogen replaced with a group chosen from alkyl, substituted alkyl, alkenyl, substituted alkenyl, cycloalkyl, and substituted cycloalkyl.

A substituted amide, for example, refers to the group —$C(\!=\!O)NR^{m}R^{n}$ wherein $R^m$ and $R^n$ are independently selected from H, alkyl, substituted alkyl, alkenyl, substituted alkenyl, cycloalkyl, and substituted cycloalkyl, provided at least one of $R^m$ or $R^n$ is a substituted moiety.

A substituted sulfonamide, for example, refers to the group —$SO_2NR^{o}R^{p}$ wherein $R^o$ and $R^p$ are independently selected from alkyl, substituted alkyl, alkenyl, substituted alkenyl, cycloalkyl, and substituted cycloalkyl, provided at least one of $R^o$ or $R^p$ is a substituted moiety.

A substituted carbamate, for example, refers to the group —$OC(\!=\!O)NR^{q}R^{r}$ wherein $R^q$ and $R^r$ are independently selected from alkyl, substituted alkyl, alkenyl, substituted alkenyl, cycloalkyl, and substituted cycloalkyl, provided at least one of $R^q$ or $R^r$ is a substituted moiety.

The term "ureido" refers to the group —$NHC(\!=\!O)NH_2$.

The term "cyano" refers to the group —$CN$.

The terms "cycloalkylalkyl" or "cycloalkylalkoxy" refer to a cycloalkyl or substituted cycloalkyl bonded to an alkyl or substituted alkyl; or an alkoxy, respectively.

The term "nitro" refers to the group —$N(O)_2$.

The term "thio" refers to the group —$SH$.

The term "alkylthio" refers to the group —$SR^s$ where $R^s$ is an alkyl, substituted alkyl, cycloalkyl, or substituted cycloalkyl.

The term "thioalkyl" refers to the group —$R^tS$ where $R^t$ is an alkyl, substituted alkyl, cycloalkyl, or substituted cycloalkyl.

The term "alkylsulfonyl" refers to the group —$S(\!=\!O)_2R^u$ where $R^u$ is an alkyl, substituted alkyl, cycloalkyl, or substituted cycloalkyl.

The term "alkylsulfinyl" refers to the group —$S(\!=\!O)R^v$ where $R^v$ is an alkyl, substituted alkyl, cycloalkyl, or substituted cycloalkyl.

The term "carboxy" refers to the group —$C(\!=\!O)OH$.

The terms "carboxyalkoxy" or "alkoxycarbonylalkoxy" refer to a carboxy, or an alkoxycarbonyl, respectively, bonded to an alkoxy.

The term "alkoxycarbonyl" refers to the group —$C(\!=\!O)OR^w$ where $R^w$ is an alkyl, substituted alkyl, cycloalkyl, substituted cycloalkyl, aryl, substituted aryl, heteroaryl, or substituted heteroaryl.

The term "arylalkoxycarbonyl" refers to an aryl or substituted aryl bonded to an alkoxycarbonyl.

The terms "alkylcarbonyloxy" or "arylcarbonyloxy" refer to the group —$OC(\!=\!O)R^x$, where $R^x$ is an alkyl or substituted alkyl, or an aryl or substituted aryl, respectively.

The term "carbamoyl" refers to the groups —$OC(\!=\!O)NH_2$, —$OC(\!=\!O)NHR^x$, and/or —$OC(\!=\!O)NR^{y}R^{z}$, wherein $R^y$ and $R^z$ are independently selected from alkyl and substituted alkyl.

The group —$NR^6(C\!=\!O)R^9$ refers to a group where $R^6$ is selected from hydrogen, lower alkyl and substituted lower alkyl, and $R^9$ is selected from hydrogen, alkyl, substituted alkyl, alkoxy, aminoalkyl, substituted aminoalkyl, alkylamino, substituted alkylamino, aryl and substituted aryl.

The term "carbonyl" refers to a $C(\!=\!O)$.

The terms "alkylcarbonyl", "aminocarbonyl", "alkylaminocarbonyl" "aminoalkylcarbonyl", or "arylaminocarbonyl"

refer to an alkyl or substituted alkyl; an amino; an alkylamino or substituted alkylamino; an aminoalkyl or substituted aminoalkyl; or an arylamino, respectively, bonded to a carbonyl.

The terms "aminocarbonylaryl" or "aminocarbonylalkyl" refer to an aminocarbonyl bonded to an aryl or substituted aryl; or an alkyl or substituted alkyl, respectively.

The term "sulfonyl" refers to the group $S(=O)_2$.

The term "sulfinyl" refers to an $S(=O)$.

The term "carboxyalkyl" refers to an alkyl or substituted alkyl bonded to a carboxy.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, 8, 1-38 (1992).

It should further be understood that solvates (e.g., hydrates) of the compounds of formula I are also with the scope of the invention. Methods of solvation are generally known in the art.

According to a further aspect of the invention, there is provided the use of a compound of the formula I, or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of formula I or a pharmaceutically acceptable salt thereof as defined herein before.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (Avastin®) and small molecules such as ZD6474 and SU6668; Vatalanib, BAY-43-9006, SU11248, CP-547632, and CEP-7055; HER 1 and HER 2 inhibitors including anti-HER2 antibodies (Herceptin); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g. Gleevec® and dasatinib; Casodex® (bicalutamide, Astra Zeneca), Tamoxifen; MEK-1 kinase inhibitors, MAPK kinase inhibitors, PI3 kinase inhibitors; PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (ixabepilone), [1S-[1R*,3R*(E), 7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g. 6-thioguanine and 6-mercaptopurine; glutamine antagonists, e.g. DON (AT-125; d-oxo-norleucine); ribonucleotide reductase inhibitors; mTOR inhibitors; and haematopoietic growth factors.

Additional cytotoxic agents include, cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component (s) of such treatment in addition to the antiproliferative treatment defined herein before may be surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, idoxifene), progestogens (for example, megestrol acetate), aromatase inhibitors (for example, anastrozole, letrozole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); Intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine, vinorelbine, vinblastine and vinflunine) and taxoids such as Taxol® (paclitaxel), Taxotere® (docetaxel) and newer microbtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as Velcade® (bortezomib).

As stated above, the formula I compounds of the invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the prostate, pancreatic ductal adreno-carcinoma, breast, colon, lung, ovary, pancreas, and thyroid;

tumors of the central and peripheral nervous system, including neuroblastoma, glioblastoma, and medullobalstoma; and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease.

The compounds of formula I are especially useful in treatment of tumors having a high incidence of tyrosine kinase activity, such as prostate, colon, brain, thyroid and pancreatic tumors. Additionally, the compounds of the invention may be useful in treatment of sarcomas and pediatric sarcomas. By the administration of a composition (or a combination) of the compounds of this invention, development of tumors in a mammalian host is reduced.

Compounds of formula I may also be useful in the treatment of other cancerous diseases (such as acute myelogenous leukemia) that may be associated with signal transduction pathways operating through kinases such as Flt-3 (Fine-like kinase-3), Tie-2, CDK2, VEGFR, FGFR and IGFR kinases.

The pharmaceutical compositions of the invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ Model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

The compounds may be administered in a dosage range of about 0.05 to 200 mg/kg/day, preferably less than 100 mg/kg/day, in a single dose or in 2 to 4 divided doses.

Biological Assays

A. CDK 2/cyclin E Kinase Assay

The assays were performed in U-bottom 384-well plates. The final assay volume was 30 µl prepared from 15 µl additions of enzyme and substrates (fluoresceinated CDK2E substrate peptide and ATP) and test compounds in assay buffer (100 mM HEPES pH 7.4, 10 mM $MgCl_2$, 0.015% Brij35 and 4 mM DTT). The reaction was initiated by the combination of bacterially expressed, CDK2E with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 30 µM; FL-peptide, 1.5 µM; CDK2E, 0.2 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

B. FLT3

The assays were performed in U-bottom 384-well plates. The final assay volume was 30 µl prepared from 15 µl additions of enzyme and substrates (fluoresceinated FLT3 substrate peptide and ATP) and test compounds in assay buffer (100 mM HEPES pH 7.4, 10 mM $MgCl_2$, 0.015% Brij35 and 4 mM DTT). The reaction was initiated by the combination of FLT3 with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays are ATP, 200 µM, FL-peptide, 1.5 µM; FLT3, 4.5 nM and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

C. GSK3-β

The assays were performed in U-bottom 384-well plates. The final assay volume was 30 µl prepared from 15 µl additions of enzyme and substrates (fluoresceinated peptide FL-GSK substrate and ATP) and test compounds in assay buffer (100 mM HEPES pH 7.2, 10 mM $MgCl_2$, 0.015% Brij35, 25 mM (β-glycerolphosphate and 4 mM DTT). The reaction was initiated by the combination of GSK3-β with substrates and test compounds. The reaction was incubated at room temperature for 60 min. and terminated by adding 30 µl of 35 mM EDTA to each sample. The reaction mixture was analyzed on the Caliper LabChip 3000 (Caliper, Hopkinton, Mass.) by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 30 µM; FL-GSK substrate, 1.5 µM; His-GSK3B, 2.4 nM; and DMSO, 1.6%.

D. IGF1-Receptor Tyrosine Kinase Assay

The assays were performed in U-bottom 384-well plates. The final assay volume was 30 µl prepared from 15 µl additions of enzyme and substrates (fluoresceinated IGF1R substrate peptide and ATP) and test compounds in assay buffer (100 mM HEPES pH 7.4, 10 mM $MnCl_2$, 0.015% Brij35 and 4 mM DTT). The reaction was initiated by the combination of IGF1-receptor with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product Inhibition data were calculated by comparison to no enzyme control reactions for 100% inhibition and vehicle-only reactions for 0% inhibition. The final concentration of reagents in the assays is ATP, 25 µM; FL-peptide, 1.5 µM; IGF1-Receptor, 14 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

Compounds described herein were tested in the above assay. The following results were obtained.

TABLE I

IGF-1R in vitro kinase IC50 (uM)

| Example | IGF1R kinase $IC_{50}$ (uM) |
| --- | --- |
| 6 | 0.043 |
| 10 | 3.166 |
| 23 | 1.757 |
| 41 | 0.122 |
| 42 | 0.170 |
| 44 | 0.098 |
| 47 | 0.361 |
| 55 | 0.072 |
| 56 | 2.840 |
| 57 | 1.522 |
| 58 | 0.174 |
| 59 | 0.880 |
| 65 | 17.740 |
| 67 | 2.507 |
| 71 | 0.428 |
| 75 | 0.462 |
| 97 | 0.058 |
| 104 | 0.002 |
| 105 | 0.004 |
| 107 | 0.016 |
| 110 | 0.002 |
| 111 | 0.007 |
| 126 | 0.370 |
| 133 | 2.724 |
| 134 | 0.034 |
| 149 | 0.912 |
| 154 | 0.021 |
| 188 | 0.028 |
| 190 | 0.232 |
| 209 | 0.002 |
| 211 | 0.001 |
| 215 | 2.070 |
| 216 | 0.005 |
| 219 | 0.001 |
| 243 | 0.005 |
| 254 | 0.001 |
| 255 | 0.000 |
| 256 | 0.002 |
| 259 | 0.002 |
| 287 | 0.003 |
| 288 | 0.001 |
| 293 | 0.002 |
| 294 | 0.005 |
| 301 | 0.002 |
| 317 | 0.014 |
| 318 | 0.003 |

E. Insulin Receptor Tyrosine Kinase Assay

The assays were performed in U-bottom 384-well plates. The final assay volume was 30 μl prepared from 15 μl additions of enzyme and substrates (fluoresceinated InsR substrate peptide and ATP) and test compounds in assay buffer (100 mM HEPES pH 7.4, 10 mM $MnCl_2$, 0.015% Brij35 and 4 mM DTT). The reaction was initiated by the combination of Insulin Receptor with substrates and test compounds. The reaction was incubated at room temperature for 60 min. and terminated by adding 30 μl of 35 mM EDTA to each sample. The reaction mixture was analyzed on the Caliper LabChip 3000 by electrophoretic separation of the fluorescent substrate and phosphorylated product Inhibition data were calculated by comparison to no enzyme control reactions for 100% inhibition and vehicle-only reactions for 0% inhibition. The final concentration of reagents in the assays is ATP, 25 μM; FL-peptide, 1.5 μM; Insulin Receptor, 14 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

F. JAK2

The assays were performed in U-bottom 384-well plates. The final assay volume was 30 μl prepared from 15 μl additions of enzyme and substrates (fluoresceinated peptide FL-JAK2 substrate and ATP) and test compounds in assay buffer (100 mM HEPES pH 7.2, 10 mM $MgCl_2$, 0.015% Brij35, 25 mM β-glycerolphosphate and 4 mM DTT). The reaction was initiated by the combination of activated JAK2 with substrates and test compounds. The reaction was incubated at room temperature for 60 min. and terminated by adding 30 μl of 35 mM EDTA to each sample. The reaction mixture was analyzed on the Caliper LabChip 3000 (Caliper, Hopkinton, Mass.) by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 30 μM; FL-JAK2 peptide, 1.5 μM; His-CDK5/p25, 2.6 nM; and DMSO, 1.6%.

G. LCK Kinase Assay

The assays were performed in U-bottom 384-well plates. The final assay volume was 30 μl prepared from 15 μl additions of enzyme and substrates (fluoresceinated LCK substrate peptide and ATP) and test compounds in assay buffer (100 mM HEPES pH 7.4, 10 mM $MnCl_2$, 0.015% Brij35 and 4 mM DTT). The reaction was initiated by the combination of LCK with substrates and test compounds. The reaction was incubated at room temperature for 60 min. and terminated by adding 30 μl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 3 μM; FL-peptide, 1.5 μM; Lck, 1 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

H. MapKapK2

The assays were performed in U-bottom 384-well plates. The final assay volume was 30 μl prepared from 15 μl additions of enzyme and substrates (fluoresceinated MK2 substrate peptide and ATP) and test compounds in assay buffer (100 mM HEPES pH 7.4, 10 mM $MgCl_2$, 0.015% Brij35 and 4 mM DTT). The reaction was initiated by the combination of MapKapK2 with substrates and test compounds. The reaction was incubated at room temperature for 60 min. and terminated by adding 30 μl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays are ATP, 1 μM; FL-peptide, 1.5 μM; MapKapK2, 0.08 nM; Brij35, 0.015% and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

I. Met Kinase Assay

Kinase reactions consisted of 0.75 ng of baculovirus expressed GST-Met, 3 ug poly(Glu/Tyr) (Sigma), 0.12 µCi 33P γ-ATP, 1 µM ATP in 30 µl kinase buffer (20 mm TRIS-Cl, 5 mM $MnCl_2$, 0.1 mg/ml BSA, 0.5 mM DTT). Reactions were incubated for 1 h at 30° C. and stopped by the addition of cold trichloroacetic acid (TCA) to a final concentration 8%. TCA precipitates were collected onto GF/C unifilter plates using a Filtermate universal harvester and the filters were quantitated using a TopCount 96-well liquid scintillation counter. Dose response curves were generated to determine the concentration required to inhibit 50% of kinase activity ($IC_{50}$). Compounds were dissolved at 10 mM in dimethylsulfoxide (DMSO) and evaluated at seven concentrations, each in triplicate.

J. p38alpha Assay

The assays were performed in U-bottom 384-well plates. The final assay volume was 30 µl prepared from 15 µl additions of enzyme and substrates (fluoresceinated P38a substrate peptide and ATP) and test compounds in assay buffer (100 mM HEPES pH 7.2, 10 mM $MgCl_2$, 0.015% Brij35 and 4 mM DTT). The reaction was initiated by the combination of activated p38alpha with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product Inhibition data were calculated by comparison to no enzyme control reactions for 100% inhibition and vehicle-only reactions for 0% inhibition. The final concentration of reagents in the assays is ATP, 20 µM; FL-peptide, 1.5 µM; p38alpha, 6 nM; and DMSO, 1.6%.

K. p38beta Assay

The assays were performed in U-bottom 384-well plates. The final assay volume was 30 µl prepared from 15 µl additions of enzyme and substrates (fluoresceinated P38b substrate peptide and ATP) and test compounds in assay buffer (100 mM HEPES pH 7.2, 10 mM $MgCl_2$, 0.015% Brij35 and 4 mM DTT). The reaction was initiated by the combination of activated p38beta with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays are ATP, 20 µM; FL-peptide, 1.5 µM; p38beta, 1 nM; and DMSO, 1.6%.

L. Protein Kinase A

The assays were performed in U-bottom 384-well plates. The final assay volume was 30 µl prepared from 15 µl additions of enzyme and substrates (fluoresceinated PKA substrate peptide and ATP) and test compounds in assay buffer (100 mM HEPES pH 7.4, 10 mM $MgCl_2$, 0.015% Brij35 and 4 mM DTT). The reaction was initiated by the combination of Protein kinase A with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product Inhibition data were calculated by comparison to no enzyme control reactions for 100% inhibition and vehicle-only reactions for 0% inhibition. The final concentration of reagents in the assays is ATP, 20 µM; FL-peptide, 1.5 µM, Protein kinase A 1 nM, and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

M. Protein Kinase C-alpha

The assays were performed in U-bottom 384-well plates. The final assay volume was 30 µl prepared from 15 µl additions of enzyme and substrates (fluoresceinated PKCa substrate peptide and ATP) and test compounds in assay buffer (100 mM HEPES pH 7.4, 10 mM $MgCl_2$, 0.015% Brij35 and 4 mM DTT). The reaction was initiated by the combination of Protein kinase C-alpha with lipids, substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 1 µM; FL-peptide, 1.5 µM; Protein kinase C-alpha, 1 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

N. TrkA Kinase Assay

Kinase reactions consisted of 0.12 ng of baculovirus expressed His-TrkA, 3 ug poly(Glu/Tyr) (Sigma), 0.24 µCi 33P γ-ATP, 30 µM ATP in 30 µl kinase buffer (20 mm MOPS, 10 mM $MgCl_2$, 1 mM EDTA, 0.015% Brij-35, 0.1 mg/ml BSA, 0.0025% Beta-Mercaptoethanol). Reactions were incubated for 1 h at 30° C. and stopped by the addition of cold trichloroacetic acid (TCA) to a final concentration 8%. TCA precipitates were collected onto GF/C unifilter plates using a Filtermate universal harvester and the filters were quantitated using a TopCount 96-well liquid scintillation counter. Dose response curves were generated to determine the concentration required to inhibit 50% of kinase activity ($IC_{50}$). Compounds were dissolved at 10 mM in dimethylsulfoxide (DMSO) and evaluated at seven concentrations, each in triplicate.

O. TrkB Kinase Assay

Kinase reactions consisted of 0.75 ng of baculovirus expressed His-TrkB, 3 ug poly(Glu/Tyr) (Sigma), 0.24 µCi 33P γ-ATP, 30 µM ATP in 30 µl kinase buffer (20 mm MOPS, 10 mM $MgCl_2$, 1 mM EDTA, 0.015% Brij-35, 0.1 mg/ml BSA, 0.0025% Beta-Mercaptoethanol). Reactions were incubated for 1 h at 30° C. and stopped by the addition of cold trichloroacetic acid (TCA) to a final concentration 8%. TCA precipitates were collected onto GF/C unifilter plates using a Filtermate universal harvester and the filters were quantitated using a TopCount 96-well liquid scintillation counter. Dose response curves were generated to determine the concentration required to inhibit 50% of kinase activity ($IC_{50}$). Compounds were dissolved at 10 mM in dimethylsulfoxide (DMSO) and evaluated at seven concentrations, each in triplicate.

P. IGF-1R Sal Tumor Model

A salivary gland adenocarcinoma that developed spontaneously in a transgenic mouse (MCI-19) was excised and cut into fragments of about 20 mg. Tumor fragments were implanted s.c. into the ventral thoracic region of a group of six female, athymic BALB/c nu/nu mice (Harley Sprague-Dawley, Indianapolis, Ind.), using a 13-gauge trocar. Once established, the salivary gland-derived tumor line was designated IGF 1R-Sal and was propagated as a tumor xenograft in nude mice. Tumors were passaged every 2 weeks, at which time the tumor reached f500 to 1,000 mm3 in size. For treatment studies, nude micebearing IGF1R-Sal tumors of about 100 mm3 in size were sorted into groups of five for treatment with vehicle (80% polyethylene glycol 400 in water) alone or the test article. Compounds were administered either on a bid schedule (oral doses 8 hours apart) or on a once a day schedule orally (qd) for 4 consecutive days. Tumors were measured at the start and end of treatment. Activity was measured as % tumor growth inhibition (% TGI). The % TGI was determined using the following formula $(C_t-T_t)/(C_t-C_o)$ where $C_t$ is defined as the median tumor size of the control group at the end of treatment, $C_o$ is defined as the median tumor size of the control group at the start of treatment, and $T_t$ is defined as the median tumor size of the treated group at the end of treatment.

Compounds described herein were tested in the above assay. The following results were obtained.

TABLE II

| In vivo efficacy in IGF-1R Sal tumor model | | | |
|---|---|---|---|
| Example | IGF-1R Sal % TGI | Dose (mpk) | Schedule |
| 3 | 80% | 6.25 | qd |
| 68 | 76% | 25 | bid |
| 85 | 76% | 25 | bid |
| 104 | 112% | 25 | bid |
| 107 | 107% | 25 | bid |
| 110 | 114% | 25 | bid |
| 111 | 80% | 25 | bid |
| 135 | 25% | 25 | bid |
| 194 | 52% | 25 | bid |
| 198 | 124% | 25 | bid |
| 206 | 111% | 50 | qd |
| 211 | 55% | 50 | qd |
| 213 | 116% | 50 | qd |
| 216 | 0% | 25 | bid |
| 217 | 0% | 25 | bid |
| 219 | 117% | 50 | qd |
| 227 | 115% | 50 | qd |
| 236 | 113% | 25 | bid |
| 243 | 21% | 50 | qd |
| 245 | 112% | 50 | qd |
| 254 | 114% | 25 | qd |
| 255 | 112% | 25 | qd |
| 256 | 119% | 50 | qd |
| 259 | 118% | 50 | qd |
| 287 | 119% | 50 | qd |
| 288 | 103% | 50 | qd |
| 293 | 46% | 50 | qd |
| 318 | 100% | 50 | qd |

Methods of Preparation

In general, the compounds of Formula (I) can be prepared in accordance with Scheme I and the general knowledge of one skilled in the art. Tautomers and solvates (e.g., hydrates) of the compounds of Formula (I) are also within the scope of the invention. Methods of solvation are generally known in the art. Accordingly, the compounds of the instant invention can be in the free or hydrate form, and can be obtained by methods exemplified in the following Schemes.

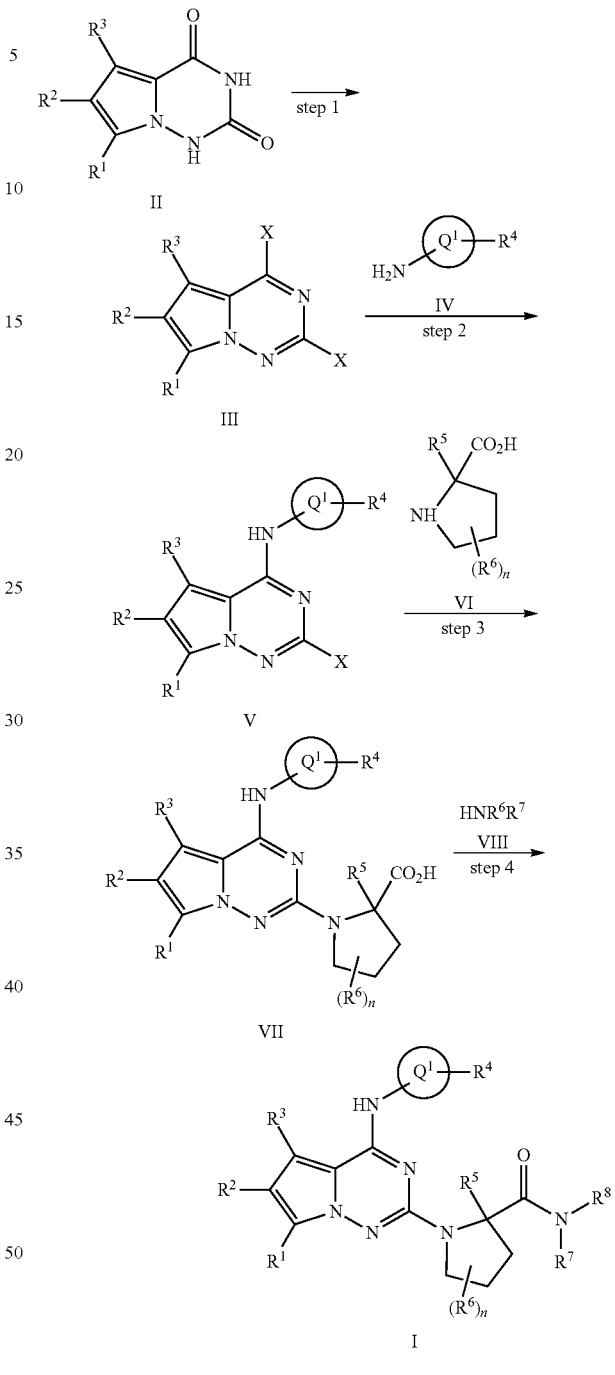

Scheme I

Step 1

Compound II can be prepared by heating a mixture of the appropriately substituted 1-amino-1H-pyrrole-2-carboxamide with a reagent, such as, for example, ethyl chloroformate and an appropriate base, such as, for example, pyridine in a solvent, such as, for example, dioxane. The resulting pyrrolotriazine-2,4-dione II can then be heated with a halogenating agent, such as, for example, phosphorus oxychloride (X=Cl) or phosphorus oxybromide (X=Br) in the presence of a base, such as for example, diisopropylethylamine to give compound III.

Step 2

Compound V is produced by treating compound III with an appropriately substituted amino compound IV in the presence of a base, such as, for example, diisopropylethylamine in a solvent, such as, for example, isopropyl alcohol. Alternatively, transition metal catalyzed methods for introduction of the amino compound IV could also be envisioned.

Step 3

Compound VII is obtained by heating compound V with an appropriately functionalized proline VI and bases, such as, for example aqueous sodium hydroxide or potassium tertiary butoxide in organic solvents such as, for example, dioxane or N-methylpyrrolidinone at elevated temperatures or in a microwave reactor. Alternatively, transition metal catalyzed methods for introduction of the amino compound VI could also be envisioned in combination with heat.

Step 4

Compound I is obtained by coupling acid VII with an amine VIII using reagents that form amide bonds such as, for example, (benzotriazol-1-yloxy)tripyrrolidinophosphonium hexafluorophosphate and a base, such as, for example, diisopropylethylamine in a solvent such as, for example, dimethylformamide. Another method involves treating compound VII with two or more equivalents of an acid chloride such as, for example, pivaloyl chloride in the presence of two or more equivalents of a base such as diisopropylethylamine in a solvent such as N-methylpyrrolidinone to generate a mixture of intermediates that will react with the alkali metal salt of an aryl or heteroaryl amine to give compound I. The latter alkali metal salt can be generated by reaction of an aryl or heteroaryl amine and an alkyl metal such as, for example, methyl or isopropyl magnesium chloride. A third method, consists of converting the acid to an alkyl ester and reacting said ester with alkali metal salt of an aryl or heteroaryl amine to give compound I. In those examples where $R_6$ is a hydroxyl group capable of forming a lactone with the acid carbonyl, such a lactone could be formed using any number of reagents known in the art to promote lactonization, such as 1-hydroxybenzotriazole hydrate and 1-[3-(dimethylamino)propyl]-3-ethyl-carbodiimide hydrochloride. This lactone could then be converted to a hydroxylamide by reacting the lactone with alkali metal salt of an aryl or heteroaryl amine to give compound I. Other amide bond forming reactions could be used and are well know in the art, see for example: "Principles of Peptide Synthesis," M. Bodanszky, $2^{nd}$ Edition, Springer-Verlag, 1993 and S.-Y. Han and Y.-A. Kim, Tetrahedron, 2004, volume 60, page 2447.

Scheme 2

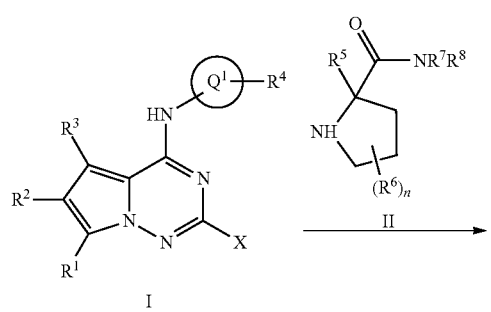

Compound V of Scheme 1

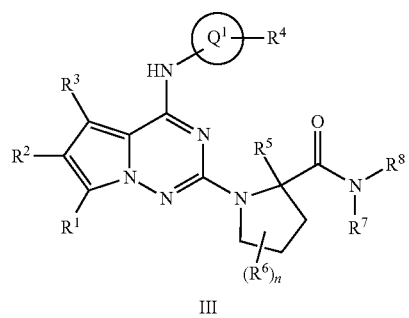

Compound I of Scheme 1

Compound I (V of Scheme 1) is heated directly with the substituted pyrrolidine carboxamide II of Scheme 2 to give compound III (I of Scheme 1). Alternatively, transition metal catalyzed methods for introduction of the amino compound II could also be envisioned in combination with heat.

Scheme 3

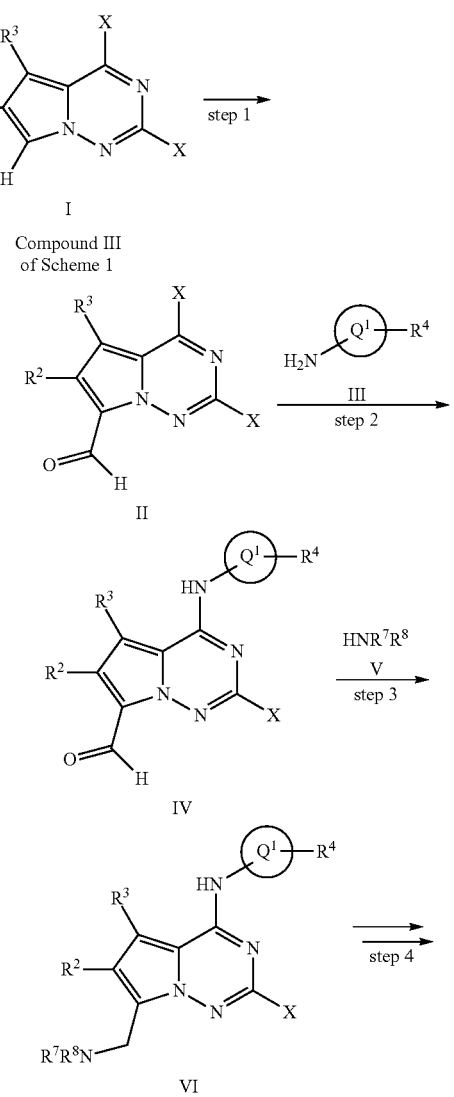

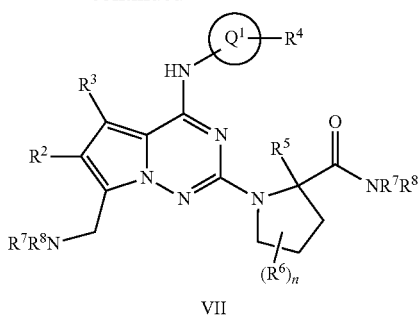

VII

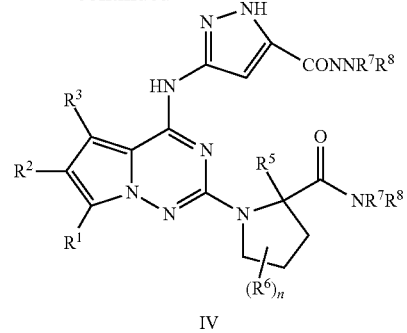

IV

Step 1

A compound III of Scheme 1, wherein $R^1$ is H, can be converted to the aldehyde II of Scheme 3 by heating with a Vilsmeier reagent, such as that generated from dimethylformamide and phosphorous oxychloride, followed by hydrolysis.

Step 2

Compound II of Scheme 3 is converted to compound IV by reaction with an appropriately substituted amino derivative III in the presence of a base, such as, for example, diisopropylethylamine in a solvent, such as, for example, isopropyl alcohol.

Step 3

Compound IV is reacted with an amino compound V in the presence of a reducing agent such as sodium triacetoxyborohydride and a catalyst such as acetic acid in a solvent such as 1,2-dichloroethane to give compound VI of Scheme 3.

Step 4

Compound VI is converted into compound VII using procedures analogous to those described in Scheme 1 or 2.

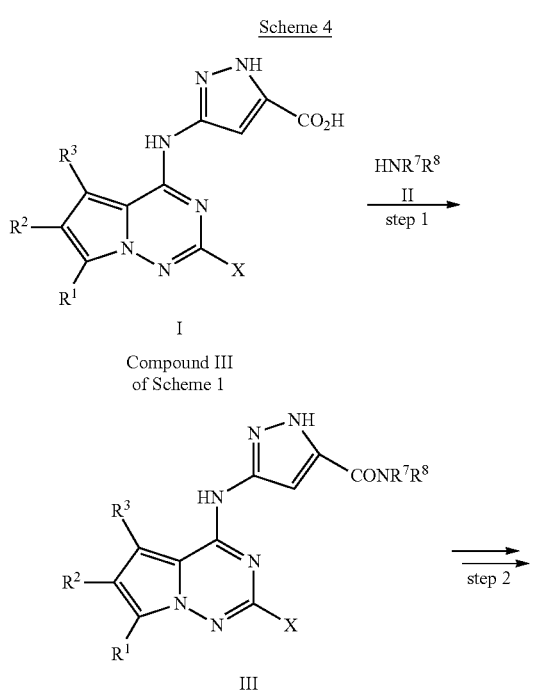

Step 1

A compound III of Scheme 1 wherein $Q^1R^4$ is a 5-pyrazolecarboxylic acid is converted to the 5-pyrazolecarboxamide III of Scheme 4 by treatment with amine II and reagents such as, for example, 1-hydroxybenzotriazole hydrate and 1-[3-(dimethylamino)propyl]-3-ethylcarbodiimide hydrochloride (EDCI) and a base, such as, for example, diisopropylethylamine in a solvent such as, for example, dimethylformamide or 1-methyl-2-pyrrolidinone (NMP). Other amide bond forming reagents could be used and are well know in the art, see for example: "Principles of Peptide Synthesis," M. Bodanszky, $2^{nd}$ Edition, Springer-Verlag, 1993 and S.-Y. Han and Y.-A. Kim, Tetrahedron, 2004, volume 60, page 2447.

Step 2

Compound III of Scheme 4 is converted to compound IV using procedures analogous to those described in Scheme 1 or 2.

EXAMPLES

The invention is further defined in the following Examples. It should be understood that these Examples are given by way of illustration only. From the above discussion and this Example, one skilled in the art can ascertain the essential characteristics of this invention, and without departing from the spirit and scope thereof, can make various changes and modifications to the invention to adapt the invention to various uses and conditions. As a result, the invention is not limited by the illustrative examples set forth hereinbelow, but rather defined by the claims appended hereto.

All temperatures are in degrees Celsius (° C.) unless indicated otherwise herein.

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm) or using a Biotage Horizon™HPFC™ system.

The following abbreviations are employed herein: HCl: hydrochloric acid, TFA: trifluoroacetic acid, $CH_3CN$: acetonitrile, MeOH: methanol, $MgSO_4$: magnesium sulfate, $NaHCO_3$: sodium bicarbonate, DMA: dimethylamine, $Cs_2CO_3$: cesium carbonate, $POCl_3$: phosphorous oxychloride, EtOH: ethanol, $CH_2Cl_2$: dichloromethane, NMP: 1-methyl-2-pyrrolidinone, DMF: N,N-dimethylformamide, Bn: benzyl, Me: methyl, Et: ethyl, min.: minute(s), h or hr(s): hour(s), L: liter, mL: milliliter, μL: microliter, g: gram(s), mg: milligram(s), mol.: moles, mmol; millimole(s), meq.: milliequivalent, RT or rt: room temperature, ret. t.: HPLC retention time (minutes), sat or sat'd: saturated, aq.: aqueous, TLC: thin layer chromatography, HPLC: high performance liquid chromatography, RP HPLC: reverse phase HPLC, Prep HPLC: preparative reverse phase HPLC, LC/MS: high performance liquid chromatography/mass spectrometry, MS: mass spectrometry, NMR: nuclear magnetic resonance, and mp: melting point.

Compounds with an epimerizable hydrogen at the C-2 position of the proline ring were obtained as a mixture of enantiomers that could be separated using chiral super critical fluid chromatography.

HPLC Conditions for Examples 1 to 103

Unless otherwise indicated herein, Analytical Reverse Phase HPLC retention times (Ret Time) were obtained using a Phenomenex S10 column 3.0×50 mm with a 4 mL/min flow rate and 2 min. linear gradient elution starting with 100% solvent A (10% MeOH, 90% $H_2O$, 0.1% TFA) and 0% solvent B, and ended with 100% solvent B (90% MeOH, 10% $H_2O$, 0.1% TFA) and 0% solvent A). UV detection was conducted at 220 nm.

Preparative Reverse Phase (RP)HPLC was performed with a linear gradient elution using $H_2O$/MeOH mixtures buffered with 0.1% trifluoroacetic acid and detection at 220 nm or 254 nm on one of the following columns: Shimadzu S5 ODS-VP 20×100 mm (flow rate=9 mL/min), or YMC S10 ODS 50×500 mm (flow rate=50 mL/min), or YMC S10 ODS 30×500 mm (flow rate=20 mL/min).

All final products were characterized by $^1H$ NMR, COSY NMR, RP HPLC, electrospray ionization (ESI MS) or atmospheric pressure ionization (API MS) mass spectrometry. $^1H$ NMR spectra were obtained on either a 500, 400 or 300 MHz Bruker instrument. $^{13}C$ NMR spectra were recorded at 100 or 125 MHz. Field strengths are expressed in units of δ (parts per million, ppm) relative to the solvent peaks, and peak multiplicities are designated as follows: s, singlet; d, doublet; dd, doublet of doublets; dm, doublet of multiplets; t, triplet; q, quartet; br s, broad singlet; m, multiplet.

Example 1

(S)-1-(4-(5-cyclopropyl-1H-pyrazol-3-ylamino)pyrrolo[1,2-f][1,2,4]triazin-2-yl)-N-(tetrahydro-2H-pyran-4-yl)pyrrolidine-2-carboxamide

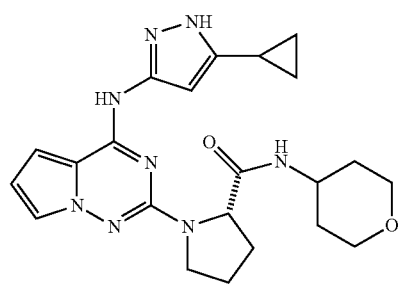 [SMILES: O=C(NC1CCOCC1)[C@@H]1CCCN1c1nc(Nc2cc(C3CC3)[nH]n2)c2cccn2n1]

1A. Pyrrolo[2,1-f][1,2,4]triazine-2,4(1H,3H)-dione

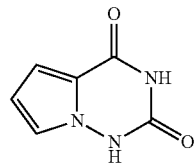 [SMILES: O=c1[nH]c(=O)c2cccn2[nH]1]

Ethyl chloroformate (4.9 ml, 51 mmole) was added dropwise to a stirred mixture of 1-amino-1H-pyrrole-2-carboxamide (5.85 gm, 46.7 mmole, Journal of Heterocyclic Chemistry, 1994, 31, 781) and dry pyridine (4.2 mL, 51 mmole) in dry dioxane (48 mL) under $N_2$ at RT. This was heated at reflux for 1 hr and then the solvent was removed. The residue was heated at 155° C. for 17 hr and then allowed to cool to RT. This was triturated with methanol and the solid was collected by filtration and washed with cold methanol to give the product, 4.43 gm (63% yield): MS: 152 $(M+H)^+$; HPLC Ret Time: 0.36 min (YMC Xterra S7 3.0×50 mm column, 2 min gradient, 5 mL/min).

1B. 2,4-Dichloropyrrolo[1,2-f][1,2,4]triazine

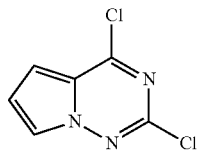 [SMILES: Clc1nc(Cl)c2cccn2n1]

A mixture of 1A (4.7 gm, 31.1 mmole), phosphorous oxychloride (8.81 mL, 3 equiv), and diisopropylethylamine (10.8 mL, 2 equiv) in toluene in a pressure vessel was heated at 125° C. for 24 hr. After cooling to RT, the reaction was poured into an ice-cooled saturated aqueous solution of $NaHCO_3$ with stirring. After 10 min, the aqueous phase was separated and washed with DCM (3×200 mL). The combined organic phases were washed with brine, dried ($Na_2SO_4$), and the solvent removed. Silica gel column chromatography (elution with DCM) afforded the product as a solid, 4.25 gm (81% yield): MS: 187.9 $(M+H)^+$; HPLC Ret Time: 1.63 min (YMC Xterra S5, 4.6×50 mm column, 2 min gradient, 5 mL/min).

1C. 2-Chloro-N-(5-cyclopropyl-1H-pyrazol-3-yl) pyrrolo[1,2-f][1,2,4]triazin-4-amine

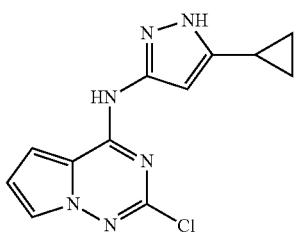 [SMILES: Clc1nc(Nc2cc(C3CC3)[nH]n2)c2cccn2n1]

A mixture of 1B (977 mg, 5.2 mmole), 5-cyclopropyl-1H-pyrazol-3-amine (640 mg, 1 equiv), and diisopropylethylamine (1.54 mL, 1.7 equiv) in isopropyl alcohol (5 mL) was stirred at RT overnight. The product was collected by filtration (1.18 gm, 83% yield): MS: 275 (M+H)+; HPLC Ret Time: 1.56 min.

1D. (S)-1-(4-(5-cyclopropyl-1H-pyrazol-3-ylamino) pyrrolo[1,2-f][1,2,4]-triazin-2-yl)pyrrolidine-2-carboxylic acid

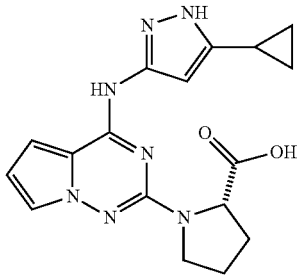 [SMILES: O=C(O)[C@@H]1CCCN1c1nc(Nc2cc(C3CC3)[nH]n2)c2cccn2n1]

A mixture of 1C (1.38 gm, 5.0 mmole), diisopropylethylamine (0.87 mL, 5.0 mmole) and S-proline (2.88 gm, 25 mmole, dissolved in an aqueous solution of NaOH (5 mL, 5.0 N, 25 mmole)) in 1,4-dioxane (10 mL) was heated in a microwave reactor (Smith Synthesizer by Personal Chemistry) at 150° C. for 4 hr. After cooling to room temperature, the organic phase was separated, diluted with ethyl acetate, and washed with water. The combined aqueous phases were washed with ethyl acetate and then acidified with 1.0 N aqueous HCl solution to give a precipitate. This was collected by filtration, washed with water, and dried under vacuum over phosphorus pentoxide to give 1.66 gm (94% yield) of the product: MS: 354 (M+H)+; HPLC Ret Time: 1.52 min.
1E.

(Benzotriazol-1-yloxy)tripyrrolidinophosphonium hexafluorophosphate (PyBOP) (52 mg, 0.10 mmole) was added to a stirred solution of diisopropylethylamine (0.47 mL, 0.27 mmole), 1D (35 mg, 0.10 mmole) and tetrahydro-2H-pyran-4-amine (21 mg, 0.20 mmole) in dry dimethylformamide (0.15 mL). The reaction was stirred overnight and the product was separated by preparative HPLC of the crude reaction mixture. The HPLC fractions that contained the product were applied onto a cartridge of Phenomenex Strata-X-C 33 um cation mixed-mode polymer. This was washed with methanol and the product was eluted with a 2 N solution of ammonia in methanol. Removal of the solvents left 1, 23 mg (53% yield): MS: 437 (M+H)+; HPLC Ret Time: 1.43 min.

Example 2

(S)-1-(4-(5-cyclopropyl-1H-pyrazol-3-ylamino)pyrrolo[1,2-f][1,2,4]triazin-2-yl)-N-phenylpyrrolidine-2-carboxamide

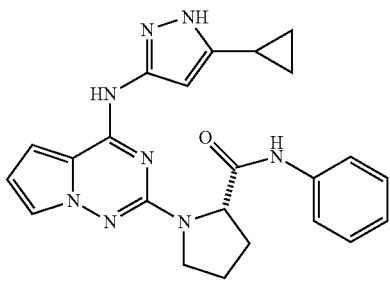 [SMILES: O=C(Nc1ccccc1)[C@@H]1CCCN1c1nc(Nc2cc(C3CC3)[nH]n2)c2cccn2n1]

Diisopropylethylamine (0.118 mL, 0.675 mmole) was added to a stirred mixture of 1D (100 mg, 0.25 mmole), aniline (47 mg, 0.50 mmole) and PyBOP (130 mg, 0.25 mmole) in dry dimethylformamide (0.30 mL). The reaction was stirred overnight and the product was separated by preparative HPLC of the crude reaction mixture. The HPLC fractions that contained the product were applied onto a cartridge of Phenomenex Strata-X-C 33 um cation mixed-mode polymer. This was washed with methanol and the product was eluted with a 2 N solution of ammonia in methanol. Removal of the solvents left 2, 45 mg (42% yield): MS: 429 (M+H)+; HPLC Ret Time: 1.57 min.

Example 3

(S)-1-(4-(5-cyclopropyl-1H-pyrazol-3-ylamino)pyrrolo[1,2-f][1,2,4]triazin-2-yl)-N-methylpyrrolidine-2-carboxamide

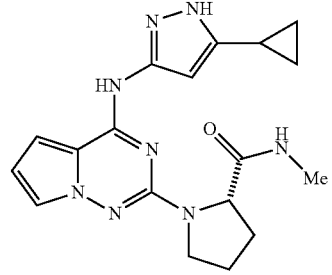 [SMILES: CNC(=O)[C@@H]1CCCN1c1nc(Nc2cc(C3CC3)[nH]n2)c2cccn2n1]

A mixture of 1C (45 mg, 0.164 mmole) and (S)-N-methylpyrrolidine-2-carboxamide (135 mg, 1.06 mmole) was heated in a sealed tube for 3 hr at 130° C. After cooling this was dissolved in methanol and the product was separated by preparative HPLC. The HPLC fractions that contained the product were applied onto a cartridge of Phenomenex Strata-X-C 33 um cation mixed-mode polymer. This was washed with methanol and the product was eluted with a 2 N solution of ammonia in methanol. Removal of the solvents left 3 (34 mg, 57% yield): MS: 367 (M+H)+; HPLC Ret Time: 1.35 min (Phenomenex-Luna S10 3.0×50 mm column, 2 min gradient, 4 mL/min).

Examples 4 to 37

Table 1 contains Examples 4 to 37 which were prepared using procedures described above in Examples 1 to 3.

TABLE 1

| Example | Compound | HPLC Ret Time (min.) | (M + H)+ |
|---|---|---|---|
| 4 | (R)-1-(4-(5-cyclopropyl-1H-pyrazol-3-ylamino)pyrrolo[1,2-f][1,2,4]triazin-2-yl)pyrrolidine-2-carboxylic acid | 1.45 | 354 |
| 5 | ((S)-1-(4-(5-cyclopropyl-1H-pyrazol-3-ylamino)pyrrolo[1,2-f][1,2,4]triazin-2-yl)pyrrolidine-2-carboxamide | 1.34 | 353 |
| 6 | (R)-1-(4-(5-cyclopropyl-1H-pyrazol-3-ylamino)pyrrolo[1,2-f][1,2,4]triazin-2-yl)pyrrolidine-2-carboxamide | 1.31 | 353 |
| 7 | (S)-1-(4-(5-cyclopropyl-1H-pyrazol-3-ylamino)pyrrolo[1,2-f][1,2,4]triazin-2-yl)-N,N-dimethylpyrrolidine-2-carboxamide | 1.39 | 381 |

TABLE 1-continued

| Example | Compound | HPLC Ret Time (min.) | (M + H)+ |
|---|---|---|---|
| 8 | 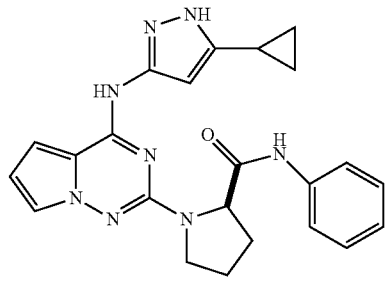<br>(R)-1-(4-(5-cyclopropyl-1H-pyrazol-3-ylamino)pyrrolo[1,2-f][1,2,4]triazin-2-yl)-N-phenylpyrrolidine-2-carboxamide | 1.60 | 429 |
| 9 | 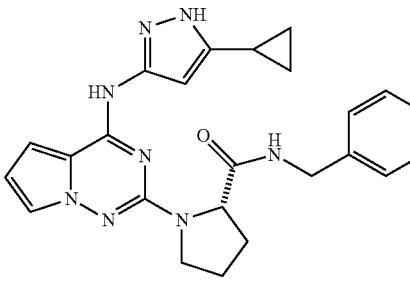<br>(S)-N-benzyl-1-(4-(5-cyclopropyl-1H-pyrazol-3-ylamino)pyrrolo[1,2-f][1,2,4]triazin-2-yl)pyrrolidine-2-carboxamide | 1.53 | 443 |
| 10 | 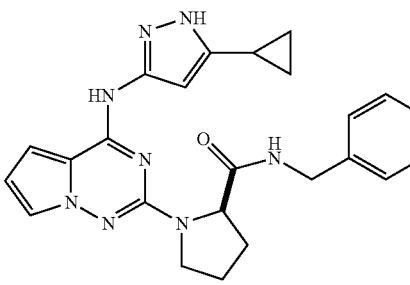<br>(R)-N-benzyl-1-(4-(5-cyclopropyl-1H-pyrazol-3-ylamino)pyrrolo[1,2-f][1,2,4]triazin-2-yl)pyrrolidine-2-carboxamide | 1.53 | 443 |
| 11 | 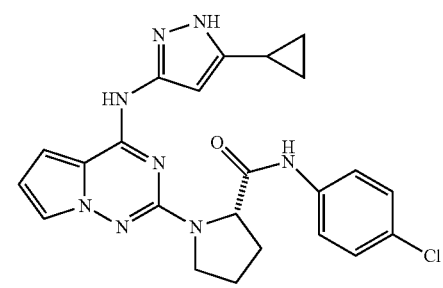<br>(S)-N-(4-chlorophenyl)-1-(4-(5-cyclopropyl-1H-pyrazol-3-ylamino)pyrrolo[1,2-f][1,2,4]triazin-2-yl)pyrrolidine-2-carboxamide | 1.73 | 463 |

TABLE 1-continued

| Example | Compound | HPLC Ret Time (min.) | (M + H)+ |
|---|---|---|---|
| 12 | (S)-N-(3-chlorophenyl)-1-(4-(5-cyclopropyl-1H-pyrazol-3-ylamino)pyrrolo[1,2-f][1,2,4]triazin-2-yl)pyrrolidine-2-carboxamide | 1.76 | 463 |
| 13 | (S)-N-cyclopentyl-1-(4-(5-cyclopropyl-1H-pyrazol-3-ylamino)pyrrolo[1,2-f][1,2,4]triazin-2-yl)pyrrolidine-2-carboxamide | 1.63 | 421 |
| 14 | (S)-N-cyclohexyl-1-(4-(5-cyclopropyl-1H-pyrazol-3-ylamino)pyrrolo[1,2-f][1,2,4]triazin-2-yl)pyrrolidine-2-carboxamide | 1.70 | 435 |
| 15 | (S)-N-tert-butyl-1-(4-(5-cyclopropyl-1H-pyrazol-3-ylamino)pyrrolo[1,2-f][1,2,4]triazin-2-yl)pyrrolidine-2-carboxamide | 1.62 | 409 |

TABLE 1-continued

| Example | Compound | HPLC Ret Time (min.) | (M + H)+ |
|---|---|---|---|
| 16 | 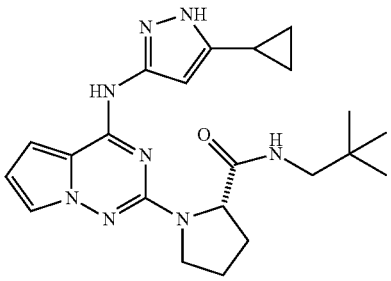<br>(S)-1-(4-(5-cyclopropyl-1H-pyrazol-3-ylamino)pyrrolo[1,2-f][1,2,4]triazin-2-yl)-N-neopentylpyrrolidine-2-carboxamide | 1.67 | 423 |
| 17 | 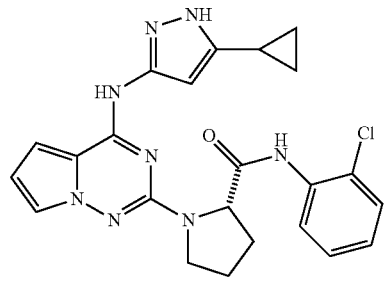<br>(S)-N-(2-chlorophenyl)-1-(4-(5-cyclopropyl-1H-pyrazol-3-ylamino)pyrrolo[1,2-f][1,2,4]triazin-2-yl)pyrrolidine-2-carboxamide | 1.81 | 463 |
| 18 | 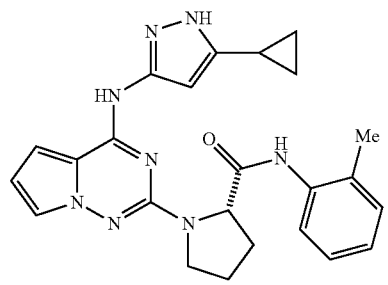<br>(S)-1-(4-(5-cyclopropyl-1H-pyrazol-3-ylamino)pyrrolo[1,2-f][1,2,4]triazin-2-yl)-N-o-tolylpyrrolidine-2-carboxamide | 1.64 | 443 |
| 19 | 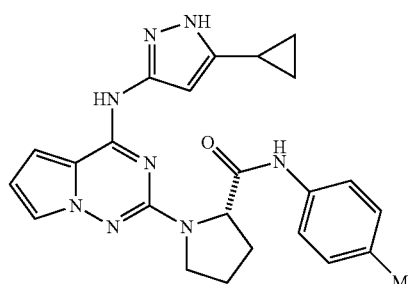<br>(S)-1-(4-(5-cyclopropyl-1H-pyrazol-3-ylamino)pyrrolo[1,2-f][1,2,4]triazin-2-yl)-N-p-tolylpyrrolidine-2-carboxamide | 1.69 | 443 |

TABLE 1-continued

| Example | Compound | HPLC Ret Time (min.) | (M + H)+ |
|---|---|---|---|
| 20 | 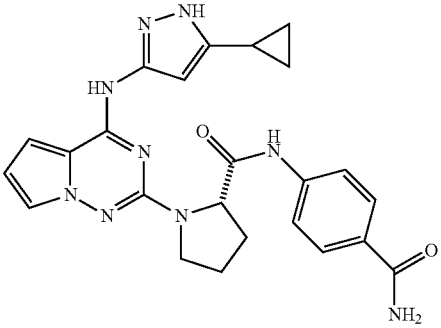<br>(S)-N-(4-carbamoylphenyl)-1-(4-(5-cyclopropyl-1H-pyrazol-3-ylamino)pyrrolo[1,2-f][1,2,4]triazin-2-yl)pyrrolidine-2-carboxamide | 1.43 | 472 |
| 21 | 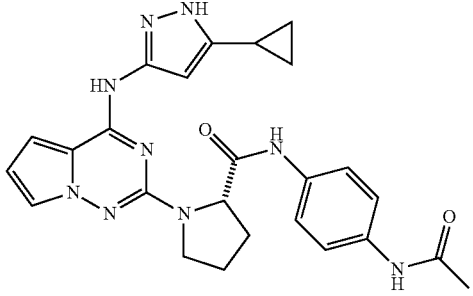<br>(S)-N-(4-acetamidophenyl)-1-(4-(5-cyclopropyl-1H-pyrazol-3-ylamino)pyrrolo[1,2-f][1,2,4]triazin-2-yl)pyrrolidine-2-carboxamide | 1.57 | 486 |
| 22 | 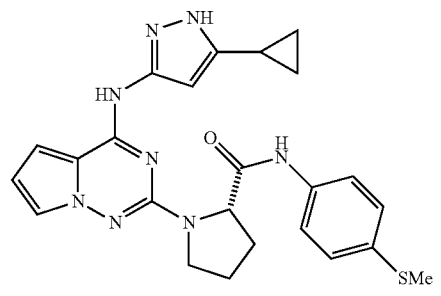<br>(S)-1-(4-(5-cyclopropyl-1H-pyrazol-3-ylamino)pyrrolo[1,2-f][1,2,4]triazin-2-yl)-N-(4-(methylthio)phenyl)pyrrolidine-2-carboxamide | 1.74 | 475 |

TABLE 1-continued
| Example | Compound | HPLC Ret Time (min.) | (M + H)+ |
|---|---|---|---|
| 23 | 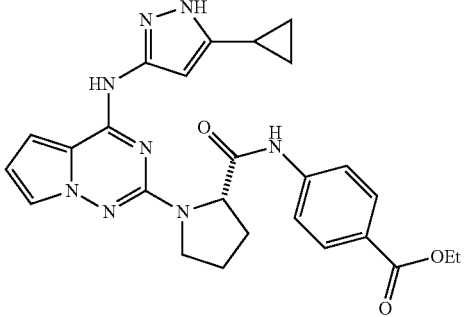<br>((S)-ethyl 4-(1-(4-(5-cyclopropyl-1H-pyrazol-3-ylamino)pyrrolo[1,2-f][1,2,4]triazin-2-yl)pyrrolidine-5-carboxamido)benzoate | 1.75 | 51 |
| 24 | 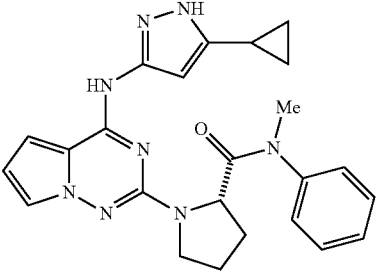<br>(S)-1-(4-(5-cyclopropyl-1H-pyrazol-3-ylamino)pyrrolo[1,2-f][1,2,4]triazin-2-yl)-N-methyl-N-phenylpyrrolidine-2-carboxamide | 1.67 | 43 |
| 25 | 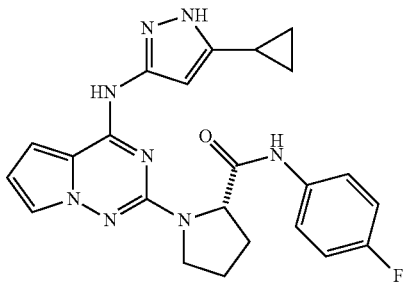<br>(S)-1-(4-(5-cyclopropyl-1H-pyrazol-3-ylamino)pyrrolo[1,2-f][1,2,4]triazin-2-yl)-N-(4-fluorophenyl)pyrrolidine-2-carboxamide | 1.62 | 447 |

TABLE 1-continued

| Example | Compound | HPLC Ret Time (min.) | (M + H)+ |
|---|---|---|---|
| 26 | (S)-N-(4-bromophenyl)-1-(4-(5-cyclopropyl-1H-pyrazol-3-ylamino)pyrrolo[1,2-f][1,2,4]triazin-2-yl)pyrrolidine-2-carboxamide | 1.98 | 508 |
| 27 | (S)-1-(4-(5-cyclopropyl-1H-pyrazol-3-ylamino)pyrrolo[1,2-f][1,2,4]triazin-2-yl)-N-(thiazol-2-yl)pyrrolidine-2-carboxamide | 1.53 | 436 |
| 29 | (S)-1-(4-(5-cyclopropyl-1H-pyrazol-3-ylamino)pyrrolo[1,2-f][1,2,4]triazin-2-yl)-N-(5-methylthiazol-2-yl)pyrrolidine-2-carboxamide | 1.59 | 450 |
| 30 | (S)-1-(4-(5-cyclopropyl-1H-pyrazol-3-ylamino)pyrrolo[1,2-f][1,2,4]triazin-2-yl)-N-(pyridin-3-yl)pyrrolidine-2-carboxamide | 1.48 | 430 |

TABLE 1-continued

| Example | Compound | HPLC Ret Time (min.) | (M + H)⁺ |
|---|---|---|---|
| 31 | (S)-1-(4-(5-cyclopropyl-1H-pyrazol-3-ylamino)pyrrolo[1,2-f][1,2,4]triazin-2-yl)-N-(6-fluoropyridin-3-yl)pyrrolidine-2-carboxamide | 1.49 | 448 |
| 32 | (S)-1-(4-(5-cyclopropyl-1H-pyrazol-3-ylamino)pyrrolo[1,2-f][1,2,4]triazin-2-yl)-N-(1-methylpiperidin-4-yl)pyrrolidine-2-carboxamide | 1.29 | 450 |
| 33 | (S)-1-(4-(5-cyclopropyl-1H-pyrazol-3-ylamino)pyrrolo[1,2-f][1,2,4]triazin-2-yl)-N-(1-isopropylpiperidin-4-yl)pyrrolidine-2-carboxamide | 1.31 | 478 |

TABLE 1-continued

| Example | Compound | HPLC Ret Time (min.) | (M + H)+ |
|---|---|---|---|
| 34 | 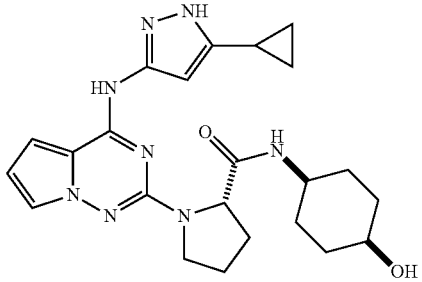 (S)-1-(4-(5-cyclopropyl-1H-pyrazol-3-ylamino)pyrrolo[1,2-f][1,2,4]triazin-2-yl)-N-((1,4-cis)-4-hydroxycyclohexyl)pyrrolidine-2-carboxamide | 1.38 | 451 |
| 35 | 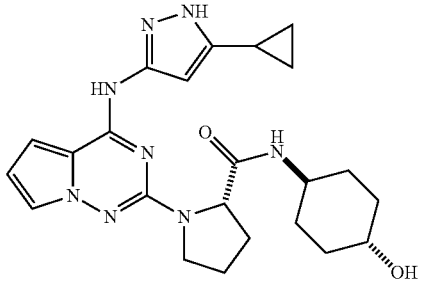 (S)-1-(4-(5-cyclopropyl-1H-pyrazol-3-ylamino)pyrrolo[1,2-f][1,2,4]triazin-2-yl)-N-((1,4-trans)-4-hydroxycyclohexyl)pyrrolidine-2-carboxamide | 1.42 | 451 |
| 36 | 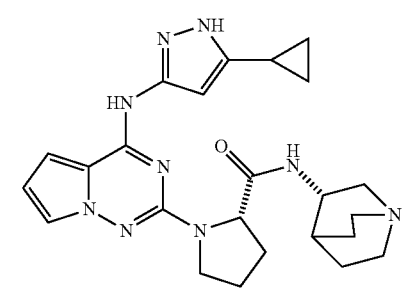 (S)-1-(4-(5-cyclopropyl-1H-pyrazol-3-ylamino)pyrrolo[1,2-f][1,2,4]triazin-2-yl)-N-((S)-quinuclidin-3-yl)pyrrolidine-2-carboxamide | 1.46 | 462 |

TABLE 1-continued

| Example | Compound | HPLC Ret Time (min.) | (M + H)+ |
|---|---|---|---|
| 37 | (S)-1-(4-(5-cyclopropyl-1H-pyrazol-3-ylamino)pyrrolo[1,2-f][1,2,4]triazin-2-yl)-N-((R)-quinuclidin-3-yl)pyrrolidine-2-carboxamide | 1.47 | 462 |

Example 38

(S)-1-(4-(5-cyclopropyl-1H-pyrazol-3-ylamino)pyrrolo[1,2-f][1,2,4]triazin-2-yl)-N-(piperidin-4-yl)pyrrolidine-2-carboxamide

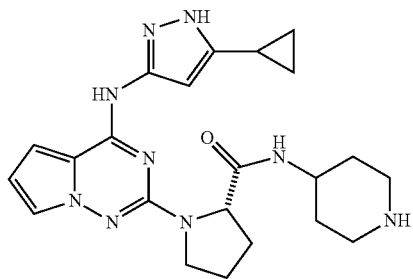 [SMILES: O=C(NC1CCNCC1)[C@@H]1CCCN1c1nc(Nc2cc(C3CC3)[nH]n2)c2cccn2n1]

PyBOP (52 mg, 0.10 mmole) was added to a stirred solution of diisopropylethylamine (0.047 mL, 0.27 mmole), 1D (35 mg, 0.10 mmole) and ten-butyl 4-aminopiperidine-1-carboxylate (40 mg, 0.20 mmole) in dry dimethylformamide (0.15 mL). The reaction was stirred overnight and the product was separated by preparative HPLC of the crude reaction mixture. The HPLC fractions that contained the product were applied onto a cartridge of Phenomenex Strata-X-C 33 um cation mixed-mode polymer. This was washed with methanol and the product was eluted with a 2 N solution of ammonia in methanol. Removal of the solvents left (S)-tert-butyl 4-(1-(4-(5-cyclopropyl-1H-pyrazol-3-ylamino)pyrrolo[1,2-f][1,2,4]triazin-2-yl)pyrrolidine-5-carboxamido)piperidine-1-carboxylate: MS: 536 (M+H)+; HPLC Ret Time: 1.72 min. It was treated with a mixture of dichloromethane (1 mL) and trifluoroacetic acid (0.5 mL) for 1.5 hr at 0° C. The solvents were removed and the product was isolated by preparative HPLC. The HPLC fractions that contained the product were applied onto a cartridge of Phenomenex Strata-X-C 33 um cation mixed-mode polymer. This was washed with methanol and the product was eluted with a 2 N solution of ammonia in methanol. Removal of the solvents left the product, 9.7 mg (22% yield): MS: 436 (M+H)+; HPLC Ret Time: 1.27 min.

Examples 39 to 60

Table 2 contains Examples 39 to 60 which were prepared using the procedure described in Example 38.

TABLE 2

| Example | Compound | HPLC ret. t. (min.) | (M + H) |
|---|---|---|---|
| 39 | (S)-N-((1,4-cis)-4-aminocyclohexyl)-1-(4-(5-cyclopropyl-1H-pyrazol-3-ylamino)pyrrolo[1,2-f][1,2,4]triazin-2-yl)pyrrolidine-2-carboxamide | 1.42 | 450 |

TABLE 2-continued

| Example | Compound | HPLC ret. t. (min.) | (M + H) |
|---|---|---|---|
| 40 | (S)-N-((1,4-trans)-4-aminocyclohexyl)-1-(4-(5-cyclopropyl-1H-pyrazol-3-ylamino)pyrrolo[1,2-f][1,2,4]triazin-2-yl)pyrrolidine-2-carboxamide | 1.32 | 450 |
| 41 | (S)-3-aminopyrrolidin-1-yl)((S)-1-(4-(5-cyclopropyl-1H-pyrazol-3-ylamino)pyrrolo[1,2-f][1,2,4]triazin-2-yl)pyrrolidin-2-yl)methanone | 1.21 | 422 |
| 42 | (R)-3-aminopyrrolidin-1-yl)((S)-1-(4-(5-cyclopropyl-1H-pyrazol-3-ylamino)pyrrolo[1,2-f][1,2,4]triazin-2-yl)pyrrolidin-2-yl)methanone | 1.18 | 422 |
| 43 | (S)-3-aminopiperidin-1-yl)((S)-1-(4-(5-cyclopropyl-1H-pyrazol-3-ylamino)pyrrolo[1,2-f][1,2,4]triazin-2-yl)pyrrolidin-2-yl)methanone | 1.24 | 436 |

TABLE 2-continued

| Example | Compound | HPLC ret. t. (min.) | (M + H) |
|---|---|---|---|
| 44 | 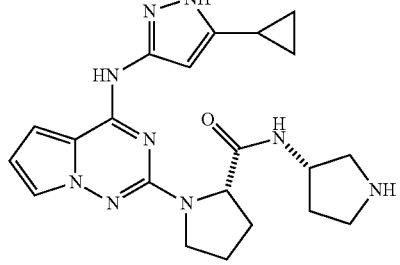<br>(S)-1-(4-(5-cyclopropyl-1H-pyrazol-3-ylamino)pyrrolo[1,2-f][1,2,4]triazin-2-yl)-N-((S)-pyrrolidin-3-yl)pyrrolidine-2-carboxamide | 1.26 | 422 |
| 45 | 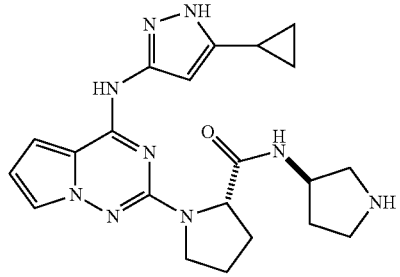<br>(S)-1-(4-(5-cyclopropyl-1H-pyrazol-3-ylamino)pyrrolo[1,2-f][1,2,4]triazin-2-yl)-N-((R)-pyrrolidine-3-yl)pyrrolidine-2-carboxamide | 1.26 | 422 |
| 46 | 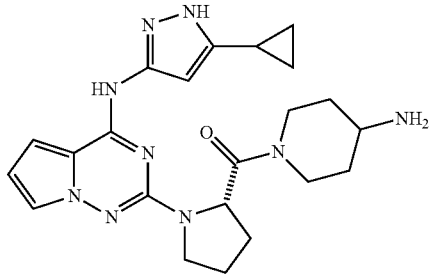<br>(S)-(4-aminopiperidin-1-yl)(1-(4-(5-cyclopropyl-1H-pyrazol-3-ylamino)pyrrolo[1,2-f][1,2,4]triazin-2-yl)pyrrolidin-2-yl)methanone | 1.15 | 436 |
| 47 | 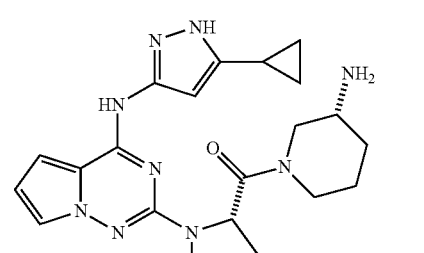<br>(R)-3-aminopiperidin-1-yl)((S)-1-(4-(5-cyclopropyl-1H-pyrazol-3-ylamino)pyrrolo[1,2-f][1,2,4]triazin-2-yl)pyrrolidin-2-yl)methanone | 1.26 | 436 |

TABLE 2-continued

| Example | Compound | HPLC ret. t. (min.) | (M + H) |
|---|---|---|---|
| 48 | (S)-N-(2-aminoethyl)-1-(4-(5-cyclopropyl-1H-pyrazol-3-ylamino)pyrrolo[1,2-f][1,2,4]triazin-2-yl)pyrrolidine-2-carboxamide | 1.24 | 396 |
| 49 | (S)-N-(azetidin-3-yl)-1-(4-(5-cyclopropyl-1H-pyrazol-3-ylamino)pyrrolo[1,2-f][1,2,4]triazin-2-yl)pyrrolidine-2-carboxamide | 1.24 | 408 |
| 50 | (R)-1-(4-(5-cyclopropyl-1H-pyrazol-3-ylamino)pyrrolo[1,2-f][1,2,4]triazin-2-yl)-N-((S)-piperidin-3-yl)pyrrolidine-2-carboxamide | 1.29 | 436 |
| 51 | (R)-1-(4-(5-cyclopropyl-1H-pyrazol-3-ylamino)pyrrolo[1,2-f][1,2,4]triazin-2-yl)-N-((R)-piperidin-3-yl)pyrrolidine-2-carboxamide | 1.45 | 436 |

TABLE 2-continued

| Example | Compound | HPLC ret. t. (min.) | (M + H) |
|---|---|---|---|
| 52 | ((S)-1-(4-(5-cyclopropyl-1H-pyrazol-3-ylamino)pyrrolo[1,2-f][1,2,4]triazin-2-yl)-N-((R)-6-oxopiperidin-3-yl)pyrrolidine-2-carboxamide | 1.33 | 450 |
| 53 | (S)-1-(4-(5-cyclopropyl-1H-pyrazol-3-ylamino)pyrrolo[1,2-f][1,2,4]triazin-2-yl)-N-((S)-6-oxopiperidin-3-yl)pyrrolidine-2-carboxamide | 1.36 | 450 |
| 54 | (S)-1-(4-(5-cyclopropyl-1H-pyrazol-3-ylamino)pyrrolo[1,2-f][1,2,4]triazin-2-yl)-N-((R)-piperidin-3-yl)pyrrolidine-2-carboxamide | 1.29 | 436 |
| 55 | (S)-1-(4-(5-cyclopropyl-1H-pyrazol-3-ylamino)pyrrolo[1,2-f][1,2,4]triazin-2-yl)-N-((S)-piperidin-3-yl)pyrrolidine-2-carboxamide | 1.33 | 436 |

TABLE 2-continued

| Example | Compound | HPLC ret. t. (min.) | (M + H) |
|---|---|---|---|
| 56 | (S)-1-(4-(5-cyclopropyl-1H-pyrazol-3-ylamino)pyrrolo[1,2-f][1,2,4]triazin-2-yl)pyrrolidin-2-yl)(1,4-diazepan-1-yl)methanone | 1.35 | 436 |
| 57 | (S)-1-(4-(5-cyclopropyl-1H-pyrazol-3-ylamino)pyrrolo[1,2-f][1,2,4]triazin-2-yl)pyrrolidin-2-yl)(piperazin-1-yl)methanone | 1.33 | 422 |
| 58 | (S)-(3-aminoazetidin-1-yl)(1-(4-(5-cyclopropyl-1H-pyrazol-3-ylamino)pyrrolo[1,2-f][1,2,4]triazin-2-yl)pyrrolidin-2-yl)methanone | 1.30 | 408 |
| 59 | (R)-2-(aminomethyl)pyrrolidin-1-yl)((S)-1-(4-(5-cyclopropyl-1H-pyrazol-3-ylamino)pyrrolo[1,2-f][1,2,4]triazin-2-yl)pyrrolidin-2-yl)methanone | 1.55 | 436 |

TABLE 2-continued

| Example | Compound | HPLC ret. t. (min.) | (M + H) |
|---|---|---|---|
| 60 | 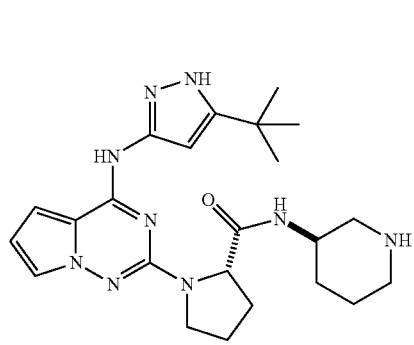 (S)-N-(azetidin-3-ylmethyl)-1-(4-(5-cyclopropyl-1H-pyrazol-3-ylamino)pyrrolo[1,2-f][1,2,4]triazin-2-yl)pyrrolidine-2-carboxamide | 1.27 | 422 |

Example 61

(S)-1-(4-(5-tert-butyl-1H-pyrazol-3-ylamino)pyrrolo[1,2-f][1,2,4]triazin-2-yl)-N-((R)-piperidin-3-yl)pyrrolidine-2-carboxamide

61A. N-(5-tert-butyl-1H-pyrazol-3-yl)-2-chloropyrrolo[1,2-f][1,2,4]triazin-4-amine

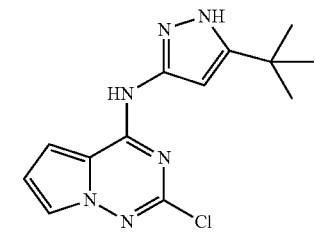 [SMILES: CC(C)(C)c1cc(Nc2nc(Cl)nn3cccc23)n[nH]1]

The compound was prepared from 5-tert-butyl-1H-pyrazol-3-amine and 1B as described for 1C: MS: 291 (M+H)+; HPLC Ret Time: 2.61 min (Phenomenex-Luna S10 4.6×30 mm column, 3 min gradient, 4 mL/min).

61B. (S)-1-(4-(5-tert-butyl-1H-pyrazol-3-ylamino)pyrrolo[1,2-f][1,2,4]triazin-2-yl)pyrrolidine-2-carboxylic acid

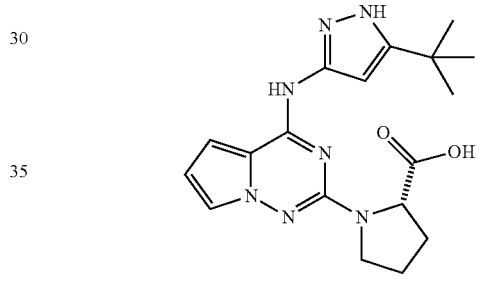

The compound was prepared from (S)-proline and 61A as described for 1D: MS: 370 (M+H)+; HPLC Ret Time: 2.34 min (Phenomenex-Luna S10 4.6×30 mm column, 3 min gradient, 4 mL/min).

PyBOP (371 mg, 0.10 mmole) was added to a stirred solution of 61B (0.25 gm, 0.68 mmole), (R)-tert-butyl piperidin-3-ylcarbamate (0.27 gm, 1.35 mmole). and diisopropylethylamine (0.32 mL, 1.8 mmole) in dry dimethylformamide (1.5 mL). at 0° C. After 30 min, the reaction was diluted with methanol, and the product was separated by preparative HPLC of the crude reaction mixture. The solvent was removed from the HPLC fractions that contained (R)-tert-butyl 3-((S)-1-(4-(5-tert-butyl-1H-pyrazol-3-ylamino)pyrrolo[1,2-f][1,2,4]triazin-2-yl)pyrrolidine-5-carboxamido)piperidine-1-carboxylate and the residue was treated with a 5.0 N solution of HCl in methanol for 1 hr at room temperature. After preparative HPLC, the fractions containing the deprotected product were applied onto a cartridge of Phenomenex Strata-X-C 33 um cation mixed-mode polymer and flushed with methanol. Elution with a 2 N solution of ammonia in methanol, followed by removal of the solvents left 61 (175 mg, 57% yield): MS: 452 (M+H)+; HPLC Ret Time: 2.35 min (Phenomenex-Luna S10 4.6×50 mm column, 3 min gradient, 4 mL/min).

Examples 62 to 67

Table 3 contains Examples 62 to 67 which were prepared using the procedure described in Example 61.

TABLE 3

| Example | Compound | HPLC ret. t. (min.) | (M + H)+ |
|---------|----------|---------------------|----------|
| 62 | 2-chloro-N-(1H-pyrazol-3-yl)pyrrolo[1,2-f][1,2,4]triazin-4-amine | 2.47[a] | 235 |
| 63 | (S)-1-(4-(1H-pyrazol-3-ylamino)pyrrolo[1,2-f][1,2,4]triazin-2-yl)pyrrolidine-2-carboxylic acid | 1.64[a] | 314 |
| 64 | (S)-1-(4-(1H-pyrazol-3-ylamino)pyrrolo[1,2-f][1,2,4]triazin-2-yl)-N-((R)-piperidin-3-yl)pyrrolidine-2-carboxamide | 1.30[a] | 396 |
| 65 | 2-chloro-N-(5-(furan-2-yl)-1H-pyrazol-3-yl)pyrrolo[1,2-f][1,2,4]triazin-4-amine | 2.92[a] | 301 |

TABLE 3-continued

| Example | Compound | HPLC ret. t. (min.) | (M + H)+ |
|---|---|---|---|
| 66 | (2S)-1-(4-(5-(furan-2-yl)-1H-pyrazol-3-ylamino)pyrrolo[1,2-f][1,2,4]triazin-2-yl)pyrroldiine-2-carboxylic acid | 2.28[a] | 380 |
| 67 | (S)-1-(4-(5-(furan-2-yl)-1H-pyrazol-3-ylamino)pyrrolo[1,2-f][1,2,4]triazin-2-yl)-N-((R)-piperidin-3-yl)pyrrolidine-2-carboxamide | 1.84[a] | 462 |

[a]Phenomenex-luna S10 4.6 x 30 mm column; 3 min gradient @ 4 mL/min

Example 68

((S)-1-(4-(5-cyclopropyl-1H-pyrazol-3-ylamino)pyrrolo[1,2-f][1,2,4]triazin-2-yl)-2-methyl-N-(pyridin-3-yl)pyrrolidine-2-carboxamide

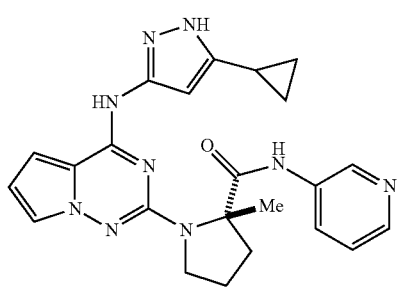

68A. (S)-1-(4-(5-cyclopropyl-1H-pyrazol-3-ylamino)pyrrolo[1,2-f][1,2,4]-triazin-2-yl)-2-methylpyrrolidine-2-carboxylic acid

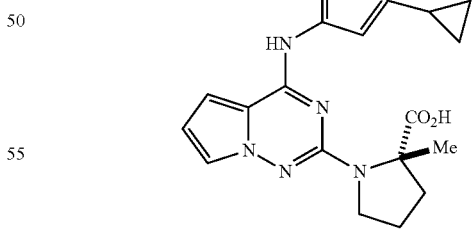

A solution of 1(S)-2-methylpyrrolidine-2-carboxylic acid (94 mg, 0.732 mmol) and tetrabutylammonium hydroxide (0.73 mL, 4 equiv, 1.0 M in MeOH) in a vial was placed under high vacuum to remove MeOH. 1C (50 mg, 0.183 mmole) and potassium carbonate (25 mg, 1 equiv) were added and the vial was sealed and heated at 160° C. for 2.5 days. After cooling, the reaction was partitioned between dichloromethane and water. The organic phase was washed with water and the pH of the combined aqueous phases was adjusted to 3 with aq. 6.0 N HCl. This gave a precipitate that was collected by filtration, washed with water and dried. The acid 68A was obtained as a solid, 34 mg (51% yield): MS: 368 (M+H)+; HPLC Ret Time: 2.50 min (Phenomenex-Luna S10 4.6×50 mm column, 3 min gradient, 4 mL/min).

Diisopropylethylamine (1.2 mL, 6.8 mmole) was added to a stirred mixture of 68A (500 mg, 1.36 mmol), 3-aminopyridine (640 mg, 6.8 mmole), and HATU (776 mg, 2.04 mmole) in dry NMP (6 mL) at RT. The mixture was heated at 45° C. for 18 hrs. Another 776 mg HATU and 1.2 ml diisopropylethylamine was added. The mixture was heated at 60° C. for 48 hrs. The crude mixture was diluted with methanol and the product was isolated by preperative HPLC. The fractions that contained the product were applied onto a MCX cartridge and then flushed with methanol. The free base product was eluted with a 2 N solution of ammonia in methanol and removal of the solvents left product (82 mg, 14% yield): MS: 444 (M+H)+.

$^1$H-NMR (CD$_3$OD, 500 MHz, δ) 8.64 (d, 1H, J=2.4 Hz), 8.20 (dd, 1H, J=1.2, 4.9 Hz), 7.91 (m, 1H), 7.40 (dd, 1H, J=1.5, 2.4 Hz), 7.32 (dd, 1H, J=4.9, 8.4 Hz), 6.83 (dd, 1H, J=1.5, 4.3 Hz), 6.50 (dd, 1H, J=2.5, 4.3 Hz), 6.14 (br, 1H), 3.91 (m, 1H), 3.72 (dt, 1H, J=10.7, 7.0 Hz), 2.48 (dt, 1H, J=11.5, 6.8 Hz), 2.18-2.04 (m, 3H), 1.79 (m, 1H), 1.74 (s, 3H), 0.89 (m, 2H), 0.74 (m, 1H), 0.69 (m, 1H).

Example 69

(S)-1-(4-(5-cyclopropyl-1H-pyrazol-3-ylamino)pyrrolo[1,2-f][1,2,4]triazin-2-yl)-2-methyl-N-((R)-piperidin-3-yl)pyrrolidine-2-carboxamide

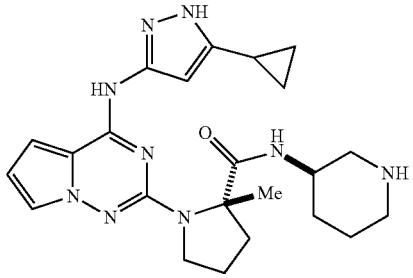

Diisopropylethylamine (0.040 mL, 0.26 mmole) was added to a stirred mixture of 68A (70 mg, 0.19 mmol), (R)-tert-butyl 3-aminopiperidine-1-carboxylate (38 mg, 0.19 mmole), and HATU (79 mg, 0.21 mmole) in dry dimethylformamide (2 mL) at RT. After 20 hr, this was diluted with a 1:1 mixture of ethyl acetate and hexane, washed with water (3 times) and dried (Na$_2$SO$_4$). Removal of the solvents followed by radial chromatography (silica gel plate eluted with mixtures of hexane containing 50 and then 75% hexane) afforded (R)-tert-butyl 3-((S)-1-(4-(5-cyclopropyl-1H-pyrazol-3-ylamino)pyrrolo[1,2-f][1,2,4]triazin-2-yl)-2-methylpyrrolidine-2-carboxamido)piperidine-1-carboxylate as an oil (41 mg, 48% yield): MS: 550 (M+H)+; HPLC Ret Time: 2.72 min (Phenomenex-Luna S10 4.6×50 mm column, 3 min gradient, 4 mL/min) This was treated with a 1:1 mixture (4 mL) of trifluoroacetic acid and dichloromethane at room temperature for 0.5 hr. The solvents were removed and the residue was dissolved in methanol and the product was isolated by preperative HPLC. The fractions that contained the product were applied onto a cartridge of Phenomenex Strata-X-C 33 um cation mixed-mode polymer and then flushed with methanol. The free base of the 69 was eluted with a 2 N solution of ammonia in methanol and removal of the solvents left 69 (18 mg, 54% yield): MS: 452 (M+H)+; HPLC Ret Time: 2.35 min (Phenomenex-Luna S10 4.6×50 mm column, 3 min gradient, 4 mL/min).

Example 70

(S)-2-methyl-1-(4-(5-methyl-1H-pyrazol-3-ylamino)pyrrolo[1,2-f][1,2,4]triazin-2-yl)-N-((R)-piperidin-3-yl)pyrrolidine-2-carboxamide

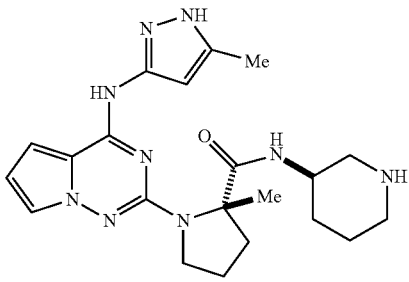

70A. 2-Chloro-N-(5-methyl-1H-pyrazol-3-yl)pyrrolo[1,2-f][1,2,4]triazin-4-amine

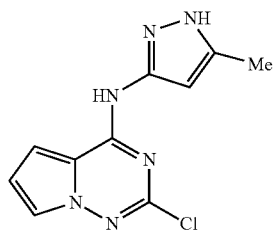 [SMILES: Cc1cc(Nc2nc(Cl)nn3cccc23)n[nH]1]

This was prepared from 1B and 5-methyl-1H-pyrazol-3-amine as described for 1C: MS: 249 (M+H)+; HPLC Ret Time: 2.04 min (Phenomenex-Luna S10 4.6×50 mm column, 3 min gradient, 4 mL/min).

70B. (S)-2-methyl-1-(4-(5-methyl-1H-pyrazol-3-ylamino)pyrrolo[1,2-f][1,2,4]triazin-2-yl)pyrrolidine-2-carboxylic acid

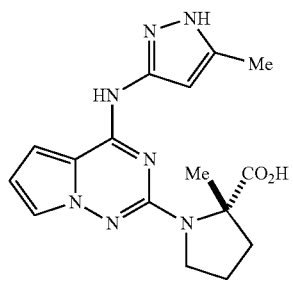 [SMILES: Cc1cc(Nc2nc(N3CCC[C@@]3(C)C(=O)O)nn3cccc23)n[nH]1]

This was prepared from 70A and 1(S)-2-methylpyrrolidine-2-carboxylic acid according to the procedure described for 68A: MS: 341 (M+H)+; HPLC Ret Time: 2.00 min (Phenomenex-Luna S10 4.6×30 mm column, 3 min gradient, 4 mL/min).

Compound 70 was prepared from 70B and (R)-tert-butyl 3-aminopiperidine-1-carboxylate according to the procedure described for 69: MS: 425 (M+H)+; HPLC Ret Time: 1.68 min (Phenomenex-Luna S10 4.6×50 mm column, 3 min gradient, 4 mL/min).

Example 71

(S)-1-(4-(5-tert-butyl-1H-pyrazol-3-ylamino)pyrrolo[1,2-f][1,2,4]triazin-2-yl)-2-methyl-N-((R)-piperidin-3-yl)pyrrolidine-2-carboxamide

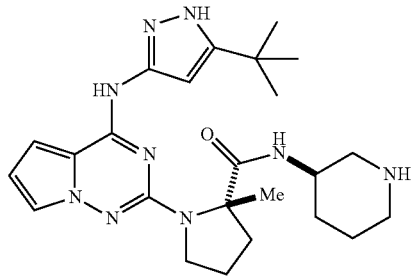

71A. (S)-1-(4-(5-tert-butyl-1H-pyrazol-3-ylamino)pyrrolo[1,2-f][1,2,4]triazin-2-yl)-2-methylpyrrolidine-2-carboxylic acid

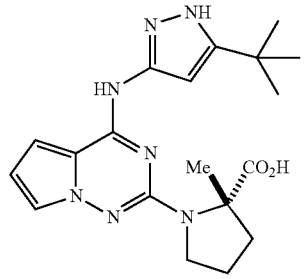 [SMILES: CC(C)(C)c1cc(Nc2nc(N3CCC[C@@]3(C)C(=O)O)nn3cccc23)n[nH]1]

Compound 71A was prepared from 61A and 1(S)-2-methylpyrrolidine-2-carboxylic acid according to the procedure described for 68A: $^1$H NMR (500 MHz, MeOH-D4) δ 1.38 (s, 9H), 1.70 (s, 3H), 2.95 (m, 1H), 2.35 (m, 1H), 3.70 (m, 2H), 3.76 (m, 2H), 6.46 (br s, 1H), 6.50 (s, 1H), 6.81 (s, 1H), 7.35 (br s, 1H).

Compound 71 was prepared from 71A and (R)-tert-butyl 3-aminopiperidine-1-carboxylate according to the procedure described for 69: MS: 466 (M+H)+; HPLC Ret Time: 2.33 min (Phenomenex-Luna S10 4.6×50 mm column, 3 min gradient, 4 mL/min).

Examples 72 to 87

Examples 72 to 87 are outlined in Table 4 and were prepared using procedures that are described above in Examples 68 to 71.

TABLE 4

| Example | Compound | HPLC ret. t. (min.) | (M + H)+ |
|---|---|---|---|
| 72 | (S)-N-(azetidin-3-yl)-1-(4-(5-cyclopropyl-1H-pyrazol-3-ylamino)pyrrolo[1,2-f][1,2,4]triazin-2-yl)-2-methylpyrrolidine-2-carboxamide | 1.99$^a$ | 422 |

TABLE 4-continued

| Example | Compound | HPLC ret. t. (min.) | (M + H)+ |
|---|---|---|---|
| 73 | (S)-N-(2-aminoethyl)-1-(4-(5-cyclopropyl-1H-pyrazol-3-ylamino)pyrrolo[1,2-f][1,2,4]triazin-2-yl)-2-methylpyrrolidine-2-carboxamide | 2.00<sup>a</sup> | 410 |
| 74 | (S)-1-(4-(5-cyclopropyl-1H-pyrazol-3-ylamino)pyrrolo[1,2-f][1,2,4]triazin-2-yl)-2-methyl-N-((S)-pyrrolidin-3-yl)pyrrolidine-2-carboxamide | 2.04<sup>a</sup> | 436 |
| 75 | (S)-1-(4-(5-cyclopropyl-1H-pyrazol-3-ylamino)pyrrolo[1,2-f][1,2,4]triazin-2-yl)-2-methyl-N-((R)-pyrrolidin-3-yl)pyrrolidine-2-carboxamide | 2.01<sup>a</sup> | 436 |

TABLE 4-continued

| Example | Compound | HPLC ret. t. (min.) | (M + H)+ |
|---------|----------|---------------------|----------|
| 76 | (S)-1-(4-(5-cyclopropyl-1H-pyrazol-3-ylamino)pyrrolo[1,2-f][1,2,4]triazin-2-yl)-2-methyl-N-((S)-piperidin-3-yl)pyrrolidine-2-carboxamide | 2.01[a] | 450 |
| 77 | (S)-(1-(4-(5-cyclopropyl-1H-pyrazol-3-ylamino)pyrrolo[1,2-f][1,2,4]triazin-2-yl)-2-methylpyrrolidin-2-yl)(piperazin-1-yl)methanone | 2.31[a] | 436 |
| 78 | (S)-N-((1,4-trans)-4-aminocyclohexyl)-1-(4-(5-cyclopropyl-1H-pyrazol-3-ylamino)pyrrolo[1,2-f][1,2,4]triazin-2-yl)-2-methylpyrrolidine-2-carboxamide | 1.71 | 464 |
| 79 | (S)-N-((1,4-cis)-4-aminocyclohexyl)-1-(4-(5-cyclopropyl-1H-pyrazol-3-ylamino)pyrrolo[1,2-f][1,2,4]triazin-2-yl)-2-methylpyrrolidine-2-carboxamide | 1.71 | 464 |

TABLE 4-continued

| Example | Compound | HPLC ret. t. (min.) | (M + H)+ |
|---|---|---|---|
| 80 | ((S)-3-aminopyrrolidin-1-yl)((S)-1-(4-(5-cyclopropyl-1H-pyrazol-3-ylamino)pyrrolo[1,2-f][1,2,4]triazin-2-yl)-2-methylpyrrolidin-2-yl)methanone | 2.31[a] | 436 |
| 81 | ((R)-3-aminopyrrolidin-1-yl)((S)-1-(4-(5-cyclopropyl-1H-pyrazol-3-ylamino)pyrrolo[1,2-f][1,2,4]triazin-2-yl)-2-methylpyrrolidin-2-yl)methanone | 2.29[a] | 436 |
| 82 | (S)-(1-(4-(5-cyclopropyl-1H-pyrazol-3-ylamino)pyrrolo[1,2-f][1,2,4]triazin-2-yl)-2-methylpyrrolidin-2-yl)(1,4-diazepan-1-yl)methanone | 2.05[a] | 450 |
| 83 | (S)-(3-aminoazetidin-1-yl)(1-(4-(5-cyclopropyl-1H-pyrazol-3-ylamino)pyrrolo[1,2-f][1,2,4]triazin-2-yl)-2-methylpyrrolidin-2-yl)methanone | 1.99[a] | 422 |

TABLE 4-continued

| Example | Compound | HPLC ret. t. (min.) | (M + H)+ |
|---|---|---|---|
| 84 | (S)-2-methyl-1-(4-(5-methyl-1H-pyrazol-3-ylamino)pyrrolo[1,2-f][1,2,4]triazin-2-yl)-N-(thiazol-2-yl)pyrrolidine-2-carboxamide | 2.39[a] | 424 |
| 85 | (S)-2-methyl-1-(4-(5-methyl-1H-pyrazol-3-ylamino)pyrrolo[1,2-f][1,2,4]triazin-2-yl)-N-(pyridin-3-yl)pyrrolidine-2-carboxamide | 1.82[a] | 418 |
| 86 | (S)-1-(4-(5-tert-butyl-1H-pyrazol-3-ylamino)pyrrolo[1,2-f][1,2,4]triazin-2-yl)-2-methyl-N-(pyridin-3-yl)pyrrolidine-2-carboxamide | 2.25[a] | 460 |
| 87 | (S)-1-(4-(5-tert-butyl-1H-pyrazol-3-ylamino)pyrrolo[1,2-f][1,2,4]triazin-2-yl)-2-methyl-N-(thiazol-2-yl)pyrrolidine-2-carboxamide | 2.74[a] | 466 |

[a]Phenomenex-luna S10 4.6 × 30 mm column; 3 min gradient @ 4 mL/min.

Example 88

(S)-1-(4-(5-cyclopropyl-1H-pyrazol-3-ylamino)pyrrolo[1,2-f][1,2,4]triazin-2-yl)-N-((1s,4R)-4-(2-(methylsulfonyl)ethylamino)cyclohexyl)pyrrolidine-2-carboxamide

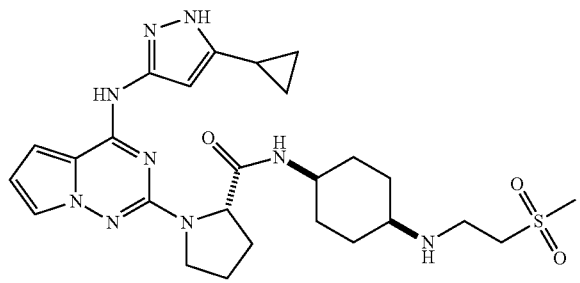

A mixture of (S)-N-((1,4-cis)-4-aminocyclohexyl)-1-(4-(5-cyclopropyl-1H-pyrazol-3-ylamino)pyrrolo[1,2-f][1,2,4]triazin-2-yl)-2-methylpyrrolidine-2-carboxamide 39 (9.6 mg, 0.021 mmole), methylvinylsulfone (6.0 mg, 0.057 mmole). in methanol (10 mL) was stirred at room temperature overnight. The product was isolated by preparative HPLC of the reaction mixture. The fractions containing the product were applied onto a cartridge of Phenomenex Strata-X-C 33 um cation mixed-mode polymer. This was washed with methanol and 88 was eluted with a 2 N solution of ammonia in methanol. Removal of the solvents left 88 (4.5 mg, 38% yield): MS: 556 (M+H)+; HPLC Ret Time: 1.28 min.

Example 89

(S)-1-(4-(5-cyclopropyl-1H-pyrazol-3-ylamino)pyrrolo[1,2-f][1,2,4]triazin-2-yl)-N-((R)-1-cyclopropylpiperidin-3-yl)pyrrolidine-2-carboxamide

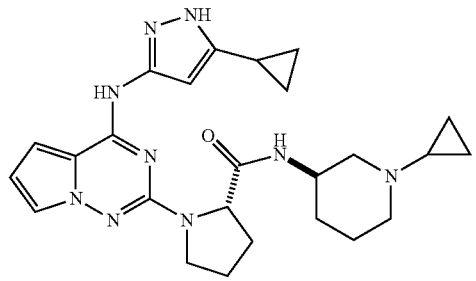

A mixture of (S)-1-(4-(5-cyclopropyl-1H-pyrazol-3-ylamino)pyrrolo[1,2-f][1,2,4]triazin-2-yl)-N-((R)-piperidin-3-yl)pyrrolidine-2-carboxamide 54 (88 mg, 0.20 mmole), (1-ethoxycyclopropoxy)trimethylsilane (0.140 mL, 0.80 mmole) sodium cyanoborohydride (0.50 mL, 1.0 N in tetrahydrofuran, 0.50 mmole) and acetic acid (0.36 mL, 10% in methanol, 0.60 mmole) in methanol (3.0 mL) was heated at 55° C. overnight. The product was isolated by preparative HPLC of the reaction mixture. The solvents were removed from the desired fractions and the residue was dissolved in methanol and applied onto a cartridge of Phenomenex Strata-X-C 33 um cation mixed-mode polymer. This was washed with methanol and 89 was eluted with a 2 N solution of ammonia in methanol. Removal of the solvents left 89 (60 mg, 62% yield): MS: 476 (M+H)+; HPLC Ret Time: 1.29 min.

Example 90

(S)-1-(4-(5-cyclopropyl-1H-pyrazol-3-ylamino)pyrrolo[1,2-f][1,2,4]triazin-2-yl)-N-((R)-1-methylpiperidin-3-yl)pyrrolidine-2-carboxamide

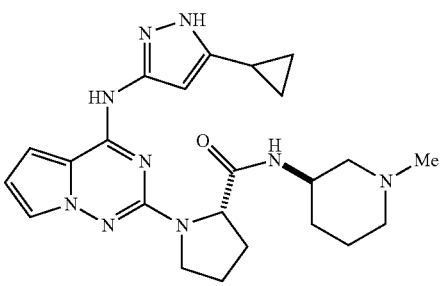

A mixture of (S)-1-(4-(5-cyclopropyl-1H-pyrazol-3-ylamino)pyrrolo[1,2-f][1,2,4]triazin-2-yl)-N-((R)-piperidin-3-yl)pyrrolidine-2-carboxamide 54 (20 mg, 0.046 mmole), formaldehyde (0.016 mL, 37 weight % solution in water), acetic acid (0.070 mL, 10% solution in methanol, 0.14 mmole) and sodium cyanoborohydride (0.15 mL, 1.0 N in tetrahydrofuran, 0.12 mmole) in methanol (0.5 mL) was stirred at room temperature for 1 hr. The product was isolated by preparative HPLC of the reaction mixture and the solvents were removed from the desired fractions. The residue was dissolved in methanol and applied onto a cartridge of Phenomenex Strata-X-C 33 um cation mixed-mode polymer. This was washed with methanol and 90 was eluted with a 2 N solution of ammonia in methanol. Removal of the solvents left 90 (17 mg, 84% yield): MS: 450 (M+H)+; HPLC Ret Time: 1.25 min.

Example 91

(S)-1-(4-(5-cyclopropyl-1H-pyrazol-3-ylamino)pyrrolo[1,2-f][1,2,4]triazin-2-yl)-N-((1S,4R)-4-(cyclopropylmethylamino)cyclohexyl)pyrrolidine-2-carboxamide

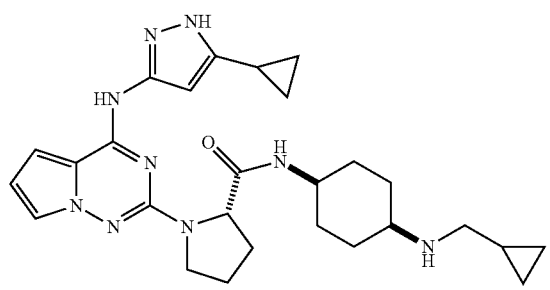

A mixture of (S)-N-((1,4-cis)-4-aminocyclohexyl)-1-(4-(5-cyclopropyl-1H-pyrazol-3-ylamino)pyrrolo[1,2-f][1,2,4]triazin-2-yl)-2-methylpyrrolidine-2-carboxamide 39 (9.0 mg, 0.020 mmole), cyclopropanecarboxaldehyde (0.005 mL, 0.067 mmole), acetic acid (0.024 mL, 10% solution in methanol, 0.040 mmole) and sodium cyanoborohydride (0.040 mL, 1.0 N in tetrahydrofuran, 0.040 mmole) in methanol (0.3 mL) was stirred at room temperature overnight. The product was isolated by preparative HPLC of the reaction mixture and the solvents were removed from the desired fractions. The residue was dissolved in methanol and applied onto a cartridge of Phenomenex Strata-X-C 33 um cation mixed-mode polymer. This was washed with methanol and 91 was eluted with a 2 N solution of ammonia in methanol. Removal of the solvents left 91 (6.2 mg, 49% yield): MS: 504 (M+H)+; HPLC Ret Time: 1.33 min.

Example 92

(S)-1-(4-(5-cyclopropyl-1H-pyrazol-3-ylamino)pyrrolo[1,2-f][1,2,4]triazin-2-yl)-N-((R)-1-(tetrahydro-2H-pyran-4-yDpiperidin-3-yl)pyrrolidine-2-carboxamide

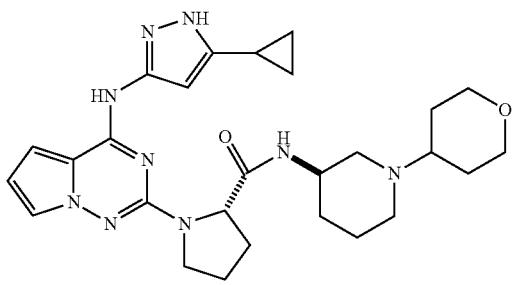

A mixture of (S)-1-(4-(5-cyclopropyl-1H-pyrazol-3-ylamino)pyrrolo[1,2-f][1,2,4]triazin-2-yl)-N-((R)-piperidin-3-yl)pyrrolidine-2-carboxamide 54 (65.0 mg, 0.15 mmole), tetrahydro-4H-pyran-4-one (0.030 mL, 0.30 mmole), acetic acid (0.18 mL, 10% solution in methanol, 0.30 mmole) and sodium cyanoborohydride (0.38 mL, 1.0 N in tetrahydrofuran, 0.38 mmole) in methanol (1.5 mL) was stirred at room temperature for 2 days. The product was isolated by preparative HPLC of the reaction mixture and the solvents were removed from the desired fractions. The residue was dissolved in methanol and applied onto a cartridge of Phenomenex Strata-X-C 33 um cation mixed-mode polymer. This was washed with methanol and 92 was eluted with a 2 N solution of ammonia in methanol. Removal of the solvents left 92 (51 mg, 66% yield): MS: 520 (M+H)+; HPLC Ret Time: 1.55 min.

Example 93

(S)-1-(4-(5-cyclopropyl-1H-pyrazol-3-ylamino)pyrrolo[1,2-f][1,2,4]triazin-2-yl)-N-((R-1-(2-methoxyethyl)piperidin-3-yl)pyrrolidine-2-carboxamide

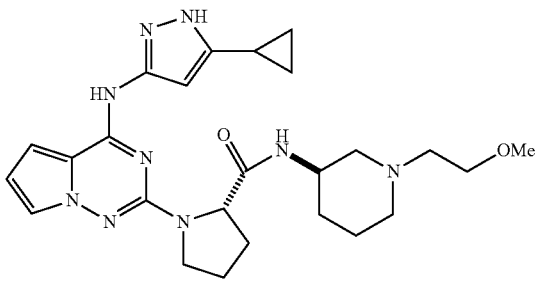

A mixture of (S)-1-(4-(5-cyclopropyl-1H-pyrazol-3-ylamino)pyrrolo[1,2-f][1,2,4]triazin-2-yl)-N-((R)-piperidin-3-yl)pyrrolidine-2-carboxamide 54 (44.0 mg, 0.10 mmole), 2-bromoethyl methyl ether (0.028 mL, 0.29 mmole) and diisopropylethylamine (0.052 mL, 0.30 mmole) in methanol (1.0 mL) was heated at 80° C. overnight. The product was isolated by preparative HPLC of the reaction mixture and the solvents were removed from the desired fractions. The residue was dissolved in methanol and applied onto a cartridge of Phenomenex Strata-X-C 33 um cation mixed-mode polymer. This was washed with methanol and 93 was eluted with a 2 N solution of ammonia in methanol. Removal of the solvents left 93 (28 mg, 57% yield): MS: 494 (M+H)+; HPLC Ret Time 1.42 min.

Example 94

(S)-1-(4-(5-cyclopropyl-1H-pyrazol-3-ylamino)pyrrolo[1,2-f][1,2,4]triazin-2-yl)-N-((R)-1-(2,2,2-trifluoroethyl)piperidin-3-yl)pyrrolidine-2-carboxamide

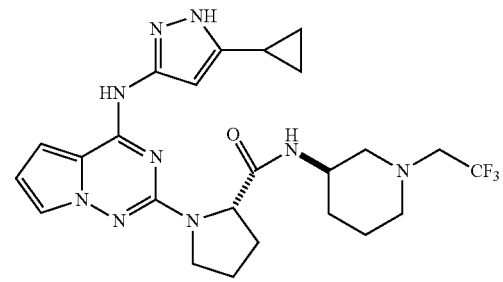

A mixture of (S)-1-(4-(5-cyclopropyl-1H-pyrazol-3-ylamino)pyrrolo[1,2-f][1,2,4]triazin-2-yl)-N-((R)-piperidin-3-yl)pyrrolidine-2-carboxamide 54 (22.0 mg, 0.051 mmole), (2,2,2-trifluoroethyl)-phenyliodonium triflate (22 mg, 0.051 mmole, Tetrahedron Letters, 1994, volume 35, page 8015) and 2,4,6-collidine (0.018 mL, 0.15 mmole) in dry dichloromethane (0.5 mL) under a dry nitrogen atmosphere was left stirring at room temperature for 30 min. The solvent was removed. The residue was dissolved in methanol and the product was isolated by preparative HPLC. After removal of the solvents from the desired fractions, the residue was dissolved in methanol and applied onto a cartridge of Phenomenex Strata-X-C 33 um cation mixed-mode polymer. This was washed with methanol and 94 was eluted with a 2 N solution of ammonia in methanol. Removal of the solvents left 94 (5 mg, 18% yield): MS: 518 (M+H)+; HPLC Ret Time: 1.50 min.

Example 95

(R)-methyl 3-((S)-1-(4-(5-cyclopropyl-1H-pyrazol-3-ylamino)pyrrolo[1,2-f][1,2,4]triazin-2-yl)pyrrolidine-5-carboxamido)piperidine-1-carboxylate

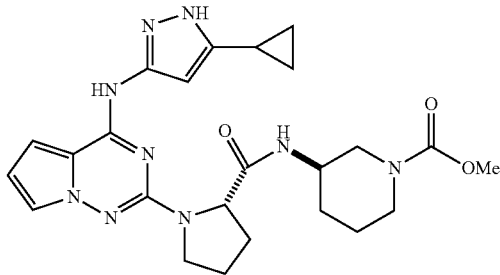

A mixture of (S)-1-(4-(5-cyclopropyl-1H-pyrazol-3-ylamino)pyrrolo[1,2-f][1,2,4]triazin-2-yl)-N-((R)-piperidin-3-yl)pyrrolidine-2-carboxamide 54 (44.0 mg, 0.10 mmole), methylchloroformate (0.014 mL, 0.15 mmole) and diisopropylethylamine (0.035 mL, 0.20 mmole) in methanol (1.0 mL) was left stirring at room temperature overnight. The product was isolated by preparative HPLC. After removal of the solvents from the desired fractions, the residue was dissolved in methanol and applied onto a cartridge of Phenomenex Strata-X-C 33 um cation mixed-mode polymer. This was washed with methanol and 95 was eluted with a 2 N solution of ammonia in methanol. Removal of the solvents left 95 (34 mg, 68% yield): MS: 494 (M+H)+; HPLC Ret Time: 1.62 min.

Example 96

(S)-1-(4-(5-cyclopropyl-1H-pyrazol-3-ylamino)pyrrolo[1,2-f][1,2,4]triazin-2-yl)-N-((R-1-(2-methoxyacetyl)piperidin-3-yl)pyrrolidine-2-carboxamide

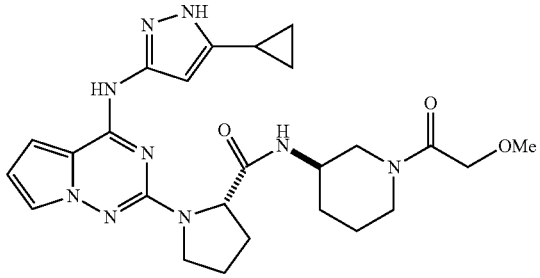

A mixture of (S)-1-(4-(5-cyclopropyl-1H-pyrazol-3-ylamino)pyrrolo[1,2-f][1,2,4]triazin-2-yl)-N-((R)-piperidin-3-yl)pyrrolidine-2-carboxamide 54 (31.0 mg, 0.07 mmole) and triethylamine (0.020 mL, 0.14 mmole) in methanol (1.0 mL) was cooled in an icebath and 2-methoxyacetyl chloride (0.070 mL, 10% solution in dry methylene chloride, 0.08 mmole) was added dropwise with stirring. After 1 hr, the product was isolated by preparative HPLC. After removal of the solvents from the desired fractions, the residue was dissolved in methanol and applied onto a cartridge of Phenomenex Strata-X-C 33 um cation mixed-mode polymer. This was flushed with methanol and the free base of the 96 was eluted with a 2 N solution of ammonia in methanol. Removal of the solvents left 96 (34 mg, 68% yield): MS: 508 (M+H)+; HPLC Ret Time: 1.74 min.

Example 97

(S)-N-((R)-1-(2-amino-2-methylpropanoyl)piperidin-3-yl)-1-(4-(5-cyclopropyl-1H-pyrazol-3-ylamino)pyrrolo[1,2-f][1,2,4]triazin-2-yl)pyrrolidine-2-carboxamide

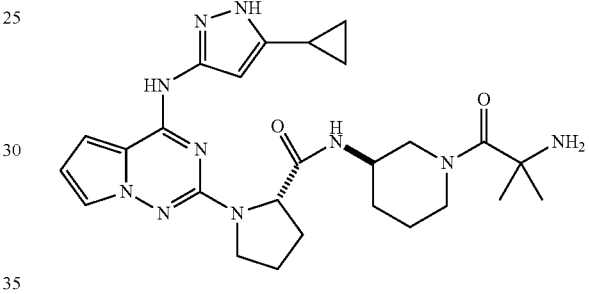

PyBOP (44 mg, 0.084 mmole) was added to a stirred solution of (S)-1-(4-(5-cyclopropyl-1H-pyrazol-3-ylamino)pyrrolo[1,2-f][1,2,4]triazin-2-yl)-N-((R)-piperidin-3-yl)pyrrolidine-2-carboxamide 54 (31.0 mg, 0.07 mmole) and diisopropylethylamine (0.033 mL, 0.19 mmole) and 2-(tert-butoxycarbonylamino)-2-methylpropanoic acid (17 mg, 0.084 mmole) in dry dimethylformamide (0.30 mL). The reaction was left stirring for 3 hr and the product was separated by preparative HPLC of the crude reaction mixture. The HPLC fractions that contained the product were applied onto a Phenomenex Strata-X-C 33 um cation mixed-mode polymer cartridge. This was washed with methanol and the product was eluted with a 2 N solution of ammonia in methanol. Removal of the solvents left tert-butyl 1-((R)-3-((S)-1-(4-(5-cyclopropyl-1H-pyrazol-3-ylamino)pyrrolo[1,2-f][1,2,4]triazin-2-yl)pyrrolidine-5-carboxamido)piperidin-1-yl)-2-methyl-1-oxopropan-2-ylcarbamate which was treated with a mixture of dichloromethane (1 mL) and trifluoroacetic acid (0.5 mL) for 1.5 hr at 0° C. The solvents were removed and the product was isolated by preparative HPLC. The HPLC fractions that contained the product were applied onto a cartridge of Phenomenex Strata-X-C 33 um cation mixed-mode polymer. This was washed with methanol and the product was eluted with a 2 N solution of ammonia in methanol. Removal of the solvents left the product 97 (18 mg, 48% yield): MS: 493 (M+H)+; HPLC Ret Time: 1.46 min.

Examples 98 to 100

Table 5 contains Examples 98 to 100 which were prepared using procedures described above in Examples 88 to 97.

TABLE 5

| Example | Compound | HPLC ret. t. (min.) | (M + H)+ |
|---|---|---|---|
| 98 | 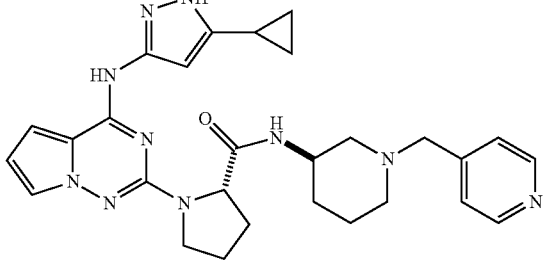<br>(S)-1-(4-(5-cyclopropyl-1H-pyrazol-3-ylamino)pyrrolo[1,2-f][1,2,4]triazin-2-yl)-N-((R)-1-(pyridin-4-ylmethyl)piperidin-3-yl)pyrrolidine-2-carboxamide | 1.24 | 527 |
| 99 | 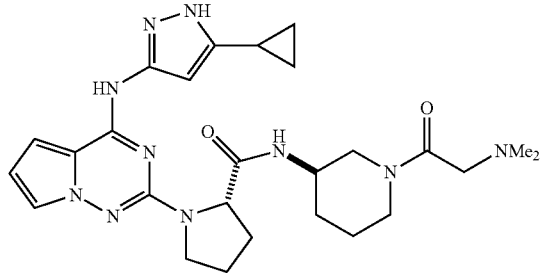<br>(S)-1-(4-(5-cyclopropyl-1H-pyrazol-3-ylamino)pyrrolo[1,2-f][1,2,4]triazin-2-yl)-N-((R)-1-(2-(dimethylamino)acetyl)piperidin-3-yl)pyrrolidine-2-carboxamide | 1.42 | 521 |
| 100 | 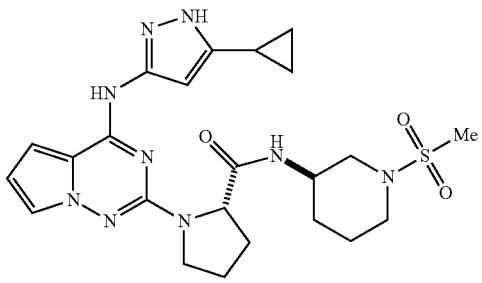<br>(S)-1-(4-(5-cyclopropyl-1H-pyrazol-3-ylamino)pyrrolo[1,2-f][1,2,4]triazin-2-yl)-N-((R)-1-(methylsulfonyl)piperidin-3-yl)pyrrolidine-2-carboxamide | 1.68 | 514 |

Example 101

((S)-1-(4-(5-cyclopropyl-1H-pyrazol-3-ylamino)-7-(piperazin-1-ylmethyl)pyrrolo[1,2-f][1,2,4]triazin-2-yl)pyrrolidine-2-carboxamide

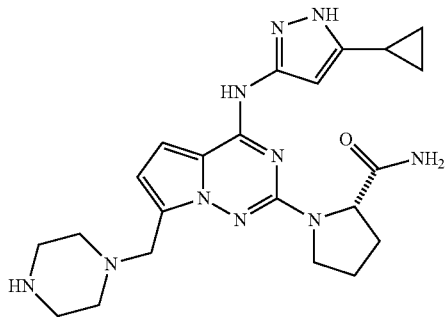 [SMILES: NC(=O)[C@@H]1CCCN1c1nc(Nc2cc(C3CC3)[nH]n2)c2ccc(CN3CCNCC3)n2n1]

101A. 2,4-dichloropyrrolo[1,2-f][1,2,4]triazine-7-carbaldehyde

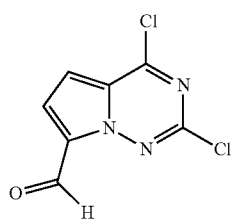 [SMILES: O=Cc1ccc2c(Cl)nc(Cl)nn12]

Dry dimethylformamide (1.03 mL, 13.3 mmole) was added to an ice-cooled solution of phosphorous oxychloride (2.47 mL, 26.6 mmole) in a vial and the mixture was stirred until homogeneous. It was allowed to warm to room temperature and 2,4-dichloropyrrolo[1,2-f][1,2,4]triazine 1B (500 mg, 2.66 mmole) was added and the vial was sealed and heated at 95° C. for 5 hr. After cooling to RT, the reaction was slowly poured into an ice-cooled, stirred mixture of saturated aqueous solution of NaHCO₃ (75 mL) and dichloromethane (25 mL). The aqueous phase was separated and extracted with additional dichloromethane. The combined organic phases were dried (Na₂SO₄) and the solvent removed. Radial silica gel chromatography (elution with mixtures of DCM:hexane=1:1 followed by 3:1) afforded the product as a solid (371 mg, 65% yield): ¹H NMR (CDCl₃) δ 7.08 (d, 1H, J=5 Hz), 7.54 (d, 1H, J=5 Hz), 10.49 (s, 1H).

101B. 2-Chloro-4-(5-cyclopropyl-1H-pyrazol-3-ylamino)pyrrolo[1,2-f][1,2,4]triazine-7-carbaldehyde

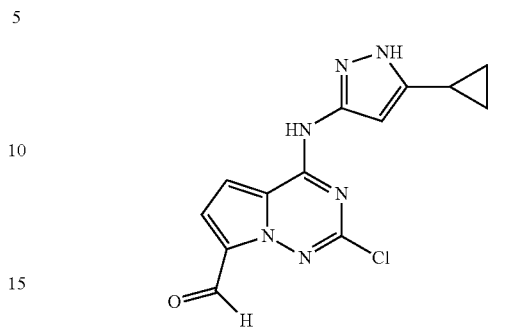

A mixture of 101A (371 mg, 1.72 mmole), 5-cyclopropyl-1H-pyrazol-3-amine (139 mg, 1 equiv), and diisopropylethylamine (0.51 mL, 1.7 equiv) in isopropyl alcohol (1.7 mL) was stirred at RT overnight. The reaction was diluted with a mixture of dichloromethane:methanol=9:1, washed with water and dried (Na₂SO₄). Removal of the solvents followed by radial silica gel chromatography (step gradient elution with mixtures of dichloromethane containing 0 to 7.5% methanol) afforded the product as a solid (279 mg, 54% yield): MS: 303 (M+H)⁺; HPLC Ret Time: 2.61 min (Phenomenex-Luna S10 3.0×50 mm column, 3 min gradient, 4 mL/min).

101C. tert-Butyl 4-((2-chloro-4-(5-cyclopropyl-1H-pyrazol-3-ylamino)pyrrolo[1,2-f][1,2,4]triazin-7-yl)methyl)piperazine-1-carboxylate

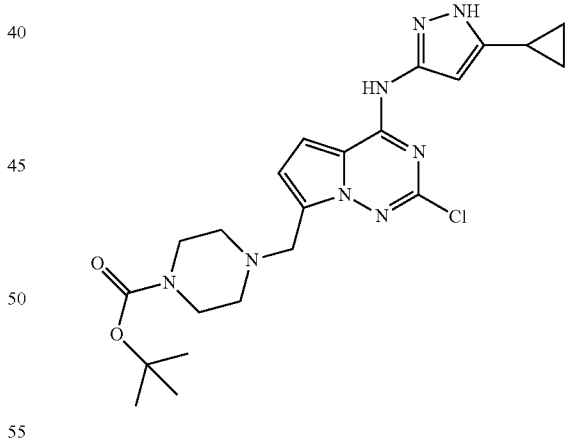

Sodium triacetoxyborohydride (88 mg, 0.42 mmole) was added to a stirred suspension of 101B (97 mg, 0.32 mmole), tert-butyl piperazine-1-carboxylate (60 mg, 0.32 mmole), and acetic acid (0.024 mL, 0.42 mmole) in dry dichloroethane. After 0.5 hr, the reaction was quenched with an aqueous solution of sodium hydroxide (3 mL, 1.0 M). The aqueous phase was extracted with methylene chloride and the combined organic phases were dried (Na₂SO₄) and the solvents removed. Radial silica gel chromatography (step gradient elution with mixtures of dichloromethane containing 0 to 7.5% methanol) afforded the product (105 mg, 70% yield):

MS: 473 (M+H)+; HPLC Ret Time: 2.27 min (Phenomenex-Luna S10 3.0×50 mm column, 3 min gradient, 4 mL/min).

A mixture of tert-butyl 4-((2-chloro-4-(5-cyclopropyl-1H-pyrazol-3-ylamino)pyrrolo[1,2-f][1,2,4]triazin-7-yl)methyl)piperazine-1-carboxylate 101C (65 mg, 0.14 mmole) and (S)-pyrrolidine-2-carboxamide (400 mg, 3.5 mmole) was heated at 120° C. for 12 hr. Preparative HPLC of the crude reaction mixture afforded (S)-tert-butyl 442-(2-carbamoylpyrrolidin-1-yl)-4-(5-cyclopropyl-1H-pyrazol-3-ylamino)pyrrolo[1,2-f][1,2,4]triazin-7-yOmethyl)piperazine-1-carboxylate which was treated with a mixture of dichloromethane:trifluoroacetic acid=1:1 (2 mL) for 0.5 hr. The solvents were removed and the residue was dissolved in methanol and applied onto a Phenomenex Strata-X-C 33 um cation mixed-mode polymer. This was eluted with methanol followed by a 2 N solution of ammonia in methanol to give, after removal of the solvents, the product 101 (24 mg, 39%): MS: 451 (M+H)+; HPLC Ret Time: 1.64 min (Phenomenex-Luna S10 3.0×50 mm column, 3 min gradient, 4 mL/min).

Examples 102 to 103

Table 6 contains Examples 102 to 103 which were prepared using procedures described above in Example 101.

TABLE 6

| Example | Compound | HPLC ret. t. (min.) | (M + H)+ |
|---|---|---|---|
| 102 | 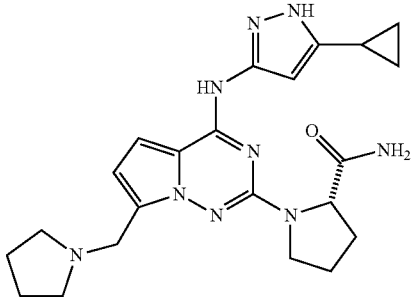<br>(S)-1-(4-(5-cyclopropyl-1H-pyrazol-3-ylamino)-7-(pyrrolidin-1-ylmethyl)pyrrolo[1,2-f][1,2,4]triazin-2-yl)pyrrolidine-2-carboxamide | 1.18 | 436 |
| 103 | 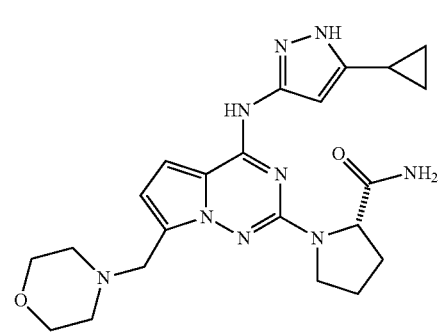<br>(S)-1-(4-(5-cyclopropyl-1H-pyrazol-3-ylamino)-7-(morpholinomethyl)pyrrolo[1,2-f][1,2,4]triazin-2-yl)pyrrolidine-2-carboxamide | 1.14 | 452 |

Example 104

(S)-1-(4-(5-cyclopropyl-1H-pyrazol-3-ylamino)pyrrolo[1,2-f][1,2,4]triazin-2-yl)-N-(6-fluoropyridin-3-yl)-2-methylpyrrolidine-2-carboxamide

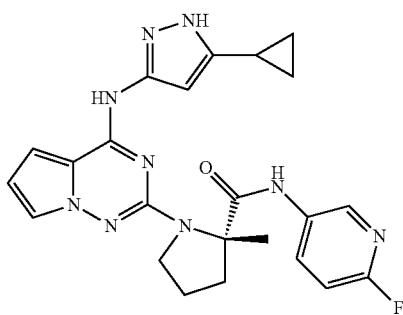 [SMILES: C[C@@]1(C(=O)Nc2ccc(F)nc2)CCCN1c1nc(Nc2cc(C3CC3)[nH]n2)c2cccn2n1]

Diisopropylethylamine (0.05 mL, 0.3 mmole) was added to a stirred mixture of 68A (40 mg, 0.11 mmol), 5-amino-2-fluoropyridine (37 mg, 0.33 mmole), and HATU (50 mg, 0.132 mmole) in dry dimethylformamide (0.5 mL) at RT. The mixture was heated at 45° C. for 18 hrs. The crude mixture was diluted with methanol and the product was isolated by preperative HPLC. The fractions that contained the product were applied onto a MCX cartridge and then flushed with methanol. The free base product was eluted with a 2 N solution of ammonia in methanol and removal of the solvents left product (9 mg, 18% yield): MS: 462 (M+H)+.

$^1$H-NMR (CD$_3$OD, 500 MHz, δ) 8.23 (d, 1H, J=1.8 Hz), 7.90 (br, 1H), 7.39 (t, 1H, J~1.8 Hz), 6.95 (dd, 1H, J=8.9, 2.8 Hz), 6.85 (dd, 1H, J=4.3, 1.2 Hz), 6.50 (dd, 1H, J=4.3, 2.4 Hz), 6.20 (br s, 1H), 3.88 (m, 1H), 3.72 (m, 1H), 2.47 (dt, 1H, J=12.5, 6.3 Hz), 2.20-2.03 (m, 3H), 1.79 (m, 1H), 1.73 (s, 3H), 0.94-0.86 (m, 2H), 0.78-0.68 (m, 2H).

Example 105

(S)-1-(4-(5-cyclopropyl-1H-pyrazol-3-ylamino)pyrrolo[1,2-f][1,2,4]triazin-2-yl)-2-methyl-N-(thiazol-2-yl)pyrrolidine-2-carboxamide

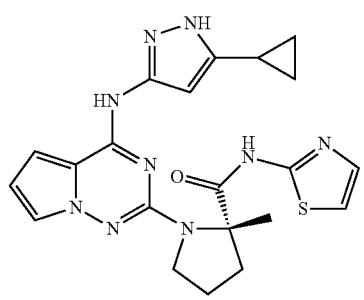 [SMILES: C[C@@]1(C(=O)Nc2nccs2)CCCN1c1nc(Nc2cc(C3CC3)[nH]n2)c2cccn2n1]

Diisopropylethylamine (0.095 mL, 0.55 mmole) was added to a stirred mixture of 68A (40 mg, 0.11 mmol), 2-Aminothiazole (50 mg, 0.5 mmole), and HATU (63 mg, 0.165 mmole) in dry dimethylformamide (0.5 mL) at RT. The mixture was heated at 45° C. for 40 hrs. The crude mixture was diluted with methanol and the product was isolated by preperative HPLC. The fractions that contained the product were applied onto a MCX cartridge and then flushed with methanol. The free base product was eluted with a 2 N solution of ammonia in methanol and removal of the solvents left product (26.2 mg, 53% yield): MS: 450 (M+H)+.

$^1$H-NMR (CD$_3$OD, 500 MHz, δ) 7.37 (dd, 1H, J=1.5, 2.4 Hz), 7.33 (d, 1H, J=3.5 Hz), 7.06 (d, 1H, J=3.5 Hz), 6.79 (dd, 1H, J=1.5, 4.3 Hz), 6.46 (dd, 1H, J=2.4, 4.3 Hz), 6.14 (br, 1H), 3.90 (m, 1H), 3.75 (dt, 1H, J=10.4, 7.2 Hz), 2.38 (dt, 1H, J=12.5, 6.8 Hz), 2.14 (m, 1H), 2.05 (m, 2H), 1.87 (tt, 1H, J=5.2, 8.4 Hz), 1.75 (s, 3H), 1.0-0.8 (m, 4H).

Example 106

(S)-1-(4-(5-cyclopropyl-1H-pyrazol-3-ylamino)pyrrolo[1,2-f][1,2,4]triazin-2-yl)-2-methyl-N-(5-methylthiazol-2-yl)pyrrolidine-2-carboxamide

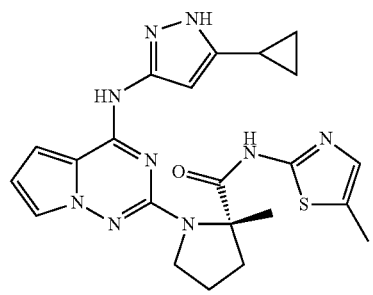 [SMILES: Cc1cnc(NC(=O)[C@]2(C)CCCN2c2nc(Nc3cc(C4CC4)[nH]n3)c3cccn3n2)s1]

Diisopropylethylamine (0.6 mL, 3.4 mmole) was added to a stirred mixture of 68A (250 mg, 0.68 mmol), 2-amino-5-methylthiazole (388 mg, 3.4 mmole), and HATU (387 mg, 1.02 mmole) in dry NMP (3 mL) at RT. The mixture was heated at 60° C. for 18 hrs. Another 387 mg HATU and 0.6 ml diisopropylethylamine was added. The mixture was heated at 60° C. for 42 hrs. The crude mixture was diluted with methanol and the product was isolated by preperative HPLC. The fractions that contained the product were applied onto a MCX cartridge and then flushed with methanol. The free base product was eluted with a 2 N solution of ammonia in methanol and removal of the solvents left product (130.7 mg, 41% yield): MS: 464 (M+H)+.

$^1$H-NMR (CD$_3$OD, 500 MHz, δ) 7.42 (dd, 1H, J=1.8, 2.5 Hz), 6.99 (q, 1H, J=1.0 Hz), 6.80 (dd, 1H, J=1.5, 4.3 Hz), 6.48 (dd, 1H, J=2.5, 4.3 Hz), 6.13 (br, 1H), 3.91 (m, 1H), 3.75 (ddd, 1H, J=10.2, 7.3, 7.2 Hz), 2.40 (m, 1H), 2.37 (d, 3H, J=1Hz) 2.19-2.02 (m, 3H), 1.91 (tt, 1H, J=8.4, 5.2 Hz), 1.75 (s, 3H), 1.02-0.82 (m, 4H).

Example 107

(S)-N-(5-chlorothiazol-2-yl)-1-(4-(5-cyclopropyl-1H-pyrazol-3-ylamino)pyrrolo[1,2-f][1,2,4]triazin-2-yl)-2-methylpyrrolidine-2-carboxamide

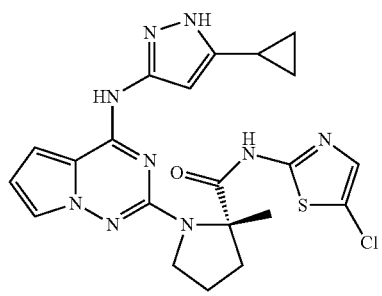 [SMILES: C[C@@]1(C(=O)Nc2ncc(Cl)s2)CCCN1c1nc(Nc2cc(C3CC3)[nH]n2)c2cccn2n1]

Diisopropylethylamine (1.2 mL, 6.8 mmole) was added to a stirred mixture of 68A (500 mg, 1.36 mmol), 2-amino-5-chlorolthiazole (915 mg, 6.8 mmole), and HATU (774 mg, 2.04 mmole) in dry NMP (3 mL) at RT. The mixture was heated at 45° C. for 18 hrs. Another 774 mg HATU and 1.2 ml diisopropylethylamine was added. The mixture was heated at 60° C. for 42 hrs. The crude mixture was diluted with methanol and the product was isolated by preperative HPLC. The fractions that contained the product were applied onto a MCX cartridge and then flushed with methanol. The free base product was eluted with a 2 N solution of ammonia in methanol and removal of the solvents left product (104 mg, 16% yield): MS: 484 (M+H)+.

$^1$H-NMR (CD$_3$OD, 500 MHz, δ) 7.39 (t, 1H, J~1.8 Hz), 7.22 (s, 1H), 6.82 (dd, 1H, J=1.5, 4.3 Hz), 6.49 (dd, 1H, J=2.5, 4.3 Hz), 6.14 (br, 1H), 3.91 (m, 1H), 3.75 (m, 1H), 2.38 (dt, 1H, J=11.9, 7.3 Hz), 2.18-2.03 (m, 3H), 1.92 (tt, 1H, J=5.2, 8.5 Hz), 1.75 (s, 3H), 1.05-0.81 (m, 4H).

Example 108

(S)-1-(4-(5-cyclopropyl-1H-pyrazol-3-ylamino)pyrrolo[1,2-f][1,2,4]triazin-2-yl)-2-methyl-N-(3-methylisothiazol-5-yl)pyrrolidine-2-carboxamide

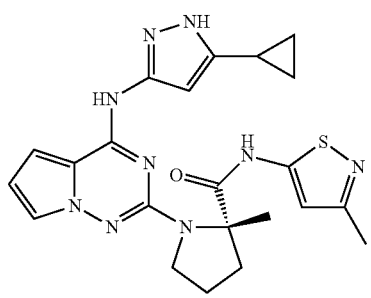 [SMILES: Cc1cc(NC(=O)[C@]2(C)CCCN2c2nc(Nc3cc(C4CC4)[nH]n3)c3cccn3n2)sn1]

Diisopropylethylamine (0.095 mL, 0.55 mmole) was added to a stirred mixture of 68A (40 mg, 0.11 mmol), 5-amino-3-methylisothiazole HCl (50 mg, 0.33 mmole), and HATU (63 mg, 0.165 mmole) in dry dimethylformamide (0.5 mL) at RT. The mixture was heated at 45° C. for 40 hrs. The crude mixture was diluted with methanol and the product was isolated by preperative HPLC. The fractions that contained the product were applied onto a MCX cartridge and then flushed with methanol. The free base product was eluted with a 2 N solution of ammonia in methanol and removal of the solvents left product (2.8 mg, 5.5% yield): MS: 464 (M+H)+.

$^1$H-NMR (CD$_3$OD, 500 MHz, δ) 7.39 (t, 1H, J~1.8 Hz), 6.82 (dd, 1H, J=1.5, 4.3 Hz), 6.65 (s, 1H), 6.49 (dd, 1H, J=2.5, 4.3 Hz), 6.08 (br, 1H), 3.92 (m, 1H), 3.73 (m, 1H), 2.37 (m, 1H), 2.31 (s, 3H), 2.18-2.00 (m, 3H), 1.90 (m, 1H), 1.78 (s, 3H), 1.02-0.90 (m, 3H), 0.85 (m, 1H).

Example 109

(S)-N-(4-chloropyridin-3-yl)-1-(4-(5-cyclopropyl-1H-pyrazol-3-ylamino)pyrrolo[1,2-f][1,2,4]triazin-2-yl)-2-methylpyrrolidine-2-carboxamide

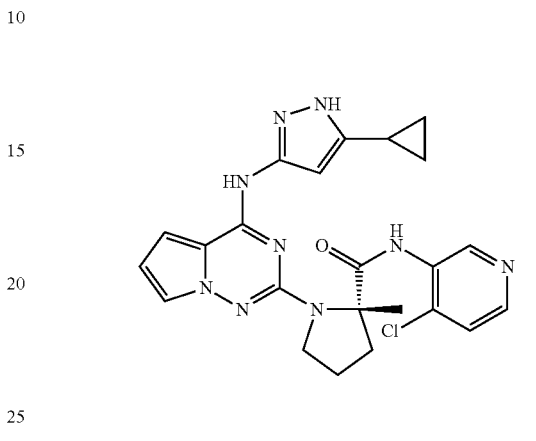

109A.

Acid 68A (8.0 g, 21.8 mmol) were dissolved in 100 ml NMP and the solution cooled to 0° C. Ethyl diisopropylamine (26.7 ml, 153 mmol, 7 equiv.) was added, followed by pivaloyl chloride (26.7 ml, 87.1 mmol, 4 equiv.). The ice bath was removed and the solution stirred at ambient temperature for 3 hours. The reaction vessel was immersed into an ice-water-bath and 200 ml sat. aq. NaHCO$_3$ solution were added. The ice bath was removed and the reaction stirred at ambient temperature for 1.5 hours, then transferred into a separating funnel loaded with water and ethyl acetate. The layers were separated, the organic layer washed with saturated aq. NaHCO$_3$ solution, then 0.5 M aq. citric acid solution, then NaHCO$_3$, then brine. Drying over MgSO$_4$, filtering, concentrating in vacuo gave 11.86 g crude product as an oil, which was used without further purification. The major isomer can be isolated analytically pure by crystallization from diethyl ether.

109B.

MeMgBr (3M in ether, 0.3 ml, 0.9 mmol) was added to a solution of 4-chloropyridin-3-amine (142 mg, 1.1 mmol) in THF (1 ml) at RT. The mixture was stirred at RT for 5mins. A solution of pivaloate 109A (47 mg, 0.11 mmol) in 0.5 ml THF was added to above mixture. After 1 hr stirring at RT, 1.5 ml of 7M NH$_3$ in MeOH was added and stirred for 20mins. The crude mixture was diluted with methanol and the product was isolated by preparative HPLC. The fractions that contained the product were applied onto a MCX cartridge and then flushed with methanol. The free base product was eluted with a 2 N solution of ammonia in methanol and removal of the solvents left product (23 mg, 44% yield): MS: 478 (M+H)+.

$^1$H-NMR (CD$_3$OD, 500 MHz, δ) 8.91 (br s, 1H), 8.22 (d, 1H, J=5.5 Hz), 7.46 (d, 1H, J=5.5 Hz), 7.42 (t, 1H, J~1.8 Hz), 6.86 (dd, 1H, J=1.2, 4.2 Hz), 6.51 (dd, 1H, J=2.4, 4.3 Hz), 6.17 (br, 1H), 3.89 (m, 1H), 3.75 (m, 1H), 2.54 (ddd, 1H, J=12.1, 6.4, 6.2 Hz), 2.21-2.07 (m, 3H), 1.78 (m, 1H), 1.74 (s, 3H), 0.87 (m, 2H), 0.73 (m, 1H), 0.67 (m, 1H).

Example 110

(S)-1-(4-(5-cyclopropyl-1H-pyrazol-3-ylamino)pyrrolo[1,2-f][1,2,4]triazin-2-yl)-2-methyl-N-(pyrazin-2-yl)pyrrolidine-2-carboxamide

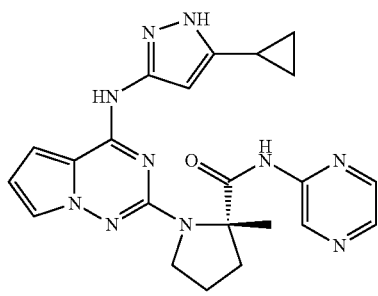 [SMILES: C[C@@]1(C(=O)Nc2cnccn2)CCCN1c1nc(Nc2cc(C3CC3)[nH]n2)c2cccn2n1]

Aminopyrazine (317 mg, 3.3 mmol, 4.75 equiv.) was dissolved in 10 ml THF and the solution cooled to −78° C. A solution of MeMgBr in ether (1.0 ml, 3 M, 3.0 mmol, 4.3 equiv.) was added and the mixture stirred at −78° C. for 5 minutes. A solution of pivaloate intermediate 109A (crystallized major isomere, 305 mg, 0.70 mmol) in 10 ml THF was added and the mixture stirred at −78° C. for 3.5 hours, then overnight at −20° C. Saturated aq. NH$_4$Cl solution (7 ml) and 7 ml aq. NH$_4$OH solution were added and the mixture stirred for 24 hours at 20° C. The mixture was poured into a separating funnel loaded with 150 ml water and 150 ml ethyl acetate and extracted. The organic layer was washed with brine, dried over MgSO$_4$ and concentrated. The crude product was purified by chromatography on silica gel, gradient hexanes—(EtOAc+1% Et$_3$N) 3:1 to 0:1 (2.881, 24 fractions), followed by prep HPLC. Product containing fractions were filtered through an MCX cartridge and the product eluted with NH$_3$ in MeOH. Evaporation of volatiles and recrystallization from acetone/water gave 183.8 mg of crystals. (59% yield). MS: 445 (M+H)+.

$^1$H-NMR (CD$_3$OD, 300 MHz, δ) 9.37 (d, 1H, J=1Hz), 8.24 (m, 2H), 7.41 (dd, 1H, J=1.7, 2.5 Hz), 6.82 (dd, 1H, J=4.5, 1.7 Hz), 6.49 (dd, 1H, J=4.5, 2.5 Hz), 6.15 (br, 1H), 3.89 (m, 1H), 3.75 (m, 1H), 2.48 (ddd, 1H, J=12.2, 6.0, 5.7 Hz), 2.21-2.03 (m, 3H), 1.84 (m, 1H), 1.74 (s, 3H), 0.99-0.93 (m, 2H), 0.85-0.75 (m, 2H).

Example 111

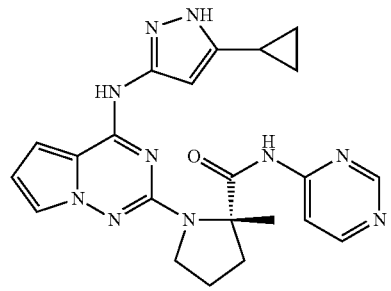 [SMILES: C[C@@]1(C(=O)Nc2ccncn2)CCCN1c1nc(Nc2cc(C3CC3)[nH]n2)c2cccn2n1]

MeMgBr (3M in ether, 0.3 ml, 0.9 mmol) was added to a solution of pyrimidin-4-amine (105 mg, 1.1 mmol) in THF (1 ml) at RT. The mixture was stirred at RT for 5mins. A solution of 109A (47 mg, 0.11 mmol) in 0.5 ml THF was added to above mixture. After 1 hr stirring at RT, 1.5 ml of 7M NH$_3$ in MeOH was added and stirred for 20mins. The crude mixture was diluted with methanol and the product was isolated by preperative HPLC. The fractions that contained the product were applied onto a MCX cartridge and then flushed with methanol. The free base product was eluted with a 2 N solution of ammonia in methanol and removal of the solvents left product (4.3 mg, 8.8% yield): MS: 445 (M+H)+.

$^1$H-NMR (CD$_3$OD, 500 MHz, δ) 8.70 (d, 1H, J=1.1 Hz), 8.56 (d, 1H, J=5.9 Hz), 8.17 (dd, 1H, J=1.1, 5.9 Hz), 7.41 (dd, 1H, J=1.6, 2.5 Hz), 6.81 (dd, 1H, J=1.6, 4.6 Hz), 6.50 (dd, 1H, J=2.5, 4.6 Hz), 6.13 (br, 1H), 3.88 (m, 1H), 3.77 (m, 1H), 2.43 (m, 1H), 2.18-2.03 (m, 3H), 1.88 (tt, 1H, J=5.5, 8.2 Hz), 1.72 (s, 3H), 1.03-0.75 (m, 4H).

Examples 112 to 163

Table 7 contains Examples 112 to 115; 117 to 128; 131 and 132 which were prepared using procedures described above in Example 104. Example 116 was a byproduct present in the above examples. Examples 129, 130, 133 to 155 were prepared using the procedure described in Example 109. Examples 156 to 162 also appear in the table.

TABLE 7

| Example | Structure | HPLC r.t. | (M + H)+ |
|---|---|---|---|
| 112 | 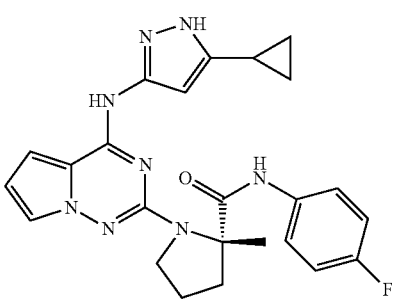(S)-1-(4-(5-cyclopropyl-1H-pyrazol-3-ylamino)pyrrolo[1,2-f][1,2,4]triazin-2-yl)-N-(4-fluorophenyl)-2-methylpyrrolidine-2-carboxamide | 1.303(a) 6.453(d) | 461 |

TABLE 7-continued

| Example | Structure | HPLC r.t. | (M + H)+ |
|---|---|---|---|
| 113 | 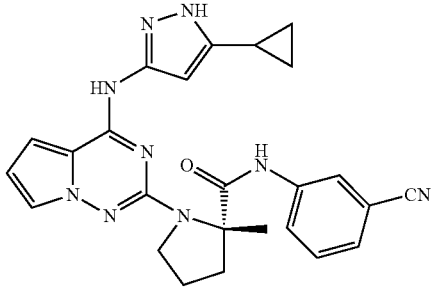<br>(S)-N-(3-cyanophenyl)-1-(4-(5-cyclopropyl-1H-pyrazol-3-ylamino)pyrrolo[1,2-f][1,2,4]triazin-2-yl)-2-methylpyrrolidine-2-carboxamide | 1.293(a)<br>6.346(d) | 468 |
| 114 | 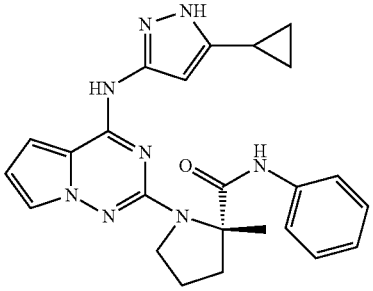<br>(S)-1-(4-(5-cyclopropyl-1H-pyrazol-3-ylamino)pyrrolo[1,2-f][1,2,4]triazin-2-yl)-2-methyl-N-phenylpyrrolidine-2-carboxamide | 1.277(a)<br>6.395(d) | 443 |
| 115 | 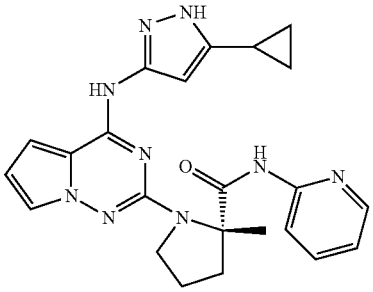<br>(S)-1-(4-(5-cyclopropyl-1H-pyrazol-3-ylamino)pyrrolo[1,2-f][1,2,4]triazin-2-yl)-2-methyl-N-(pyridin-2-yl)pyrrolidine-2-carboxamide | 1.203(a)<br>5.793(d) | 444 |
| 116 | 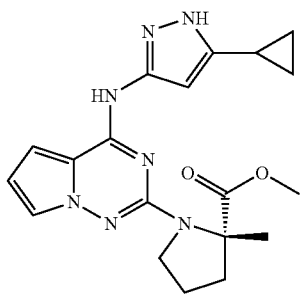<br>(S)-methy-1-(4-(5-cyclopropyl-1H-pyrazol-3-ylamino)pyrrolo[1,2-f][1,2,4]triazin-2-yl)-2-methylpyrrolidine-2-carboxylate | 1.248(a)<br>6.38(d) | 382 |

TABLE 7-continued

| Example | Structure | HPLC r.t. | (M + H)+ |
|---|---|---|---|
| 117 | (S)-1-(4-(5-cyclopropyl-1H-pyrazol-3-ylamino)pyrrolo[1,2-f][1,2,4]triazin-2-yl)-2-methyl-N-(thiazol-2-ylmethyl)pyrrolidine-2-carboxamide | 1.195(j) 6.73(h) 8.36(i) | 464 |
| 118 | (S)-1-(4-(5-cyclopropyl-1H-pyrazol-3-ylamino)pyrrolo[1,2-f][1,2,4]triazin-2-yl)-N-(4-methoxyphenyl)-2-methylpyrrolidine-2-carboxamide | 1.29(a) 6.27(b) | 473 |
| 119 | (S)-1-(4-(5-cyclopropyl-1H-pyrazol-3-ylamino)pyrrolo[1,2-f][1,2,4]triazin-2-yl)-N-(3-fluoro-4-methoxyphenyl)-2-methylpyrrolidine-2-carboxamide | 1.322(a) 6.42(b) | 491 |

TABLE 7-continued

| Example | Structure | HPLC r.t. | (M + H)+ |
|---|---|---|---|
| 120 | (S)-1-(4-(5-cyclopropyl-1H-pyrazol-3-ylamino)pyrrolo[1,2-f][1,2,4]triazin-2-yl)-N,N,2-trimethylpyrrolidine-2-carboxamide | 2.177(e) | 395 |
| 121 | (S)-1-(4-(5-cyclopropyl-1H-pyrazol-3-ylamino)pyrrolo[1,2-f][1,2,4]triazin-2-yl)-N-(4-fluoro-3-methylphenyl)-2-methylpyrrolidine-2-carboxamide | 1.407(a) 6.915(b) | 475 |
| 122 | (S)-1-(4-(5-cyclopropyl-1H-pyrazol-3-ylamino)pyrrolo[1,2-f][1,2,4]triazin-2-yl)-N-(4-fluoro-2-hydroxyphenyl)-2-methylpyrrolidine-2-carboxamide | 1.302(a) 6.421(b) | 477 |

TABLE 7-continued

| Example | Structure | HPLC r.t. | (M + H)+ |
|---|---|---|---|
| 123 | (S)-1-(4-(5-cyclopropyl-1H-pyrazol-3-ylamino)pyrrolo[1,2-f][1,2,4]triazin-2-yl)-N-(3,4-dimethoxyphenyl)-2-methylpyrrolidine-2-carboxamide | 1.58(c) 6.281(d) | 503 |
| 124 | (S)-1-(4-(5-cyclopropyl-1H-pyrazol-3-ylamino)pyrrolo[1,2-f][1,2,4]triazin-2-yl)-2-methyl-N-(4-methylthiazol-2-yl)pyrrolidine-2-carboxamide | 1.675(c) 6.576(d) | 464 |
| 125 | (S)-N-(5-cyclopropyl-1,3,4-thiadiazol-2-yl)-1-(4-(5-cyclopropyl-1H-pyrazol-3-ylamino)pyrrolo[1,2-f][1,2,4]triazin-2-yl)-2-methylpyrrolidine-2-carboxamide | 1.728(c) 6.836(d) | 491 |
| 126 | (S)-1-(4-(5-cyclopropyl-1H-pyrazol-3-ylamino)pyrrolo[1,2-f][1,2,4]triazin-2-yl)-2-methyl-N-(1,3,4-thiadiazol-2-yl)pyrrolidine-2-carboxamide | 1.57(c) 6.14(d) | 451 |

TABLE 7-continued

| Example | Structure | HPLC r.t. | (M + H)+ |
|---|---|---|---|
| 127 | (S)-1-(4-(5-cyclopropyl-1H-pyrazol-3-ylamino)pyrrolo[1,2-f][1,2,4]triazin-2-yl)-N-(1-ethyl-1H-pyrazol-5-yl)-2-methylpyrrolidine-3-carboxamide | 1.127(a) 5.905(d) | 461 |
| 128 | (S)-1-(4-(5-cyclopropyl-1H-pyrazol-3-ylamino)pyrrolo[1,2-f][1,2,4]triazin-2-yl)-N-(6-methoxypyridin-3-yl)-2-methylpyrrolidine-2-carboxamide | 1.220(a) 6.063(d) | 474 |
| 129 | (S)-1-(4-(5-cyclopropyl-1H-pyrazol-3-ylamino)pyrrolo[1,2-f][1,2,4]triazin-2-yl)-2-methyl-N-(3-methylisoxazol-5-yl)pyrrolidine-2-carboxamide | 1.308(j) 7.99(h) 9.32(i) | 448 |
| 130 | (S)-1-(4-(5-cyclopropyl-1H-pyrazol-3-ylamino)pyrrolo[1,2-f][1,2,4]triazin-2-yl)-2-methyl-N-(5-methylisoxazol-3-yl)pyrrolidine-2-carboxamide | 1.34(j) 7.93(h) 9.40(i) | 448 |

TABLE 7-continued

| Example | Structure | HPLC r.t. | (M + H)+ |
|---------|-----------|-----------|----------|
| 131 | 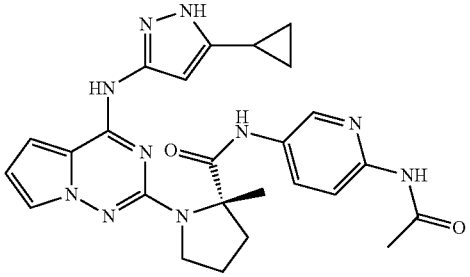<br>(S)-N-(6-acetamidopyridin-3-yl)-1-(4-(5-cyclopropyl-1H-pyrazol-3-ylamino)pyrrolo[1,2-f][1,2,4]triazin-2-yl)-2-methylpyrrolidine-2-carboxamide | 1.528(f) | 501 |
| 132 | 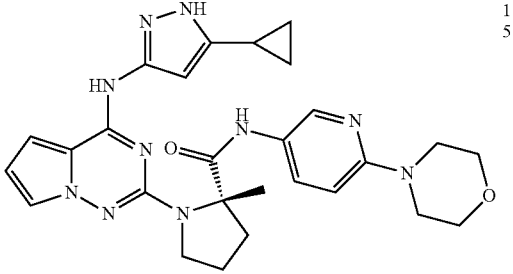<br>(S)-1-(4-(5-cyclopropyl-1H-pyrazol-3-ylamino)pyrrolo[1,2-f][1,2,4]triazin-2-yl)-2-methyl-N-(6-morpholinopyridin-3-yl)pyrrolidine-2-carboxamide | 1.157(a)<br>5.443(b) | 529 |
| 133 | 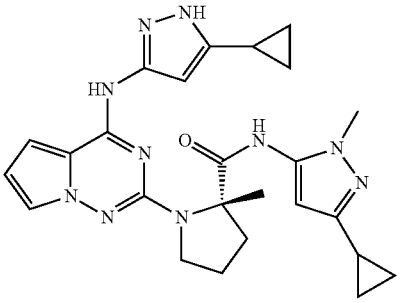<br>(S)-N-(3-cyclopropyl-1-methyl-1H-pyrazol-5-yl)-1-(4-(5-cyclopropyl-1H-pyrazol-3-ylamino)pyrrolo[1,2-f][1,2,4]triazin-2-yl)-2-methylpyrrolidine-2-carboxamide | 1.21(a)<br>6.146(b) | 487 |

TABLE 7-continued

| Example | Structure | HPLC r.t. | (M + H)⁺ |
|---|---|---|---|
| 134 | (S)-N-(5-cyclopropyl-1H-pyrazol-3-yl)-1-(4-(5-cyclopropyl-1H-pyrazol-3-ylamino)pyrrolo[1,2-f][1,2,4]triazin-2-yl)-2-methylpyrrolidine-2-carboxamide | 1.165(a) 5.97(b) | 473 |
| 135 | (S)-1-(4-(5-cyclopropyl-1H-pyrazol-3-ylamino)pyrrolo[1,2-f][1,2,4]triazin-2-yl)-2-methyl-N-(5-methyl-1H-pyrazol-3-yl)pyrrolidine-2-carboxamide | 1.088(a) 5.613(b) | 447 |
| 136 | (S)-1-(4-(5-cyclopropyl-1H-pyrazol-3-ylamino)pyrrolo[1,2-f][1,2,4]triazin-2-yl)-2-methyl-N-(1H-pyrazol-3-yl)pyrrolidine-2-carboxamide | 1.053(a) 5.563(b) | 433 |
| 137 | (S)-1-(4-(5-cyclopropyl-1H-pyrazol-3-ylamino)pyrrolo[1,2-f][1,2,4]triazin-2-yl)-2-methyl-N-(6-methylpyridin-3-yl)pyrrolidine-2-carboxamide | 1.167(a) 5.573(b) | 458 |

TABLE 7-continued

| Example | Structure | HPLC r.t. | (M + H)+ |
|---|---|---|---|
| 138 | (S)-N-(6-chloropyridin-3-yl)-1-(4-(5-cyclopropyl-1H-pyrazol-3-ylamino)pyrrolo[1,2-f][1,2,4]triazin-2-yl)-2-methylpyrrolidine-2-carboxamide | 1.302(a) 6.35(b) | 478 |
| 139 | (S)-N-(6-cyanopyridin-3-yl)-1-(4-(5-cyclopropyl-1H-pyrazol-3-ylamino)pyrrolo[1,2-f][1,2,4]triazin-2-yl)-2-methylpyrrolidine-2-carboxamide | 1.295(a) 6.325(b) | 469 |
| 140 | (S)-1-(4-(5-cyclopropyl-1H-pyrazol-3-ylamino)pyrrolo[1,2-f][1,2,4]triazin-2-yl)-N-(6-fluoro-5-methylpyridin-3-yl)-2-methylpyrrolidine-2-carboxamide | 1.29(a) 6.375(b) | 476 |
| 141 | (S)-N-(2-chloropyridin-3-yl)-1-(4-(5-cyclopropyl-1H-pyrazol-3-ylamino)pyrrolo[1,2-f][1,2,4]triazin-2-yl)-2-methylpyrrolidine-2-carboxamide | 1.338(a) 6.45(d) | 478 |

TABLE 7-continued

| Example | Structure | HPLC r.t. | (M + H)+ |
|---|---|---|---|
| 142 | (S)-N-(4-chloropyridin-3-yl)-1-(4-(5-cyclopropyl-1H-pyrazol-3-ylamino)pyrrolo[1,2-f][1,2,4]triazin-2-yl)-2-methylpyrrolidine-2-carboxamide | 1.267(a) 6.036(d) | 478 |
| 143 | (S)-1-(4-(5-cyclopropyl-1H-pyrazol-3-ylamino)pyrrolo[1,2-f][1,2,4]triazin-2-yl)-N-(2,5-dichloropyridin-3-yl)-2-methylpyrrolidine-2-carboxamide | 1.568(a) 7.631(d) | 512 |
| 144 | (S)-1-(4-(5-cyclopropyl-1H-pyrazol-3-ylamino)pyrrolo[1,2-f][1,2,4]triazin-2-yl)-N-(2,6-dichloropyridin-3-yl)-2-methylpyrrolidine-2-carboxamide | 1.51(a) 7.106(d) | 512 |
| 145 | (S)-N-(6-chloro-2-methylpyridin-3-yl)-1-(4-(5-cyclopropyl-1H-pyrazol-3-ylamino)pyrrolo[1,2-f][1,2,4]triazin-2-yl)-2-methylpyrrolidine-2-carboxamide | 1.308(a) 6.183(d) | 492 |

TABLE 7-continued

| Example | Structure | HPLC r.t. | (M + H)⁺ |
|---|---|---|---|
| 146 | (S)-1-(4-(5-cyclopropyl-1H-pyrazol-3-ylamino)pyrrolo[1,2-f][1,2,4]triazin-2-yl)-N-(5-fluoropyridin-2-yl)-2-methylpyrrolidine-2-carboxamide | 1.343(a) 6.513(d) | 462 |
| 147 | (S)-N-(5-cyanopyridin-2-yl)-1-(4-(5-cyclopropyl-1H-pyrazol-3-ylamino)pyrrolo[1,2-f][1,2,4]triazin-2-yl)-2-methylpyrrolidine-2-carboxamide | 1.368(a) 6.601(d) | 469 |
| 148 | (S)-N-(5-chloropyrazin-2-yl)-1-(4-(5-cyclopropyl-1H-pyrazol-3-ylamino)pyrrolo[1,2-f][1,2,4]triazin-2-yl)-2-methylpyrrolidine-2-carboxamide | 1.395(a) 6.943(d) | 479 |
| 149 | (S)-1-(4-(5-cyclopropyl-1H-pyrazol-3-ylamino)pyrrolo[1,2-f][1,2,4]triazin-2-yl)-2-methyl-N-(6-(trifluoromethyl)pyridin-3-yl)pyrrolidine-2-carboxamide | 1.425(a) 6.711(d) | 512 |

TABLE 7-continued

| Example | Structure | HPLC r.t. | (M + H)+ |
|---|---|---|---|
| 150 | (S)-1-(4-(5-cyclopropyl-1H-pyrazol-3-ylamino)pyrrolo[1,2-f][1,2,4]triazin-2-yl)-2-methyl-N-(pyridin-4-yl)pyrrolidine-2-carboxamide | 1.21(a) 5.79(b) | 444 |
| 151 | (S)-N-(2-chloropyridin-4-yl)-1-(4-(5-cyclopropyl-1H-pyrazol-3-ylamino)pyrrolo[1,2-f][1,2,4]triazin-2-yl)-2-methylpyrrolidine-2-carboxamide | 1.35(a) 6.786(b) | 478 |
| 152 | (S)-1-(4-(5-cyclopropyl-1H-pyrazol-3-ylamino)pyrrolo[1,2-f][1,2,4]triazin-2-yl)-N-(2-fluoropyridin-4-yl)-2-methylpyrrolidine-2-carboxamide | 1.31(a) 6.556(b) | 462 |
| 153 | (S)-1-(4-(5-cyclopropyl-1H-pyrazol-3-ylamino)pyrrolo[1,2-f][1,2,4]triazin-2-yl)-2-methyl-N-(pyrimidin-4-yl)pyrrolidine-2-carboxamide | 1.178(a) 6.101(b) | 445 |

TABLE 7-continued

| Example | Structure | HPLC r.t. | (M + H)+ |
|---|---|---|---|
| 154 | (S)-1-(4-(5-cyclopropyl-1H-pyrazol-3-ylamino)pyrrolo[1,2-f][1,2,4]triazin-2-yl)-2-methyl-N-(pyrimidin-2-yl)pyrrolidine-2-carboxamide | 1.11(a) 5.53(b) | 445 |
| 155 | (S)-N-(5-chloropyrimidin-2-yl)-1-(4-(5-cyclopropyl-1H-pyrazol-3-ylamino)pyrrolo[1,2-f][1,2,4]triazin-2-yl)-2-methylpyrrolidine-2-carboxamide | 1.227(a) 6.12(b) | 479 |
| 156 | (S)-N-(5-bromopyrazin-2-yl)-1-(4-(3-cylcopropyl-1H-pyrazol-5-ylamino)pyrrolo[1,2-f][1,2,4]triazin-2-yl)-2-methylpyrrolidine-2-carboxamide | 3.39(k) | 523 |
| 157 | (S)-N-(5-aminopyrazin-2-yl)-1-(4-(3-cyclopropyl-1H-pyrazol-5-ylamino)pyrrolo[1,2-f][1,2,4]triazin-2-yl)-2-methylpyrrolidine-2-carboxamide | 2.77(k) | 460 |

TABLE 7-continued

| Example | Structure | HPLC r.t. | (M + H)+ |
|---|---|---|---|
| 158 | (S)-1-(4-(3-cyclopropyl-1H-pyrazol-5-ylamino)pyrrolo[1,2-f][1,2,4]triazin-2-yl)-2-methyl-N-(5-(methylamino)pyrazin-2-yl)pyrrolidine-2-carboxamide | 2.80(k) | 474 |
| 159 | (S)-1-(4-(3-cyclopropyl-1H-pyrazol-5-ylamino)pyrrolo[1,2-f][1,2,4]triazin-2-yl)-N-(5-(dimethylamino)pyrazin-2-yl)-2-methylpyrrolidine-2-carboxamide | 3.02(k) | 488 |
| 160 | (S)-1-(4-(3-cyclopropyl-1H-pyrazol-5-ylamino)pyrrolo[1,2-f][1,2,4]triazin-2-yl)-N-(4-hydroxypyridin-3-yl)-2-methylpyrrolidine-2-carboxamide | 1.71(l) | 460 |
| 161 | (S)-1-(4-(3-cyclopropyl-1H-pyrazol-5-ylamino)pyrrolo[1,2-f][1,2,4]triazin-2-yl)-N-(6-hydroxypyridin-3-yl)-2-methylpyrrolidine-2-carboxamide | 2.72(k) | 460 |

TABLE 7-continued

| Example | Structure | HPLC r.t. | (M + H)+ |
|---|---|---|---|
| 162 | (S)-1-(4-(3-cyclopropyl-1H-pyrazol-5-ylamino)pyrrolo[1,2-f][1,2,4]triazin-2-yl)-2-methyl-N-(1,2,4-thiadiazol-5-yl)pyrrolidine-2-carboxamide | 2.79(m) | 451 |

HPLC Conditions for Examples 104 to 162 a: Phenomenex C18 4.6×30 mm column, 2 min gradient, 0-100% B, 5 mL/min. Solvent A: 5% CH$_3$CN-95% H$_2$O-10 mm Ammonium Acetate; Solvent B: 95% CH$_3$CN-5% H$_2$O-10 mm Ammonium Acetate.

b: Phenomenex C18 4.6×50 mm column, 10 min gradient, 0-100% B, 5 mL/min. Solvent A: 10% CH$_3$OH-90% H$_2$O-0.1% TFA; Solvent B: 90% CH$_3$OH-10% H$_2$O-0.1% TFA.

c: Phenomenex C18 4.6×30 mm column, 2 min gradient, 0-100% B, 5 mL/min. Solvent A: 10% CH$_3$OH-90% H$_2$O-0.1% TFA; Solvent B: 90% CH$_3$OH-10% H$_2$O-0.1% TFA.

d: Xterra MS C18 4.6×50 mm column, 10 min gradient, 0-100% B, 5 mL/min. Solvent A: 10% CH$_3$OH-90% H$_2$O-0.1% TFA; Solvent B: 90% CH$_3$OH-10% H$_2$O-0.1% TFA.

e: Phenomenex C18 4.6×30 mm column, 3 min gradient, 0-100% B, 4 mL/min. Solvent A: 10% CH$_3$OH-90% H$_2$O-0.1% TFA; Solvent B: 90% CH$_3$OH-10% H$_2$O-0.1% TFA.

f: Phenomenex C18 4.6×30 mm column, 3 min gradient, 0-100% B, 5 mL/min. Solvent A: 5% CH$_3$CN-95% H$_2$O-10 mm Ammonium Acetate; Solvent B: 95% CH$_3$CN-5% H$_2$O-10 mm Ammonium Acetate.

g: Phenomenex C18 3.0×50 mm column, 10 um, 2 min gradient, 0-100% B, 5 mL/min. Solvent A: 10% CH$_3$OH-90% H$_2$O-0.1% TFA; Solvent B: 90% CH$_3$OH-10% H$_2$O-0.1% TFA.

h: Waters Sunfire C18 4.6×150 mm column, 3.5 um, 10 min gradient, 10-90% B, 1 mL/min. Solvent A: 5% CH$_3$CN-95% H$_2$O-0.1% TFA; Solvent B: 90% CH$_3$CN-10% H$_2$O-0.1% TFA.

i: Waters Sunfire C18 4.6×150 mm column, 3.5 um, 10 min gradient, 10-90% B, 1 mL/min. Solvent A: 5% CH$_3$CN-95% H$_2$O-10 mM Ammonium Acetate; Solvent B: 90% CH$_3$CN-10% H$_2$O-10 mM Ammonium Acetate.

j: Phenomenex C18 4.6×50 mm column, 2 min gradient, 0-100% B, 5 mL/min. Solvent A: 5% CH$_3$CN-95% H$_2$O-10 mm Ammonium Acetate; Solvent B: 95% CH$_3$CN-5% H$_2$O-10 mm Ammonium Acetate.

k: column Phenomenex-Luna 4.6×50 mm S10, 4 min gradient, 0-100% B, 4 mL/min, Solvent A: 10% methanol-90% water-0.1% TFA; Solvent B: 90% methanol-10% water-0.1% TFA.

l: column Phenomenex-Luna 3.0×50 mm S10, 2 min gradient, 0-100% B, 4 mL/min, Solvent A: 10% methanol-90% water-0.1% TFA; Solvent B: 90% methanol-10% water-0.1% TFA.

Example 163

(S)-1-(4-(3-Cyclopropyl-1H-pyrazol-5-ylamino)pyrrolo[1,2-f][1,2,4]triazin-2-yl)-4,4-dimethyl-N-((R)-1-methylpiperidin-3-yl)pyrrolidine-2-carboxamide

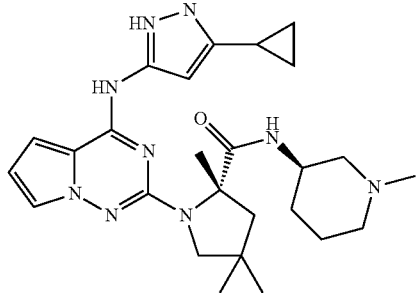 [SMILES: CN1CCC[C@@H](NC(=O)[C@]2(C)CC(C)(C)CN2c2nc(Nc3cc(C4CC4)[nH]n3)c3cccn3n2)C1]

163A. (S)-1-tert-Butyl 2-ethyl 5-oxopyrrolidine-1,2-dicarboxylate

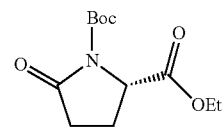 [SMILES: CCOC(=O)[C@@H]1CCC(=O)N1C(=O)OC(C)(C)C]

To a solution of (S)-ethyl 5-oxopyrrolidine-2-carboxylate (20 g, 0.127 mol) and di-tert-butyl-dicarbonate (30.5 g, 0.14 mol) in acetonitrile (150 mL) was added 4-(dimethylamino)pyridine (1.55 g, 0.013 mol) at 0° C. The reaction mixture was stirred at room temperature overnight and concentrated in vacuo. The residue was purified by flash chromatography (30% EtOAc/hexane) to give 163A (32.5 g, 100%) as an oil.
$^1$H NMR (CDCl$_3$, 400 MHz) δ 4.58 (1H, dd, J=3.0, 9.5 Hz), 4.22 (2H, q, J=7.3 Hz), 2.56-2.66 (1H, m), 2.48 (1H, ddd, J=3.8, 9.6, 13.1 Hz), 2.25-2.35 (1H, m), 1.97-2.04 (1H, m), 1.48 (9H, s), and 1.28 (3H, t, J=7.3 Hz).

163B. (S)-1-tert-Butyl 2-ethyl 4,4-dimethylpyrrolidine-1,2-dicarboxylate

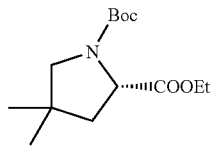 [SMILES: CCOC(=O)[C@@H]1CC(C)(C)CN1C(=O)OC(C)(C)C]

(S)-1-tert-Butyl 2-ethyl 4,4-dimethylpyrrolidine-1,2-dicarboxylate was prepared from (S)-1-tert-butyl 2-ethyl 5-oxopyrrolidine-1,2-dicarboxylate according to the procedures described in *J. Org. Chem.*, 59, 1994, 4327-4331.

163C. (S)-4,4-Dimethylpyrrolidine-2-carboxylic acid

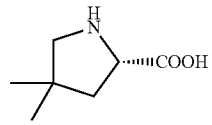

To a solution of (S)-1-tert-butyl 2-ethyl 4,4-dimethylpyrrolidine-1,2-dicarboxylate (1.0 g, 3.7 mmol) in MeOH/H$_2$O/THF (20/15/10 mL) was added lithium hydroxide monohydrate (0.78 g, 18.5 mmol), and the resulting mixture was stirred at room temperature overnight. The solvent was removed and the resulting residue was acidified with phorsphoric acid to pH 3. The aqueous layer was extracted with EtOAc, washed with brine, dried over Na$_2$SO$_4$, and filtered. The filtrate was evaporated to furnish the crude product (0.82 g, 91%).

$^1$H NMR (CD$_3$OD, 400 MHz) δ 4.21 (m, 1H), 3.24-3.29 (m, 1H), 3.11-3.14 (m, 1H), 2.08 (m, 1H), 1.75 (m, 1H), 1.40 (s, 9H), 1.11 (s, 3H), and 1.04 (s, 3H).

The crude material from above was dissolved in methylene chloride (30 mL), and trifluoroacetic acid (5 mL) was added. The reaction mixture was stirred at room temperature for 4 h. After concentrating to dryness, the residue was passed through a MCX cartridge, the cartridge was eluted with a 2 N solution of ammonia in methanol and removal of the solvents gave (163C) as a solid (450 mg, 93%).

$^1$H NMR (CD$_3$OD, 400 MHz) δ 3.28 (m, 1H), 3.11 (m, 1H), 2.24-2.30 (m, 1H), 1.95-2.00 (m, 1H), 1.17 (s, 3H), and 1.16 (s, 3H).

163D. (S)-1-tert-Butyl 2-ethyl 4,4-dimethyl-5-oxopyrrolidine-1,2-dicarboxylate

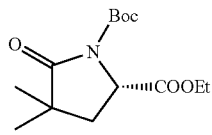 [SMILES: CCOC(=O)[C@@H]1CC(C)(C)C(=O)N1C(=O)OC(C)(C)C]

(S)-1-tert-Butyl 2-ethyl 4,4-dimethyl-5-oxopyrrolidine-1,2-dic arboxylate (163D) was prepared from (S)-1-tert-butyl 2-ethyl 5-oxopyrrolidine-1,2-dicarboxylate according to the procedures described in *J. Org. Chem.*, 59, 1994, 4327-4331.

163E. 1-tert-Butyl 2-ethyl 2,4,4-trimethylpyrrolidine-1,2-dicarboxylate

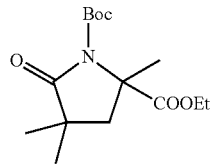 [SMILES: CCOC(=O)C1(C)CC(C)(C)C(=O)N1C(=O)OC(C)(C)C]

To a solution of (S)-1-tert-butyl 2-ethyl 4,4-dimethyl-5-oxopyrrolidine-1,2-dicarboxylate (163D) (10 g, 0.035 mol) in dry THF (60 mL) stirred at −78° C. under nitrogen was added a 1 M solution of lithium hexmethyldisilazide in THF (38.5 mL, 0.038 mol). The mixture was stirred at −78° C. for 30 min, iodomethane (5.4 g, 0.038 mol) in THF (5 mL) was added, and the mixture was then stirred 1 h, warmed up to room temperature and continued stirring for additional 3 h. The reaction mixture was quenched with saturated ammonium chloride solution and extracted with CH$_2$Cl$_2$ (3×100 mL). The combined organic layers were dried over Na$_2$SO$_4$, filtered, and evaporated to dryness. The residue was purified by flash chromatography (10-20% EtOAc/hexanxe) to furnish (163E) (8.2 g, 72%).

$^1$H NMR (CDCl$_3$, 400 MHz)) δ 4.17 (2H, q, J=7.2 Hz), 2.12 (1H, d, J=13.6 Hz), 1.84 (1H, d, J=13.6 Hz), 1.68 (3H, s), 1.48 (9H, s), 1.24 (3H, t, J=7.2 Hz), 1.25 (3H, s), and 1.22 (3H, s). $^{13}$C NMR (CDCl$_3$, 100 MHz) δ 179.00, 173.41, 149.65, 83.51, 62.61, 61.61, 45.62, 40.96, 27.95 (3C), 27.51, 26.75, 25.06, and 14.06.

163F. 1-tert-Butyl 2-ethyl 2,4,4-trimethylpyrrolidine-1,2-dicarboxylate

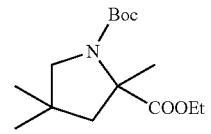 [SMILES: CCOC(=O)C1(C)CC(C)(C)CN1C(=O)OC(C)(C)C]

A 1.0 M solution of lithium triethylborohydride in THF (36 mL, 0.036 mol) was added to a solution of 1-tert-butyl 2-ethyl 2,4,4-trimethylpyrrolidine-1,2-dicarboxylate (163E) (9 g, 0.031 mol) in THF (60 mL) at −78° C. under nitrogen. After 2 h, the reaction mixture was quenched with saturated NaHCO$_3$ (20 mL) and warmed to 0° C. A solution of H$_2$O$_2$ (30%, 8 mL) was added and the mixture was stirred at 0° C. for 30 min. The organic solvent was removed in vacuo and the aqueous layer was extracted with CH$_2$Cl$_2$ (3×100 mL). The combined organic layers were dried over Na$_2$SO$_4$, filtered, and evaporated to dryness. The crude product was used without further purification.

A solution of the crude product from above and triethylsilane (3.65 g, 0.032 mol) in CH$_2$Cl$_2$ (50 mL) was cooled to −78° C., and boron trifluoride etherate (4.54 g 0.032 mol) was added dropwise under nitrogen. After 30 min, 3.65 g triethylsilane and 4.54 g boron trifluoride etherate were added, and the resulting mixture was stirred for 2 h at −78° C. The reaction mixture was quenched with saturated NaHCO$_3$ solution, extracted with CH₂Cl₂ (3×100 mL), and dried over Na₂SO₄. Evaporation of the solvent and furification by flash chromatography (20% EtOAc/hexane) yielded 1-tert-butyl 2-ethyl 2,4,4-trimethylpyrrolidine-1,2-dicarboxylate (163F) (5.65 g, 62%).

163G. 2,4,4-Trimethylpyrrolidine-2-carboxylic acid

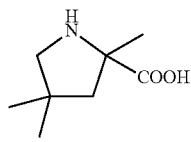

To a solution of 1-tert-butyl 2-ethyl 2,4,4-trimethylpyrrolidine-1,2-dicarboxylate (5 g, 0.018 mol) in MeOH (15 mL), was added NaOH (2.1 g, 0.053 mol) in water (10 mL). The reaction mixture was heated at 45° C. overnight. After concentration, the residue was acidified to pH 3 with phorsphoric acid. The aqueous layer was extracted with EtOAc, the combined organic layer was washed with brine, dried over Na₂SO₄, and filtered. The filtrate was evaporated to give a solid which was used for the next step without separation.

The crude acid from above was dissolved in methylene chloride (40 mL), Trifluoroacetic acid (5 mL) was added, and the reaction mixture was stirred at room temperature overnight. The reaction mixture was concentrated, the residue was passed through a MCX cartridge and eluted with a 2 N solution of ammonia in methanol and removal of the solvents gave (163G) (2.17 g, 79%) as a solid.

¹H NMR (CD₃OD, 400 MHz)) δ 3.14 (1H, d, J=11.6 Hz), 3.01 (1H, d, J=11.6 Hz), 2.37 (1H, d, J=13.6 Hz), 1.75 (1H, d, J=13.2 Hz), 1.55 (3H, s), 1.15 (3H, s), and 1.10 (3H, s). ¹³C NMR (CD₃OD, 100 MHz)) δ 177.56, 71.68, 57.92, 51.50, 40.15, 27.41, 26.86, and 24.63.

163H. 1-(4-(3-cyclopropyl-1H-pyrazol-5-ylamino)pyrrolo[1,2-f][1,2,4]triazin-2-yl)-2,4,4-trimethylpyrrolidine-2-carboxylic acid

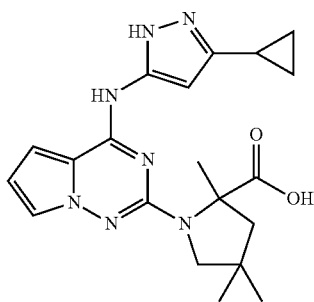 [SMILES: CC1(C)CN(c2nc(Nc3cc(C4CC4)n[nH]3)c3cccn3n2)C(C)(C(=O)O)C1]

2,4,4-Trimethylpyrrolidine-2-carboxylic acid hydrochloride salt 163G (500 mg, 2.58 mmole) was dissolved in NMP (3 mL). 1C (160 mg, 0.57 mmole) and potassium tert-butoxide (565 mg, 5.03 mmol) were added and the mixture was heated in a microwave at 200° C. for 20 hr. After cooling to room temperature, the crude product was purified by prep. HPLC to give compound 163H (146 mg, 65%). MS: 396 (M+H)+; HPLC Ret Time: 3.57 min (Phenomenex-Luna S10 4.6×50 mm column, 4 min gradient, 4 mL/min).

163I. (R)-1-methylpiperidin-3-amine

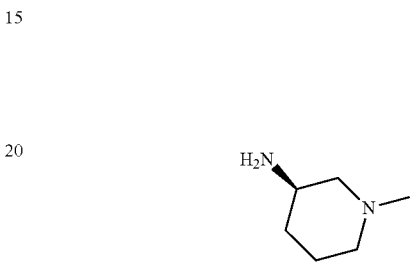

Sodium cyanoborohydride (4.51 g, 0.075 mol) was added in portion to a mixture of (R)-tert-butyl piperidin-3-ylcarbamate (10 g, 0.05 mol), 30% water solution of formaldehyde (7.5 mL), and methanol (75 mL) at 0° C. The reaction mixture was stirred at room temperature overnight and concentrated in vacuo. The residue was dissolved in ethyl acetate and water. After extraction, the organic layers were washed with water, brine, and dried over Na₂SO₄. Concentration in vacuo, gave the N-methyl compound as an oil which was used directly without further purification. To a solution of the crude material previously obtained in methanol (60 mL) was added 4N HCl dioxane (10 mL). The reaction mixture was stirred at room temperature for 6 h. After concentration in vacuo, the residue was triturated with ether. The resuting precipitate was filtered and washed with ice-cold methanol to give the title compound as a solid (4.01 g, 72%). ¹H NMR (CD₃OD, 400 MHz) δ 3.54 (1H, m), 2.81 (1H, m), 2.62 (1H, m), 2.23 (3H, s), 1.97 (1H, m), 1.67-1.87 (3H, m), 1.56-1.61 (1H, m), 1.41 (9H, s), 1.15-1.42 (1H, m).

Diisopropylethylamine (509 mg, 3.95 mmole) was added to a mixture of (S)-1-(4-(3-cyclopropyl-1H-pyrazol-5-ylamino)pyrrolo[1,2-f][1,2,4]triazin-2-yl)-4,4-dimethylpyrrolidine-2-carboxylic acid (163H) (300 mg, 0.79 mmol), (R)-1-methylpiperidin-3-amine (221 mg, 1.58 mmol), and 1-hydroxybenzotriazole (130 mg, 0.95 mmol), N-(3-dimethylaminopropyl)-N'-ethyl-carbodiimide hydrochloride (455 mg, 2.37 mmol) in dry dimethylformamide (3 mL) at room temperature. The reaction mixture was stirred at room temperature overnight. The crude product was purified by preparative HPLC. The fractions that contained the product were applied onto a MCX cartridge and then flushed with methanol. The free base of the was eluted with a 2N solution of ammonia in methanol and removal of the solvents gave (163) (150 mg, 40% yield): MS: 478 (M+H)⁺HPLC Ret Time: 2.62 min (Phenomenex-Luna S10 4.6×50 mm column, 3 min gradient, 4 mL/min).

Example 164

(S)-1-(4-(3-Cyclopropyl-1H-pyrazol-5-ylamino)pyrrolo[1,2-f][1,2,4]triazin-2-yl)-N-((R)-1-cyclopropylpiperidin-3-yl)-4,4-dimethylpyrrolidine-2-carboxamide

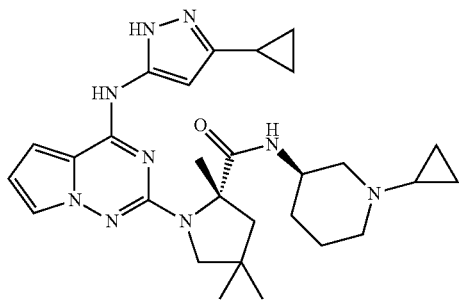 [SMILES: CC1(C)CN(c2nc(Nc3cc(C4CC4)n[nH]3)c3cccn3n2)[C@](C)(C(=O)N[C@@H]2CCCN(C3CC3)C2)C1]

164A.

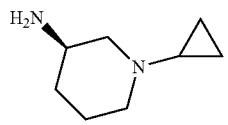

(R)-1-cyclopropylpiperidin-3-amine was prepared using a method similar to that described for example 163I.

(S)-1-(4-(3-Cyclopropyl-1H-pyrazol-5-ylamino)pyrrolo[1,2-f][1,2,4]triazin-2-yl)-N-((R)-1-cyclopropylpiperidin-3-yl)-4,4-dimethylpyrrolidine-2-carboxamide was prepared using the same procedures as described for compound (163). MS: 478 (M+H)⁺ HPLC Ret Time: 2.62 min (Phenomenex-Luna S10 4.6×50 mm column, 3 min gradient, 4 mL/min).

Example 165

(S)-1-(4-(3-Cyclopropyl-1H-pyrazol-5-ylamino)pyrrolo[1,2-f][1,2,4]triazin-2-yl)-N-(6-fluoropyridin-3-yl)-2,4,4-trimethylpyrrolidine-2-carboxamide

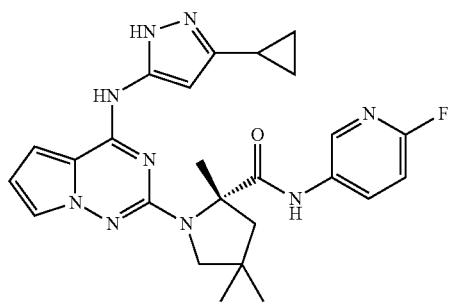 [SMILES: CC1(C)CN(c2nc(Nc3cc(C4CC4)n[nH]3)c3cccn3n2)[C@](C)(C(=O)Nc2ccc(F)nc2)C1]

(S)-1-(4-(3-Cyclopropyl-1H-pyrazol-5-ylamino)pyrrolo[1,2-f][1,2,4]triazin-2-yl)-N-(6-fluoropyridin-3-yl)-2,4,4-trimethylpyrrolidine-2-carboxamide was prepared using the same method as described for 104. The racemic mixture was separated by SFC chiralcel OD-H column, 4.6×250 mm, 5 um over 10 min. The fractions with t=6.77 min were collected.

$^1$H NMR (CD$_3$OD, 400 MHz) δ 8.17 (1H, s), 7.82 (1H, m), 7.41 (1H, m), 6.91-6.94 (1H, m), 6.86 (1H, m), 6.49-6.51 (1H, m), 6.03 (1H, s), 3.48-3.55 (2H, m), 2.48 (1H, d, J=13.3 Hz), 1.99 (1H, d, J=13.1 Hz), 1.71 (3 h, s), 1.64 (1H, m), 1.18 (3H, s), 1.16 (3H, s), 0.78-0.82 (2H, m), 0.78 (1H, m) and 0.57 (1H, m).

HPLC Ret Time=20.22 min. (waters Xterra column 4 6×150 mm, 3.5 um over 30 min.). MS: 490 (M+H)⁺ HPLC Ret Time: 3.29 min (Phenomenex-Luna S10 4.6×50 mm column, 3 min gradient, 4 mL/min).

Analytical HPLC Conditions for Examples 166 to 225, 240 to 240A, 244 to 246 and 251 to 317

LC/MS Analysis:

All LC/MS data (unless otherwise noted) was obtained on a Shimadzu HPLC in conjunction with a Micro-Mass positive ion mass spectrometer using a Phenomenex-Luna 4.6×50 mm 10 micron column, at a flow rate of 4 mL/min and a linear gradient from 100% A (10% Methanol-90% Water-0.1% TFA) to 100% B (90% Methanol-10% Water-0.1% TFA) over 3 min. UV detection was conducted at either 220 or 254 nM. The ret. t. obtained from this LC/MS data is reported as LC/MS ret. t=x min.

Preparative Reverse Phase (RP)HPLC:

This was performed using a Waters Atlantis 30×100 mm 5 micron column or a Phenomenex-Luna 30×100 mm 10 micron column with linear gradient elution using the stated ratio of solvent A (10% Methanol-90% Water-0.1% TFA). and solvent B (90% Methanol-10% Water-0.1% TFA) over the stated time period (typically from 10-13 min) using a flow rate of either 35 or 36 mL/min. A typical example would have the linear gradient from 15% B (85% A) to 90% B (10% A) over 12 min. UV detection was conducted at 254 nM.

Several of the final products are isolated as their free bases by passing the appropriate fractions from the preparative HPLC purification (using the method described above) through a 1 gram (20 cc) or 6 gram (35 cc) Waters Oasis® MCX Extraction Cartridge. Elution with HPLC methanol serves to concentrate the product on the cartridge and to remove the TFA. Subsequent elution with 2.0M NH$_3$ in methanol (Aldrich), followed by evaporation, gives the free base of the final products.

Preparative and Analytical Normal Phase Silca Gel Chromatography:

Preparative silica gel chromatography was performed on a Biotage Horizon™ HPFC™ system (unless indicated otherwise) using Biotage commercially available pre-packed cartridges (FLASH 25+™, FLASH 40+™, FLASH 65i™ cartridges) using the conditions (flow rate, sample loading, column volume size, fraction size collected, etc) recommended in the Biotage manual for the appropriate cartridge. The elution solvent and gradient conditions varied and are described in the applicable examples cited below. Fractions were analyzed for purity by silica gel Thin Layer Chromatography (TLC) using Merck KGaA silica gel 60 F$_{254}$ precoated plates for thin layer chromatography (2.5×7.5 cm, 250 µm thickness) purchased from VWR Scientific. Compounds were visualized on these TLC plates by either UV or appropriate staining (ie I$_2$) techniques.

In the examples below, the Analytical Reverse Phase HPLC ret. t. were obtained on a Shimadzu HPLC system with one or more of the following methods (unless otherwise noted):

Method A: Waters X-Terra HPLC column, 4.6×150 mm, 3.5 micron, 1 mL/min flow rate, linear gradient from 95% A (95:5 Water:CH$_3$CN, 10 mM NH$_4$OAc, pH 6.8)/5% B (90:10 CH$_3$CN:Water, 10 mM NH$_4$OAc, pH 6.8) to 100% B over 15 min. UV detection was conducted at 254 nM.

Method B: Phenomenex Gemini HPLC column, 4.6×150 mm, 5 micron, 1 mL/min flow rate, linear gradient from 95% A (95:5 Water:CH$_3$CN, 10 mM NH$_4$OAc, pH 6.8)/5% B (90:10 CH$_3$CN: Water, 10 mM NH$_4$OAc, pH 6.8) to 100% B over 15 min. UV detection was conducted at 254 nM.

Method C: Waters X-Bridge HPLC column, 4.6×150 mm, 5 micron, 1 mL/min flow rate, linear gradient from 95% A (95:5 Water:CH$_3$CN, 10 mM NH$_4$OAc, pH 6.8)/5% B (90:10 CH$_3$CN:Water, 10 mM NH$_4$OAc, pH 6.8) to 100% B over 20 min. UV detection was conducted at 254 nM.

Method D: Phenomenex Luna HPLC column, 4.6×150 mm, 5 micron, 1.5 mL/min flow rate, linear gradient from 100% A (90:10 HPLC Water:Methanol, 0.1% TFA)/0% B (90:10 HPLC Methanol:Water, 0.1% TFA) to 100% B over 15 min. UV detection was conducted at 254 nM.

Method E: Waters X-Terra HPLC column, 4.6×150 mm, 3.5 micron, 1 mL/min flow rate, linear gradient from 95% A (95:5 Water:CH$_3$CN, 10 mM NH$_4$HCO$_3^-$, pH 7.8)/5% B (90:10 CH$_3$CN:Water, 10 mM NH$_4$HCO$_3^-$, pH 7.8) to 100% B over 20 min. UV detection was conducted at 254 nM. The ret. t. obtained from the analytical HPLC data (methods A-E) is reported in minutes.

Method F: Waters Atlantis C18 HPLC column, 4.6×150 mm, 3 micron, 1 mL/min flow rate, linear gradient from 95% A (95:5 Water:CH$_3$CN, 10 mM NH$_4$OAc, pH 6.8)/5% B (90:10 CH$_3$CN:Water, 10 mM NH$_4$OAc, pH 6.8) to 100% B over 30 min. UV detection was conducted at 254 nM.

Example 166

(S)-3-(2-(2-(thiazol-2-ylcarbamoyl)pyrrolidin-1-yl)pyrrolo[1,2-f][1,2,4]triazin-4-ylamino)-1H-pyrazole-5-carboxamide

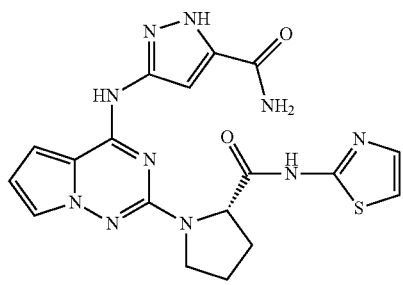 [SMILES: NC(=O)c1cc(Nc2nc(N3CCC[C@H]3C(=O)Nc3nccs3)nn3cccc23)n[nH]1]

166A. 3-Amino-1H-pyrazole-5-carboxylic acid, sodium salt

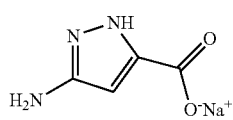

To a stirred solution of 3-nitro-1H-pyrazole-5-carboxylic acid (6 g, 38.2 mmol) in methanol (300 mL) under nitrogen was added 750 mg Pearlman's catalyst and 750 mg DeGussa catalyst. The reaction was flushed with nitrogen, then purged with hydrogen and allowed to stir for 16 h under 1 atm of hydrogen. The reaction was monitored by LC/MS and when complete, was flushed well with nitrogen and 38.2 mL 1.0 M NaOH was added. The catalyst was filtered off through a bed of Celite and the solvent removed in vacuo to give the title compound in quantitative yield: MS: 255 (2M+H)$^+$; LC/MS ret. t=0.18 min (Phenomenex-Luna 4.6×50 mm 10 micron column, flow rate of 5 mL/min and a linear gradient from 100% A (10% Methanol-90% Water-0.1% TFA) to 40% B (90% Methanol-10% Water-0.1% TFA) over 3 min).

166B. 3-(2-chloropyrrolo[1,2-f][1,2,4]-triazin-4-ylamino)-1H-pyrazole-5-carboxylic acid, sodium salt

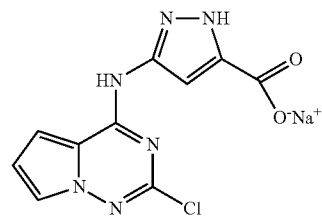

To a stirred solution of compound from 1B (2.4 g, 12.7 mmol) in isopropyl alcohol (120 mL) was added a solution of 166A (2.04 g, 13.7 mmol) dissolved in HPLC water (60 mL), followed by N,N-diisopropylethylamine (4.4 mL, 25.4 mmol). The resulting solution was allowed to stir at room temperature for 18 h. The reaction was cooled at −20 C for 30 min., the solid was collected by filtration and then dried in vacuo for 18 h to give the title compound (2.0 g, 53%) as a solid: MS: 279,281 (M+H)$^+$, LC/MS ret. t=2.11 min; $^1$H NMR (d6-DMSO) δ 12.62 (br s, 1H), 11.12 (br s, 1H), 7.72 (s, 1H); 7.39 (br s, 1H), 6.81 (s, 1H), 6.69 (s, 1H).

166C. 3-(2-chloropyrrolo[1,2-f][1,2,4]-triazin-4-ylamino)-1H-pyrazole-5-carboxamide

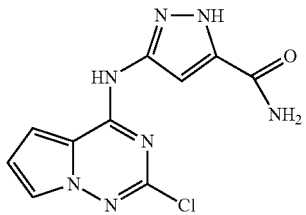 [SMILES: NC(=O)c1cc(Nc2nc(Cl)nn3cccc23)n[nH]1]

To a stirred solution of the material from 166B (9.5 g, 31.56 mmol) in anhydrous DMF (70 mL) was added ammonium chloride (17 g, 315.6 mmol) and 1-hydroxybenzotriazole hydrate (4.3 g, 31.56 mmol) and the resulting suspension was flushed with nitrogen and allowed to stir for 15 min at RT. 1-(3-dimethylaminopropyl)-3-ethylcarbodiimide hydrochloride (12.1 g, 63.12 mmol) and N,N-diisopropylethylamine (110 mL, 631 mmol) were added and the reaction was flushed with nitrogen and allowed to stir at RT overnight. LC/MS showed a mixture of starting material as well as desired product. Additional 1-(3-dimethylaminopropyl)-3-ethylcarbodiimide hydrochloride (3 g, 15.65 mmol), ammonium chloride (4.25 g, 79.4 mmol), and N,N-diisopropylethylamine (28 mL, 158 mmol) was added and the reaction was allowed to stir at RT for 16 h. LC/MS showed the reaction to be complete. The insoluble material was filtered off and washed with 150 mL DMF and the solvent removed in vacuo to afford an oil. HPLC grade water (475 mL) was added and a precipitate formed which was collected by filtration, washed with a small amount of water, and dried in vacuo to give the title compound (7.75 g, 88%) as a solid. MS: 278,280 (M+H)⁺, LC/MS ret. t=1.88 min; ¹H NMR (d6-DMSO): δ 13.32 (s, 1H), 11.14 (s, 1H), 8.08 (s, 1H), 7.77 (s, 1H), 7.51 (s, 1H), 7.43-7.13 (m, 2H), 6.72 (s, 1H).

166D. (S)-1-(4-(5-carbamoyl-1H-pyrazol-3-ylamino)pyrrolo[1,2-f][1,2,4]triazin-2-yl)pyrrolidine-2-carboxylic acid

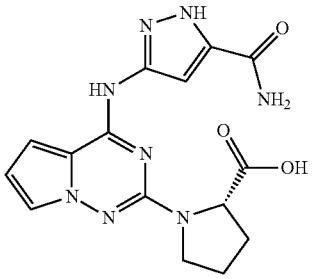 [SMILES: NC(=O)c1cc(Nc2nc(N3CCC[C@H]3C(=O)O)nn3cccc23)n[nH]1]

To a stirred solution of the material from 166C (550 mg, 1.98 mmol) in anhydrous NMP (15 mL) is added a solution of (S)-pyrrolidine-2-carboxylic acid (7.4 g, 64 mmol) that had been previously treated with 5 M NaOH (9 mL, 45 mmol). to form its sodium salt. N,N-diisopropylethylamine (345 µL, 1.98 mmol) was then added and the reaction is flushed with nitrogen and heated to 100° C. for 24 h in a pressure bottle. The product is purified by preparative HPLC (using 5% solvent B to 100% solvent B over 11 min) and the desired fractions containing the product concentrated on a Speed Vac to give 485 mg (69%) of the title compound as a solid: MS: 357 (M+H)⁺, LC/MS ret. t=1.98 min.

To a stirred solution of material from 166D (28 mg, 0.078 mmol) in anhydrous N,N-dimethylformamide (1.1 mL) is added 2-aminothiazole (23.5 mg, 0.234 mmol), and 1-hydroxybenzotriazole hydrate (4 mg, 0.03 mmol). The solution is flushed with nitrogen and benzotriazole-1-yl-oxy-tris-pyrrolidino-phosphonium hexafluorophosphate (89 mg, 0.172 mmol) and N,N-diisopropylethylamine (824 µL, 0.473 mmol) are added and the resulting solution is allowed to stir at RT for 6 h, then heated 50 C for 1 h. The product is purified by preparative HPLC (using 0% solvent B to 100% solvent B over 11 min) and the desired fractions containing the product are processed to the title compound 166, obtained as its free base, using a 1 gram (20 cc) Waters Oasis® MCX Extraction Cartridge using the general method described above to give 9.6 mg of a solid, as a mixture of enantiomers: MS: 439 (M+H)⁺, LC/MS ret. t=2.07 min; HPLC (Method D) ret. t.=13.2 min.

Examples 167 to 178

Table 8 contains Examples 167 to 178 which were prepared using the procedures described in Example 166E. Note that 1-[3-(dimethylamino)propyl]-3-ethylcarbodiimide hydrochloride is used interchangeably with benzotriazole-1-yloxy-tris-pyrrolidino-phosphonium hexafluorophosphate; 1-hydroxybenzotriazole hydrate is used interchangeably with 1-hydroxy-7-azabenzotriazole; DMF is used interchangeably with NMP; and N-methylmorpholine is used interchangeably with N,N-diisopropylethylamine Note: In Examples 167 to 178, the compounds are TFA Salts and mixtures of enantiomers, and were obtained by evaporation in vacuo of the preparative chromatography fractions.

(#) HPLC Method
(*) HPLC retention time
(&) LC/MS (M+H)⁺

TABLE 8

| Example | Compound | # | * | & |
|---|---|---|---|---|
| 167 | (S)-3-(2-(2-((4-chlorophenyl)carbamoyl)pyrrolidin-1-yl)pyrrolo[1,2-f][1,2,4]triazin-4-ylamino)-1H-pyrazole-5-carboxamide | D | 15.2 | 466, 468 |

| Example | Compound | # | * | & |
|---|---|---|---|---|
| 168 | (S)-3-(2-(2-(pyridin-3-ylcarbamoyl)pyrrolidin-1-yl)pyrrolo[1,2-f][1,2,4]triazin-4-ylamino)-1H-pyrazole-5-carboxamide | D | 12.4 | 433 |
| 169 | (S)-3-(2-(2-((6-fluoropyridin-3-yl)carbamoyl)pyrrolidin-1-yl)pyrrolo[1,2-f][1,2,4]triazin-4-ylamino)-1H-pyrazole-5-carboxamide | D | 13.8 | 451 |
| 170 | (S)-3-(2-(2-((2-(4-chloro-1H-pyrazol-1-yl)ethyl)carbamoyl)pyrrolidin-1-yl)pyrrolo[1,2-f][1,2,4]triazin-4-ylamino)-1H-pyrazole-5-carboxamide | D | 14.5 | 484, 486 |
| 171 | (S)-3-(2-(2-((5-methylthiazol-2-yl)carbamoyl)pyrrolidin-1-yl)pyrrolo[1,2-f][1,2,4]triazin-4-ylamino)-1H-pyrazole-5-carboxamide | D | 15.0 | 453 |

TABLE 8-continued

| Example | Compound | # | * | & |
|---|---|---|---|---|
| 172 | (S)-3-(2-(2-((1,3,4-thiadiazol-2-yl)carbamoyl)pyrrolidin-1-yl)pyrrolo[1,2-f][1,2,4]triazin-4-ylamino)-1H-pyrazole-5-carboxamide | A | 7.7 | 440 |
| 173 | (S)-3-(2-(2-((1-methyl-1H-pyrazol-3-yl)carbamoyl)pyrrolidin-1-yl)pyrrolo[1,2-f][1,2,4]triazin-4-ylamino)-1H-pyrazole-5-carboxamide | A | 7.9 | 436 |
| 174 | (S)-3-(2-(2-((6-methoxypyridin-3-yl)carbamoyl)pyrrolidin-1-yl)pyrrolo[1,2-f][1,2,4]triazin-4-ylamino)-1H-pyrazole-5-carboxamide | A | 9.1 | 463 |
| 175 | (S)-3-(2-(2-((6-methylpyridin-3-yl)carbamoyl)pyrrolidin-1-yl)pyrrolo[1,2-f][1,2,4]triazin-4-ylamino)-1H-pyrazole-5-carboxamide | A | 8.34 | 447 |

TABLE 8-continued

| Example | Compound | # | * | & |
|---|---|---|---|---|
| 176 | 3-(2-((S)-2-((tetrahydrothiophen-3-yl-1,1-dioxide)carbamoyl)pyrrolidin-1-yl)pyrrolo[1,2-f][1,2,4]triazin-4-ylamino)-1H-pyrazole-5-carboxamide | A | 7.7 | 474 |
| 177 | (S)-3-(2-(2-(benzo[d]thiazol-2-ylcarbamoyl)pyrrolidin-1-yl)pyrrolo[1,2-f][1,2,4]triazin-4-ylamino)-1H-pyrazole-5-carboxamide | B | 10.6 | 489 |
| 178 | (S)-3-(2-(2-((4,5-dimethylthiazol-2-yl)carbamoyl)pyrrolidin-1-yl)pyrrolo[1,2-f][1,2,4]triazin-4-ylamino)-1H-pyrazole-5-carboxamide | B | 9.8 | 467 |

(#) HPLC Method
(*) HPLC retention time
(&) LC/MS (M + H)⁺

Example 179

(S)-1-(4-(5-carbamoyl-1H-pyrazol-3-ylamino)pyrrolo[1,2-f][1,2,4]triazin-2-yl)-2-methylpyrrolidine-2-carboxylic acid

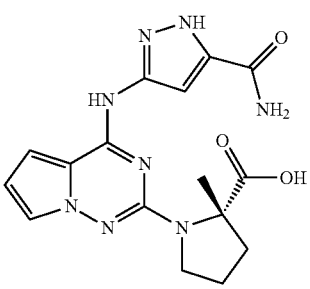 [SMILES: C[C@@]1(C(=O)O)CCCN1c1nc(Nc2cc(C(N)=O)[nH]n2)c2cccn2n1]

To a flame dried 100 mL pressure bottle under nitrogen is added (S)-2-methylpyrrolidine-2-carboxylic acid (7.4 g, 57.4 mmol), potassium tert-butoxide (6.24 g, 55.6 mmol), and 13.6 mL of anhydrous 1-methyl-2-pyrrolidinone. The resulting pink suspension is flushed with nitrogen, magnetically stirred, and sonnicated until almost all solids have dissolved. The compound from 166C (1.4 g, 4.97 mmol) is then added followed by N,N-diisopropylethylamine (866 µL, 4.97 mmol) and the resulting solution was flushed with nitrogen, then heated to 155° C. for 72 h. The product is purified by preparative HPLC (using 15% solvent B to 90% solvent B over 10 min). and the desired fractions containing the product are concentrated to give 1.2 g (66%). of the title compound as a solid: MS: 371 (M+H)$^+$, LC/MS ret. t=2.25 min; HPLC (Method A) ret. t. 6.2 min.

Examples 180 to 190

Table 9 contains Examples 180 to 190 which were prepared using the procedures described in Example 166E.

Note: In the following Examples, 1-[3-(dimethylamino)propyl]-3-ethylcarbodiimide hydrochloride and benzotriazole-1-yl-oxy-tris-pyrrolidino-phosphonium hexafluorophosphate and 1-hydroxy-7-azabenzotriazole were used interchangeably; DMF is used interchangeably with NMP and N-methylmorpholine is used interchangeably with N,N-diisopropylethylamine (#) HPLC Method
(*) HPLC retention time
(&) LC/MS (M+H)$^+$

TABLE 9

| Example | Compound | # | * | & |
|---|---|---|---|---|
| 180 | (S)-3-(2-(2-methyl-2-(thiazol-2-ylcarbamoyl)pyrrolidin-1-yl)pyrrolo[1,2-f][1,2,4]triazin-4-ylamino)-1H-pyrazole-5-carboxamide | A | 9.25 | 453 |
| 181 | (S)-3-(2-(2-((5-chlorothiazol-2-yl)carbamoyl)-2-methylpyrrolidin-1-yl)pyrrolo[1,2-f][1,2,4]triazin-4-ylamino)-1H-pyrazole-5-carboxamide | A | 10.88 | 487 |

TABLE 9-continued

| Example | Compound | # | * | & |
|---|---|---|---|---|
| 182 | 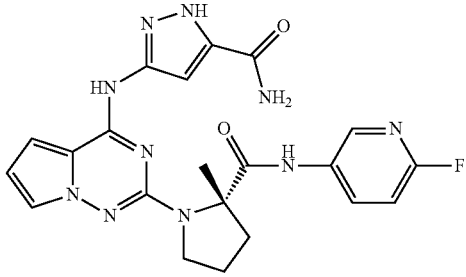<br>(S)-3-(2-(2-((6-fluoropyridin-3-yl)carbamoyl)-2-methylpyrrolidin-1-yl)pyrrolo[1,2-f][1,2,4]triazin-4-ylamino)-1H-pyrazole-5-carboxamide | A | 9.45 | 465 |
| 183 | 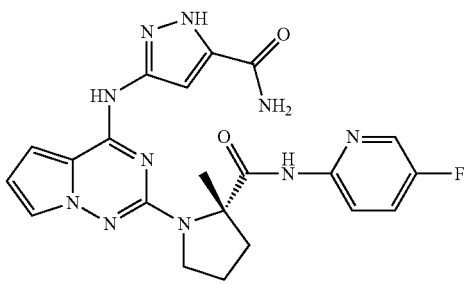<br>(S)-3-(2-(2-((5-fluoropyridin-2-yl)carbamoyl)-2-methylpyrrolidin-1-yl)pyrrolo[1,2-f][1,2,4]triazin-4-ylamino)-1H-pyrazole-5-carboxamide | A | 10.0 | 465 |
| 184 | 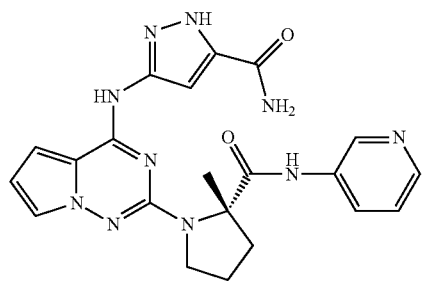<br>(S)-3-(2-(2-methyl-2-(pyridin-3-ylcarbamoyl)pyrrolidin-1-yl)pyrrolo[1,2-f][1,2,4]triazin-4-ylamino)-1H-pyrazole-5-carboxamide | A | 8.42 | 447 |
| 185 | 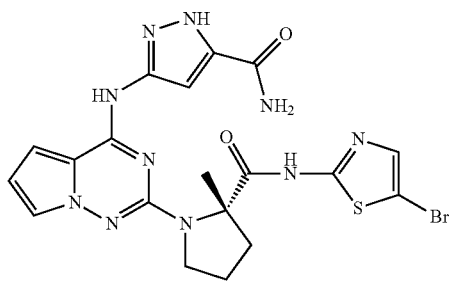<br>(S)-3-(2-(2-((5-bromothiazol-2-yl)carbamoyl)-2-methylpyrrolidin-1-yl)pyrrolo[1,2-f][1,2,4]triazin-4-ylamino)-1H-pyrazole-5-carboxamide | A | 11.15 | 531, 533 |

TABLE 9-continued

| Example | Compound | # | * | & |
|---|---|---|---|---|
| 186 | (S)-3-(2-(2-methyl-2-((5-methylthiazol-2-yl)carbamoyl)pyrrolidin-1-yl)pyrrolo[1,2-f][1,2,4]triazin-4-ylamino)-1H-pyrazole-5-carboxamide | A | 10.22 | 467 |
| 187 | (S)-3-(2-(2-methyl-2-((4-methylthiazol-2-yl)carbamoyl)pyrrolidin-1-yl)pyrrolo[1,2-f][1,2,4]triazin-4-ylamino)-1H-pyrazole-5-carboxamide | A | 10.41 | 467 |
| 188 | (S)-3-(2-(2-((6-aminopyridin-3-yl)carbamoyl)-2-methylpyrrolidin-1-yl)pyrrolo[1,2-f][1,2,4]triazin-4-ylamino)-1H-pyrazole-5-carboxamide | A | 8.57 | 462 |
| 189 | 3-(2-((S)-2-methyl-2-(piperidin-3-ylcarbamoyl)pyrrolidin-1-yl)pyrrolo[1,2-f][1,2,4]triazin-4-ylamino)-1H-pyrazole-5-carboxamide | A | 7.75 | 453 |

TABLE 9-continued

| Example | Compound | # | * | & |
|---------|----------|---|---|---|
| 190 | 3-(2-((S)-2-((1-(cyclopropylmethyl)piperidin-3-yl)carbamoyl)-2-methylpyrrolidin-1-yl)pyrrolo[1,2-f][1,2,4]triazin-4-ylamino)-1H-pyrazole-5-carboxamide | A | 9.14 | 507 |

Example 191

191A. 2-Chloro-N-(5-cyclobutyl-1H-pyrazol-3-yl)pyrrolo [1,2-f][1,2,4]triazin-4-amine 5-Cyclobutyl-1H-pyrazol-3-amine (see J. Med. Chem., 2001, 44(26), 4628-4660) (89 mg, 0.65 mmol) is dissolved in isopropyl alcohol (2-3 mL), N,N-diisopropylethylamine (174 µL, 1.0 mmol) is then added, followed by the compound from 1B (85 mg, 0.45 mmol). The reaction mixture is then stirred at RT for 22 h and the solid precipitate is collected by filtration, washed with a few mL of cold isopropyl alcohol, and dried in vacuo to give 106 mg (81.5%) of the title compound as a solid: MS: 289,291 (M+H)+, LC/MS ret. t=2.02 min.; HPLC (Method D) ret. time 15.35 min.

191B. (S)-1-(4-(5-cyclobutyl-1H-pyrazol-3-ylamino)pyrrolo[1,2-f][1,2,4]-triazin-2-yl)pyrrolidine-2-carboxamide

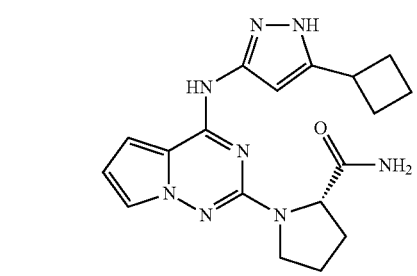 [SMILES: NC(=O)[C@@H]1CCCN1c1nc(Nc2cc(C3CCC3)[nH]n2)c2cccn2n1]

To a dry 20 mL vial under nitrogen was added material from 191A (45 mg, 0.156 mmol) and (S)-pyrrolidine-2-carboxamide (89 mg, 0.78 mmol). The vial was sealed and heated neat to 95° C. for 72 h. The product is purified by preparative HPLC (using 5% solvent B to 100% solvent B over 11 min) and the desired fractions containing the product are processed to the title compound, obtained as its free base, using a 1 gram (20 cc) Waters Oasis® MCX Extraction Cartridge using the general method described above to give 36 mg of the free base of the title compound as a solid: MS: 367 (M+H)+, LC/MS ret. t=1.58 min; HPLC (Method D) ret. t.=12.43 min.

Example 192

(R)-1-(4-(5-cyclobutyl-1H-pyrazol-3-ylamino)pyrrolo[1,2-f][1,2,4]triazin-2-yl)pyrrolidine-2-carboxamide

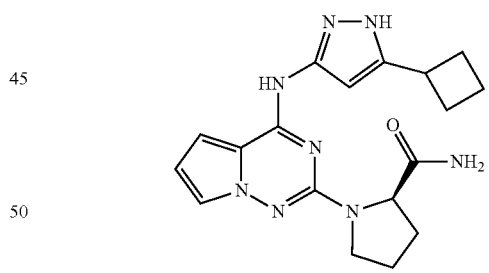

To a dry 20 mL vial under nitrogen is added material from 191A (45 mg, 0.156 mmol) and (R)-pyrrolidine-2-carboxamide (89 mg, 0.78 mmol). The vial is sealed and heated neat to 95° C. for 72 h. The product is purified by preparative HPLC (using 5% solvent B to 100% solvent B over 11 min) and the desired fractions containing the product are processed to the title compound, obtained as its free base, using a 1 gram (20 cc) Waters Oasis® MCX Extraction Cartridge using the general method described above to give 50 mg of the free base of the title compound as a solid: MS: 367 (M+H)+, LC/MS ret. t=1.59 min; HPLC (Method D) ret. t.=12.61 min.

Example 193

193A. 1-(3-(2-chloropyrrolo[1,2-f][1,2,4]triazin-4-ylamino)-1H-pyrazol-5-yl)cyclopropanol

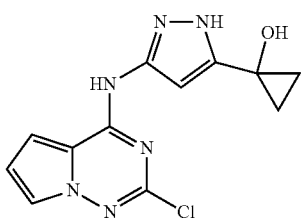 [SMILES: OC1(c2cc(Nc3nc(Cl)nn4cccc34)n[nH]2)CC1]

1-(3-Amino-1H-pyrazol-5-yl)cyclopropanol (see J. Med. Chem., 2001, 44(26), 4628-4660 for related procedure) (288 mg, 2.07 mmol) in isopropyl alcohol (15 mL) is reacted with the material from 1B (300.1 mg, 1.60 mmol) using the method described in 191A. The solvent is evaporated in vacuo and the residue is dissolved in methylene chloride and purified by silica gel chromatography using a Biotage instrument (see above for general details) with a Flash 25+M cartridge using a gradient from 100% dichloromethane to 10-12% 2 M ammonia in methanol: 88-90% methylene chloride over 12 column volumes. The desired fractions containing the product were evaporated in vacuo to give 148.5 mg (32%) of the title compound as a solid; MS: 291, 293 (M+H)$^+$, LC/MS ret. t=2.41 min.

193B. (S)-1-(4-(5-(1-hydroxycyclopropyl)-1H-pyrazol-3-ylamino)pyrrolo[1,2-f][1,2,4]triazin-2-yl)pyrrolidine-2-carboxylic acid

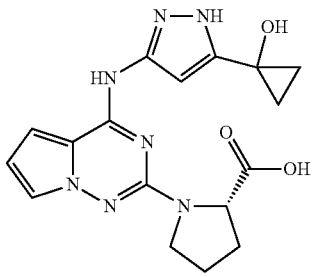 [SMILES: O=C(O)[C@@H]1CCCN1c1nc(Nc2cc(C3(O)CC3)[nH]n2)c2cccn2n1]

To a stirred solution of the material from 193A (190 mg, 0.65 mmol) in anhydrous NMP (3.5 mL) is added a solution of (S)-pyrrolidine-2-carboxylic acid (647 mg, 5.62 mmol) in 5 M NaOH (1.1 mL, 5.5 mmol). N-methylmorpholine (142 µL, 1.29 mmol) is then added and the reaction is flushed with nitrogen. The vial is then sealed and heated to 100° C. for 24 h. The product is purified by preparative HPLC (using 10% solvent B to 100% solvent B over 12 min) and the desired fractions containing the product were concentrated in vacuo to obtain 65.2 mg (27%). of the title compound: MS: 370 (M+H)$^+$, LC/MS ret. t=2.66 min.

193C. (S)-1-(4-(5-(1-hydroxycyclopropyl)-1H-pyrazol-3-ylamino)pyrrolo[1,2-f][1,2,4]triazin-2-yl)-N-(thiazol-2-yl)pyrrolidine-2-carboxamide

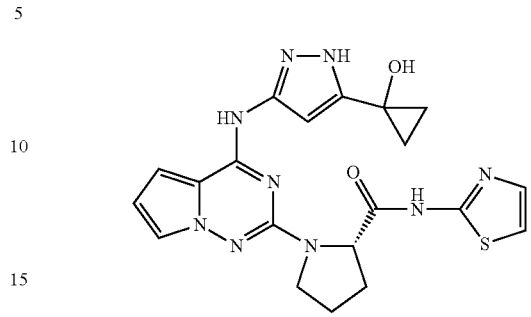

To a stirred solution of material from 193B (36.5 mg, 0.099 mmol) in anhydrous NMP (1 mL) is added 2-aminothiazole (29.7 mg, 0.297 mmol), and 1-hydroxybenzotriazole hydrate (6.7 mg, 0.05 mmol). The solution is flushed with nitrogen and 1-[3-(dimethylamino)propyl]-3-ethylcarbodiimide hydrochloride (38 mg, 0.198 mmol) and N-methylmorpholine (824 µL, 0.469 mmol) are added. The resulting solution is allowed to stir at RT for 18 h and the product is purified by preparative HPLC (using 10% solvent B to 100% solvent B over 12 min). The desired fractions containing the product were concentrated in vacuo to obtain 22.9 mg of the title compound as its TFA salt and as a mixture of enantiomers: MS: 452 (M+H)$^+$, LC/MS ret. t=2.01 min; HPLC (Method A), ret. t.=11.87 min.

Example 194

(S)-1-(4-(5-(1-methylcyclopropyl)-1H-pyrazol-3-ylamino)pyrrolo[1,2-f][1,2,4]triazin-2-yl)-N-((R)-piperidin-3-yl)pyrrolidine-2-carboxamide

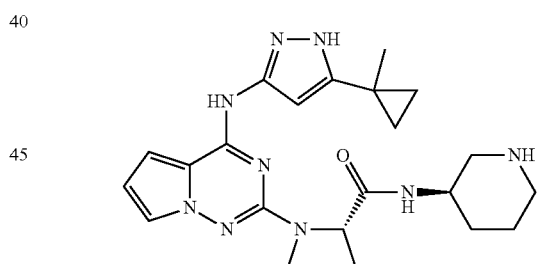

194A. 2-Chloro-N-(5-(1-methylcyclopropyl)-1H-pyrazol-3-yl)pyrrolo[1,2-f][1,2,4]triazin-4-amine

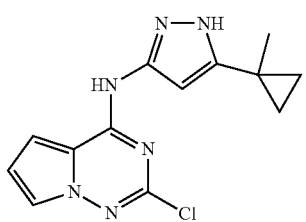 [SMILES: CC1(c2cc(Nc3nc(Cl)nn4cccc34)n[nH]2)CC1]

5-(1-methylcyclopropyl)-1H-pyrazol-3-amine (see J. Med. Chem., 2001, 44(26), 4628-4660 for related procedure) (1.31 g, 9.56 mmol) was treated with the compound from 1B (1.5 g, 7.98 mmol) using the procedure described in 191A to give the title compound (2.31 g, 100%) as a solid. MS: 289, 291 (M+H)$^+$, LC/MS ret. t=2.64 min.

194B. (S)-1-(4-(5-(1-methylcyclopropyl)-1H-pyrazol-3-ylamino)pyrrolo[1,2-f][1,2,4]triazin-2-yl)pyrrolidine-2-carboxylic acid

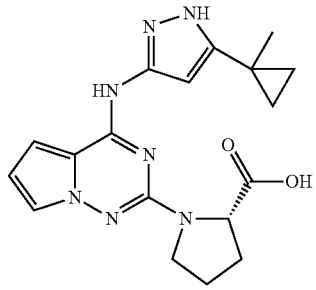 [SMILES: CC1(c2cc(Nc3nc(N4CCC[C@H]4C(=O)O)nn4cccc34)n[nH]2)CC1]

To a stirred solution of the material from 194A (870 mg, 3.0 mmol) in anhydrous NMP (17 mL) is added a solution of (S)-pyrrolidine-2-carboxylic acid (4.2 g, 36.4 mmol) in 5 M NaOH (6.9 mL, 34.5 mmol). The reaction is flushed with nitrogen, sealed, and heated to 135° C. for 18 h. The crude reaction mixture is poured into water (225 mL) and dichloromethane (150 mL). The organic layer is removed and the aqueous layer is treated with aqueous 1.0 N HCl (40 mL, 40 mmol) and extracted with ethyl acetate (2×300 mL). The ethyl acetate layers were combined, washed water (2×30 mL) and brine (30 mL), and dried (Na$_2$SO$_4$). Concentration in vacuo gives the title compound (1.34 g) as a solid; MS: 368 (M+H)$^+$, LC/MS ret. t=2.37 min.

A vial containing the compound from 194B (573 mg, 1.56 mmol), (R)-tert-butyl 3-aminopiperidine-1-carboxylate (407 mg, 2.03 mmol), and 1-hydroxybenzotriazole hydrate (158 mg, 1.17 mmol) is treated with THF (11 mL) and N-methylmorpholine (893 μL, 8.12 mmol), followed by 1-[3-(dimethylamino)propyl]-3-ethylcarbodiimide hydrochloride (538 mg, 2.81 mmol). The reaction is stirred at rt for 1 h and the volatiles are evaporated. The resulting solids are dissolved in dichloromethane (15 mL), trifluoroacetic acid (4 mL) is added, and the resulting solution allowed to stir at room temperature for 45 min. The product is purified by preparative HPLC (using 10% solvent B to 80% solvent B over 10 min) and the desired fractions containing the product are processed to the title compound, obtained as its free base, using three 1 gram (20 cc) Waters Oasis® MCX Extraction Cartridges, using the general method described above, to give the title compound (194) (510 mg, 73%) as a solid: MS: 450 (M+H)$^+$, LC/MS ret. t=2.01 min.; HPLC (Method A) ret. t.=10.8 min; 500 MHz $^1$H NMR (CD$_3$OD) δ 7.40-7.32 (m, 1H), 6.87-6.78 (m, 1H), 6.53-6.31 (m, 2H), 4.55-4.44 (m, 1H), 3.87-3.70 (m, 2H), 3.64-3.50 (m, 1H), 2.99-2.89 (m, 1H), 2.85-2.75 (m, 1H), 2.52-2.34 (m, 2H), 2.31-2.20 (m, 1H), 2.18-2.08 (m, 1H), 2.05-1.92 (m, 2H), 1.76-1.65 (m, 1H), 1.62-1.51 (m, 1H), 1.46 (s, 3H), 1.44-1.26 (m, 2H), 1.04-0.95 (m, 2H), 0.84-0.74 (m, 2H).

Example 195

(S)-N-((R)-1-(cyclopropylmethyl)piperidin-3-yl)-1-(4-(5-(1-methylcyclopropyl)-1H-pyrazol-3-ylamino)pyrrolo[1,2-f][1,2,4]triazin-2-yl)pyrrolidine-2-carboxamide

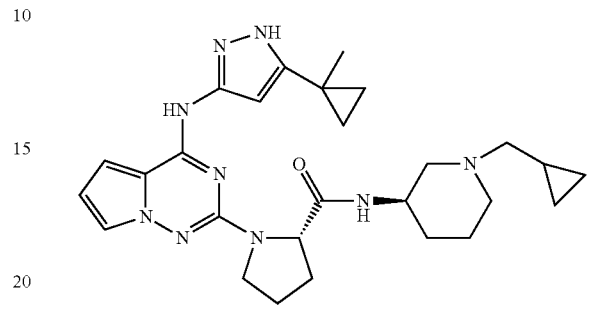

To a solution of material from 194C (60 mg, 0.134 mmol) in methanol (2.5 mL) is added glacial acetic acid (6 μL) and cyclopropanecarbaldehyde (47 μL, 0.63 mmol). Sodium cyanoborohydride (1.0M in THF, 536 μL, 0.536 mmol) is added and the resulting solution is allowed to stand at room temperature for 30 min. The product is purified by preparative HPLC (using 15% solvent B to 80% solvent B over 11 min) and the desired fractions containing the product are processed to the title compound, obtained as its free base, using a 1 gram (20 cc) Waters Oasis® MCX Extraction Cartridge using the general method described above to give 64 mg (96%) of the title compound: MS: 504 (M+H)$^+$, LC/MS ret. t=2.08 min; HPLC (Method A) ret. t.=12.2 min.

Example 196

(S)-N-((R)-1-cyclopropylpiperidin-3-yl)-1-(4-(5-(1-methylcyclopropyl)-1H-pyrazol-3-ylamino)pyrrolo[1,2-f][1,2,4]triazin-2-yl)pyrrolidine-2-carboxamide

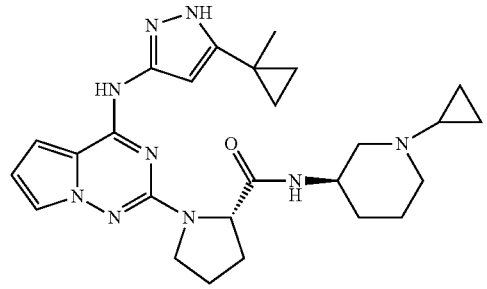 [SMILES: CC1(c2cc(Nc3nc(N4CCC[C@H]4C(=O)N[C@@H]4CCCN(C5CC5)C4)nn4cccc34)n[nH]2)CC1]

To a solution of the compound from 194C (60 mg, 0.134 mmol) in methanol (2.5 mL) is added glacial acetic acid (6 μL) and (1-ethoxycyclopropyloxy). trimethylsilane (148 μL, 0.74 mmol). Sodium cyanoborohydride (1.0M in THF, 536 μL, 0.536 mmol) is then added and the resulting solution is heated at 48° C. overnight. The product is purified by preparative HPLC (using 15% solvent B to 80% solvent B over 11 min) and the desired fractions containing the product are processed to the title compound, obtained as its free base, using a 1 gram (20 cc) Waters Oasis® MCX Extraction Cartridge using the general method described above to give 48.1 mg (73%). of the title compound as a solid: MS: 490 (M+H)+, LC/MS ret. t=2.06 min; HPLC (Method A) ret. t.=13.0 min; 500 MHz $^1$H NMR (CD$_3$OD) δ 7.38 (brs, 1H), 6.88-6.80 (m, 1H), 6.56-6.40 (m, 2H), 4.61-4.47 (m, 1H), 3.92-3.83 (m, 1H), 3.77-3.65 (m, 1H), 3.62-3.50 (m, 1H), 2.78-1.83 (m, 8H), 1.62-1.21 (m, 8H), 1.05-0.91 (m, 2H), 0.85-0.69 (m, 2H), 0.45-0.30 (m, 2H), 0.28-0.11 (m, 2H).

Example 197

(S)-2-methyl-1-(4-(5-(1-methylcyclopropyl)-1H-pyrazol-3-ylamino)pyrrolo[1,2-f][1,2,4]triazin-2-yl)-N-(thiazol-2-yl)pyrrolidine-2-carboxamide

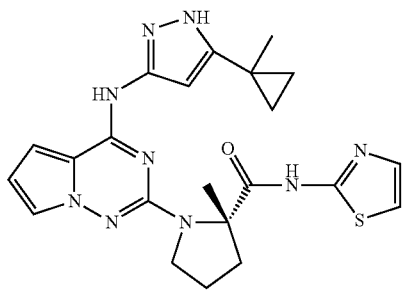 [SMILES: CC1(c2cc(Nc3nc(N4CCC[C@@]4(C)C(=O)Nc4nccs4)nn4cccc34)n[nH]2)CC1]

197A. (S)-2-methyl-1-(4-(5-(1-methylcyclopropyl)-1H-pyrazol-3-ylamino)pyrrolo[1,2-f][1,2,4]triazin-2-yl)pyrrolidine-2-carboxylic acid

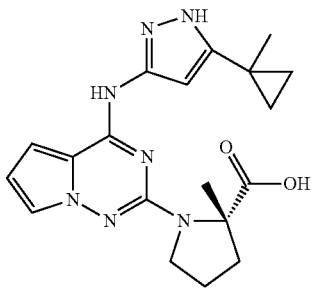 [SMILES: CC1(c2cc(Nc3nc(N4CCC[C@@]4(C)C(=O)O)nn4cccc34)n[nH]2)CC1]

To a solution of material from 194A (400 mg, 1.38 mmol) in anhydrous NMP (17 mL) is added a solution of (S)-2-methylpyrrolidine-2-carboxylic acid (2.15 g, 16.6 mmol) in 5 M NaOH (3.22 mL, 16.11 mmol,). The resulting solution is heated to 155° C. for 50 h. The reaction is poured into water (85 mL) and extracted with dichloromethane (65 mL). The organic layer is discarded and the aqueous layer is acidified with 1 N HCl to a final pH of 2-3 and then extracted with ethyl acetate (3×75 mL). The organic layers are combined, washed with water (50 mL) and brine (50 mL), and dried (Na$_2$SO$_4$). Evaporation in vacuo gives the crude title compound as an oil: MS: 382 (M+H)+, LC/MS ret. t=2.45 min.

A vial containing the compound from 197A (66 mg), 2-aminothiazole (173 mg), and 1-hydroxybenzotriazole hydrate (26 mg), is treated sequentially with NMP (1 mL), N-methylmorpholine (101 μL), and 1-[3-(dimethylamino)propyl]-3-ethylcarbodiimide hydrochloride (40 mg). The reaction is heated at 55° C. for 9 h and purified by preparative HPLC (using 15% solvent B to 95% solvent B over 11 min). The desired fractions containing the product are processed to the title compound, obtained as its free base, using a 1 gram (20 cc) Waters Oasis® MCX Extraction Cartridge, following the general method described above, to give 6.0 mg of the title compound (197) as a solid: MS: 464 (M+H)+, LC/MS ret. t=2.62 min.; HPLC (Method A) ret. t.=13.7 min.

Example 198

(2S,4R)-1-(4-(5-cyclopropyl-1H-pyrazol-3-ylamino)pyrrolo[1,2-f][1,2,4]triazin-2-yl)-4-fluoro-N-(thiazol-2-yl)pyrrolidine-2-carboxamide

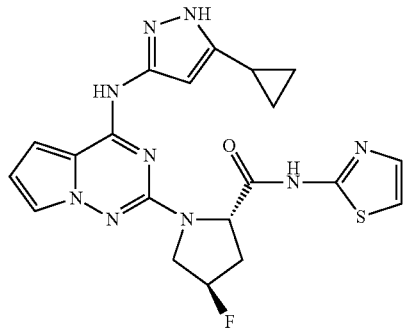 [SMILES: O=C(Nc1nccs1)[C@@H]1C[C@@H](F)CN1c1nc(Nc2cc(C3CC3)[nH]n2)c2cccn2n1]

198A. (2S,4R)-1-(4-(5-cyclopropyl-1H-pyrazol-3-ylamino)pyrrolo[1,2-f][1,2,4]triazin-2-yl)-4-fluoropyrrolidine-2-carboxylic acid

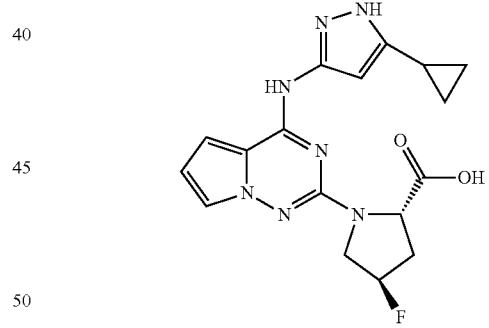

A mixture of the material from 1C (1.77 g, 6.43 mmol) and (2S, 4R-4-fluoropyrrolidine-2-carboxylic acid (1.989 g, 14.9 mmol) in a 48 mL pressure bottle is treated with NMP (20 mL) followed by N,N-diisopropylethylamine (1.43 mL, 8.20 mmol). To this stirred mixture is then added 5 M NaOH (2.88 mL, 14.4 mmol). The reaction is flushed with nitrogen, sealed, and heated at 115° C. for 45 h, at 135° C. for 24 h, and finally at 117° C. for 15 h. The crude reaction mixture is poured into water (300 mL) and dichloromethane (200 mL). The organic layer is removed and the aqueous layer is extracted with additional dichloromethane (3×50 mL). The water layer is treated with aqueous 1.0 N HCl (18-20 mL,) to pH 2-3 and extracted with ethyl acetate (2×400 mL). The ethyl acetate layers were combined, washed water (2×50 mL) and brine (50 mL), and dried (Na$_2$SO$_4$). Concentration in vacuo gives the title compound (1.97 g) as a solid which is 70% pure by HPLC and is used as is for the reactions described below; MS: 372 (M+H)+, LC/MS ret. t=1.83 min; HPLC (Method A) ret. t.=6.8 min; 300 MHz $^1$HNMR (CD$_3$OD) δ 7.38 (s, 1H), 6.91-6.81 (m, 1H), 6.52-6.44 (m, 1H), 6.34 (s, 1H), 5.41 (d, 1H, J=53.4 Hz), 4.73 (t, 1H, J=8.1 Hz), 4.14-3.70 (m, 2H), 2.87-2.64 (m, 1H), 2.44-2.21 (m, 1H), 2.00-1.86 (m, 1H), 1.06-0.92 (m, 2H), 0.88-0.72 (m, 2H).

A vial containing the compound from 198A (415 mg), 2-aminothiazole (780 mg), and 1-hydroxybenzotriazole hydrate (146 mg), is treated sequentially with NMP (8 mL), N-methylmorpholine (640 µL), and 1-[3-(dimethylamino) propyl]-3-ethylcarbodiimide hydrochloride (365 mg). The reaction is stirred at rt for 2 h, heated at 48° C. for 16 h, and then purified by preparative HPLC (using 20% solvent B to 86% solvent B over 11 min). The desired fractions containing the product are processed to the title compound, obtained as its free base, using two 1 gram (20 cc). Waters Oasis® MCX Extraction Cartridges, following the general method described above, to give 181.5 mg of the pure title compound (198) (36%) as a solid: MS: 454 (M+H)+, LC/MS ret. t=2.6 min.; HPLC (Method A) ret. t.=12.5 min.

Example 199

(2S,4R)-1-(4-(5-cyclopropyl-1H-pyrazol-3-ylamino) pyrrolo[1,2-f][1,2,4]triazin-2-yl)-4-fluoro-N-((R)-piperidin-3-yl)pyrrolidine-2-carboxamide

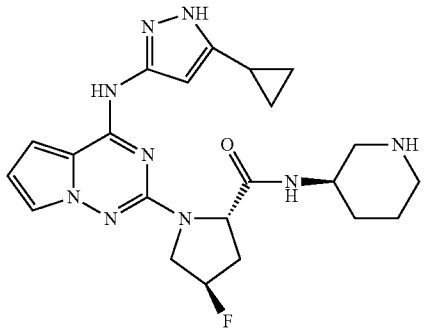 [SMILES: O=C(N[C@@H]1CCCNC1)[C@@H]1C[C@@H](F)CN1c1nc(Nc2cc(C3CC3)[nH]n2)c2cccn2n1]

A vial containing the compound from 198A (147 mg), (R)-tert-butyl 3-aminopiperidine-1-carboxylate (105 mg), and 1-hydroxy-7-azabenzotriazole (40 mg). is treated with THF (3 mL) and N-methylmorpholine (225 µL), followed by 1-[3-(dimethylamino)propyl]-3-ethylcarbodiimide hydrochloride (130 mg). The reaction is stirred at RT for 1.5-2 h and the volatiles are evaporated. The resulting solids are dissolved in dichloromethane (3 mL), trifluoroacetic acid (3 mL) is added, and the resulting solution allowed to stir at room temperature for 45 min. The product is purified by preparative HPLC (using 20% solvent B to 80% Solvent B over 12 min). and the desired fractions containing the product are processed to the title compound, obtained as its free base, using three 1 gram (20 cc) Waters Oasis® MCX Extraction Cartridges, using the general method described above, to give 33 mg of the title compound as a solid: MS: 454 (M+H)+, LC/MS ret. t 1.94 min.; HPLC (Method A). ret. t.=15.3 min.

Example 200

(2S,4R)-1-(4-(5-cyclopropyl-1H-pyrazol-3-ylamino) pyrrolo[1,2-f][1,2,4]triazin-2-yl)-N-((R)-1-(cyclo-propylmethyl)piperidin-3-yl)-4-fluoropyrrolidine-2-carboxamide

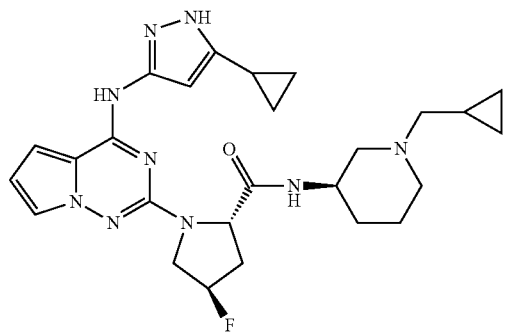 [SMILES: O=C(N[C@@H]1CCCN(CC2CC2)C1)[C@@H]1C[C@@H](F)CN1c1nc(Nc2cc(C3CC3)[nH]n2)c2cccn2n1]

The method described in Example 195 was used. Starting with compound 199 (13 mg, 0.029 mmol), followed by preparative HPLC (15% solvent B to 90% solvent B over 11 min), and processing the desired fractions containing the product to its free base with a 1 gram (20 cc) Waters Oasis® MCX Extraction Cartridge using the general method described above, gives 10.5 mg (72%) of the pure title compound as a solid: MS: 508 (M+H)+, LC/MS ret. t=2.3 min; HPLC (Method A) ret. t.=16.5 min.

Example 201

(2S,4R)-1-(4-(5-cyclopropyl-1H-pyrazol-3-ylamino) pyrrolo[1,2-f][1,2,4]triazin-2-yl)-N-((R)-1-cyclopropylpiperidin-3-yl)-4-fluoropyrrolidine-2-carboxamide

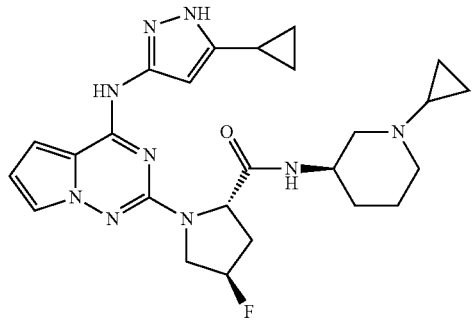 [SMILES: O=C(N[C@@H]1CCCN(C2CC2)C1)[C@@H]1C[C@@H](F)CN1c1nc(Nc2cc(C3CC3)[nH]n2)c2cccn2n1]

The method described in Example 196 was used. Starting with example 199 (13 mg, 0.029 mmol), followed by preparative HPLC (15% solvent B to 90% solvent B over 11 min), and processing the desired fractions containing the product to its free base with a 1 gram (20 cc) Waters Oasis® MCX Extraction Cartridge using the general method described above, gives 9.8 mg (69%) of the pure title compound: MS: 494 (M+H)+, LC/MS ret. t=1.96 min; HPLC (Method A) ret. t.=15.34 min.

Example 202

(2S,4R)-1-(4-(5-cyclopropyl-1H-pyrazol-3-ylamino)pyrrolo[1,2-f][1,2,4]triazin-2-yl)-4-fluoro-N-(6-fluoropyridin-3-yl)pyrrolidine-2-carboxamide

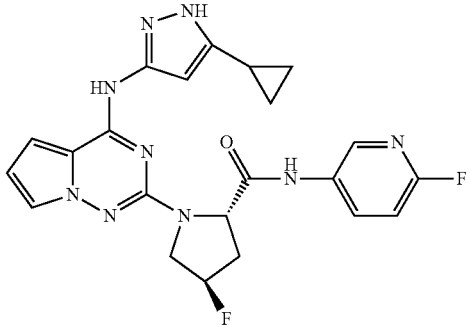 [SMILES: O=C(Nc1ccc(F)nc1)[C@@H]1C[C@@H](F)CN1c1nc(Nc2cc(C3CC3)[nH]n2)c2cccn2n1]

The compound from 198A (777 mg), 2-fluoro-5-aminopyridine (2.35 g), and 1-hydroxybenzotriazole hydrate (256 mg), is treated sequentially with NMP (10 mL), N-methylmorpholine (2.1 mL), and 1-[3-(dimethylamino)propyl]-3-ethylcarbodiimide hydrochloride (777 mg). The reaction is stirred at rt for 16 h, and then purified by preparative HPLC (using 14% solvent B to 82% solvent B over 11 min). The desired fractions containing the product are processed to the title compound, obtained as its free base, using two 6 gram (35 cc) Waters Oasis® MCX Extraction Cartridges, following the general method described above, to give 374.4 mg of the pure title compound (38.4%) as a solid: MS: 466 (M+H)$^+$, LC/MS ret. t=1.85 min.; HPLC (Method A) ret. t.=11.16 min; 500 MHz $^1$H NMR (CD$_3$OD) δ 8.24 (s, 1H), 8.01 (brs, 1H), 7.36 (s, 1H), 7.01-6.93 (m, 1H), 6.87-6.78 (m, 1H), 6.47 (s, 1H), 6.33 (brs, 1H), 5.40 (d, 1H, J=53.7 Hz), 4.77 (t, 1H), 4.28-4.11 (m, 1H), 3.95-3.76 (m, 1H), 2.79-2.62 (m, 1H), 2.46-2.27 (m, 1H), 1.87-1.73 (m, 1H), 0.97-0.84 (m, 2H), 0.77-0.61 (m, 2H).

Example 203

(2S,4R)-N-(4-chloropyridin-3-yl)-1-(4-(5-cyclopropyl-1H-pyrazol-3-ylamino)pyrrolo[1,2-f][1,2,4]triazin-2-yl)-4-fluoropyrrolidine-2-carboxamide

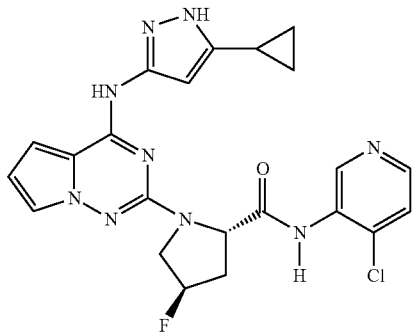 [SMILES: O=C(Nc1cnccc1Cl)[C@@H]1C[C@@H](F)CN1c1nc(Nc2cc(C3CC3)[nH]n2)c2cccn2n1]

203A. (2S,4R)-methyl 1-(4-(5-cyclopropyl-1H-pyrazol-3-ylamino)pyrrolo[1,2-f][1,2,4]triazin-2-yl)-4-fluoropyrrolidine-2-carboxylate

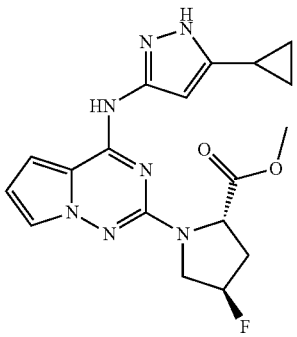 [SMILES: COC(=O)[C@@H]1C[C@@H](F)CN1c1nc(Nc2cc(C3CC3)[nH]n2)c2cccn2n1]

To a solution of compound 198A (2.21 g, 4.7 mmol) in 40 ml methanol were added 1-hydroxybenzotriazole (1.08 g, 8 mmol), N-methylmorpholine (1.76 ml, 16 mmol), and 1-[3-(dimethylamino)propyl]-3-ethylcarbodiimide hydrochloride (1.53 g, 8 mmol). The mixture was stirred at ambient temperature. After a total time of 4 hours the mixture was concentrated, dissolved in ethyl acetate, washed with a saturated aqueous NaHCO$_3$ solution, water and brine, dried over MgSO$_4$, filtered and concentrated. The product was purified by chromatography on a Horizon Biotage system, using a 40-M cartridge (conditioned with 95% dichloromethane+5% ethyl acetate) and eluted with a gradient from 5% ethyl acetate in dichloromethane to 100% ethyl acetate. 997.8 mg of the title compound were isolated. LCMS m/e=385, [M+H]+, Ret.time. 1.45 min.

3-Amino-4-chloro-pyridine (142 mg, 1.1 mmol) was dissolved in 5 ml THF and cooled to 0° C. A solution of isopropyl magnesium chloride (2M in THF, 0.5 ml, 1.0 mmol) was added and the mixture stirred for 5 minutes. Then a solution of compound 203A (37 mg, 0.095 mmol, in 5 ml THF) was added. The mixture was stirred for 1 hour at 0° C., then 1 hour at ambient temperature. The reaction vessel is briefly immersed into an acetone/dry ice bath and the reaction quenched by addition of a mixture of 1 ml trifluoroacetic acid and 5 ml methanol. After evaporation of volatiles the product is purified by prep HPLC. The fractions containing the product are processed to the title compound, obtained as its free base, using a one gram (20 cc) Waters Oasis MCX Extraction Cartridge, following the general method described above, to give 18.0 mg of the pure title compound as a pale brown solid. LCMS m/e=482 ([M+H]+), Ret. Time 1.20 min on Phenomenex 10u, 4.6×50 mm column, gradient over 2 minutes from 5% CH$_3$CN in water to 95% CH$_3$CN+5% water, buffered with 10 mM NH$_4$OAc. Analytical HPLC Ret. Time 4.95 min, on Waters Sunfire C18 4.6×150 mm column, 3.5 um, 5 min gradient, 10-90% B, 1 mL/min flow rate. Solvent A: 5% CH$_3$CN-95% H$_2$O-0.1% TFA; Solvent B: 90% CH$_3$CN-10% H$_2$O-0.1% TFA.

Examples 204 TO 206

Table 10 contains Examples 204 to 206 which were prepared using the procedure described for Example 203, starting from 203A and using the appropriate heteroarylamine. LCMS (a) and analytical HPLC (b) conditions are as described in Example 203.

TABLE 10

| Example | Compound | Ret. t. | LCMS [M + H]+ |
|---|---|---|---|
| 204 | (2S,4R)-1-(4-(5-cyclopropyl-1H-pyrazol-3-ylamino)pyrrolo[1,2-f][1,2,4]triazin-2-yl)-4-fluoro-N-(pyridin-3-yl)pyrrolidine-2-carboxamide | 1.14(a) 5.03(b) | 448 |
| 205 | (2S,4R)-1-(4-(5-cyclopropyl-1H-pyrazol-3-ylamino)pyrrolo[1,2-f][1,2,4]triazin-2-yl)-4-fluoro-N-(3-methylisothiazol-5-yl)pyrrolidine-2-carboxamide | 1.24(a) 5.34(b) | 468 |
| 206 | (2S,4R)-1-(4-(5-cyclopropyl-1H-pyrazol-3-ylamino)pyrrolo[1,2-f][1,2,4]triazin-2-yl)-4-fluoro-N-(pyrazin-2-yl)pyrrolidine-2-carboxamide | 1.13(a) 4.35(b) | 449 |

Example 207

3-(2-((2S,4R)-4-fluoro-2-(thiazol-2-ylcarbamoyl)pyrrolidin-1-yl)pyrrolo[1,2-f][1,2,4]triazin-4-ylamino)-1H-pyrazole-5-carboxamide

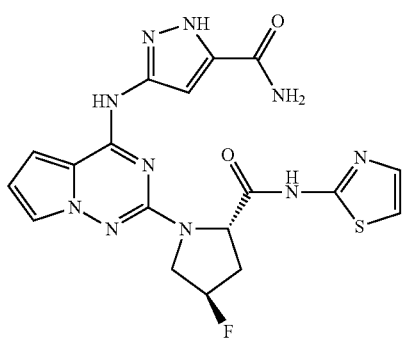 [SMILES: NC(=O)c1cc(Nc2nc(N3C[C@H](F)C[C@H]3C(=O)Nc3nccs3)nn3cccc23)n[nH]1]

207A. (2S,4R)-1-(4-(5-carbamoyl-1H-pyrazol-3-ylamino)pyrrolo[1,2-f][1,2,4]triazin-2-yl)-4-fluoropyrrolidine-2-carboxylic acid

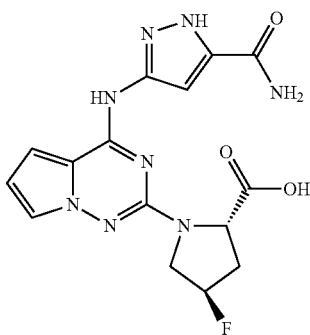 [SMILES: NC(=O)c1cc(Nc2nc(N3C[C@H](F)C[C@H]3C(=O)O)nn3cccc23)n[nH]1]

A mixture of the material from 166C (91.1 mg, 0.328 mmol) and (2S, 4R-4-fluoropyrrolidine-2-carboxylic acid (253 mg, 1.90 mmol) is treated with NMP (2 mL) followed by 5 M NaOH (304 µL, 1.52 mmol). The reaction is flushed with nitrogen, sealed, and heated at 112° C. for 5 days. The crude reaction mixture is purified by preparative HPLC (using 10% solvent B to 100% solvent B over 11 min). The desired fractions containing the product are concentrated in vacuo to give 74.4 mg of the title compound (possible TFA salt); MS: 375 (M+H)$^+$, LC/MS ret. t=2.45 min.

A vial containing the compound from 207A (74.4 mg), 2-aminothiazole (144 mg), and 1-hydroxybenzotriazole hydrate (44 mg), is treated sequentially with DMF (2 mL), 1[3-(dimethylamino)propyl]-3-ethylcarbodiimide hydrochloride (188 mg), and then N-methylmorpholine (250 µL). The reaction is stirred at rt for 16 h and then purified by preparative HPLC (using 5% solvent B to 85% solvent B over 12 min) to give the pure title compound 207; MS: 457 (M+H)$^+$, LC/MS ret. t=2.41 min; HPLC (Method A) ret. t.=12.49 min.

Example 208

(2S,4S)-1-(4-(5-cyclopropyl-1H-pyrazol-3-ylamino)pyrrolo[1,2-f][1,2,4]triazin-2-yl)-N-(6-fluoropyridin-3-yl)-4-hydroxypyrrolidine-2-carboxamide

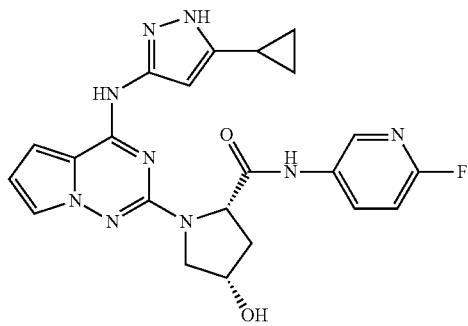 [SMILES: O=C(Nc1ccc(F)nc1)[C@@H]1C[C@H](O)CN1c1nc(Nc2cc(C3CC3)[nH]n2)c2cccn2n1]

208A. (2S,4S)-1-(4-(5-cyclopropyl-1H-pyrazol-3-ylamino)pyrrolo[1,2-f][1,2,4]triazin-2-yl)-4-hydroxypyrrolidine-2-carboxylic acid

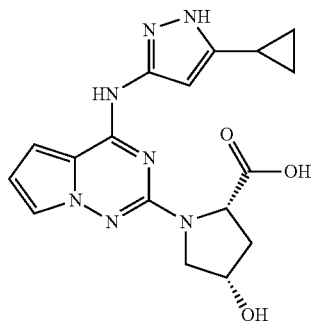 [SMILES: O=C(O)[C@@H]1C[C@H](O)CN1c1nc(Nc2cc(C3CC3)[nH]n2)c2cccn2n1]

A mixture of the material from 1C (7.06 g, 25.7 mmol) and (2S,4S)-4-hydroxypyrrolidine-2-carboxylic acid (24.3 g, 185 mmol) in a 350 mL pressure bottle is treated with NMP (100 mL). To this stirred mixture is then added 5 M NaOH (36.8 mL, 184 mmol) and N,N-diisopropylethylamine (5.0 mL, 28.7 mmol), and the reaction is flushed with nitrogen, sealed, and heated at 133° C. for 24 h. The crude reaction mixture is cooled to rt and then poured into water (500 mL) and dichloromethane (350 mL). The organic layer is extracted with additional water (1×100 mL). The combined water layers are slowly treated with aqueous 1.0 N HCl (194 mL,) to pH 2-3 to give a precipitate, which is filtered, washed with water (2×50 mL), and dried for 24 h under high vacuum at 30° C. to give 4.20 g of 90% pure title compound as a solid. The water filtrate is then extracted with ethyl acetate mixed with 2% methanol (2×500 mL). The organic layer is washed with water (75 mL), and filtered to remove precipitated product, which is dried in vacuo to give 1.98 g of additional 95% pure title compound. Finally, the combined organic layers were slowly evaporated to a total volume of about 50-75 mL, and filtered to give 2.36 g of >95% pure title compound as a solid. The combined weight of title compound is 8.54 g (90%); MS: 370 (M+H)$^+$, LC/MS ret. t=1.94 min; 500 MHz $^1$H NMR (d$_6$-DMSO). δ 12.17 (brs, 2H), 10.19 (s, 1H), 7.38 (s, 1H), 7.07 (s, 1H), 6.47-6.31 (m, 2H), 4.96 (brs, 1H), 4.51 (brs, 1H), 4.39-4.29 (m, 1H), 3.72 (brs, 1H), 3.50-3.08 (m, 1H), 2.57-2.38 (m, 1H), 2.01-1.91 (m, 1H), 1.90-1.78 (m, 1H), 0.97-0.86 (m, 2H), 0.83-0.69 (m, 2H).

208B. (1S,4R)-5-(4-(5-cyclopropyl-1H-pyrazol-3-ylamino)pyrrolo[1,2-f][1,2,4]-triazin-2-yl)-2-oxa-5-azabicyclo[2.2.1]heptan-3-one

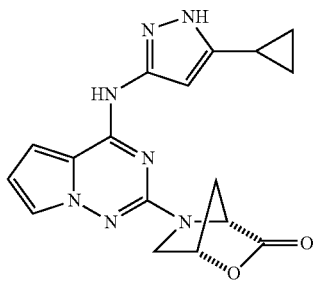

A mixture of the compound from 208A (4.20 g, 11.4 mmol) and 1-hydroxybenzotriazole hydrate (500 mg), is treated sequentially with THF (400 mL), N-methylmorpholine (3.80 mL), and 1-[3-(dimethylamino)propyl]-3-ethylcarbodiimide hydrochloride (3.20 g) is then added last. The reaction is stirred at rt for 10 min and then heated to reflux under nitrogen for 1 h. The volatiles are evaporated and the crude material is dissolved in ethyl acetate (800 mL) and water (600 mL). The organic layer is washed with water (2×100 mL) and brine (100 mL), and dried ($Na_2SO_4$). Concentration in vacuo gives 1.89 g of the title compound as a solid which is 89% pure by LC/MS and is used directly as described below without further purification: MS: 352 (M+H)$^+$, LC/MS ret. t=2.11 min. 300 MHz $^1$H NMR (CD$_3$OD) δ 7.48-7.38 (m, 1H), 6.97-6.84 (m, 1H), 6.68-6.42 (m, 2H), 5.26 (brs, 1H), 4.91-4.84 (m, 1H), 3.79 (d, 1H, J=10.8 Hz), 3.54 (d, 1H, J=10.8 Hz), 2.46-2.16 (m, 2H), 2.00-1.89 (m, 1H), 1.04-0.91 (m, 2H), 0.85-0.77 (m, 2H); IR (KBr) 1789 cm$^{-1}$.

A cold solution of 2-fluoro-5-aminopyridine (382 mg, 3.41 mmol) in THF (2 mL) under nitrogen is treated slowly with swirling with isopropylmagnesium chloride (2.0 M in THF; 1.62 mL, 3.24 mmol). After 10-15 min, the compound of 208B is added (0.357 mmol) and the mixture is rapidly swirled under nitrogen. After 40 min at rt, a solution of TFA (260 μL, 3.4 mmol) in methanol (8 mL) was added and the mixture is then purified by preparative HPLC (using 15% solvent B to 81% solvent B over 12 min). The desired fractions containing the product are processed to the title compound, obtained as its free base, using a one gram (20 cc) Waters Oasis® MCX Extraction Cartridge, following the general method described above, to give 106.1 mg of the pure title compound 208 (64% for 2 steps) as a solid: MS: 464 (M+H)$^+$, LC/MS ret. t=1.57 min.; HPLC (Method A) ret. t.=11.35 min; 300 MHz $^1$H NMR (CD$_3$OD) δ 8.32 (brs, 1H), 8.04 (brs, 1H), 7.42 (brs, 1H), 7.00 (dd, 1H, J=2.9, 8.8 Hz), 6.91-6.82 (m, 1H), 6.55-6.45 (m, 1H), 6.34 (brs, 1H), 4.81-4.68 (m, 1H), 4.63-4.49 (m, 1H), 3.82-3.67 (m, 2H), 2.71-2.44 (m, 1H), 2.42-2.26 (m, 1H), 1.95-1.73 (m, 1H), 1.02-0.84 (m, 2H), 0.80-0.58 (m, 2H).

Example 209

(2S,4S)-1-(4-(5-cyclopropyl-1H-pyrazol-3-ylamino)pyrrolo[1,2-f][1,2,4]triazin-2-yl)-4-hydroxy-N-(pyrazin-2-yl)pyrrolidine-2-carboxamide

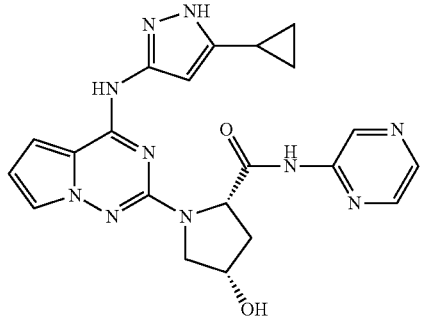 [SMILES: O=C(Nc1cnccn1)[C@@H]1C[C@H](O)CN1c1nc(Nc2cc(C3CC3)[nH]n2)c2cccn2n1]

Using the method described in 208C, but substituting 2-fluoro-5-aminopyridine with 2-aminopyrazine, the compound from 208B (0.326 mmol) is converted to 102 mg (70% for 2 steps) of the pure title compound as a solid. The preparative HPLC purification had a gradient using 15% solvent B to 83% solvent B over 12 min. MS: 447 (M+H)$^+$, LC/MS ret. t=2.1 min.; HPLC (Method A) ret. t.=9.97 min; 500 MHz $^1$H NMR (CD$_3$OD) δ 9.45 (s, 1H), 8.26 (s, 2H), 7.41 (brs, 1H), 6.94-6.77 (m, 1H), 6.49 (brs, 1H), 6.31 (brs, 1H), 4.80-4.64 (m, 1H), 4.62-4.44 (m, 1H), 3.91-3.60 (m, 2H), 2.68-2.47 (m, 1H), 2.42-2.27 (m, 1H), 1.92-1.67 (m, 1H), 1.02-0.85 (m, 2H), 0.82-0.61 (m, 2H).

Example 210

(2S,4S)-N-(4-chloropyridin-3-yl)-1-(4-(5-cyclopropyl-1H-pyrazol-3-ylamino)pyrrolo[1,2-f][1,2,4]triazin-2-yl)-4-hydroxypyrrolidine-2-carboxamide

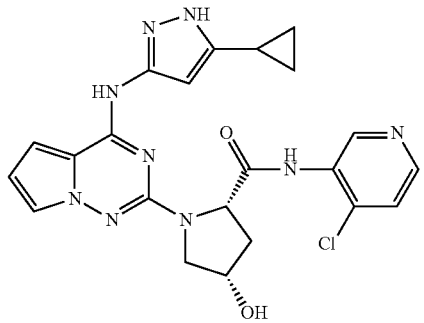 [SMILES: O=C(Nc1cnccc1Cl)[C@@H]1C[C@H](O)CN1c1nc(Nc2cc(C3CC3)[nH]n2)c2cccn2n1]

Using the method described in 208C, but substituting 2-fluoro-5-aminopyridine with 3-amino-4-chloropyridine, the compound from 208B (0.236 mmol) is converted to 69 mg (61% for 2 steps) of the pure title compound as a solid. The preparative HPLC purification had a gradient using 15% solvent B to 85% solvent B over 12 min)-MS: 480, 482 (M+H)$^+$, LC/MS ret. t=2.07 min.

Example 211

(2S,4S)-1-(4-(5-cyclopropyl-1H-pyrazol-3-ylamino)pyrrolo[1,2-f][1,2,4]triazin-2-yl)-4-hydroxy-N-(pyridin-3-yl)pyrrolidine-2-carboxamide

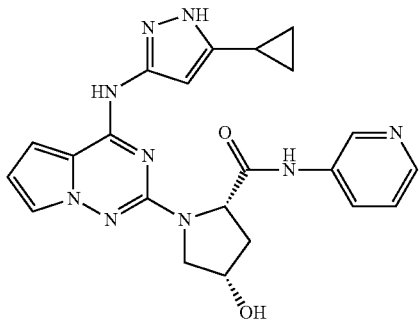 [SMILES: O=C(Nc1cccnc1)[C@@H]1C[C@H](O)CN1c1nc(Nc2cc(C3CC3)[nH]n2)c2cccn2n1]

Using the method described in 208C, but substituting 2-fluoro-5-aminopyridine with 3-aminopyridine, example 208B (0.241 mmol) is converted to 61 mg (57% for 2 steps) of the pure title compound as a solid. The preparative HPLC purification had a gradient using 15% solvent B to 85% solvent B over 11 min): MS: 446 (M+H)$^+$, LC/MS ret. t=1.84 min.; HPLC (Method A) ret. t.=8.61 min; 500 MHz $^1$H NMR (CD$_3$OD) δ 8.69 (s, 1H), 8.30-8.12 (m, 1H), 7.98, (brs, 1H), 7.39 (s, 1H), 7.36-7.27 (m, 1H), 6.84 (brs, 1H), 6.47 (s, 1H), 6.32 (brs, 1H), 4.77-4.65 (m, 1H), 4.62-4.42 (m, 1H), 3.73 (s, 2H), 2.65-2.43 (m, 1H), 2.41-2.23 (m, 1H), 1.90-1.68 (m, 1H), 1.00-0.80 (m, 2H), 0.77-0.53 (m, 2H).

Example 212

(2S,4S)-1-(4-(5-cyclopropyl-1H-pyrazol-3-ylamino)pyrrolo[1,2-f][1,2,4]triazin-2-yl)-4-hydroxy-N-(3-methylisothiazol-5-yl)pyrrolidine-2-carboxamide

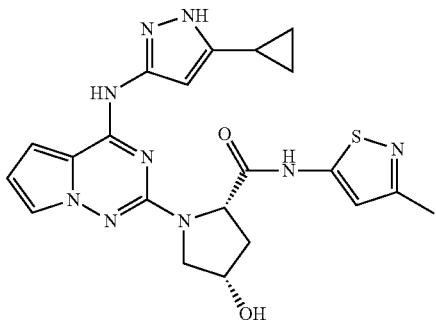 [SMILES: Cc1cc(NC(=O)[C@@H]2C[C@H](O)CN2c2nc(Nc3cc(C4CC4)[nH]n3)c3cccn3n2)sn1]

Using the method described in 208C, but substituting 2-fluoro-5-aminopyridine with 5-amino-3-methyl-isothiazole hydrochloride (with twice the amount of isopropylmagnesium chloride added to account for the neutralization of the HCl salt), the compound from 208B (0.241 mmol) is converted to 62.8 mg (56% for 2 steps) of the pure title compound as a solid. The preparative HPLC purification had a gradient using 15% solvent B to 85% solvent B over 11 min): MS: 466 (M+H)$^+$, LC/MS ret. t=2.07 min.; HPLC (Method A) ret. t.=10.48 min; 500 MHz $^1$H NMR (CD$_3$OD) δ 7.39 (s, 1H), 6.92-6.77 (m, 1H), 6.69 (s, 1H), 6.48 (brs, 1H), 6.18 (brs, 1H), 4.97-4.68 (m, 1H), 4.53 (brs, 1H), 3.81-3.64 (m, 2H), 2.59-2.43 (m, 1H), 2.40-2.21 (m, 1H), 2.35 (s, 3H), 1.89-1.75 (m, 1H), 1.04-0.85 (m, 2H), 0.80-0.62 (m, 2H).

Example 213

(2S,4S)-1-(4-(5-cyclopropyl-1H-pyrazol-3-ylamino)pyrrolo[1,2-f][1,2,4]triazin-2-yl)-4-hydroxy-N-(thiazol-2-yl)pyrrolidine-2-carboxamide

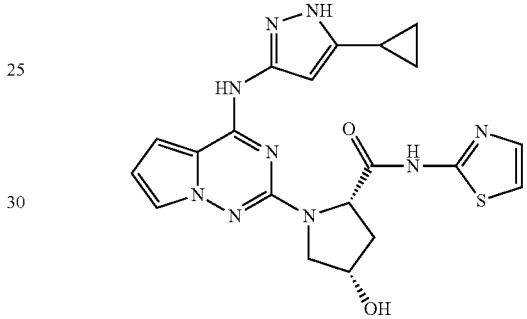

A mixture of the compound from 208A (228 mg, 0.617 mmol) and 1-hydroxybenzotriazole hydrate (75 mg), is treated sequentially with THF (8 mL), N-methylmorpholine (205 μL), and 1-[3-(dimethylamino)propyl]-3-ethylcarbodiimide hydrochloride (EDCI) (196 mg) is then added last. The reaction is stirred at rt for 1 h and then at 50° C. for 2 h. This is called reaction "A". In a separate vial, a cold solution of 2-aminothiazole (370 mg, 3.69 mmol) in THF (3 mL) under nitrogen is prepared. This solution is then treated slowly with swirling with ethylmagnesium bromide (1.0 M in THF; 3.1 mL, 3.1 mmol). After 5 min, this solution was added to the above reaction "A" vial and the mixture is rapidly swirled under nitrogen. After 25 min, NMP (3 mL) is added and the mixture is stirred at rt for 1.5 h, cooled to −20° C., and quenched with TFA (290 μL, 3.8 mmol). The reaction mixture is then purified by preparative HPLC (using 14% solvent B to 83% solvent B over 12 min). The desired fractions containing the product are processed to the title compound, obtained as its free base, using two one gram (20 cc) Waters Oasis® MCX Extraction Cartridges, following the general method described above, to give 140.8 mg of the pure title compound (51% for 2 steps) as a solid: MS: 452 (M+H)$^+$, LC/MS ret. t=2.16 min.; HPLC (Method A) ret. t.=11.06 min; 300 MHz $^1$H NMR (CD$_3$OD) δ 7.40-7.36 (m, 1H), 7.35 (d, 1H, J=3.35 Hz), 7.08 (d, 1H, J=3.35 Hz), 6.83-6.80 (m, 1H), 6.48-6.44 (m, 1H), 6.24 (brs, 1H), 4.92-4.73 (m, 1H), 4.53 (brs, 1H), 3.84-3.68 (m, 2H), 2.59-2.47 (m, 1H), 2.33 (d, 1H, J=13.7 Hz), 1.82 (brs, 1H), 0.95-0.88 (m, 2H), 0.79-0.69 (m, 2H).

Example 214

(2S,4S)-N-(5-chlorothiazol-2-yl)-1-(4-(5-cyclopropyl-1H-pyrazol-3-ylamino)pyrrolo[1,2-f][1,2,4]triazin-2-yl)-4-hydroxypyrrolidine-2-carboxamide

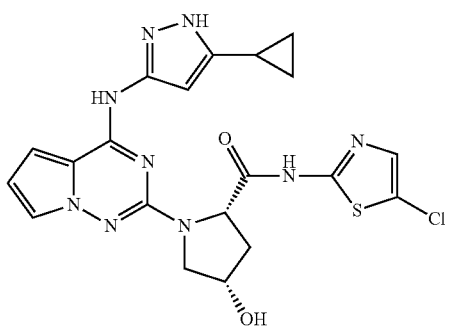 [SMILES: O=C(Nc1ncc(Cl)s1)[C@@H]1C[C@H](O)CN1c1nc(Nc2cc(C3CC3)[nH]n2)c2cccn2n1]

Using the method described in 208C, but substituting 2-fluoro-5-aminopyridine with 2-amino-5-chlorothiazole hydrochloride (with twice the amount of isopropylmagnesium chloride added to account for the neutralization of the HCl salt), the compound from 208B (4.52 mmol) is converted to 108 mg (40% for 2 steps). of the pure title compound as a solid. The preparative HPLC purification had a gradient using 17% solvent B to 89% solvent B over 12 min): MS: 488, 486 (M+H)$^+$, LC/MS ret. t=2.53 min.; HPLC (Method A) ret. t.=12.3 min; 500 MHz $^1$H NMR (CD$_3$OD) δ 7.39 (brs, 1H), 7.25-7.24 (m, 1H), 6.84 (brs, 1H), 6.48 (brs, 1H), 6.23 (brs, 1H), 4.80 (d, 1H, J=9.8 Hz), 4.53 (brs, 1H), 3.79-3.70 (m, 2H), 2.58-2.48 (m, 1H), 2.31 (d, 1H, J=13.7 Hz), 1.84 (brs, 1H), 0.98-0.90 (m, 2H), 0.79-0.70 (m, 2H).

Example 215

(2S,4S)-1-(4-(5-cyclopropyl-1H-pyrazol-3-ylamino)pyrrolo[1,2-f][1,2,4]triazin-2-yl)-N-(cyclopropylsulfonyl)-4-hydroxypyrrolidine-2-carboxamide

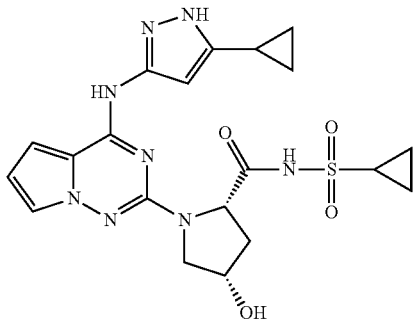 [SMILES: O=C(NS(=O)(=O)C1CC1)[C@@H]1C[C@H](O)CN1c1nc(Nc2cc(C3CC3)[nH]n2)c2cccn2n1]

Using the method described in 208C, but substituting 2-fluoro-5-aminopyridine with cyclopropylsulfonamide, the compound from 208B (0.127 mmol). is converted to 43.3 mg (72% for 2 steps) of the title compound as a solid. The preparative HPLC purification had a gradient using 15% solvent B to 85% solvent B over 11 min. MS: 473 (M+H)$^+$, LC/MS ret. t=1.96 min.; HPLC (Method E) ret. t.=9.06 min; 400 MHz $^1$H NMR (CD$_3$OD) δ 7.41-7.30 (m, 1H), 6.89-6.70 (m, 1H), 6.51-6.38 (m, 1H), 6.23 (brs, 1H), 4.60-4.49 (m, 1H), 4.47-4.38 (m, 1H), 3.80-3.64 (m, 2H), 2.87-2.71 (m, 1H), 2.58-2.43 (m, 1H), 2.23-2.10 (m, 1H), 2.00-1.84 (m, 1H), 1.12-0.88 (m, 4H), 0.84-0.65 (m, 4H).

Example 216

(2S,4R)-1-(4-(5-cyclopropyl-1H-pyrazol-3-ylamino)pyrrolo[1,2-f][1,2,4]triazin-2-yl)-4-hydroxy-N-(thiazol-2-yl)pyrrolidine-2-carboxamide

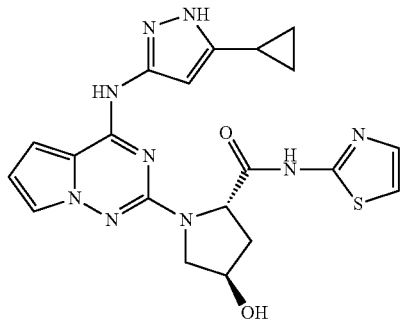 [SMILES: O=C(Nc1nccs1)[C@@H]1C[C@@H](O)CN1c1nc(Nc2cc(C3CC3)[nH]n2)c2cccn2n1]

216A. (2S,4R)-1-(4-(5-cyclopropyl-1H-pyrazol-3-ylamino)pyrrolo[1,2-f][1,2,4]triazin-2-yl)-4-hydroxypyrrolidine-2-carboxylic acid

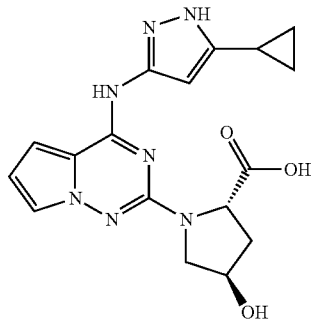 [SMILES: O=C(O)[C@@H]1C[C@@H](O)CN1c1nc(Nc2cc(C3CC3)[nH]n2)c2cccn2n1]

A mixture of the material from 1C (1.114 g, 4.05 mmol) and (2S,4R)-4-hydroxypyrrolidine-2-carboxylic acid (6.46 g, 49.3 mmol) in a 48 mL pressure bottle is treated with NMP (23 mL). To this stirred mixture is then added 5 M NaOH (9.4 mL, 47 mmol) and the reaction is flushed with nitrogen, sealed, and heated at 135° C. for 23 h. The crude reaction mixture is poured into water (300 mL) and dichloromethane (200 mL). The organic layer is removed and the water layer is treated with aqueous 1.0 N HCl (50 mL,) to pH 2-3 to give a precipitate. Ethyl acetate (350 mL) is added and the precipitate dissolves. The organic layer is washed with water (2×30 mL) and brine (75 mL), and dried (Na$_2$SO$_4$). Concentration in vacuo gives the title compound (1.51 g, 100%) as a solid (81% pure by HPLC). This material is used as is as described below: MS: 370 (M+H)$^+$, LC/MS ret. t=1.27 min; HPLC (Method A) ret. t.=5.33 min.

A vial containing the compound from 216A (227 mg), 2-aminothiazole (480 mg), and 1-hydroxybenzotriazole hydrate (107 mg), is treated sequentially with NMP (3.5 mL), N-methylmorpholine (615 μL), and 1-[3-(dimethylamino)propyl]-3-ethylcarbodiimide hydrochloride (240 mg). The reaction is stirred at rt for 20 h and then at 50° C. for 60 h. The product is purified by preparative HPLC (using 15% solvent B to 85% solvent B over 12 min) to give 61.0 mg (22%) of the title compound 216 as a solid; MS: 452 (M+H)⁺, LC/MS ret. t=1.8 min; HPLC (Method A) ret. t.=8.84 min; 300 MHz ¹H NMR (CD₃OD) δ 7.41 (d, 1H, J=3.7 Hz), 7.38-7.34 (m, 1H), 7.11 (d, 1H, J=3.7 Hz), 6.84-6.80 (m, 1H), 6.50-6.45 (m, 1H), 6.29 (brs, 1H), 4.99-4.78 (m, 1H), 4.64-4.52 (m, 1H), 3.97-3.88 (m, 1H), 3.86-3.77 (m, 1H), 2.49-2.21 (m, 2H), 1.93-1.77 (m, 1H), 1.01-0.88 (m, 2H), 0.83-0.69 (m, 2H).

Example 217

(2S,4R)-1-(4-(5-cyclopropyl-1H-pyrazol-3-ylamino)pyrrolo[1,2-f][1,2,4]triazin-2-yl)-N-(6-fluoropyridin-3-yl)-4-hydroxypyrrolidine-2-carboxamide

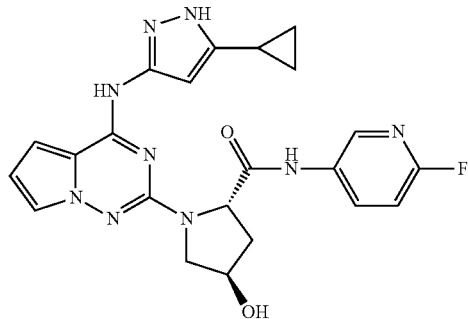 [SMILES: O=C(Nc1ccc(F)nc1)[C@@H]1C[C@@H](O)CN1c1nc(Nc2cc(C3CC3)[nH]n2)c2cccn2n1]

A vial containing the compound from 216A (103 mg), 2-fluoro-5-aminopyridine (237 mg), and 1-hydroxybenzotriazole hydrate (38 mg), is treated sequentially with NMP (2.5 mL), N-methylmorpholine (330 µL), and 1-[3-(dimethylamino)propyl]-3-ethylcarbodiimide hydrochloride (130 mg). The reaction is stirred at rt for 18 h and at 48° C. for 3 h. The product is purified by preparative HPLC (using 15% solvent B to 85% solvent B over 12 min) to give 32.3 mg (25%). of the title compound as a solid; MS: 464 (M+H)⁺, LC/MS ret. t=2.25 min; HPLC (Method A) ret. t.=10.62 min; 500 MHz ¹H NMR (CD₃OD) δ 8.24 (s, 1H), 8.00 (brs, 1H), 7.36 (brs, 1H), 6.99-6.94 (m, 1H), 6.85-6.80 (m, 1H), 6.46 (brs, 1H), 6.35 (brs, 1H), 4.79-4.73 (m, 1H), 4.59-4.54 (m, 1H), 3.90-3.81 (m, 1H), 3.80-3.72 (m, 1H), 2.44-2.25 (m, 2H), 1.84-1.79 (m, 1H), 0.94-0.83 (m, 2H), 0.76-0.61 (m, 2H).

Example 218

(2S,4R)-1-(4-(5-cyclopropyl-1H-pyrazol-3-ylamino)pyrrolo[1,2-f][1,2,4]triazin-2-yl)-4-methoxy-N-(thiazol-2-yl)pyrrolidine-2-carboxamide

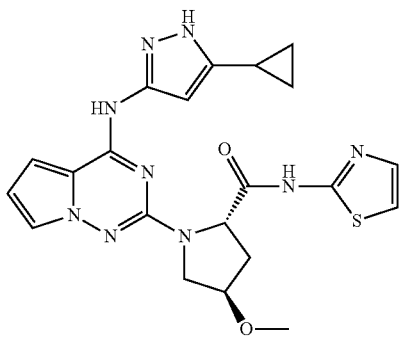 [SMILES: CO[C@@H]1C[C@@H](C(=O)Nc2nccs2)N(c2nc(Nc3cc(C4CC4)[nH]n3)c3cccn3n2)C1]

218A. (2S,4R)-4-methoxypyrrolidine-2-carboxylic acid hydrochloride

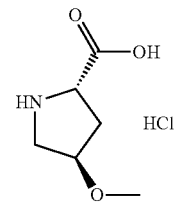

A stirred solution of (2S,4R)-1-(tert-butoxycarbonyl)-4-hydroxypyrrolidine-2-carboxylic acid (25.6 g, 111 mmol), is treated under nitrogen with sodium hydride (9.3 g, 388 mmol) and methyl iodide (31.5 g, 222 mmol), using a procedure similar to that published for the CBZ analog in J. Med. Chem. 1988, 31, 875, except that reflux is carried out for 16 h. The crude extracted product of this alkylation reaction, (2S,4R)-1-(tert-butoxycarbonyl)-4-methoxypyrrolidine-2-carboxylic acid, is then dissolved in dichloromethane (200 mL), cooled to 0° C., treated with 4 N HCl in dioxane (100 mL), and then stirred at room temperature overnight. After further cooling at −20° C. for 3 h, the precipitate is collected by filtration, washed with ethyl ether, and dried in vacuo to give 18.5 g (92%) of the pure mono HCl salt of (2S,4R)-4-methoxypyrrolidine-2-carboxylic acid: MS: 146 (M+H)⁺; ¹H NMR (d6-DMSO) δ 14.02 (brs, 1H), 10.30 (brs, 1H), 8.98 (brs, 1H), 4.33-4.22 (m, 1H), 4.10 (brs, 1H), 3.43-3.34 (m, 1H), 3.24 (s, 3H), 3.26-3.19 (m, 1H), 2.45-2.36 (m, 1H), 2.10-2.00 (m, 1H); [α]²²_D -29.7 (CH₃OH).

218B. (2S,4R)-1-(4-(5-cyclopropyl-1H-pyrazol-3-ylamino)pyrrolo[1,2-f][1,2,4]triazin-2-yl)-4-methoxypyrrolidine-2-carboxylic acid

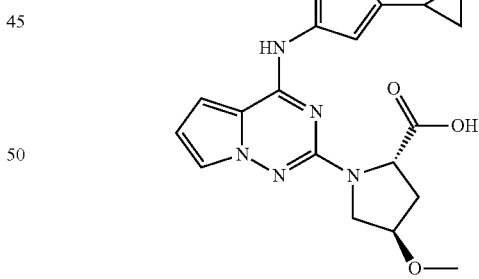

A mixture of the compound from 1C (2.0 g, 7.3 mmol) and (2S,4R)-4-methoxypyrrolidine-2-carboxylic acid-HCl salt, 218A (8.07 g, 44.4 mmol) in a 150 mL pressure bottle is treated with NMP (50 mL) followed by 5 M NaOH (17.4 mL, 87 mmol). N,N-diisopropylethylamine (1.53 mL, 8.8 mmol) is then added and the stirred mixture is flushed with nitrogen, sealed, and heated at 135° C. for 26 h. The crude reaction mixture is cooled and poured into water (500 mL) and dichloromethane (500 mL). The organic layer is removed and the aqueous layer is extracted with additional dichloromethane (1×100 mL). The combined dichloromethane layers are extracted with water (150 mL) and the combined aqueous layers are then acidified with 1.0 N HCl (47 mL) to pH 2-3 and extracted with ethyl acetate (600 mL). The ethyl acetate layer is washed water (1×100 mL) and brine (100 mL), and dried (Na₂SO₄). The extract is concentrated in vacuo to a volume of about 25 mL and then slowly added to rapidly stirred ethyl ether (220 mL) to give a precipitate. Filtration and drying in vacuo gives 1.50 g of the title compound (54%). as a solid which is >95% pure by HPLC: MS: 384 (M+H)⁺, LC/MS ret. t=2.14 min.

A vial containing the compound from 218B (30 mg, 0.078 mmol), 2-aminothiazole (78 mg), and 1-hydroxybenzotriazole hydrate (11.6 mg), is treated sequentially with NMP (2 mL), 1-[3-(dimethylamino)propyl]-3-ethylcarbodiimide hydrochloride (18 mg), and then N-methylmorpholine (51 µL). The reaction is stirred at rt for 18 h and then purified by preparative HPLC (using 15% solvent B to 80% solvent B over 11 min). The desired fractions containing the product are processed to the title compound 218, obtained as its free base, using a one gram (20 cc) Waters Oasis® MCX Extraction Cartridge, following the general method described above, to give 12 mg of the pure title compound (33%) as a solid; MS: 466 (M+H)⁺, LC/MS ret. t=2.23 min; HPLC (Method A) ret. t.=10.04 min; 500 MHz ¹H NMR (CD₃OD). δ 7.39 (d, 1H, J=3.7 Hz), 7.34 (brs, 1H), 7.09 (d, 1H, J=3.7 Hz), 6.83-6.78 (m, 1H), 6.47-6.43 (m, 1H), 6.28 (brs, 1H), 4.85-4.75 (m, 1H), 4.20-4.13 (m, 1H), 3.95-3.89 (m, 1H), 3.88-3.81 (m, 1H), 3.38 (s, 3H), 2.55-2.46 (m, 1H), 2.32-2.24 (m, 1H), 1.86-1.78 (m, 1H), 0.97-0.87 (m, 2H), 0.78-0.69 (m, 2H).

Example 219

(2S,4R)-1-(4-(5-cyclopropyl-1H-pyrazol-3-ylamino) pyrrolo[1,2-f][1,2,4]triazin-2-yl)-N-(6-fluoropyridin-3-yl)-4-methoxypyrrolidine-2-carboxamide

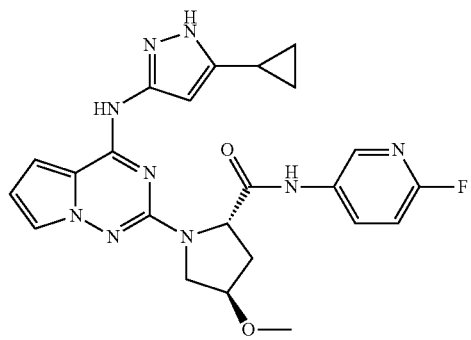

A vial containing the compound from 218B (34 mg, 0.089 mmol), 2-fluoro-5-aminopyridine (99 mg), and 1-hydroxybenzotriazole hydrate (13 mg), is treated sequentially with NMP (1.5 mL), 1-[3-(dimethylamino)propyl]-3-ethylcarbodiimide hydrochloride (20 mg), and then N-methylmorpholine (58 µL). The reaction is stirred at rt for 18 h and then purified by preparative HPLC (using 17% solvent B to 77% solvent B over 12 min). The desired fractions containing the product are processed to the title compound, obtained as its free base, using a one gram (20 cc) Waters Oasis® MCX Extraction Cartridge, following the general method described above, to give 26 mg of the pure title compound (61%) as a solid; MS: 478 (M+H)⁺, LC/MS ret. t=2.21 min; HPLC (Method A) ret. t.=9.85 min; 500 MHz ¹H NMR (CD₃OD) δ 8.24brs, 1H), 8.00 (brs, 1H), 7.36 (brs, 1H), 6.97 (dd, 1H, J=8.85, 2.75 Hz), 6.85-6.81 (m, 1H), 6.50-6.44 (m, 1H), 6.32 (brs, 1H), 4.73-4.67 (m, 1H), 4.23-4.16 (m, 1H), 3.93-3.87 (m, 1H), 3.85-3.78 (m, 1H), 3.39 (s, 3H), 2.51-2.41 (m, 1H), 2.37-2.27 (m, 1H), 1.84-1.75 (m, 1H), 0.93-0.85 (m, 2H), 0.72-0.63 (m, 2H).

Example 220

(2S,4S)-1-(4-(5-cyclopropyl-1H-pyrazol-3-ylamino) pyrrolo[1,2-f][1,2,4]triazin-2-yl)-N-(6-fluoropyridin-3-yl)-4-hydroxy-4-methylpyrrolidine-2-carboxamide

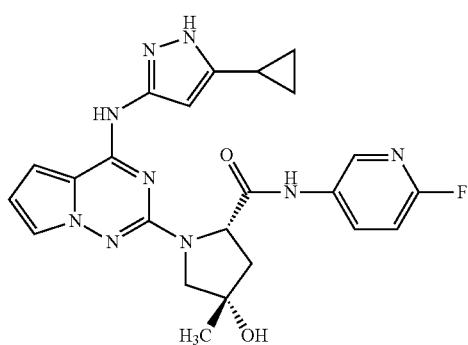 [SMILES: C[C@]1(O)C[C@@H](C(=O)Nc2ccc(F)nc2)N(c2nc(Nc3cc(C4CC4)[nH]n3)c3cccn3n2)C1]

220A. (2S,4S)-1-(4-(5-cyclopropyl-1H-pyrazol-3-ylamino)pyrrolo[1,2-f][1,2,4]triazin-2-yl)-4-hydroxy-4-methylpyrrolidine-2-carboxylic acid

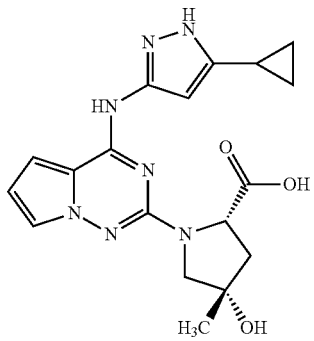 [SMILES: C[C@]1(O)C[C@@H](C(=O)O)N(c2nc(Nc3cc(C4CC4)[nH]n3)c3cccn3n2)C1]

A mixture of the material from 1C (300 mg, 1.09 mmol) and 3.38 mmol of (2S,4S)-4-hydroxy-4-methylpyrrolidine-2-carboxylic acid' TFA salt [prepared from(S)-1-(tert-butoxycarbonyl)-4-oxopyrrolidine-2-carboxylic acid and methylmagnesium bromide (3 M in diethyl ether), using a procedure similar to that published in J. Med. Chem. 1988, 31, 1148 for the corresponding CBZ analog and phenylmagnesium bromide. The N-boc group was removed with TFA in dichloromethane followed by concentration and drying in vacuo to a constant weight] in a 38 mL pressure bottle is treated with NMP (8 mL) followed by N,N-diisopropylethylamine (1.14 mL, 6.54 mmol). To this stirred mixture is then added 5 M NaOH (1.28 mL, 6.4 mmol). The reaction is flushed with nitrogen, sealed, and heated at 135° C. for 24 h, additional 5 M NaOH is added (0.8 mL), and the mixture is then heated at 135° C. for 36 h. The crude reaction mixture is purified by preparative HPLC (using 10% solvent B to 100% solvent B over 11 min) and the desired fractions containing the product are partially concentrated in vacuo and extracted with ethyl acetate (2×85 mL) to give 236 mg (56%) of the title compound as a solid: MS: 384 (M+H)+, LC/MS ret. t=2.1 min; 400 MHz $^1$H NMR (CD$_3$OD) δ 7.54-7.48 (m, 1H), 7.06-7.00 (m, 1H), 6.62-6.56 (m, 1H), 6.11 (brs, 1H), 4.69 (dd, 1H, J=9.1, 3.0 Hz), 3.72-3.66 (m, 1H), 3.59-3.53 (m, 1H), 2.44-2.28 (m, 2H), 2.01-1.91 (m, 1H), 1.45 (s, 3H), 1.09-1.04 (m, 2H), 0.85-0.81 (m, 2H).

220B. (1S,4R)-5-(4-(5-cyclopropyl-1H-pyrazol-3-ylamino)pyrrolo[1,2-f][1,2,4]-triazin-2-yl)-1-methyl-2-oxa-5-azabicyclo[2.2.1]heptan-3-one

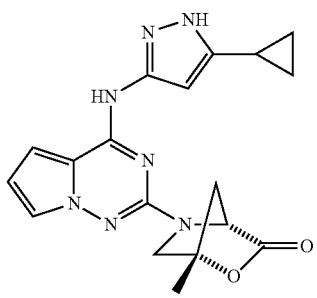

A mixture of the compound from 220A (36.7 mg, 0.096 mmol) and 1-hydroxybenzotriazole hydrate (14 mg), is treated sequentially with NMP (1.5 mL), N-methylmorpholine (58 μL), and 1-[3-(dimethylamino)propyl]-3-ethylcarbodiimide hydrochloride (22 mg) is then added last. The reaction is stirred at rt for 16 h and then purified by preparative HPLC (using 10% solvent B to 100% solvent B over 11 min). The desired fractions containing the product are processed to the title compound, obtained as its free base, using a one gram (20 cc) Waters Oasis® MCX Extraction Cartridge, following the general method described above, to give 15.2 mg of the pure title compound (43%) as a solid; MS: 366 (M+H)+, LC/MS ret. t=2.19 min.

Using a procedure similar to that described in 208C, the compound of 220B (16.3 mg, 0.045 mmol) is transformed into the pure title compound. The preparative HPLC purification used a gradient consisting of 15% solvent B to 85% solvent B over 11 min. The desired fractions containing the product are processed to the title compound, obtained as its free base, using a one gram (20 cc) Waters Oasis® MCX Extraction Cartridge, following the general method described above, to give 11.8 mg (55%) of the pure title compound 220 as a solid: MS: 478 (M+H)+, LC/MS ret. t=2.23 min; HPLC (Method A) ret. t.=12.93 min; 500 MHz $^1$H NMR (CD$_3$OD). δ 8.30 (s, 1H), 8.03 (brs, 1H), 7.39 (s, 1H), 6.97 (dd, 1H, J=8.9, 2.8 Hz), 6.86-6.82 (m, 1H), 6.50-6.45 (m, 1H), 6.30 (brs, 1H), 4.76-4.69 (m, 1H), 3.76-3.67 (m, 1H), 3.58-3.52 (m, 1H), 2.46-2.37 (m, 1H), 2.36-2.29 (m, 1H), 1.85-1.76 (m, 1H), 1.47 (s, 3H), 0.92-0.86 (m, 2H), 0.75-0.59 (m, 2H).

Example 221

(2S,4S)-1-(4-(5-cyclopropyl-1H-pyrazol-3-ylamino)pyrrolo[1,2-f][1,2,4]triazin-2-yl)-4-hydroxy-4-methyl-N-(thiazol-2-yl)pyrrolidine-2-carboxamide

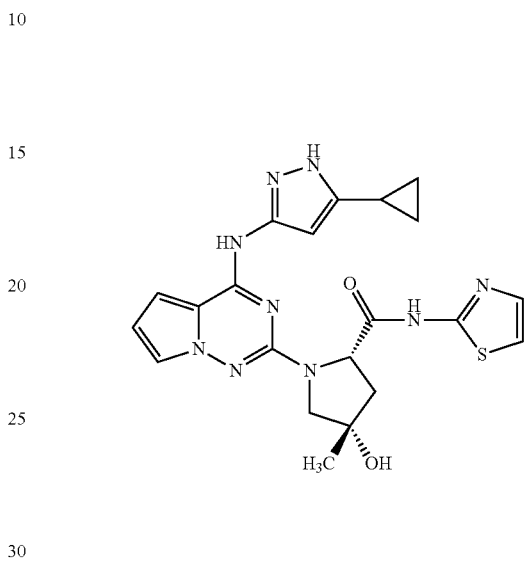

A mixture of the compound from 220A (30 mg, 0.078 mmol) and 1-hydroxybenzotriazole hydrate (11.6 mg), is treated sequentially with THF (1.1 mL), N-methylmorpholine (43 μL), and 1-[3-(dimethylamino)propyl]-3-ethylcarbodiimide hydrochloride (18 mg) is then added last. The reaction is stirred at rt for 1 h. This is called reaction "A". In a separate vial, a cold solution of 2-aminothiazole (196 mg, 1.96 mmol) in THF (1 mL) under nitrogen is prepared. This solution is then treated slowly with swirling with ethylmagnesium bromide (1.0 M in THF; 1.57 mL, 1.57 mmol). After 10 min, this solution was added to the above reaction "A" vial and the mixture is rapidly swirled under nitrogen. After 30 min, a solution of TFA (121 μL) in methanol (5 mL) is added and the mixture is then purified by preparative HPLC (using 15% solvent B to 85% solvent B over 11 min). The desired fractions containing the product are processed to the title compound, obtained as its free base, using a one gram (20 cc) Waters Oasis® MCX Extraction Cartridge, following the general method described above, to give 14.8 mg of the pure title compound (41% for 2 steps) as a solid: MS: 466 (M+H)+, LC/MS ret. t=2.22 min; HPLC (Method A). ret. t.=15.15 min; 500 MHz $^1$H NMR (CD$_3$OD) δ7.41-7.37 (m, 1H), 7.36-7.33 (m, 1H), 7.10-7.06 (m, 1H), 6.85-6.80 (m, 1H), 6.49-6.45 (m, 1H), 6.23 (brs, 1H), 4.85-4.78 (m, 1H), 3.80-3.71 (m, 1H), 3.57-3.52 (m, 1H), 2.46-2.38 (m, 1H), 2.35-2.29 (m, 1H), 1.86-1.78 (m, 1H), 1.45 (brs, 3H), 0.95-0.88 (m, 2H), 0.78-0.68 (m, 2H).

Example 222

(2S,4S)-1-(4-(5-cyclopropyl-1H-pyrazol-3-ylamino)pyrrolo[1,2-f][1,2,4]triazin-2-yl)-4-(1,3-dioxoisoindolin-2-yl)-N-(6-fluoropyridin-3-yl)pyrrolidine-2-carboxamide

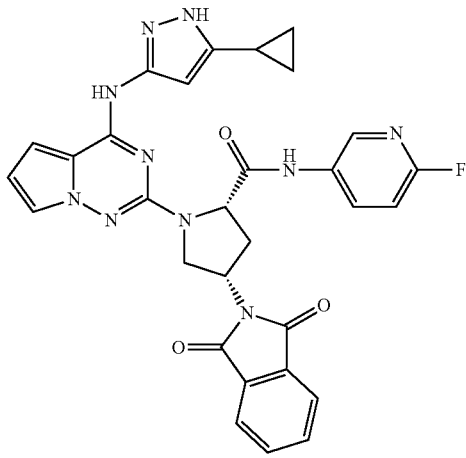 [SMILES: O=C(Nc1ccc(F)nc1)[C@@H]1C[C@H](N2C(=O)c3ccccc3C2=O)CN1c1nc(Nc2cc(C3CC3)[nH]n2)c2cccn2n1]

To a magnetically stirred suspension of the compound from Example 217 (79.6 mg, 0.172 mmol), phthalimide (68.1 mg), and triphenylphosphine (145.7 mg) in anhydrous THF (3.4 mL) is added diisopropyl azodicarboxylate (106 μL). The reaction is stirred at rt for 45 min, quenched with water, and then purified by preparative HPLC (using 20% solvent B to 100% solvent B over 15 min) Three fourths of the fractions containing the product of this example are processed below as described in Example 223. One fourth of the desired fractions containing the product are evaporated in vacuo to give 2.5 mg of the pure title compound (as a TFA salt) as a solid: MS: 593 (M+H)$^+$, LC/MS ret. t=2.59 min; 500 MHz $^1$H NMR (CD$_3$OD) δ 8.34 (brs, 1H), 8.12-8.05 (m, 1H), 7.90-7.85 (m, 2H), 7.84-7.78 (m, 2H), 7.48-7.44 (m, 1H), 7.03-6.98 (m, 1H), 6.97-6.92 (m, 1H), 6.59-6.53 (m, 1H), 6.18 (s, 1H), 5.10-5.01 (m, 1H), 4.79-4.72 (m, 1H), 4.31-4.21 (m, 2H), 3.01-2.92 (m, 1H), 2.85-2.78 (m, 1H), 1.93-1.84 (m, 1H), 1.03-0.95 (m, 2H), 0.80-0.73 (m, 2H).

Example 223

(2S,4S)-4-amino-1-(4-(5-cyclopropyl-1H-pyrazol-3-ylamino)pyrrolo[1,2-f][1,2,4]triazin-2-yl)-N-(6-fluoropyridin-3-yl)pyrrolidine-2-carboxamide

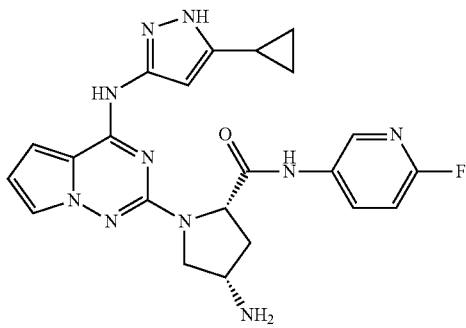 [SMILES: N[C@H]1C[C@@H](C(=O)Nc2ccc(F)nc2)N(c2nc(Nc3cc(C4CC4)[nH]n3)c3cccn3n2)C1]

Three fourths of the fractions containing the product of Example 222 above are applied to a one gram (20 cc) Waters Oasis® MCX Extraction Cartridge, following the general method described above, to give a solution in about 15 mL of the 2 M ammonia in methanol eluent. This solution was then treated with hydrazine hydrate (300 μL), stirred at rt for 14 h, and purified by preparative HPLC (using 15% solvent B to 85% solvent B over 12 min). The desired fractions containing the product are processed to the title compound, obtained as its free base, using a one gram (20 cc) Waters Oasis® MCX Extraction Cartridge, following the general method described above, to give 3.8 mg of the pure title compound as a solid: MS: 463 (M+H)$^+$, LC/MS ret. t=1.88 min; HPLC (Method A) ret. t.=9.76 min; 500 MHz $^1$H NMR (CD$_3$OD) δ 8.26 (s, 1H), 8.05 (brs, 1H), 7.36 (brs, 1H), 6.98 (dd, 1H, 8.9, 3.1 Hz), 6.86-6.81 (m, 1H), 6.49-6.45 (m, 1H), 6.29 (brs, 1H), 4.70-4.63 (m, 1H), 3.95-3.87 (m, 1H), 3.74-3.65 (m, 1H), 3.61-3.53 (m, 1H), 2.68-2.60 (m, 1H), 2.13-2.06 (m, 1H), 1.83-1.74 (m, 1H), 0.92-0.85 (m, 2H), 0.70-0.64 (m, 2H).

Example 224

(2S,4S)-4-azido-1-(4-(5-cyclopropyl-1H-pyrazol-3-ylamino)pyrrolo[1,2-f][1,2,4]triazin-2-yl)-N-(6-fluoropyridin-3-yl)pyrrolidine-2-carboxamide

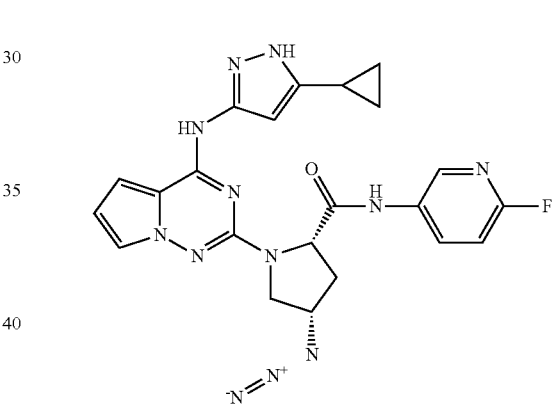

224A. (2S,4S)-4-azido-1-(4-(5-cyclopropyl-1H-pyrazol-3-ylamino)pyrrolo[1,2-f][1,2,4]triazin-2-yl)pyrrolidine-2-carboxylic acid

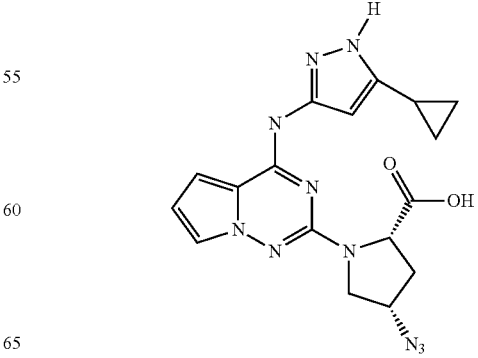

A solution of (2S,4S)-Boc-4-azidoproline (1.0 g, 3.90 mmol) is dissolved in methylene chloride (20 mL) and treated with TFA (about 5 mL). The solution is stirred at rt for 1.5 h, evaporated in vacuo into a 48 mL pressure bottle, then dried under high vacuum overnight to give syrup. To this is added the compound of 1C (300 mg, 1.09 mmol), NMP (4.5 mL), N,N-diisopropylethylamine (1.5 mL, 8.6 mmol), and 5 M NaOH (2.2 mL, 11 mmol). The reaction is flushed with nitrogen, sealed, and heated to 130° C. for 3 h and then at 108° C. for 117 h. The product is purified by preparative HPLC (using 10% solvent B to 85% solvent B over 11 min). and the desired fractions containing the product were partially concentrated in vacuo and extracted with ethyl acetate to obtain, following evaporation in vacuo, 217 mg (50%) of the title compound which was 70% pure by HPLC and was used directly as described below: MS: 395 (M+H)$^+$, LC/MS ret. t=2.25 min; HPLC (Method A) ret. t.=9.88 min.

Using the procedure described in Example 219, the compound of 224A (75 mg) and 2-fluoro-5-aminopyridine (191 mg) are transformed into the title compound 224 following purification by preparative HPLC (using 15% solvent B to 85% solvent B over 12 min). The desired fractions containing the product are processed using a one gram (20 cc) Waters Oasis® MCX Extraction Cartridge, following the general method described above, to give 9.9 mg of the title compound (11%), obtained as its free base, as a solid which was 91% pure by analytical HPLC: MS: 489 (M+H)$^+$, LC/MS ret. t=2.41 min; HPLC (Method A) ret. t.=14.31 min; 500 MHz $^1$H NMR (CD$_3$OD) δ 8.29 (brs, 1H), 8.01 (brs, 1H), 7.42 (brs, 1H), 6.99 (dd, 1H, J=8.9, 2.8 Hz), 6.89-6.85 (m, 1H), 6.52-6.48 (m, 1H), 6.28 (brs, 1H), 4.76-4.71 (m, 1H), 4.50-4.45 (m, 1H), 3.86-3.80 (m, 1H), 3.77-3.72 (m, 1H), 2.66-2.58 (m, 1H), 2.50-2.43 (m, 1H), 1.80-1.73 (m, 1H), 0.91-0.81 (m, 2H), 0.71-0.65 (m, 1H), 0.59-0.50 (m, 1H).

Example 225

(2S,4S)-1-(4-(5-cyclopropyl-1H-pyrazol-3-ylamino) pyrrolo[1,2-f][1,2,4]triazin-2-yl)-4-(dimethylamino)-N-(6-fluoropyridin-3-yl)pyrrolidine-2-carboxamide 225A.
(2S,4S)-4-(dimethylamino)pyrrolidine-2-carboxylic acid

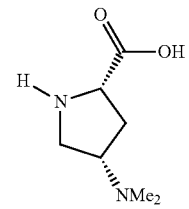

To a stirred solution of (S)-1-tert-butyl 2-methyl 4-oxopyrrolidine-1,2-dicarboxylate (Boc-Pro(4-keto)-OMe; 2.42 g, 9.95 mmol), is added under nitrogen dimethylamine (2.0 M in THF; 13 mL, 26 mmol) and glacial acetic acid (950 mg, 16 mmol). To this solution is added sodium cyanoborohydride (1.0 M in THF; 21 mL, 21 mmol) and the reaction is stirred at rt for 1 h. Additional dimethylamine (2.0 M in THF; 10 mL, 20 mmol) is then added, the reaction is stirred at rt for 1 h, and evaporated in vacuo. The resulting crude solid is digested with ethyl acetate (250 mL), saturated aqueous sodium bicarbonate (100 mL), and water (50 mL). The ethyl acetate layer is washed with water (30 mL) and brine (125 mL), dried (Na$_2$SO$_4$), and evaporated in vacuo to give 2.49 g of a syrup. This material is dissolved in dioxane (65 mL) and water (30 mL) and treated with aqueous 2 M sodium hydroxide (9.5 mL, 19 mmol). The reaction mixture is stirred at rt for 3 h, evaporated to dryness in vacuo, and then dried on high vacuum for 30 min. The resulting material is treated with methylene chloride (60 mL) and slowly TFA is added (about 30 mL). The reaction mixture is allowed to stand at rt for 1 h, concentrated in vacuo, and further dried on high vacuum to give 11.2 g of a viscous syrup of the crude title compound. The syrup is dissolved in methanol (30 mL), treated with N,N-diisopropylethylamine (2.0 mL), evaporated into a 48 mL pressure bottle, dried on high vacuum for 2 h, and then used directly:MS: 159 (M+H)$^+$, LC/MS ret. t=0.23 min. (Phenomenex-Luna 4.6×50 mm 10 micron column, flow rate of 4 mL/min and a linear gradient from 100% A (10% Methanol-90% Water-0.1% TFA) to 10% B (90% Methanol-10% Water-0.1% TFA) over 4 min).

225B. (2S,4S)-1-(4-(5-cyclopropyl-1H-pyrazol-3-ylamino)pyrrolo[1,2-f][1,2,4]triazin-2-yl)-4-(dimethylamino)pyrrolidine-2-carboxylic acid

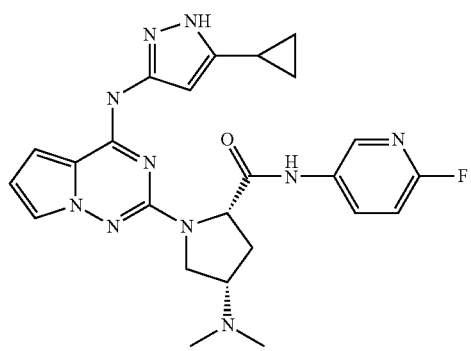 [SMILES: CN(C)[C@H]1C[C@@H](C(=O)Nc2ccc(F)nc2)N(c2nc(Nc3cc(C4CC4)[nH]n3)c3cccn3n2)C1]

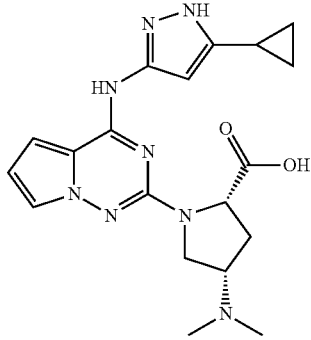 [SMILES: CN(C)[C@H]1C[C@@H](C(=O)O)N(c2nc(Nc3cc(C4CC4)[nH]n3)c3cccn3n2)C1]

The entire amount of the crude material from 225A (2S, 4S)-4-(dimethylamino)pyrrolidine-2-carboxylic acid; maximum 9.95 mmol) in a 48 mL pressure bottle is treated with NMP (15 mL) and N,N-diisopropylethylamine (2.0 mL, 11.5 mmol). To this stirred mixture is then added 5 M NaOH (8.0 mL, 40 mmol) followed by the material from 1C (414 mg, 1.51 mmol). The reaction is flushed with nitrogen, sealed, and heated at 120° C. for 44 h. The crude reaction mixture is cooled to rt, treated with a few mL of methanol, filtered through Celite, and then filtered through a Supelco 10 g DSC-18 cartridge, using some methanol to wash the material from the cartridge. The solution is evaporated partially and then purified by preparative HPLC (using 15% solvent B to 100% solvent B over 11 min). The desired fractions containing the product are concentrated in vacuo to give 238.7 mg (39.9%) of the title compound (>90% pure) as a solid; MS 397 (M+H)$^+$, LC/MS ret. t=1.58 HPLC (Method A) ret. t.=10.00 min; 500 MHz $^1$H NMR (CD$_3$OD) δ7.45-7.41 (m, 1H), 6.93-6.88 (m, 1H), 6.57-6.52 (m, 1H), 6.26 (s, 1H), 4.72-4.67 (m, 1H), 4.27-4.21 (m, 1H), 4.03-3.95 (m, 1H), 3.82-3.75 (m, 1H), 3.01 (s, 6H), 3.05-2.92 (m, 1H), 2.38-2.30 (m, 1H), 2.00-1.92 (m, 1H), 1.08-1.02 (m, 2H), 0.89-0.84 (m, 2H).

The compound from 225B (30 mg, 0.076 mmol), 2-fluoro-5-aminopyridine (90 mg), and 1-hydroxybenzotriazole hydrate (16 mg), is treated sequentially with NMP (2 mL), N-methylmorpholine (120 μL), and 1-[3-(dimethylamino)propyl]-3-ethylcarbodiimide hydrochloride (55 mg). The reaction is stirred at rt for 15 h, and then purified by preparative HPLC (using 15% solvent B to 82% solvent B over 11 min). The desired fractions containing the product are processed to the title compound, obtained as its free base, using a one gram (20 cc). Waters Oasis® MCX Extraction Cartridge, following the general method described above, to give 9.4 mg of the title compound 225 (nearly equal mixture of C-2 proline epimers) as a solid. Separation of these epimers is achieved by preparative silica gel chromatography using a (0.5 mm Whatman plate with a preconcentrating zone). The plate is developed with ethyl acetate:methanol (92:8) containing 0.5% triethylamine The fastest eluting band is the title compound, obtained by eluting the cut silica gel with ethyl acetate/methanol and evaporation in vacuo to give 5.8 mg of the pure title compound as a solid: MS: 491 (M+H)$^+$, LC/MS ret. t=1.78 min; HPLC (Method A). ret. t.=11.50 min; 500 MHz $^1$H NMR (CD$_3$OD) δ 8.26 (brs, 1H), 8.07-7.98 (m, 1H), 7.42-7.32 (m, 1H), 7.00-6.94 (m, 1H), 6.89-6.80 (m, 1H), 6.52-6.44 (m, 1H), 6.23 (brs, 1H), 4.65-4.59 (m, 1H), 4.23-4.15 (m, 1H), 3.58-3.51 (m, 1H), 2.94-2.85 (m, 1H), 2.74-2.65 (m, 1H), 2.37 (s, 6H), 2.12-2.03 (m, 1H), 1.86-1.78 (m, 1H), 0.94-0.84 (m, 2H), 0.73-0.66 (m, 2H).

Example 226

(2S,4S)-1-(4-(5-cyclopropyl-1H-pyrazol-3-ylamino)pyrrolo[1,2-f][1,2,4]triazin-2-yl)-N-(6-fluoropyridin-3-yl)-4-hydroxy-2-methylpyrrolidine-2-carboxamide

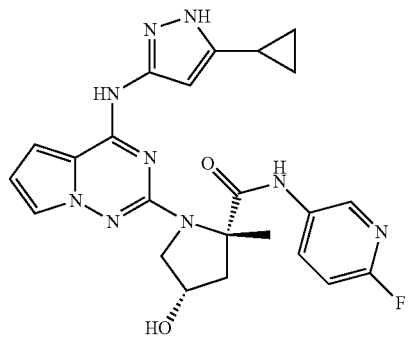 [SMILES: C[C@@]1(C(=O)Nc2ccc(F)nc2)C[C@H](O)CN1c1nc(Nc2cc(C3CC3)[nH]n2)c2cccn2n1]

226A. (2S,4S)-1-tert-butyl 2-methyl 4-(tert-butyldimethylsilyloxy)pyrrolidine-1,2-dicarboxylate

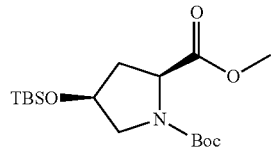 [SMILES: COC(=O)[C@@H]1C[C@H](O[Si](C)(C)C(C)(C)C)CN1C(=O)OC(C)(C)C]

A mixture of (2S,4S)-1-tert-butyl 2-methyl 4-hydroxypyrrolidine-1,2-dicarboxylate (10 g, 40.7 mmol), imidazole (5.54 g, 81.4 mmol) and t-butyldimethylsilyl chloride (6.6 g, 45 mmol) in DMF (50 ml) was stirred and r.t. for 4 days. The mixture was diluted with EtOAc and washed with H$_2$O and sat. NH$_4$Cl. The organic layer was dried over MgSO$_4$ and concentrated. 14 g of an oil product was obtained and used without further purification.

226B. (4S)-1-tert-butyl 2-methyl 4-(tert-butyldimethylsilyloxy)-2-methylpyrrolidine-1,2-dicarboxylate

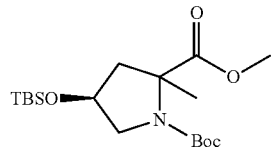 [SMILES: COC(=O)C1(C)C[C@H](O[Si](C)(C)C(C)(C)C)CN1C(=O)OC(C)(C)C]

LDA (2M in Heptane/THF/ethylbenzene, 48.5 ml, 97 mmol) was mixed with 100 ml THF at −78° C. and stirred for 5mins. (2S,4S)-1-tert-butyl 2-methyl 4-(tert-butyldimethylsilyloxy)pyrrolidine-1,2-dicarboxylate (14 g, 38.92 mmol) in 80 ml THF was added dropwise at −78° C. The mixture was stirred at −40° C. for 1 hr. Then the mixture was stirred at −78° C. for 10 mins. MeI (4.85 ml, 77.8 mmol) was slowly added and the mixture was stirred from −78° C. to r.t. overnight. The mixture was diluted with ether and quenched with 5% HCl. The organic layer was separated and washed with NaHCO$_3$, brine, dried over MgSO$_4$ and concentrated. 18.5 g of crude product as a diastereomeric mixture at C-2 was obtained.

226C. (2S,4S)-1-(4-(5-cyclopropyl-1H-pyrazol-3-ylamino)pyrrolo[1,2-f][1,2,4]triazin-2-yl)-4-hydroxy-2-methylpyrrolidine-2-carboxylic acid

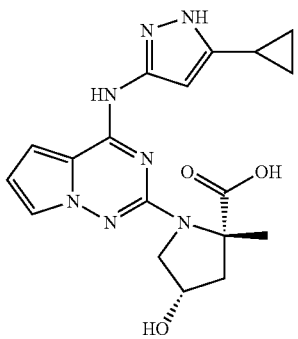 [SMILES: C[C@@]1(C(=O)O)C[C@H](O)CN1c1nc(Nc2cc(C3CC3)[nH]n2)c2cccn2n1]

A mixture of the compound IC (500 mg, 1.8 mmol) and 226B (2250 mg, 6 mmol) and KOH (320 mg, 5.7 mmol) in a 25 ml microwave tube is treated with NMP (4 mL) and heated at 180° C. for 10mins. This mixture was then sealed and heated in a microwave reactor for 20 hours at 195° C. The crude reaction mixture is cooled to r.t. and then poured into aq. NaHCO$_3$ and dichloromethane. The organic layer is extracted with additional water 2 times. The combined water layers are slowly treated with aqueous 1.0 N HCl to pH 2-3. This aqueous layer was applied onto a 6 g HLB cartridge, washed with water and eluted with MeOH, then concentrated. The solid was dissolved in MeOH and purified by prep-HPLC to give 100 mg of the title compound. MS: 384 (M+H)+

226D. (1S,4S)-5-(4-(5-cyclopropyl-1H-pyrazol-3-ylamino)pyrrolo[1,2-f][1,2,4]-triazin-2-yl)-4-methyl-2-oxa-5-azabicyclo[2.2.1]heptan-3-one

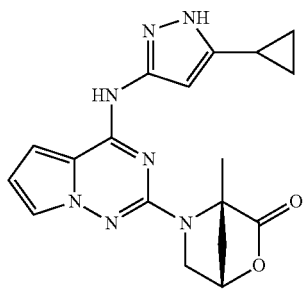 [SMILES: C[C@@]12C[C@@H](CN1c1nc(Nc3cc(C4CC4)[nH]n3)c3cccn3n1)OC2=O]

A mixture of compound 226C (92 mg, 0.24 mmol), HOBt (49 mg, 0.36 mmol), N-methylmorpholine (0.1 ml) and 1-[3-(dimethylamino)propyl]-3-ethylcarbodiimide hydrochloride (67 mg, 0.36 mmol) was suspended in 10 ml THF and stirred at r.t. for 2 days. The mixture was concentrated and used as is in the next step. MS: 366 (M+H)+.

A cold solution of 2-fluoro-5-aminopyridine (81 mg, 0.73 mmol) in THF (1 mL) is treated slowly with stirring with isopropylmagnesium chloride (2.0 M in THF; 0.35 mL, 0.7 mmol). After 5 min, the crude compound 226D [(1S,4R)-5-(4-(5-cyclopropyl-1H-pyrazol-3-ylamino)pyrrolo[1,2-f][1,2,4]triazin-2-yl)-4-methyl-2-oxa-5-azabicyclo[2.2.1]heptan-3-one](<0.13 mmol) in 3 ml THF is added and the mixture is rapidly stirred for 1 hour at r.t. The mixture was blown to dryness under N$_2$ stream, re-dissolved in MeOH and purified by preparative HPLC. The fractions containing the product are processed to the title compound, obtained as its free base, using a one gram (20 cc) Waters Oasis® MCX Extraction Cartridge, following the general method described above, to give 10.8 mg of the pure title compound. HPLC R.t.=5.56 min, conditions "d" as defined in table 7, LCMS R.t.=1.06 min, conditions "a" as defined in table 7, MS: 478 (M+H)$^+$.

Example 227

(2S,4S)-1-(4-(5-cyclopropyl-1H-pyrazol-3-ylamino)pyrrolo[1,2-f][1,2,4]triazin-2-yl)-4-hydroxy-2-methyl-N-(pyrazin-2-yl)pyrrolidine-2-carboxamide

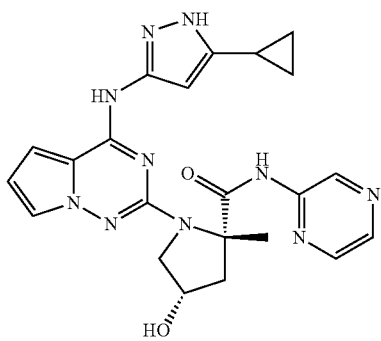 [SMILES: C[C@@]1(C(=O)Nc2cnccn2)C[C@H](O)CN1c1nc(Nc2cc(C3CC3)[nH]n2)c2cccn2n1]

A cold solution of pyrazin-2-amine (69 mg, 0.73 mmol) in THF (1 mL) is treated slowly with stirring with isopropylmagnesium chloride (2.0 M in THF; 0.35 mL, 0.7 mmol). After 5 min, the crude compound 226D [(1S,4S)-5-(4-(5-cyclopropyl-1H-pyrazol-3-ylamino)pyrrolo[1,2-f][1,2,4]triazin-2-yl)-4-methyl-2-oxa-5-azabicyclo[2.2.1]heptan-3-one](<0.13 mmol) in 3 ml THF is added and the mixture is rapidly stirred for 1 hour at r.t. The mixture was blown to dryness under N2 stream, re-dissolved into MeOH and purified by preparative HPLC. The fractions containing the product are processed to the title compound, obtained as its free base, using a one gram (20 cc) Waters Oasis® MCX Extraction Cartridge, following the general method described above, to give 5.4 mg of the pure title compound. HPLC R.t. =5.37 min, conditions "d" as defined in table 7, LCMS R.t.=1.02 min, conditions "a" as defined in table 7, MS: 461 (M+H)$^+$.

HPLC Conditions for Examples 228 to 240

Unless otherwise indicated herein, Analytical Reverse Phase HPLC retention times (Ret Time) were obtained using a Phenomenex S10 column 4.6×50 mm with a 4 mL/min flow rate and 3 min. linear gradient elution starting with 100% solvent A (10% MeOH, 90% H$_2$O, 0.1% TFA) and 0% solvent B, and ended with 100% solvent B (90% MeOH, 10% H$_2$O, 0.1% TFA) and 0% solvent A). UV detection was conducted at 220 nm.

Preparative Reverse Phase (RP)HPLC was performed with a linear gradient elution using H$_2$O/MeOH mixtures buffered with 0.1% trifluoroacetic acid and detection at 220 nm on one of the following columns. Shimadzu S5ODS-VP 20×100 mm (flow rate=9 mL/min), or YMC S10 ODS 50×500 mm (flow rate=50 mL/min), or YMC S10 ODS 30×500 mm (flow rate=20 mL/min).

Example 228

(S)-1-(4-(1-isopropyl-1H-imidazol-4-ylamino)pyrrolo[1,2-f][1,2,4]triazin-2-yl)-N-((R)-piperidin-3-yl)pyrrolidine-2-carboxamide

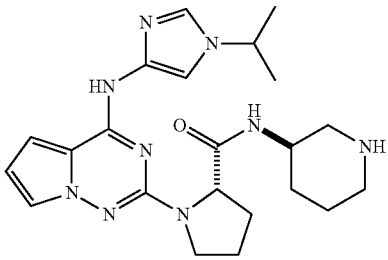

228A. 1-Isopropyl-4-nitro-1H-imidazole

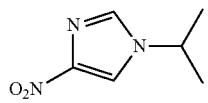

A mixture of 4-nitro-1H-imidazole (1.0 gm, 8.8 mmole), 2-bromopropane (1.1 gm, 8.8 mmole), potassium carbonate (1.8 gm, 13 mmole) and tetrabutylammonium iodide (0.10 gm, 0.27 mmole) in dry acetonitrile (10 mL) was heated at reflux for 7 hr. After cooling to room temperature, the reaction was filtered and the solvents removed from the filtrate. The residue was chromatograped (silica gel column, gradient elution with mixtures of dichloromethane containing 0 to 50% ethyl acetate) to afford the product as a solid (0.52 gm, 39% yield). HPLC retention time=1.12 min; MS (M+H)$^+$=155, $^1$H NMR (500 MHz, CD$_3$OD) δ 1.56 (d, J=6.71 Hz, 6 H) 4.53-4.61 (m, 1 H) 7.85 (s, 1 H) 8.27 (s, 1 H).

228B. 2-Chloro-N-(1-isopropyl-1H-imidazol-4-yl)pyrrolo[1,2-f][1,2,4]triazin-4-amine

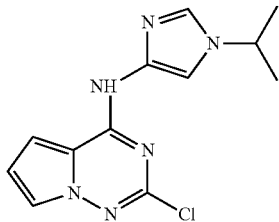 [SMILES: CC(C)n1cnc(Nc2nc(Cl)nn3cccc23)c1]

A mixture of 1-isopropyl-4-nitro-1H-imidazole (5.0 gm, 34 mmole) and 10% palladium on carbon (5.0 gm) in isopropanol (25 mL) under hydrogen (balloon). was vigorously stirred for 15 hr. The catalyst was removed by filtration and the filtrate was treated with 1B (5.0 gm, 26 mmole) and diisopropylethylamine (9.1 mL, 52 mmole) for 1 hr at room temperature. The product, 228B, was collected by filtration, washed with a little cold isopropanol, and dried (5.0 gm, 74% yield). HPLC retention time=2.11 min; MS (M+H)$^+$=279.

A mixture of 228B (0.25 gm, 0.91 mmole), S-proline (0.523 gm, 4.6 mmole), diisopropylethylamine (0.15 mL, 0.91 mmole) and an aqueous solution of NaOH (0.91 mL, 5.0 N, 4.6 mmole) in 1,4-dioxane (3 mL) was heated in a microwave reactor at 150° C. for 4.5 hr. After cooling to room temperature, the solvents were removed. The residue was diluted with water and washed with methylene chloride. The aqueous phase was acidified with hydrochloric acid and the product was isolated by preparative HPLC. The fractions containing the desired product were combined and the solvents removed to leave the trifluoroacetic acid salts of (S)-1-(4-(1-isopropyl-1H-imidazol-4-ylamino)pyrrolo[1,2-f][1,2,4]triazin-2-yl)pyrrolidine-2-carboxylic acid: MS: 356 (M+H)+; HPLC Ret Time: 1.98 min (Phenomenex-Luna S10 3.0×50 mm column, 3 min gradient, 4 mL/min). A portion (103 mg, 0.29 mmole) of this was taken and treated with (R)-tert-butyl piperidin-3-ylcarbamate (0.116 gm, 0.58 mmole) and diisopropylethylamine (0.05 mL, 0.29 mmole) in dry dimethylformamide (1.0 mL) at 0° C. PyBOP (158 mg, 0.3 mmole) was added with stirring and after 1 hr, the reaction was diluted with methanol, the product was separated by preparative HPLC. The solvent was removed from the HPLC fractions that contained (R)-tert-butyl 3-((S)-1-(4-(1-isopropyl-1H-imidazol-4-ylamino)pyrrolo[1,2-f][1,2,4]triazin-2-yl)pyrrolidine-5-carboxamido)piperidine-1-carboxylate and the residue was treated with a 5.0 N solution of HCl in methanol for 1 hr at room temperature. This was applied onto a cartridge of Phenomenex Strata-X-C 33 um cation mixed-mode polymer, flushed with methanol and then the product was eluted with a 2 N solution of ammonia in methanol. Removal of the solvents left 228 (100 mg, 96% yield). HPLC retention time=1.60 min; MS (M+H)$^+$=438.

Examples 229 to 235

Table 11 contains Examples 229 to 235 which were prepared using the procedure described in Example 228.

TABLE 11

| Example | Compound | HPLC ret. t. (min.) | (M + H)$^+$ |
|---|---|---|---|
| 229 | 2-chloro-N-(1-methyl-1H-imidazol-4-yl)pyrrolo[1,2-f][1,2,4]triazin-4-amine | 1.85 | 249 |

TABLE 11-continued

| Example | Compound | HPLC ret. t. (min.) | (M + H)+ |
|---|---|---|---|
| 230 | (S)-1-(4-(1-methyl-1H-imidazol-4-ylamino)pyrrolo[1,2-f][1,2,4]triazin-2-yl)pyrrolidine-2-carboxylic acid | 1.60 | 328 |
| 231 | (S)-1-(4-(1-methyl-1H-imidazol-4-ylamino)pyrrolo[1,2-f][1,2,4]triazin-2-yl)-N-((R)-piperidin-3-yl)pyrrolidine-2-carboxamide | 1.67 | 410 |
| 232 | 2-chloro-N-(1-ethyl-1H-imidazol-4-yl)pyrrolo[1,2-f][1,2,4]triazin-4-amine | 1.75 | 263 |
| 233 | (S)-1-(4-(1-ethyl-1H-imidazol-4-ylamino)pyrrolo[1,2-f][1,2,4]triazin-2-yl)pyrrolidine-2-carboxylic acid | 1.88 | 342 |

TABLE 11-continued

| Example | Compound | HPLC ret. t. (min.) | (M + H)+ |
|---|---|---|---|
| 234 | 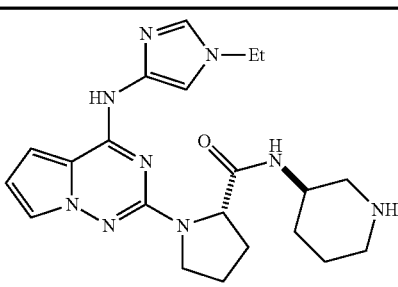<br>(S)-1-(4-(1-ethyl-1H-imidazol-4-ylamino)pyrrolo[1,2-f][1,2,4]triazin-2-yl)-N-((R)-piperidin-3-yl)pyrrolidine-2-carboxamide | 1.61 | 424 |
| 235 | 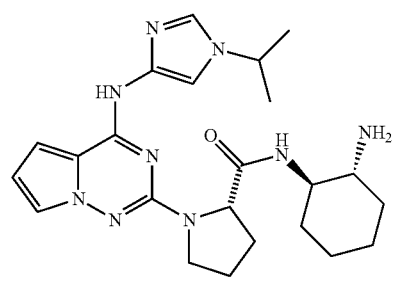<br>(S)-N-((1R,2R)-2-aminocyclohexyl)-1-(4-(1-isopropyl-1H-imidazol-4-ylamino)pyrrolo[1,2-f][1,2,4]triazin-2-yl)pyrrolidine-2-carboxamide | 1.65 | 452 |

Example 236

(S)-1-(4-(1-Isopropyl-1H-imidazol-4-ylamino)pyrrolo[1,2-f][1,2,4]triazin-2-yl)-N-((R)-1-methylpiperidin-3-yl)pyrrolidine-2-carboxamide

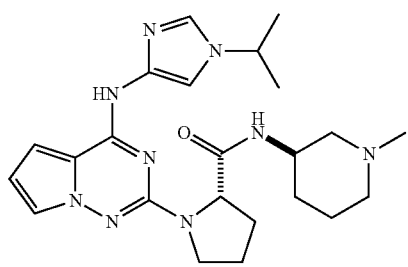

A mixture of 228 (0.06 gm, 0.14 mmole), formaldehyde (37 wt % in water) (48 ul, 1.1 mmole), sodium cyanoborohydride, 1.0 M solution in tetrahydrofuran (0.35 mL, 0.35 mmole) and acetic acid (0.007 mL, 0.42 mmole) in methanol (1.5 mL) was stirred for 1 hr at room temperature. The product was isolated by preparative HPLC. The fractions containing the desired product were combined and applied onto a cartridge of Phenomenex Strata-X-C 33 um cation mixed-mode polymer, flushed with methanol, and the product was eluted with a 2 N solution of ammonia in methanol. Removal of the solvents left 236 (45 mg, 71% yield). HPLC retention time=2.03 min; MS (M+H)+=452.

Example 237

(S)-1-(4-(1-cyclopropyl-1H-imidazol-4-ylamino)pyrrolo[1,2-f][1,2,4]triazin-2-yl)-N-((R)-piperidin-3-yl)pyrrolidine-2-carboxamide

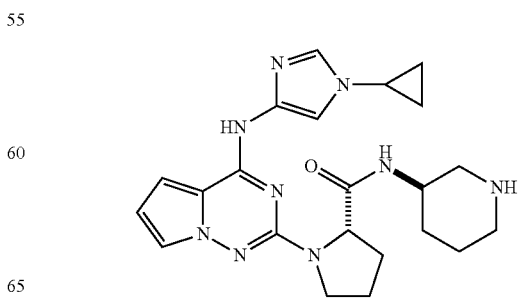

237A.
Ethyl-1-cyclopropyl-1H-imidazole-4-carboxylate

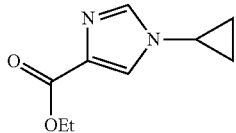 [SMILES: CCOC(=O)c1cn(C2CC2)cn1]

This was prepared from cyclopropylamine using the procedure described in Organic Letters, 2002, 4, 4133. HPLC retention time=1.02 min; MS (M+H)+=181; 1H NMR (500 MHz, CDCl3) δ 0.96-1.01 (m, 2 H) 1.02-1.07 (m, 2 H) 1.35 (t, J=7.02 Hz, 3 H) 3.37 (dt, J=7.02, 3.05 Hz, 1 H) 4.33 (q, J=7.02 Hz, 2H) 7.59 (s, 1 H). 7.63 (d, J=1.22 Hz, 1 H).

237B.
1-Cyclopropyl-1H-imidazole-4-carbohydrazide

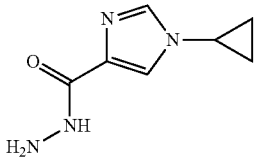 [SMILES: NNC(=O)c1cn(C2CC2)cn1]

Compound 237A was converted to 237B using a procedure analogous to that described in Journal of Fluorine Chemistry, 2001, 107, 147: HPLC retention time=0.28 min; MS (M+H)+= 167, 1H NMR (500 MHz, CD3OD) δ1.02-1.10 (m, 4 H) 3.54 (ddd, J=7.40, 3.59, 3.36 Hz, 1 H) 7.70 (s, 1 H) 7.74 (s, 1 H).

237C. 1-Cyclopropyl-1H-imidazole-4-carbonyl azide

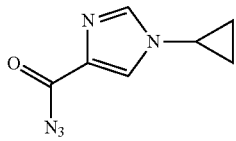

Compound 237B was converted to 237C using a procedure analogous to that described in Journal of Fluorine Chemistry, 2001, 107, 147: HPLC retention time=0.76 min; MS (M+H)+= 178; 1H NMR (500 MHz, CD3OD) δ ppm 1.05-1.12 (m, 4 H) 3.58 (ddd, J=10.91, 7.10, 3.97 Hz, 1 H) 7.87 (s, 1 H) 7.95 (s, 1 H).

237D. tert-Butyl 1-cyclopropyl-1H-imidazole-4-ylcarbamate

Compound 237C was converted to 237D using a procedure analogous to that described in Journal of Fluorine Chemistry, 2001, 107, 147: HPLC retention time=1.23 min; MS (M+H)+= 224: 1H NMR (500 MHz, CDCl3) δ 0.92-0.97 (m, 4 H) 1.46-1.53 (m, 9 H) 3.30 (s, 1 H) 7.07 (s, 1 H) 7.30 (s, 1 H) 7.82 (s, 1 H).

237E. 1-Cyclopropyl-1H-imidazole-4-amine

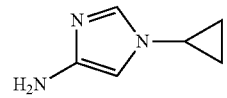

A solution of 237D (0.60 gm, 2.3 mmole) in a 5.0 N solution of HCl in methanol was left stirring at room temperature for 1 hr. This was applied onto a Phenomenex Strata-X-C 33 um cation mixed-mode polymer, flushed with methanol, and the product was eluted with a 2 N solution of ammonia in methanol. Removal of the solvents left 237E, (0.20 gm; 59% yield). 1H NMR (500 MHz, CDCl3) δ 0.87 (m, 4 H) 3.21 (s, 1 H) 6.27 (s, 1 H) 7.16 (br s, 1 H).

237F. 2-Chloro-N-(1-cyclopropyl-1H-imidazol-4-yl)pyrrolo[1,2-f][1,2,4]triazin-4-amine

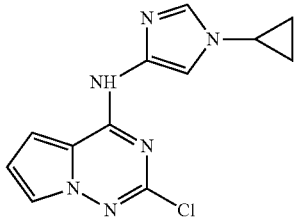 [SMILES: Clc1nc(Nc2cn(C3CC3)cn2)c2cccn2n1]

This was prepared from 1-cyclopropyl-1H-imidazole-4-amine and 237E as described for 1C: HPLC retention time=2.15 min; MS (M+H)+=277.

A mixture of 237F (0.2 gm, 0.73 mmole), S-proline (0.42 gm, 3.6 mmole), diisopropylethylamine (0.12 mL, 0.73 mmole) and an aqueous solution of NaOH (0.73 mL, 5.0 N, 3.7 mmole) in 1,4-dioxane (3 mL) was heated in a microwave reactor at 150° C. for 10 hr. After cooling to room temperature, the solvents were removed. The residue was diluted with water and washed with methylene chloride. The aqueous phase was acidified with hydrochloric acid and the product was isolated by preparative HPLC. The fractions containing the desired product were combined and the solvents removed to leave the trifluoroacetic acid salts of (S)-1-(4-(1-cyclopropyl-1H-imidazol-4-ylamino)pyrrolo[1,2-f][1,2,4]triazin-2-yl)pyrrolidine-2-carboxylic acid: HPLC Ret Time: 2.27 min (Phenomenex-Luna S10 4.6×50 mm column, 3 min gradient, 4 mL/min); MS: 354 (M+H)+. A portion (110 mg, 0.3 mmole) of this was taken and treated with (R)-tert-butyl piperidin-3-ylcarbamate (0.12 gm, 0.6 mmole) and diisopropylethylamine (0.052 mL, 0.3 mmole) in dry dimethylformamide (1.5 mL) at 0° C. PyBOP (164 mg, 0.3 mmole) was added with stirring and after 1 hr, the reaction was diluted with methanol, and the product was separated by preparative HPLC. The solvent was removed from the HPLC fractions that contained (R)-tert-butyl 3-((S)-1-(4-(1-cyclopropyl-1H-imidazol-4-ylamino)pyrrolo[1,2-f][1,2,4]triazin-2-yl)pyrrolidine-5-carboxamido)piperidine-1-carboxylate and the residue was treated with a 5.0 N solution of HCl in methanol for 1 hr at room temperature. This was then applied onto a cartridge of Phenomenex Strata-X-C 33 um cation mixed-mode polymer, flushed with methanol, and the product was eluted with a 2 N solution of ammonia in methanol. Removal of the solvents left 237 (80 mg, 68% yield). HPLC retention time=2.12 min; MS $(M+H)^+$=436.

Example 238

(S)-N-(6-fluoropyridin-3-yl)-1-(4-(1-isopropyl-1H-imidazol-4-ylamino)pyrrolo[1,2-f][1,2,4]triazin-2-yl)-2-methylpyrrolidine-2-carboxamide

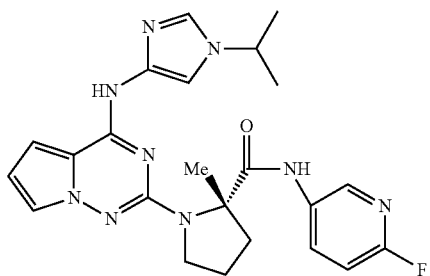 [SMILES: CC(C)n1cnc(Nc2nc(N3CCC[C@@]3(C)C(=O)Nc3ccc(F)nc3)nn3cccc23)c1]

238A. (S)-1-(4-(1-Isopropyl-1H-imidazol-4-ylamino)pyrrolo[1,2-f][1,2,4]-triazin-2-yl)-2-methylpyrrolidine-2-carboxylic acid

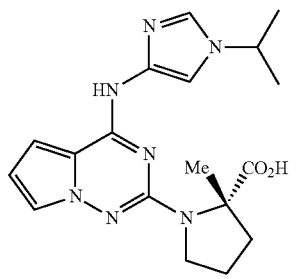 [SMILES: CC(C)n1cnc(Nc2nc(N3CCC[C@@]3(C)C(=O)O)nn3cccc23)c1]

A mixture of 228B (0.15 gm, 0.5 mmole), 1(S)-2-methylpyrrolidine-2-carboxylic acid (0.35 gm, 2.7 mmole), sodium tert-butoxide (0.256 gm, 2.7 mmole). and $K_2CO_3$ (75 mg, 0.5 mmole) in 1-methyl-2-pyrrolidinone (4 mL) was heated in a microwave reactor at 190° C. for 20 hr. After cooling to room temperature, the product was isolated by preparative HPLC. The fractions containing the desired product were combined and the solvents removed to leave the trifluoroacetic acid salts: HPLC retention time=1.5 min; MS $(M+H)^+$=370.

The mixture obtained from Example 238A (0.1 gm, 0.27 mmole), 6-fluoropyridine-3-amine (0.3 gm, 2.7 mmole), diisopropylethylamine (0.060 mL, 0.35 mmole) and HATU (0.1 gm, 0.27 mmole) in dry dimethylformamide (0.15 mL) was stirred 16 hr at room temperature. The product was isolated by preparative HPLC. The fractions containing the desired product were combined and applied onto a cartridge of Phenomenex Strata-X-C 33 um cation mixed-mode polymer, flushed with methanol and the product eluted with a 2 N solution of ammonia in methanol. Removal of the solvents left 238 (75 mg, 60% yield): HPLC retention time=2.09 min; MS $(M+H)^+$=464.

Example 239

(S)-1-(4-(1-cyclopropyl-1H-imidazol-4-ylamino)pyrrolo[1,2-f][1,2,4]triazin-2-yl)-N-(6-fluoropyridin-3-yl)-2-methylpyrrolidine-2-carboxamide

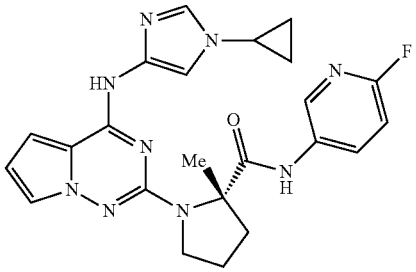 [SMILES: C[C@@]1(C(=O)Nc2ccc(F)nc2)CCCN1c1nc(Nc2cn(C3CC3)cn2)c2cccn2n1]

This was prepared from 237F and (S)-2-methylpyrrolidine-2-carboxylic acid according to the procedure described for 238: HPLC retention time=2.02 min; MS $(M+H)^+$=462.

Example 240

(2S,4S)-4-hydroxy-1-(4-(1-isopropyl-1H-imidazol-4-ylamino)pyrrolo[1,2-f][1,2,4]triazin-2-yl)-N-((R)-piperidin-3-yl)pyrrolidine-2-carboxamide

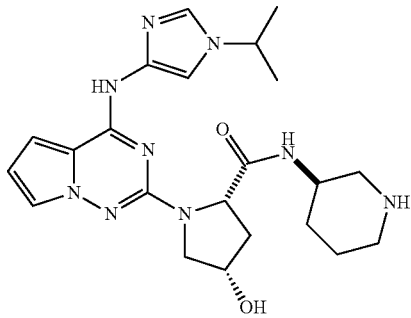

240A. (2S,4S)-4-hydroxy-1-(4-(1-isopropyl-1H-imidazol-4-ylamino)pyrrolo[1,2-f][1,2,4]triazin-2-yl)pyrrolidine-2-carboxylic acid

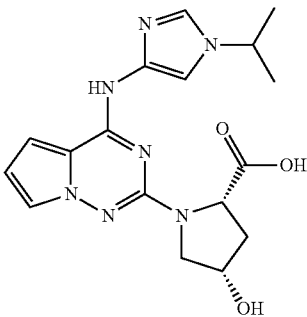 [SMILES: CC(C)n1cnc(Nc2nc(N3C[C@@H](O)C[C@H]3C(=O)O)nn3cccc23)c1]

A mixture of 2-chloro-N-(1-isopropyl-1H-imidazol-4-yl)pyrrolo[1,2-f][1,2,4]triazin-4-amine 228B (140 mg, 0.507 mmol) and (2S,4S)-4-hydroxypyrrolidine-2-carboxylic acid (Bachem, 997 mg, 7.61 mmol) in a 15 mL pressure bottle is treated with NMP (4.5 mL). To this stirred mixture is then added 5 M NaOH (1.48 mL, 7.4 mmol) and N,N-diisopropylethylamine (140 μL, 0.811 mmol), and the reaction is flushed with nitrogen, sealed, and heated at 135° C. for 15 h. The crude reaction mixture is cooled to rt, filtered through a 45 mμ frit and purified by preparative HPLC (using 10% solvent B to 70% solvent B over 10 min). The desired fractions containing the product are evaporated to dryness to give 205 mg of the title compound as a possible TFA salt; MS: 372 (M+H)+, LC/MS ret. t=1.52 min.

The title compound was prepared from 240A and (R)-tert-butyl piperidin-3-ylcarbamate (0.2 gm, 1.0 mmole) according to the procedure describe for 228: HPLC retention time=1.47 min; MS (M+H)+=454.

Example 241

(2S,4S)-4-Hydroxy-1-(4-(1-isopropyl-1H-imidazol-4-ylamino)pyrrolo[1,2-f][1,2,4]triazin-2-yl)-N-((R)-1-methylpiperidin-3-yl)pyrrolidine-2-carboxamide

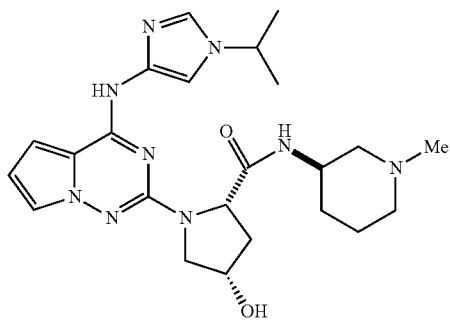

The title compound was prepared from 240 and formaldehyde (37 wt % in water) according to the procedure described for 236: HPLC retention time=1.48 min; MS (M+H)+=468.

Example 242

(2S,4S)-N-((R)-1-Cyclopropylpiperidin-3-yl)-4-hydroxy-1-(4-(1-isopropyl-1H-imidazol-4-ylamino)pyrrolo[1,2-f][1,2,4]triazin-2-yl)pyrrolidine-2-carboxamide

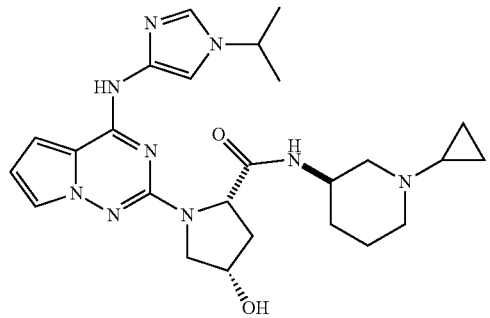

The title compound was prepared from 240 and (1-ethoxycyclopropoxy)trimethylsilane as described for 89: HPLC retention time=1.82 min; MS (M+H)+=492.

Example 243

(2S,4S)-4-hydroxy-1-(4-(1-isopropyl-1H-imidazol-4-ylamino)pyrrolo[1,2-f][1,2,4]triazin-2-yl)-N-((R)-1-isopropylpiperidin-3-yl)pyrrolidine-2-carboxamide

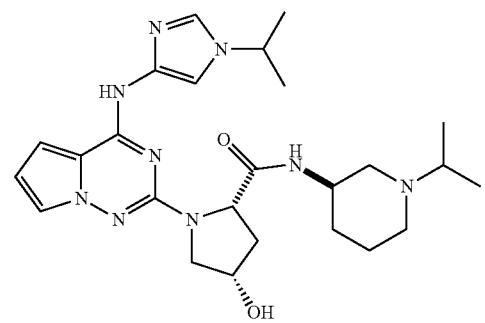

The title compound was prepared from 240 and acetone as described for 92: HPLC retention time=1.83 min; MS (M+H)+=494.

HPLC Conditions for Examples 244 to 246

In the examples below, the Analytical Reverse Phase HPLC ret. t. were obtained on a Shimadzu HPLC system with the following solvents. UV detection was conducted at 254 nM. Waters X-Terra HPLC column, 4.6×150 mm, 3.5 micron, 1 mL/min flow rate, linear gradient from 95% A (95:5 Water: $CH_3CN$, 10 mM $NH_4OAc$, pH 6.8)/5% B (90:10 $CH_3CN$: Water, 10 mM $NH_4OAc$, pH 6.8) to 100% B over 15 min. UV detection was conducted at 254 nM.

Preparative Reverse Phase (RP)HPLC was performed using a Waters Atlantis 30×100 mm 5 micron column with linear gradient elution using the stated ratio of solvent A (10% Methanol-90% Water-0.1% TFA) and solvent B (90% Methanol-10% Water-0.1% TFA) over the stated time period (typically from 10-13 min) A typical example would have the linear gradient from 15% B (85% A) to 90% B (10% A) over 12 min. UV detection was conducted at 254 nM.

Several of the final products are isolated as their free bases by passing the appropriate fractions from the preparative HPLC purification (using the method described above) through a 1 gram (20 cc) or 6 gram (35 cc) Waters Oasis® MCX Extraction Cartridge. Elution with HPLC methanol serves to concentrate the product on the cartridge and to remove the TFA. Subsequent elution with 2.0M $NH_3$ in methanol (Aldrich), followed by evaporation, gives the free base of the final products.

Example 244

(2S,4S)-N-(6-fluoropyridin-3-yl)-4-hydroxy-1-(4-(1-isopropyl-1H-imidazol-4-ylamino)pyrrolo[1,2-f][1,2,4]triazin-2-yl)pyrrolidine-2-carboxamide

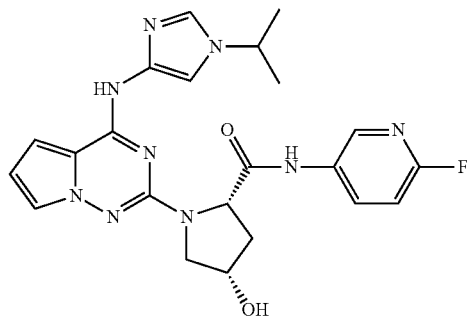 [SMILES: CC(C)n1cnc(Nc2nc(N3C[C@@H](O)C[C@H]3C(=O)Nc3ccc(F)nc3)nn3cccc23)c1]

244A. (1S,4R)-5-(4-(1-isopropyl-1H-imidazol-4-ylamino)pyrrolo[1,2-f][1,2,4]-triazin-2-yl)-2-oxa-5-azabicyclo[2.2.1]heptan-3-one

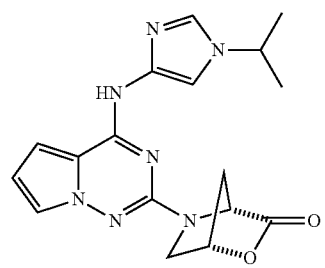

A mixture of the compound from 240A (102 mg, 0.275 mmol) and 1-hydroxy-7-azabenzotriazole (19 mg), is treated sequentially with THF (4 mL), N-methylmorpholine (181 μL), and 1-[3-(dimethylamino)propyl]-3-ethylcarbodiimide hydrochloride (58 mg). The reaction is stirred at rt for 1 h, and then the volatiles are evaporated and the crude material is dried under high vacuum and used directly as described below without further purification: MS: 352 $(M+H)^+$, LC/MS ret. t=2.11 min.

A magnetically stirred solution of 2-fluoro-5-aminopyridine (184 mg, 1.64 mmol) in THF (7 mL) under nitrogen is cooled in an ice water bath and is then treated slowly with isopropylmagnesium chloride (2.0 M in THF; 800 μL, 1.6 mmol). After 15 min, the material from 244A (0.137 mmol) is added and the mixture is rapidly stirred under nitrogen. After 30 min at rt, the reaction mixture is cooled again in an ice bath and a cold solution of TFA (123 μL, 3 mmol) in methanol (3 mL) is added. The mixture is then purified by preparative HPLC (using 10% solvent B to 70% solvent B over 11 min). The desired fractions containing the product are processed to the title compound, obtained as its free base, using a one gram (20 cc) Waters Oasis® MCX Extraction Cartridge, following the general method described above, to give 26 mg of the pure title compound as a solid: MS: 466 $(M+H)^+$, LC/MS ret. t=1.67 min.; HPLC (Method A) ret. t.=13.39 min; 500 MHz $^1$H NMR (CD$_3$OD) δ 8.35 (s, 1H), 8.05-7.99 (m, 1H), 7.48 (s, 1H), 7.42-7.38 (m, 2H), 6.97 (dd, 1H, J=8.9, 2.8 Hz), 6.86 (brs, 1H), 6.49-6.46 (m, 1H), 4.72 (d, 1H, J-10.0 Hz), 4.58-4.54 (m, 1H), 4.34-4.28 (m, 1H), 3.81-3.73 (m, 2H), 2.60-2.53 (m, 1H), 2.36-2.31 (m, 1H), 1.45-1.37 (m, 6H).

Example 245

(2S,4S)-4-hydroxy-1-(4-(1-isopropyl-1H-imidazol-4-ylamino)pyrrolo[L2-f][1,2,4]triazin-2-yl)-N-(pyrazin-2-yl)pyrrolidine-2-carboxamide

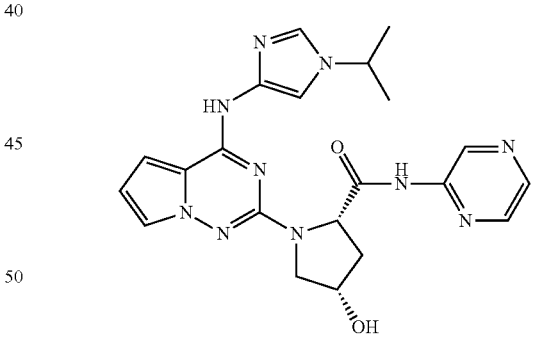

Using the method described in 244, but substituting 2-fluoro-5-aminopyridine with 2-aminopyrazine, the compound from 244A (0.137 mmol) is converted to 23.5 mg of the pure title compound as a solid. The preparative HPLC purification has a gradient using 10% solvent B to 70% solvent B over 11 min. MS: 449 $(M+H)^+$, LC/MS ret. t=1.62 min.; HPLC (Method A) ret. t.=15.8 min; 500 MHz $^1$H NMR (d$_6$-DMSO-) δ 10.37 (brs, 1H), 9.99 (brs, 1H), 9.34 (s, 1H), 8.33 (brs, 2H), 7.55 (brs, 1H), 7.42 (brs, 1H), 7.41 (brs, 1H), 7.15 (brs, 1H), 6.42-6.38 (m, 1H), 5.27 (brs, 1H), 4.73-4.67 (m, 1H), 4.44-4.40 (m. 1H), 4.39-4.32 (m, 1H), 3.70-3.62 (m, 2H), 2.58-2.51 (m, 1H), 2.16-2.09 (m, 1H), 1.43-1.35 (m, 6H).

Example 246

(2S,4R)-N-(6-fluoropyridin-3-yl)-1-(4-(1-isopropyl-1H-imidazol-4-ylamino)pyrrolo[1,2-f][1,2,4]triazin-2-yl)-4-methoxypyrrolidine-2-carboxamide

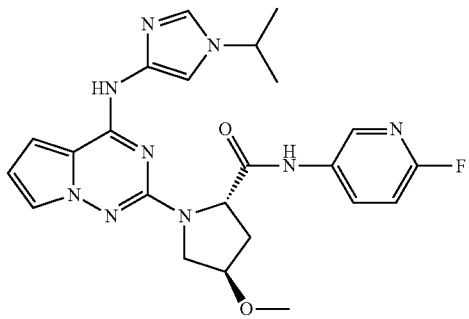 [SMILES: CO[C@@H]1C[C@@H](C(=O)Nc2ccc(F)nc2)N(c2nc(Nc3cn(C(C)C)cn3)c3cccn3n2)C1]

246A. (2S,4R)-1-(4-(1-isopropyl-1H-imidazol-4-ylamino)pyrrolo[1,2-f][1,2,4]triazin-2-yl)-4-methoxypyrrolidine-2-carboxylic acid

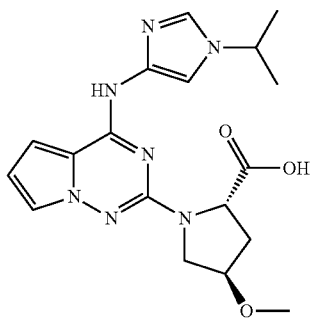 [SMILES: CO[C@@H]1C[C@@H](C(=O)O)N(c2nc(Nc3cn(C(C)C)cn3)c3cccn3n2)C1]

A mixture of 2-chloro-N-(1-isopropyl-1H-imidazol-4-yl)pyrrolo[1,2-f][1,2,4]triazin-4-amine 228B (154 mg, 0.556 mmol) and (2S,4R)-4-methoxypyrrolidine-2-carboxylic acid-HCl salt (218A) (984 mg, 5.42 mmol) in a 15 mL pressure bottle is treated with NMP (5 mL). To this stirred mixture is then added 5 M NaOH (2.14 mL, 10.7 mmol) and N,N-diisopropylethylamine (140 μL, 0.811 mmol), and the reaction is flushed with nitrogen, sealed, and heated at 135° C. for 22 h. The crude reaction mixture is cooled to rt, filtered, and purified by preparative HPLC (using 10% solvent B to 80% solvent B over 11 min). The desired fractions containing the product are evaporated to dryness to give 187 mg of the title compound as possible TFA salt; MS: 386 (M+H)$^+$, LC/MS ret. t=1.68 min.

Following the procedure described in 219, 246A (0.221 mmol) is converted (the preparative HPLC purification conditions used are 15% B to 80% B over 11 min) to the free base of the title compound as a solid.; MS: 480 (M+H)$^+$, LC/MS ret. t=1.76 min; HPLC (Method A) ret. t=12.94 min; 500 MHz $^1$H NMR (CD$_3$OD) δ 8.29 (s, 1H), 8.04-7.98 (m, 1H), 7.49 (brs, 1H), 7.42 (brs, 1H), 7.36 (brs, 1H), 6.98 (dd, 1H, J=8.9, 2.8 Hz), 6.84 (brs, 1H), 6.49-6.46 (m, 1H), 4.68 (t, 1H), 4.36-4.29 (m, 1H), 4.21-4.16 (m, 1H), 3.98-3.93 (m, 1H), 3.92-3.87 (m, 1H), 3.39 (s, 3H), 2.57-2.50 (m, 1H), 2.34-2.27 (m, 1H), 1.43 (d, 6H, J=6.7 Hz).

Example 247

1-(4-(1-Isopropyl-1H-imidazol-4-ylamino)pyrrolo[1,2-f][1,2,4]triazin-2-yl)-2,4,4-trimethylpyrrolidine-2-carboxylic acid

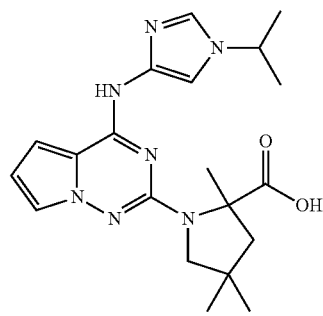 [SMILES: CC(C)n1cnc(Nc2nc(N3CC(C)(C)CC3(C)C(=O)O)nn3cccc23)c1]

1-(4-(1-Isopropyl-1H-imidazol-4-ylamino)pyrrolo[1,2-f][1,2,4]triazin-2-yl)-2,4,4-trimethylpyrrolidine-2-carboxylic acid was prepared using the same method described in example 163H using 228B and 163G as starting materials. MS: 398 (M+H)+; HPLC Ret Time: 2.74 min (Phenomenex-Luna S10 4.6×50 mm column, 4 min gradient, 4 mL/min).

Example 248

(S)-N-(6-fluoropyridin-3-yl)-1-(4-(1-isopropyl-1H-imidazol-4-ylamino)pyrrolo[1,2-f][1,2,4]triazin-2-yl)-2,4,4-trimethylpyrrolidine-2-carboxamide

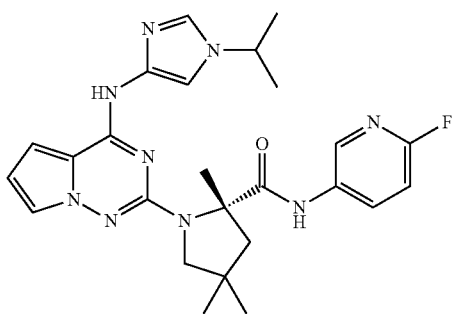 [SMILES: CC(C)n1cnc(Nc2nc(N3CC(C)(C)C[C@@]3(C)C(=O)Nc3ccc(F)nc3)nn3cccc23)c1]

(S)-N-(6-fluoropyridin-3-yl)-1-(4-(1-isopropyl-1H-imidazol-4-ylamino)pyrrolo[1,2-f][1,2,4]triazin-2-yl)-2,4,4-trimethylpyrrolidine-2-carboxamide was prepared using the same method as described for Example 165. The racemic mixture was separated by SFC chiracel OD-H column, 4.6× 250 mm, 5 um over 25 min. The fraction s with t=14.51 min. were collected. $^1$H NMR (CD$_3$OD, 400 MHz). δ 8.15 (1H, m), 7.82 (1H, m), 7.39 (1H, m), 7.15 (1H, s), 6.93 (1H, dd, J=2.8, 8.0 Hz), 6.84 (1H, br s), 6.48 (1H, dd, J=2.5, 4.3 Hz), 4.11 (1H, m), 3.64 (1H, d, J=10.6 Hz), 3.46 (1H, d, J=10.9 Hz), 2.42 (1H, d, J=13.3 Hz), 2.04 (1H, d, J=13.4 Hz), 1.73 (3H, s), 1.29 (3H, d, J=6.8 Hz), 1.23 (9H, m). MS: 492

Example 249

(S)-1-(4-(1-isopropyl-1H-imidazol-4-ylamino)pyrrolo[1,2-f][1,2,4]triazin-2-yl)-2,4,4-trimethyl-N-(pyrazin-2-yl)pyrrolidine-2-carboxamide

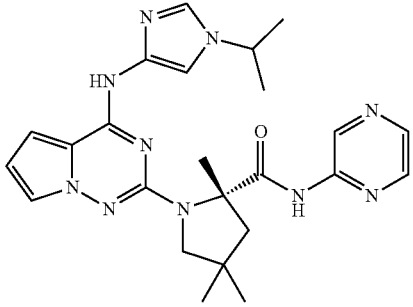 [SMILES: CC(C)n1cnc(Nc2nc(N3CC(C)(C)C[C@@]3(C)C(=O)Nc3cnccn3)nn3cccc23)c1]

(S)-1-(4-(1-Isopropyl-1H-imidazol-4-ylamino)pyrrolo[1,2-f][1,2,4]triazin-2-yl)-2,4,4-trimethyl-N-(pyrazin-2-yl)pyrrolidine-2-carboxamide was prepared using the same method as described for example 248. The racemic mixture was separated by SFC chiracel OD-H column, 4.6×250 mm, 5 um over 20 min. The fractions with t=8.52 min were collected. $^1$H NMR (CD$_3$OD, 400 MHz) δ 9.31 (1H, s), 8.23 (1H, m), 8.22 (1H, m), 7.36-7.39 (2H, m), 7.17 (1H, s), 6.81 (1H, br s), 6.46 (1H, dd, J=2.5, 4.5 Hz), 4.23 (1H, h, J=6.8 Hz), 3.63 (1H, d, J=10.6 Hz), 3.49 (1H, d, J=10.8 Hz), 2.46 (1H, d, J=13.3 Hz), 2.02 (1H, d, J=13.4 Hz), 1.73 (3H, s), 1.38 (3H, d, J=6.8 Hz), 1.34 (3H, d, J=6.8 Hz), 1.22 (3H, s), 1.20 (3H, s). HPLC (phenomenex-luna 4.6×150 mm over 25 min) Ret Time=16.90 min. MS: 475 (M+H)$^+$HPLC Ret Time: 3.22 min (Phenomenex-Luna S10 4.6×50 mm column, 3 min gradient, 4 mL/min).

Example 250

(S)-1-(4-(3-cyclopropyl-1H-pyrazol-5-ylamino)pyrrolo[1,2-f][1,2,4]triazin-2-yl)-4,4-difluoro-N-((R)-1-methylpiperidin-3-yl)pyrrolidine-2-carboxamide

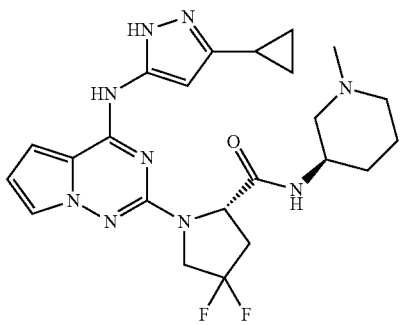 [SMILES: CN1CCC[C@@H](NC(=O)[C@@H]2CC(F)(F)CN2c2nc(Nc3cc(C4CC4)n[nH]3)c3cccn3n2)C1]

250A. (S)-4,4-difluoropyrrolidine-2-carboxylic acid

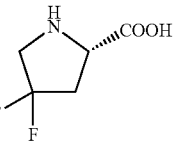

To a solution of (S)-1-(tert-butoxycarbonyl)-4,4-difluoropyrrolidine-2-carboxylic acid (500 mg, 1.99 mmol) in methanol (30 mL) was added 4N HCl dioxane (3 mL). The reaction mixture was stirred at rt for 6 h. Concentration gave an oil which was used for the next step without purification (480 mg, 100%). $^1$H NMR (CD$_3$OD, 400 MHz) δ 4.76 (1H, t, J=8.5 Hz), 3.79-3.87 (2H, m), 2.91-3.03 (1H, m), 2.73-2.82 (1H, m).

250B. (S)-1-(4-(3-cyclopropyl-1H-pyrazol-5-ylamino)pyrrolo[1,2-f][1,2,4]-triazin-2-yl)-4,4-difluoropyrrolidine-2-carboxylic acid

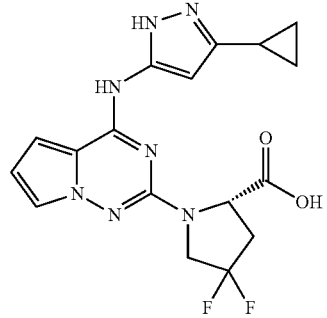 [SMILES: O=C(O)[C@@H]1CC(F)(F)CN1c1nc(Nc2cc(C3CC3)n[nH]2)c2cccn2n1]

A mixture of 1C (250 mg, 0.91 mmol), diisopropylethylamine (117 mg, 0.91 mmol), (S)-4,4-difluoropyrrolidine-2-carboxylic acid hydrochloride (920 mg, 4.55 mmol), 5 N NaOH aqueous solution (0.85 mL, 4.32 mmol), and N-methylpyrrolidinone (3 mL) was heated to 160° C. in microwave for 20 h. After cooling to room temperature, the crude product was purified by prep. HPLC to give compound (250) (163 mg, 46%). MS: 390 (M+H)$^+$;HPLC Ret Time: 3.71 min (Phenomenex-Luna S10 4.6×50 mm column, 5 min gradient, 4 mL/min).

Compound 250 was prepared using 4,4-difluoro. $^1$H NMR (CD$_3$OD, 400 MHz) δ 7.37 (1H, m), 6.83 (1H, m), 6.47 (1H, dd, J=2.5, 4.5 Hz), 6.30 (1H, br s), 4.71 (1H, dd, J=3.8, 10.1 Hz), 3.92-4.02 (3H, m), 2.79-2.91 (1H, m), 2.41-2.61 (3H, m), 2.16 (3H, s), 1.88-1.99 (3H, m), 1.39-1.58 (3H, m), 1.21-1.26 (1H, m), 0.94-0.98 (2H, m), 0.81 (2H, m). HPLC (phenomenex-luna 4.6×150 mm over 25 min) Ret Time=16.75 min. MS: 486 (M+H)$^+$HPLC Ret Time: 2.81 min (Phenomenex-Luna S10 4.6×50 mm column, 3 min gradient, 4 mL/min).

Example 251

(2S,4S)-4-methoxypyrrolidine-2-carboxylic acid

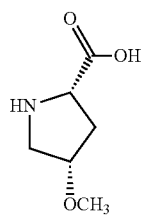

A stirred solution of (2S,4S)-1-(benzyloxycarbonyl)-4-hydroxypyrrolidine-2-carboxylic acid (35.9 g, 135.4 mmol) in dry THF (870 mL) is treated under nitrogen with sodium hydride (11.78 g, 491 mmol) and methyl iodide (38.5 g, 271 mmol), using a procedure similar to that published in J. Med. Chem. 1988, 31, 875, except that reflux is carried out for 16 h. The crude extracted product of this alkylation reaction, (2S,4S)-1-(benzyloxycarbonyl)-4-methoxypyrrolidine-2-carboxylic acid, is then dissolved in methanol (200 mL), treated with 6.2 g of 20% palladium hydroxide on carbon, and stirred at room temperature overnight under 1 atmosphere of hydrogen. The reaction mixture is filtered, washed with methanol, and evaporated in vacuo. The resulting solid is suspended in dichloromethane (450 mL). and filtered to give 11.5 g (91%) of the pure title compound: MS: 146 $(M+H)^+$; 500 MHz $^1$H NMR (d6-DMSO) δ

Example 252

(2S,4S)-1-(4-(5-cyclopropyl-1H-pyrazol-3-ylamino)pyrrolo[1,2-f][1,2,4]triazin-2-yl)-4-methoxypyrrolidine-2-carboxylic acid

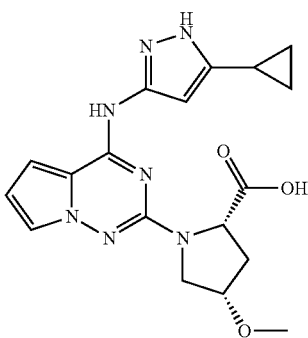 [SMILES: CO[C@H]1C[C@@H](C(=O)O)N(c2nc(Nc3cc(C4CC4)[nH]n3)c3cccn3n2)C1]

To solid (2S,4S)-4-methoxypyrrolidine-2-carboxylic acid (2.43 g, 16.7 mmol) in a 48 mL pressure bottle is added NMP (18 mL)) followed by 5 M NaOH (3.2 mL, 16 mmol). N,N-diisopropylethylamine (3.0 mL, 17.2 mmol) is added and the stirred mixture is treated with the compound from Example 1C (2.05 g, 7.45 mmol). The vessel is flushed with nitrogen, sealed, and heated at 135° C. for 21 h. The crude reaction mixture is cooled and poured into water (400 mL) and acidified slowly with 1 NHCL (30 mL) to pH 2-3. The resulting precipitate is collected by filtration, washed with water (50 mL) and dried in vacuo to give 1.8 g (63%) of the title compound, 89% pure by HPLC. The combined aqueous layers are then extracted with ethyl acetate (700 mL). The ethyl acetate layer is washed water (2×100 mL). and brine (200 mL), and dried (Na$_2$SO$_4$). The extract is concentrated in vacuo to give 1.40 g of additional title compound as a solid which is >92% pure by HPLC: MS: 384 $(M+H)^+$, LC/MS ret. t=2.14 min.

Example 253

(2S,4S)-methyl 1-(4-(5-cyclopropyl-1H-pyrazol-3-ylamino)pyrrolo[1,2-f][1,2,4]triazin-2-yl)-4-methoxypyrrolidine-2-carboxylate

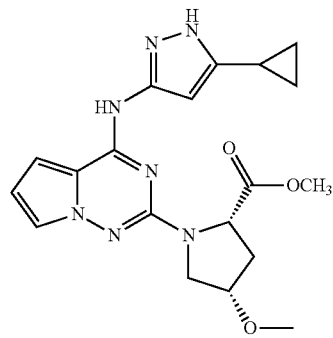 [SMILES: COC(=O)[C@@H]1C[C@H](OC)CN1c1nc(Nc2cc(C3CC3)[nH]n2)c2cccn2n1]

The entire amount of the compound from Example 252 (3.2 g) is dissolved in methanol (500 mL) and treated with 1-hydroxy-7-aza-benzotriazole (90 mg), N-methylmorpholine (800 mL), and 1-[3-(dimethylamino)propyl]-3-ethylcarbodiimide hydrochloride (2.03 g, 10.6 mmol). The reaction is stirred at room temperature overnight, concentrated in vacuo, and extracted with ethyl acetate (450 mL). The ethyl acetate layer is washed with water (2×275 mL) and brine (100 mL), and dried (Na$_2$SO$_4$). The solvent is evaporated in vacuo and the residue is dissolved in methylene chloride and purified by silica gel chromatography using a Biotage instrument (see above for general details) with a Flash 40+M cartridge using a gradient from 100% dichloromethane to 10% methanol in dichloromethane. The desired fractions containing the product were evaporated in vacuo to give 2.70 g (91%) of the title compound as a solid which is used directly as described below: MS: 398 $(M+H)^+$, LC/MS ret. t=2.34 min.

Example 254

(2S,4S)-1-(4-(5-cyclopropyl-1H-pyrazol-3-ylamino)pyrrolo[1,2-f][1,2,4]triazin-2-yl)-N-(6-fluoropyridin-3-yl)-4-methoxypyrrolidine-2-carboxamide

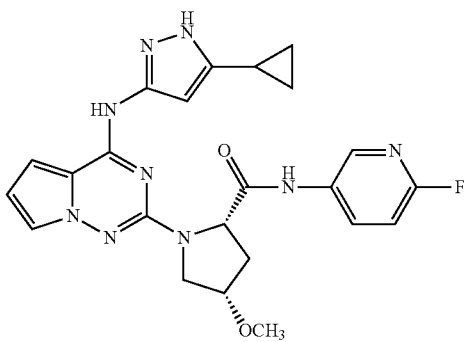 [SMILES: CO[C@H]1C[C@@H](C(=O)Nc2ccc(F)nc2)N(c2nc(Nc3cc(C4CC4)[nH]n3)c3cccn3n2)C1]

A cold solution of 2-fluoro-5-aminopyridine (3.30 g, 29.4 mmol) in dry THF (40 mL) under nitrogen at 0° C. is treated slowly with stirring with isopropylmagnesium chloride (2.0 M in THF; 13.8 mL, 27.6 mmol). After 10-15 min, the compound of Example 253 is added (1.06 g, 2.68 mmol) and the mixture is stirred at rt for 70 min. A cold solution of TFA (2.5 mL) in methanol (20 mL) is added and the mixture is then purified by preparative HPLC (using 23% solvent B to 80% solvent B over 11 min). The desired fractions containing the product (ret t=10.41 min) are processed to the title compound, obtained as its free base, using a 6 gram (35 cc) and a 1 gram (20 cc) Waters Oasis® MCX Extraction Cartridge, following the general method described above, to give 566.2 mg (44.4%) of the pure title compound of Example 254 as a solid: MS: 478 (M+H)$^+$, LC/MS ret. t=2.35 min.; HPLC (Method A but with a 30 min rather than a 15 min gradient) ret. t.=15.61 min; 500 MHz $^1$H NMR (CD$_3$OD) δ 8.32 (s, 1H), 8.04 (brs, 1H), 7.43 (s, 1H), 7.00 (dd, 1H, J=2.8, 8.9 Hz), 6.88 (d, 1H, J=3.4 Hz), 6.52-6.50 (m, 1H), 6.34 (brs, 1H), 4.72 (d, 1H, J=10.4 Hz), 4.15 (brs, 1H), 3.90-3.86 (m, 1H), 3.71 (dd, 1H, J=4.0, 11.6 Hz), 3.37 (s, 3H), 2.55 (d, 1H, J=13.7 Hz), 2.49-2.41 (m, 1H), 1.86-1.78 (m, 1H), 0.96-0.85 (m, 2H), 0.77-0.71 (m, 1H), 0.66-0.60 (m, 1H). Note that during preparative HPLC, a lesser amount of the earlier eluting C-2 proline ring epimer can be obtained similarly.

Example 255

(2S,4S)-1-(4-(5-cyclopropyl-1H-pyrazol-3-ylamino)pyrrolo[1,2-f][1,2,4]triazin-2-yl)-4-methoxy-N-(pyrazin-2-yl)pyrrolidine-2-carboxamide

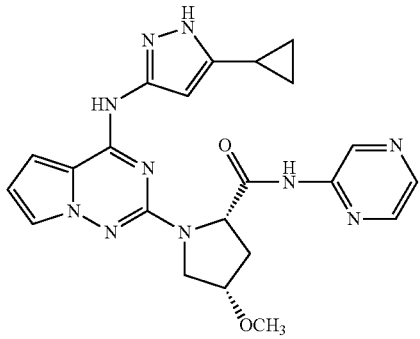 [SMILES: CO[C@H]1C[C@@H](C(=O)Nc2cnccn2)N(c2nc(Nc3cc(C4CC4)[nH]n3)c3cccn3n2)C1]

A cold solution of 2-aminopyrazine (7.2 g, 75.8 mmol) in dry THF (125 mL) under nitrogen at 0° C. is treated slowly with stirring with isopropylmagnesium chloride (2.0 M in THF; 36.0 mL, 72.0 mmol). After 10-15 min, the compound of Example 253 is added (2.00 g, 5.04 mmol) and the mixture is stirred at rt for 45 min. A cold solution of TFA (5.8 mL) in methanol (12 mL) is added and the mixture is then purified by preparative HPLC (using 15% solvent B to 85% solvent B over 11 min). The desired fractions containing the product (ret t=10.61 min) are processed to the title compound, obtained as its free base, using one 6 gram (35 cc) and two 1 gram (20 cc) Waters Oasis® MCX Extraction Cartridges, and one 5 gram (60 cc) Phenomenex strata-XL-C cartridge following the general method described above, to give 1.07 g (46%) of the pure title compound of Example 255 as a solid: MS: 461 (M+H)$^+$, LC/MS ret. t=2.27 min.; HPLC (Method A but with a 30 min rather than a 15 min gradient) ret. t.=14.57 min; 500 MHz $^1$H NMR (CD$_3$OD) δ 9.46 (s, 1H), 8.29 (s, 2H), 7.43 (s, 1H), 6.87 (s, 1H), 6.51 (s, 1H,), 6.31 (brs, 1H), 4.74 (d, 1H, J=10.4 Hz), 4.17 (brs, 1H), 3.94-3.86 (m, 1H), 3.70 (dd, 1H, J=4.0, 11.6 Hz), 3.33 (s, 3H), 2.57 (d, 1H, J=14.0 Hz), 2.51-2.45 (m, 1H), 1.87-1.78 (m, 1H), 0.96-0.90 (m, 2H), 0.79-0.72 (m, 1H), 0.71-0.64 (m, 1H). Note that during preparative HPLC, a lesser amount of the earlier eluting C-2 proline ring epimer can be obtained similarly.

Example 256

(2S,4S)-1-(4-(5-cyclopropyl-1H-pyrazol-3-ylamino)pyrrolo[1,2-f][1,2,4]triazin-2-yl)-4-methoxy-N-(1,2,4-thiadiazol-5-yl)pyrrolidine-2-carboxamide

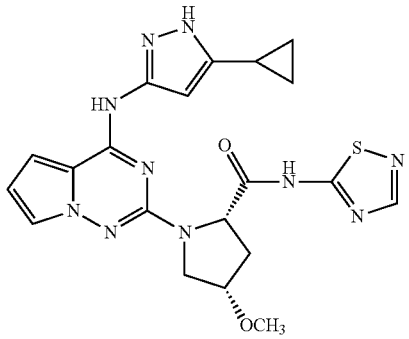 [SMILES: CO[C@H]1C[C@@H](C(=O)Nc2ncns2)N(c2nc(Nc3cc(C4CC4)[nH]n3)c3cccn3n2)C1]

A cold solution of 5-amino-1,2,4-thiadiazole (532 mg, 5.26 mmol) in dry THF (20 mL) under nitrogen at 0° C. is treated slowly with stirring with isopropylmagnesium chloride (2.0 M in THF; 2.50 mL, 5.0 mmol). After 10-15 min, the compound of Example 253 is added (235 mg, 0.591 mmol) and the mixture is stirred at rt for 18 h. A cold solution of TFA (455 μL) in methanol (8 mL) is added and the mixture is then purified by preparative HPLC (using 20% solvent B to 80% solvent B over 11 min). The desired fractions containing the product (ret t=10.22 min) are processed to the title compound, obtained as its free base, using a 1 gram (20 cc) Waters Oasis® MCX Extraction Cartridge following the general method described above, to give 112 mg (41%) of the pure title compound of Example 256 as a solid: MS: 467 (M+H)$^+$, LC/MS ret. t=2.44 min.; HPLC (Method A) ret. t.=10.01 min; 500 MHz $^1$H NMR (CD$_3$OD) δ.8.29 (s, 1H), 7.44-7.41 (m, 1H), 6.87 (d, 1H, J=4.3 Hz), 6.51 (dd, 1H, J=2.4, 4.3 Hz), 6.16 (brs, 1H), 4.96-4.90 (m, 1H), 4.16 (brs, 1H), 3.34-3.39 (m, 3H), 3.9 (d, 1H, J=12.2 Hz), 1.03 (dd, 1H, J=3.7, 11.6 Hz), 2.58-2.46 (m, 2H), 1.89-1.76 (m, 1H), 0.98-0.91 (m, 2H), 0.75-0.68 (m, 2H). Note that during preparative HPLC, a lesser amount of the earlier eluting C-2 proline ring epimer can be obtained similarly.

Example 257

(2S,4S)-4-hydroxy-1-(4-(5-(1-methylcyclopropyl)-1H-pyrazol-3-ylamino)pyrrolo[1,2-f][1,2,4]triazin-2-yl)pyrrolidine-2-carboxylic acid

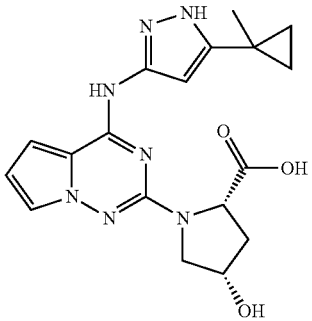 [SMILES: CC1(c2cc(Nc3nc(N4C[C@@H](O)C[C@H]4C(=O)O)nn4cccc34)n[nH]2)CC1]

To solid (2S,4S)-4-hydroxypyrrolidine-2-carboxylic acid (8.38 g, 63.9 mmol) in a 100 mL pressure bottle is added NMP (35 mL) followed by 5 M NaOH (12.8 mL, 64.0 mmol). N,N-diisopropylethylamine (1.31 mL, 7.52 mmol) is added and the stirred mixture is treated with the compound from Example 194A (1.88 g, 6.51 mmol). The vessel is flushed with nitrogen, sealed, and heated at 135° C. for 27 h. The crude reaction mixture is cooled to rt and then poured into water (250 mL) and slowly treated with aqueous 1.0 N HCl (75 mL,) to pH 2-3 to give a precipitate, which is filtered, washed with diethyl ether (3×15 mL), and dried under high vacuum to give 518 mg (21%) of the title compound of Example 257 as a solid. The water filtrate is extracted with ethyl acetate (5×300 mL), the organic layers are combined, washed with water (75 mL), brine (50 mL), dried over sodium sulfate and evaporated in vacuo to give a thick oil that contains the remainder of the product wet with NMP; MS: 384 (M+H)$^+$, LC/MS ret. t=2.26 min.

Example 258

(1S,4R)-5-(4-(5-(1-methylcyclopropyl)-1H-pyrazol-3-ylamino)pyrrolo[1,2-f][1,2,4]triazin-2-yl)-2-oxa-5-azabicyclo[2.2.1]heptan-3-one

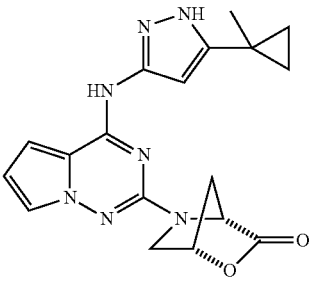

A mixture of the compound from Example 257 (2.45 g, 6.4 mmol) in dry THF (100 mL) is treated sequentially with 1-hydroxy-7-aza-benzotriazole (222 mg), N-methylmorpholine (2.46 mL, 22.4 mmol), and 1-[3-(dimethylamino)propyl]-3-ethylcarbodiimide hydrochloride (1.29 g, 6.72 mmol). The reaction is stirred at rt for 20 min, heated to reflux under nitrogen for 1.5 h then stirred at rt for 18 h. The volatiles are evaporated in vacuo and the crude material is dissolved in ethyl acetate (600 mL). The organic layer is washed with water (6×200 mL) and brine (200 mL), and dried (Na$_2$SO$_4$). Concentration in vacuo gives 2.38 g of the title compound of Example 258 as a solid which is used directly as described below without further purification: MS: 366 (M+H)$^+$, LC/MS ret. t=2.40 min.

Example 259

(2S,4S)-4-hydroxy-1-(4-(5-(1-methylcyclopropyl)-1H-pyrazol-3-ylamino)pyrrolo[1,2-f][1,2,4]triazin-2-yl)-N-(pyrazin-2-yl)pyrrolidine-2-carboxamide

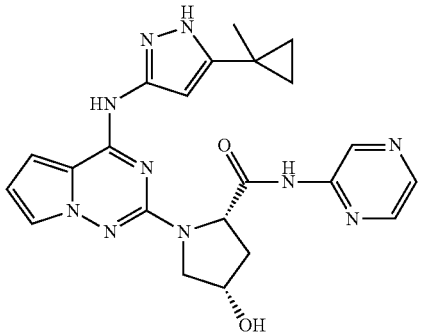 [SMILES: CC1(c2cc(Nc3nc(N4C[C@@H](O)C[C@H]4C(=O)Nc4cnccn4)nn4cccc34)n[nH]2)CC1]

A cold solution of 2-aminopyrazine (2.1 g, 22.1 mmol) in dry THF (40 mL) under nitrogen at 0° C. is treated slowly with stirring with isopropylmagnesium chloride (2.0 M in THF; 10.5 mL, 21.0 mmol). After 20 min, the compound of Example 258 is added (634 mg, 1.74 mmol) and the mixture is stirred at rt for 30 min. A cold solution of TFA (1.7 mL) in methanol (15 mL) is added and the mixture is then purified by preparative HPLC (using 20% solvent B to 80% solvent B over 11 min). The desired fractions containing the product (ret t=10.1 min) are processed to the title compound, obtained as its free base using a 5 gram (60 cc) Phenomenex strata-XL-C cartridge following the general method described above, to give 238 mg (30%) of the pure title compound of Example 259 as a solid: MS: 461 (M+H)$^+$, LC/MS ret. t=2.14 min.; HPLC (Method A but with a 30 min rather than a 15 min gradient) ret. t.=13.24 min; 500 MHz $^1$H NMR (d$_6$-DMSO) δ 12.07 (brs, 1H), 10.34 (s, 1H), 9.91 (s, 1H), 9.41 (d, 1H, J=1.2 Hz), 8.41-8.36 (m, 2H), 7.49-7.47 (m, 1H), 7.19 (brs, 1H), 6.52-6.46 (m, 2H), 5.26 (brs, 1H), 4.70 (dd, 1H, J=1.8, 9.8 Hz), 4.49-4.44 (m, 1H), 3.76-3.66 (m, 2H), 2.59-2.51 (m, 1H), 2.20 (d, 1H, J=13.1 Hz), 1.41 (s, 3H), 0.97-0.90 (m. 2H), 0.78-0.73 (m, 2H).

Example 260

(2S,4S)-N-(6-fluoropyridin-3-3-yl)-4-hydroxy-1-(4-(5-(1-methylcyclopropyl)-1H-pyrazol-3-ylamino)pyrrolo[L2-f][1,2,4]triazin-2-yl)pyrrolidine-2-carboxamide

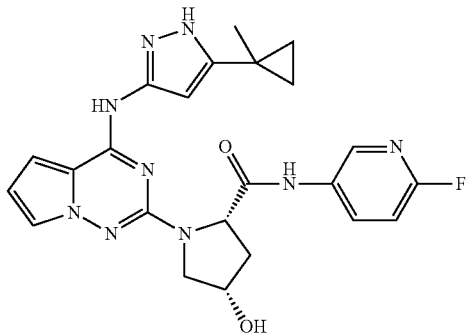 [SMILES: CC1(c2cc(Nc3nc(N4C[C@@H](O)C[C@H]4C(=O)Nc4ccc(F)nc4)nn4cccc34)n[nH]2)CC1]

A cold solution of 2-fluoro-5-aminopyridine (695 mg, 6.2 mmol) in dry THF (12 mL) under nitrogen at 0° C. is treated slowly with stirring with isopropylmagnesium chloride (2.0 M in THF; 3.02 mL, 6.04 mmol). After 10-15 min, the compound of Example 258 is added (171 mg, 0.468 mmol) and the mixture is stirred at rt for 45 min. A cold solution of TFA (310 μL) in methanol (10 mL) is added and the mixture is then purified by preparative HPLC (using 15% solvent B to 85% solvent B over 11 min). The desired fractions containing the product (ret t=10.07 min) are processed to the title compound, obtained as its free base, using a 1 gram (20 cc) Phenomenex Strata-XL-C Extraction Cartridge, following the general method described above, to give 147 mg (66%) of the pure title compound of Example 260 as a solid: MS: 478 (M+H)$^+$, LC/MS ret. t=2.13 min.; HPLC (Method A but with a 20 min rather than a 15 min gradient) ret. t.=11.25 min. 500 MHz $^1$H NMR (CD$_3$OD) δ.8.28 (s, 1H), 8.04-7.97 (m, 1H), 7.40 (s, 1H), 6.97 (dd, 1H, J=2.8, 8.9 Hz), 6.86 (d, 1H), 6.49 (s, 1H), 6.38 (s, 1H), 4.78-4.72 (m, 1H), 4.56-4.52 (m, 1H), 3.78-3.69 (m, 2H), 2.55-2.45 (m, 1H), 2.41-2.33 (m, 1H), 1.36 (s, 3H), 0.92-0.82 (m, 2H), 0.74-0.67 (m, 2H).

Example 261

(2S,4S)-N-(5-chlorothiazol-2-yl)-4-hydroxy-1-(4-(5-(1-methylcyclopropyl)-1H-pyrazol-3-ylamino)pyrrolo[1,2-f][1,2,4]triazin-2-yl)pyrrolidine-2-carboxamide

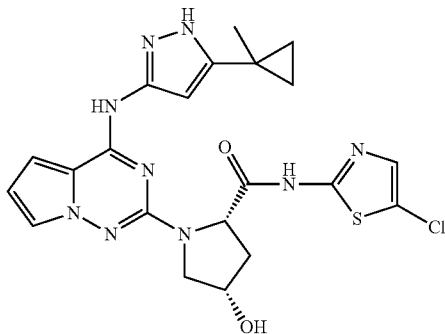 [SMILES: CC1(c2cc(Nc3nc(N4C[C@@H](O)C[C@H]4C(=O)Nc4ncc(Cl)s4)nn4cccc34)n[nH]2)CC1]

A cold solution of 2-amino-5-chlorothiazole hydrochloride (1.56 g, 9.1 mmol) in dry THF (20 mL) under nitrogen at 0° C. is treated slowly with stirring with isopropylmagnesium chloride (2.0 M in THF; 9.0 mL, 18.0 mmol). After 10-15 min, the compound of Example 258 is added (171 mg, 0.468 mmol) and the mixture is stirred at rt for 18 h. A cold solution of TFA (1.5 mL) in methanol (5 mL) is added and the mixture is then purified by preparative HPLC (using 40% solvent B to 100% solvent B over 12 min). The desired fractions containing the product (ret t=9.6 min). are processed to the title compound, obtained as its free base, using a 1 gram (20 cc) Phenomenex Strata-XL-C Extraction Cartridge, following the general method described above, to give 138 mg (59%) of the pure title compound of Example 261 as a solid: MS: 500, 502 (M+H)$^+$, LC/MS ret. t=2.57 min.; HPLC (Method A but with a 20 min rather than a 15 min gradient) ret. t.=13.31 min. 500 MHz $^1$H NMR (CD$_3$OD) δ 7.42-7.37 (m, 1H), 7.25 (s, 1H), 6.88-6.80 (m, 1H), 6.52-6.44 (m, 1H), 6.30 (brs, 1H), 4.85-4.77 (m, 1H), 4.53 (brs, 1H), 3.79-3.69 (m, 2H), 2.57-2.45 (m, 1H), 2.34 (d, 1H, J=13.4 Hz), 1.41 (s, 3H), 0.96-0.87 (m, 2H), 0.77-0.72 (m, 2H).

Example 262

(2S,4R)-methyl 1-(4-(5-cyclopropyl-1H-pyrazol-3-ylamino)pyrrolo[1,2-f][1,2,4]triazin-2-yl)-4-methoxypyrrolidine-2-carboxylate

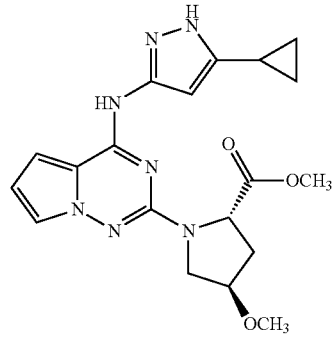 [SMILES: COC(=O)[C@@H]1C[C@@H](OC)CN1c1nc(Nc2cc(C3CC3)[nH]n2)c2cccn2n1]

The compound from Example 218B (4.36 mmol) is dissolved in methanol (350 mL) and treated with 1-hydroxy-7-aza-benzotriazole (250 mg and 1-[3-(dimethylamino)propyl]-3-ethylcarbodiimide hydrochloride (836 mg, 4.36 mmol). The reaction is stirred at room temperature for 5.5 h, concentrated in vacuo, and extracted with ethyl acetate (500 mL). The ethyl acetate layer is washed with water (3×150 mL) and brine (150 mL), and dried (Na$_2$SO$_4$). The solvent is evaporated in vacuo and the solid obtained as the title compound of Example 262 is used directly as described below: MS: 398 (M+H)$^+$, LC/MS ret. t=2.28 min.

Example 263

(2S,4R)-1-(4-(5-cyclopropyl-1H-pyrazol-3-ylamino)pyrrolo[1,2-f][1,2,4]triazin-2-yl)-4-methoxy-N-(pyrazin-2-yl)pyrrolidine-2-carboxamide

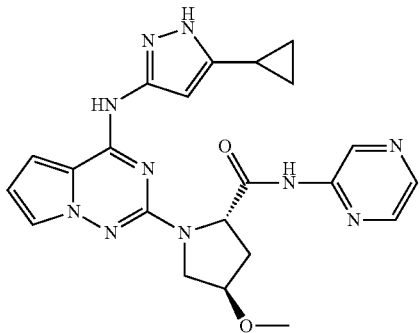 [SMILES: CO[C@@H]1C[C@@H](C(=O)Nc2cnccn2)N(c2nc(Nc3cc(C4CC4)[nH]n3)c3cccn3n2)C1]

A cold solution of 2-aminopyrazine (3.5 g, 36.3 mmol) in dry THF (200 mL) under nitrogen at 0° C. is treated slowly with stirring with isopropylmagnesium chloride (2.0 M in THF; 18.0 mL, 36.0 mmol). After 20 min, the compound of Example 262 is added (1.2 g, 3.02 mmol) and the mixture is stirred at rt for 1 h then warmed to 40° C. for 1.5 h. A cold solution of TFA (3.1 mL) in methanol (40 mL) is added and the mixture is then purified by preparative HPLC (using 16% solvent B to 87% solvent B over 11 min). The desired fractions containing the product (ret t=9.45 min) are processed to the title compound, obtained as its free base using a 6 gram (35 cc) Waters Oasis® MCX Extraction Cartridge, following the general method described above, to give 735 mg (53%) of the pure title compound of Example 263; MS: 461 (M+H)$^+$, LC/MS ret. t=2.17 min; HPLC (Method A but with a 20 min rather than a 15 min gradient) ret. t.=15.84 min; 500 MHz $^1$H NMR (d$_6$-DMS)) δ 12.01 (brs, 1H), 10.79 (s, 1H), 10.20 (s, 1H), 9.23 (s, 1H), 8.40-8.31 (m, 2H), 7.35 (brs, 1H), 7.10 (brs, 1H), 6.45 (brs, 1H), 6.39 (brs, 1H), 4.77 (brs, 1H), 4.13-4.08 (m, 1H), 3.77-3.73 (m, 2H), 3.28 (s, 3H), 2.51-2.48 (m, 1H), 2.22-2.15 (m, 1H), 1.78 (brs, 1H), 0.88-0.74 (m, 2H), 0.67-0.60 (m, 2H).

Example 264

(2S,4R)-4-fluoro-1-(4-(5-(1-methylcyclopropyl)-1H-pyrazol-3-ylamino)pyrrolo[1,2-f][1,2,4]triazin-2-yl)pyrrolidine-2-carboxylic acid

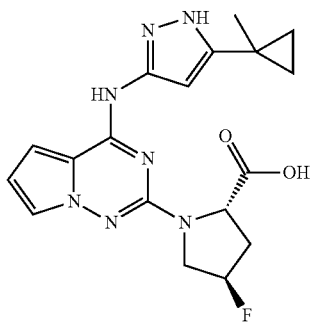 [SMILES: CC1(c2cc(Nc3nc(N4C[C@H](F)C[C@H]4C(=O)O)nn4cccc34)n[nH]2)CC1]

To solid (2S,4R)-4-fluoropyrrolidine-2-carboxylic acid (3.15 g, 23.7 mmol) in a 100 mL pressure bottle is added NMP (15 mL) followed by 5 M NaOH (4.7 mL, 23.5 mmol). N,N-diisopropylethylamine (4.13 mL, 23.7 mmol) is added and the stirred mixture is treated with the compound from Example 194A (1.88 g, 6.51 mmol). The vessel is flushed with nitrogen, sealed, and heated at 135° C. for 72 h. The crude reaction mixture is cooled and poured into water (300 mL) and dichloromethane (200 mL). The organic layer is removed and the aqueous layer is extracted with additional dichloromethane (1×50 mL). The aqueous layer is acidified with 1.0 N HCl (26.5 mL) to pH 2-3 and extracted with ethyl acetate (2×400 mL). The ethyl acetate layers are combined, washed with water (2×50 mL) and brine (50 mL), dried (Na$_2$SO$_4$) and evaporated in vacuo to give a thick oil that contains the title compound of Example 264, wet with NMP, which was used directly as described below; MS: 386 (M+H)$^+$, LC/MS ret. t=2.55 min.

Example 265

(2S,4R)-methyl 4-fluoro-1-(4-(5-(1-methylcyclopropyl)-1H-pyrazol-3-ylamino)pyrrolo[1,2-f][1,2,4]triazin-2-yl)pyrrolidine-2-carboxylate

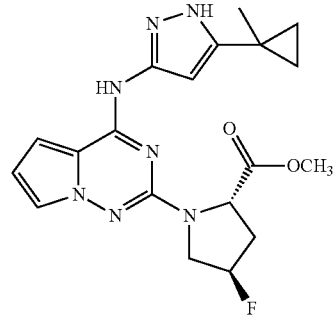 [SMILES: COC(=O)[C@@H]1C[C@@H](F)CN1c1nc(Nc2cc(C3(C)CC3)[nH]n2)c2cccn2n1]

Material from Example 264 (1.58 mmol) is dissolved in methanol (300 mL) and treated with 1-hydroxybenzotriazole hydrate (107 mg), and 1-[3-(dimethylamino)propyl]-3-ethyl-carbodiimide hydrochloride (319 mg, 1.66 mmol). The reaction is stirred at room temperature for 1.5 h, concentrated in vacuo, and extracted with ethyl acetate (750 mL). The ethyl acetate layer is washed with water (5×150 mL) and brine (750 mL), dried (Na$_2$SO$_4$) and evaporated in vacuo to give 740 mg of the title compound of Example 265 that is used below without further purification; MS: 400 (M+H)$^+$, LC/MS ret. t=2.70 min.

Example 266

(2S,4R)-4-fluoro-1-(4-(5-(1-methylcyclopropyl)-1H-pyrazol-3-ylamino)pyrrolo[1,2-f][1,2,4]triazin-2-yl)-N-(pyrazin-2-yl)pyrrolidine-2-carboxamide

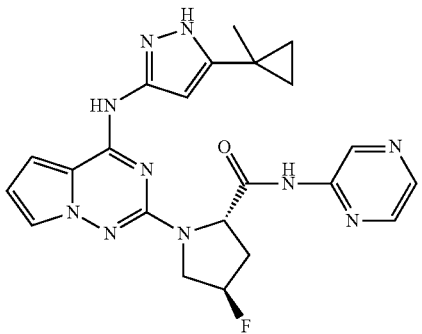 [SMILES: CC1(c2cc(Nc3nc(N4C[C@H](F)C[C@H]4C(=O)Nc4cnccn4)nn4cccc34)n[nH]2)CC1]

A cold solution of 2-aminopyrazine (280 mg, 2.95 mmol) in dry THF (20 mL) under nitrogen at 0° C. is treated slowly with stirring with isopropylmagnesium chloride (2.0 M in THF; 1.3 mL, 2.6 mmol). After 20 min, the compound of Example 265 (0.227 mmol) is added and the mixture is stirred at rt for 55 min. A cold solution of TFA (215 μL) in methanol (10 mL) is added and the mixture is then purified by preparative HPLC (using 20% solvent B to 95% solvent B over 11 min). The desired fractions containing the product (ret t=9.27 min) are processed to the title compound, obtained as its free base using a 1 gram (20 cc) Waters Oasis® MCX Extraction Cartridge, following the general method described above, to give 61.3 mg (59%) of the pure title compound of Example 266; MS: 463 (M+H)$^+$, LC/MS ret. t=2.42 min; HPLC (Method A but with a 30 min rather than a 15 min gradient) ret. t.=16.10 min; 500 MHz $^1$H NMR (CD$_3$OD) δ 9.30 (brs, 1H), 8.38-8.26 (m, 2H), 7.36 (brs, 1H), 6.83 (brs, 1H), 6.52-6.36 (m, 2H), 5.43 (d, 1H, J=52.2 Hz), 4.89-4.83 (m, 1H), 4.33-4.19 (m, 1H), 3.99-3.83 (m, 1H), 2.84-2.69 (m, 1H), 2.50-2.33 (m, 1H), 1.41 (s, 3H), 0.97-0.86 (m, 2H), 0.80-0.70 (m, 2H).

Example 267

(2S,4R)-4-methoxy-1-(4-(5-(1-methylcyclopropyl)-1H-pyrazol-3-ylamino)pyrrolo[1,2-f][1,2,4]triazin-2-yl)pyrrolidine-2-carboxylic acid

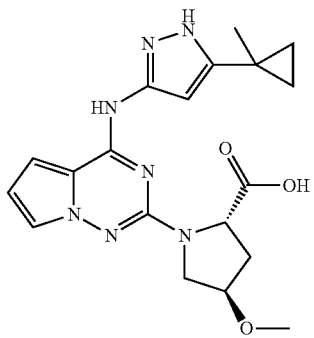 [SMILES: CO[C@@H]1C[C@@H](C(=O)O)N(c2nc(Nc3cc(C4(C)CC4)[nH]n3)c3cccn3n2)C1]

To solid (2S,4R)-4-methoxypyrrolidine-2-carboxylic acid HCl salt, 218A (7.85 g, 43.3 mmol) in a 150 mL pressure bottle is added NMP (40 mL) followed by 5 M NaOH (16.96 mL, 84.80 mmol). N,N-diisopropylethylamine (1.81 mL, 10.4 mmol) is added and the stirred mixture is treated with the compound from Example 194A (2.50 g, 8.65 mmol). The vessel is flushed with nitrogen, sealed, and heated at 135° C. for 20 h and then stirred at rt for 72 h. The crude reaction mixture is cooled and poured into water (250 mL) and acidified with 1.0 N HCl (46.5 mL) to pH 2-3. The resulting solid is collected by filtration and dried in vacuo to obtain 2.38 g (69.4%) of the product of Example 267. The aqueous layer is extracted with ethyl acetate (3×300 mL). The ethyl acetate layers are combined, washed with brine (50 mL), dried (Na$_2$SO$_4$), and evaporated in vacuo to give a thick oil that contains additional title compound of Example 267, wet with NMP. This thick oil was used directly as described below in Example 268; MS: 398 (M+H)$^+$, LC/MS ret. t=2.41 min.

Example 268

(2S,4R)-methyl 4-methoxy-1-(4-(5-(1-methylcyclopropyl)-1H-pyrazol-3-ylamino)pyrrolo[1,2-f][1,2,4]triazin-2-yl)pyrrolidine-2-carboxylate

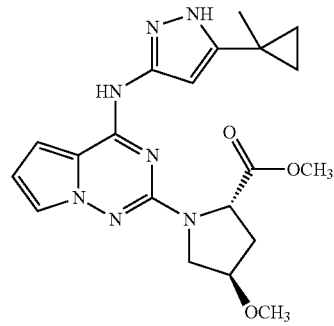 [SMILES: COC(=O)[C@@H]1C[C@@H](OC)CN1c1nc(Nc2cc(C3(C)CC3)[nH]n2)c2cccn2n1]

Using the procedure as described in Example 262, the thick oil from Example 267 is converted to the title compound of Example 268 that is used below without further purification; MS: 412 (M+H)$^+$, LC/MS ret. t=2.74 min.

Example 269

(2S,4R)-4-methoxy-1-(4-(5-(1-methylcyclopropyl)-1H-pyrazol-3-ylamino)pyrrolo[1,2-f][1,2,4]triazin-2-yl)-N-(pyrazin-2-yl)pyrrolidine-2-carboxamide

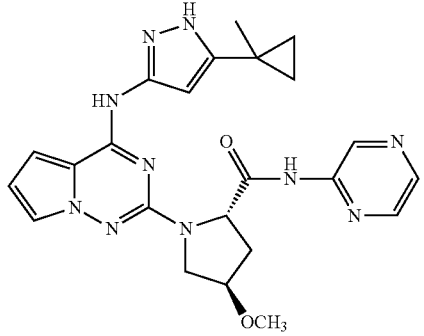 [SMILES: CO[C@@H]1C[C@@H](C(=O)Nc2cnccn2)N(c2nc(Nc3cc(C4(C)CC4)[nH]n3)c3cccn3n2)C1]

Using the procedure as described in Example 266, the compound from Example 268 is converted to the title compound of Example 269 in 61% yield; MS: 475 (M+H)$^+$, LC/MS ret. t=2.43 min.; HPLC (Method A but with a 20 min rather than a 15 min gradient) ret. t.=11.77 min; 500 MHz $^1$H NMR (CD$_3$OD) δ 9.32 (s, 1H), 8.32 (brs, 1H), 8.28 (d, 1H, J=2.4 Hz), 7.37 (s, 1H), 6.84 (s, 1H), 6.48 (s, 1H), 6.42 (brs, 1H), 4.78 (t, 1H, J=7.5 Hz), 4.23-4.18 (m, 1H), 3.98-3.93 (m, 1H), 3.90-3.83 (m, 1H), 3.41 (s, 3H), 2.55-2.47 (m, 1H), 2.42-2.33 (m, 1H), 1.39 (s, 3H), 0.93-0.87 (m, 2H), 0.77-0.70 (m, 2H).

Example 270

(2S,4R)-1-(4-(1-isopropyl-1H-imidazol-4-ylamino)pyrrolo[1,2-f][1,2,4]triazin-2-yl)-4-methoxypyrrolidine-2-carboxylic acid

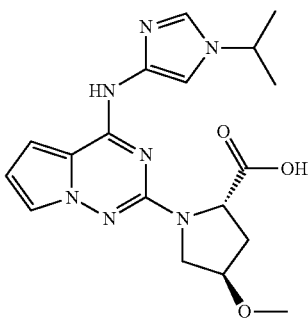 [SMILES: CO[C@@H]1C[C@@H](C(=O)O)N(c2nc(Nc3cn(C(C)C)cn3)c3cccn3n2)C1]

A mixture of the compound from Example 228B (154 mg, 0.556 mmol). and (2S,4R)-4-methoxypyrrolidine-2-carboxylic acid HCl salt, 218A (984 mg, 5.42 mmol) in a 15 mL pressure bottle is treated with NMP (5 mL) followed by 5 M NaOH (2.14 mL, 10.7 mmol). N,N-diisopropylethylamine (140 μL, 0.811 mmol) is then added and the stirred mixture is flushed with nitrogen, sealed, and heated at 135° C. for 15 h. The reaction mixture is then purified by preparative HPLC (using 10% solvent B to 80% solvent B over 11 min). The desired fractions containing the product (ret t=8.69 min) are evaporated to dryness to give 187 mg of the title compound (possible TFA salt) of Example 270 which is used directly as described below; MS: 386 (M+H)+, LC/MS ret. t=1.68 min.

Example 271

(2S,4R)-N-(6-fluoropyridin-3-yl)-1-(4-(1-isopropyl-1H-imidazol-4-ylamino)pyrrolo[1,2-f][1,2,4]triazin-2-yl)-4-methoxypyrrolidine-2-carboxamide

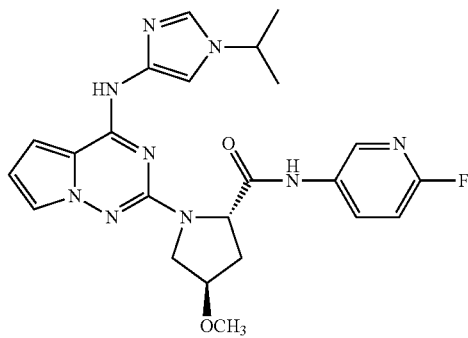 [SMILES: CO[C@@H]1C[C@@H](C(=O)Nc2ccc(F)nc2)N(c2nc(Nc3cn(C(C)C)cn3)c3cccn3n2)C1]

The compound from Example 270 (85 mg, 0.221 mmol), 2-fluoro-5-aminopyridine (336 mg), and 1-hydroxy-7-azabenzotriazole (34 mg) is treated sequentially with NMP (4 mL), 1-[3-(dimethylamino)propyl]-3-ethylcarbodiimide hydrochloride (52 mg), and N-methylmorpholine (242 μL). The reaction is stirred at rt for 4 h, and at 45° C. for 45 min, and then purified by preparative HPLC (using 15% solvent B to 80% solvent B over 11 min). The desired fractions containing the product (ret t=8.30 min) are processed to the title compound, obtained as its free base, using a 1 gram (20 cc) Waters Oasis® MCX Extraction Cartridge, following the general method described above, to give 45.8 mg of the pure title compound (43%) as a solid: MS: 480 (M+H)+, LC/MS ret. t=1.76 min.; HPLC (Method A but with a 20 min rather than a 15 min gradient) ret. t.=12.94 min; 500 MHz $^1$H NMR (CD$_3$OD) δ 8.30 (s, 1H), 8.05-7.98 (m, 1H), 7.49 (s, 1H), 7.43 (s, 1H), 7.36 (s, 1H), 6.98 (dd, 1H, J=2.8, 8.9 Hz), 6.84 (brs, 1H), 6.47 (dd, 1H, J=2.6, 4.4 Hz), 4.68 (t, 1 H, J=7.80 Hz), 4.37-4.30 (m, 1H), 4.21-4.16 (m, 1H), 3.98-3.93 (m, 1H), 3.92-3.87 (m, 1H), 3.39 (s, 3H), 2.57-2.50 (m, 1H), 2.34-2.27 (m, 1H), 1.43 (d, 6H, J=6.7 Hz).

Example 272

(S)-methyl 1-(4-(5-carbamoyl-1H-pyrazol-3-ylamino)pyrrolo[1,2-f][1,2,4]triazin-2-yl)-2-methylpyrrolidine-2-carboxylate

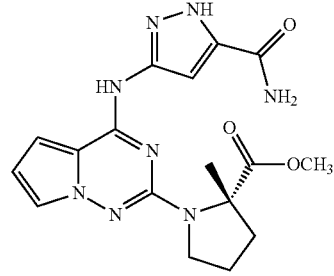 [SMILES: COC(=O)[C@]1(C)CCCN1c1nc(Nc2cc(C(N)=O)[nH]n2)c2cccn2n1]

The compound from Example 179 (8.1 mmol) is dissolved in methanol (300 mL) and treated with 1-hydroxy-7-azabenzotriazole (540 mg and 1-[3-(dimethylamino)propyl]-3-ethylcarbodiimide hydrochloride (1.73 g). The reaction is stirred at room temperature for 18 h, concentrated in vacuo, and partitioned with ethyl acetate (350 mL) and water (300 mL). The ethyl acetate layer is washed with water (2×100 mL) and brine (100 mL), and dried (Na$_2$SO$_4$). The solvent is evaporated in vacuo and the residue is purified by silica gel chromatography using a Biotage instrument (see above for general details) with a Flash 65+M cartridge using a gradient from 100% dichloromethane to 10% methanol in dichloromethane. The desired fractions containing the product were evaporated in vacuo to give 726 mg (23%) of the pure title compound as a solid which is used directly as described below. In addition, there is obtained 386 mg of less pure title compound: MS: 385 (M+H)+, LC/MS ret. t=2.41 min.

Example 273

(S)-methyl 1-(4-(5-cyano-1H-pyrazol-3-ylamino)pyrrolo[1,2-f][1,2,4]triazin-2-yl)-2-methylpyrrolidine-2-carboxylate

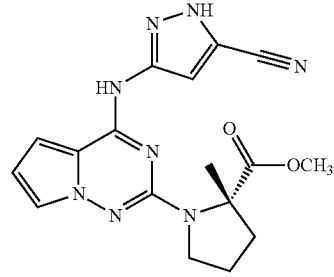 [SMILES: COC(=O)[C@]1(C)CCCN1c1nc(Nc2cc(C#N)[nH]n2)c2cccn2n1]

219

The compound from Example 272 (256 mg, 0.665 mmol) and imidazole (146.5 mg, 2.154 mmol) is dissolved in anhydrous pyridine (4 mL), cooled to −10° C., and phosphorous oxychloride (350 μL, 3.82 mmol) is then added over 1 min. The reaction is stored at −20° C. overnight, warmed to rt over 15 min, and poured onto 10 g of ice. Methanol (60 mL) is then added, the mixture was partially concentrated in vacuo, and then purified by preparative reverse phase HPLC using a Waters X-Bridge Prep C18 30×100 mm, 5 micron column, with linear gradient elution using the a ratio of 88% solvent C (5% acetonitrile-95% Water-10 mmol ammonium acetate). and 85% solvent D (90% acetonitrile-10% Water-10 mmol ammonium acetate). over 11 min with a flow rate of 35 mL/min. The desired fractions containing the product (ret t=9.6 min) are processed to the title compound, obtained as its free base, by extraction with ethyl acetate (700 mL), followed by washing with water (40 mL) and brine (100 mL), drying over $Na_2SO_4$, and concentration in vacuo to give 198.7 mg (82%) of the pure title compound as a solid; MS: 367 (M+H)$^+$, LC/MS ret. t=2.66 min.

Example 274

(S)-1-(4-(5-cyano-1H-pyrazol-3-ylamino)pyrrolo[1,2-f][1,2,4]triazin-2-yl)-N-(6-fluoropyridin-3-yl)-2-methylpyrrolidine-2-carboxamide

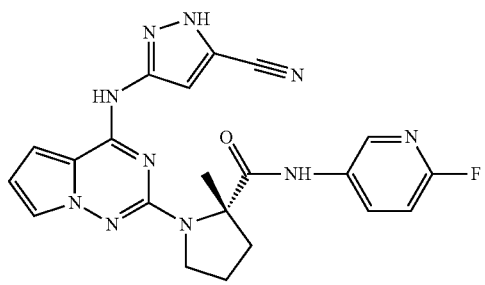 [SMILES: C[C@@]1(C(=O)Nc2ccc(F)nc2)CCCN1c1nc(Nc2cc(C#N)[nH]n2)c2cccn2n1]

A cold solution of 2-fluoro-5-aminopyridine (270 mg, 2.41 mmol) in dry THF (5 mL) under nitrogen at 0° C. is treated slowly with stirring with isopropylmagnesium chloride (2.0 M in THF; 1.08 mL, 2.0 mmol). After 10 min, the compound of Example 273 is added (72 mg, 0.197 mmol) and the mixture is stirred at rt for 21 h. A cold solution of TFA (176 μL) in methanol (5 mL) is added and the mixture is then purified by preparative reverse phase HPLC using a Waters X-Bridge Prep C18 30×100 mm, 5 micron column, with linear gradient elution using the a ratio of 88% solvent C (5% acetonitrile-95% Water-10 mmol ammonium acetate). and 83% solvent D (90% acetonitrile-10% Water-10 mmol ammonium acetate). over 11 min with a flow rate of 35 mL/min. The desired fractions containing the product (ret t=8.9 min) are processed to the title compound, obtained as its free base, by extraction with ethyl acetate (170 mL), followed by washing with water (10 mL) and brine (100 mL), drying over $Na_2SO_4$, and concentration in vacuo to give 60.1 mg (68%) of the pure title compound as a solid; MS: 447 (M+H)$^+$, LC/MS ret. t=2.47 min. HPLC (Method A but with a 20 min rather than a 15 min gradient) ret. t.=14.85 min; IR (KBr) 2243 cm$^{-1}$; 500 MHz $^1$H NMR (CD$_3$OD) δ 8.22 (s, 1H), 8.14-8.06 (m, 1H), 7.45 (s, 1H), 6.95 (dd, 1H, J=2.7, 8.9 Hz), 6.87 (brs, 1H), 6.54 (brs, 1H), 6.47 (brs, 1H), 3.99-3.89 (m, 1H), 3.78-3.70 (m, 1H), 2.46-2.38 (m, 1H), 2.21-2.08 (m, 3H), 1.67 (s, 3H).

220

Example 275

(2S,4S)-ethyl 1-(4-(5-cyclopropyl-1H-pyrazol-3-ylamino)pyrrolo[1,2-f][1,2,4]triazin-2-yl)-4-hydroxypyrrolidine-2-carboxylate

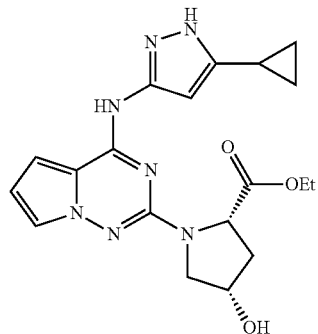 [SMILES: CCOC(=O)[C@@H]1C[C@H](O)CN1c1nc(Nc2cc(C3CC3)[nH]n2)c2cccn2n1]

The compound from Example 208B (2.5 mmol) is dissolved in absolute ethanol (100 mL) and THF (50 mL). Triethylamine (9 mL) and magnesium ethoxide (2.65 g, 23.2 mmol) is added and the mixture is refluxed for 30-45 min and the solvent is evaporated in vacuo. The residue is partitioned with ethyl acetate (300 mL). and aqueous citric acid solution (pH 2, 300 mL). The ethyl acetate layer is washed with water (200 mL) and brine (200 mL), and dried (Na$_2$SO$_4$). The solvent is evaporated in vacuo and the residue is purified by silica gel chromatography using a Biotage instrument (see above for general details) with a Flash 40+M cartridge using a gradient from 100% dichloromethane to 100% ethyl acetate. The desired fractions containing the product were evaporated in vacuo to give 838 mg (85%) of the title compound which is used directly as described below: MS: 398 (M+H)$^+$, LC/MS ret. t=2.27 min.

Example 276

((2S,4R)-ethyl 4-chloro-1-(4-(5-cyclopropyl-1H-pyrazol-3-ylamino)pyrrolo[1,2-f][1,2,4]triazin-2-yl) pyrrolidine-2-carboxylate (major isomer) and (2S,4S)-ethyl 4-chloro-1-(4-(5-cyclopropyl-1H-pyrazol-3-ylamino)pyrrolo[1,2-f]-1,2,4]-triazin-2-yl) pyrrolidine-2-carboxylate (minor isomer)

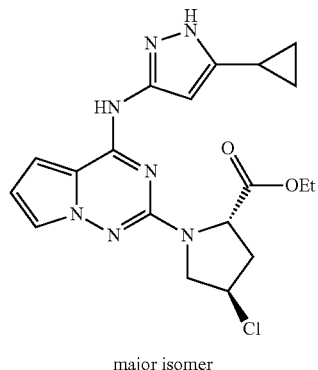

major isomer

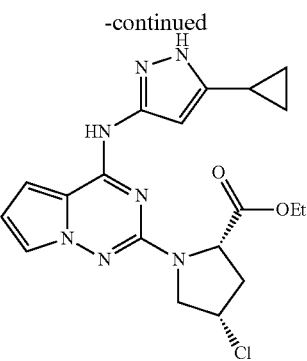

minor isomer

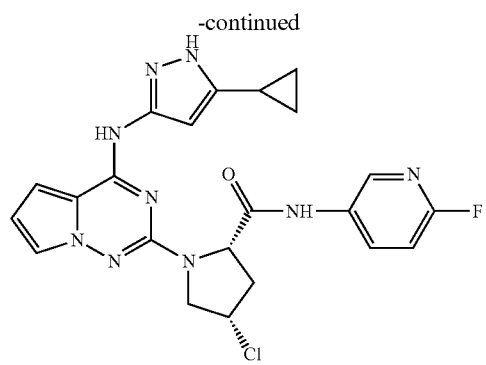

minor isomer

The compound from Example 275 (525 mg, 1.32 mmol) in dry pyridine (7 mL) is cooled under nitrogen to 0° C. and treated slowly over 30 min with methanesulfonyl chloride (0.75 mL, 9.70 mmol). The reaction is warmed to rt overnight, the solvent is evaporated in vacuo and the residue is partitioned with ethyl acetate (165 mL), water (45 mL), and brine (30 mL). The organic layer is washed with water and brine and dried ($Na_2SO_4$). The solvent is evaporated in vacuo and the residue is dissolved in dichloromethane, evaporated in vacuo, and dried under high vacuum. The residue is dissolved in dry dichloromethane (8 mL), transferred to a 50 mL pressure bottle, flushed with nitrogen and treated with tetrabutylammonium cyanide (2.00 g, 7.46 mmol). The reaction is heated at 50° C. for 1.5 h, most of the solvent is removed under a stream of nitrogen, and dry DMF (4 mL) was then added. The reaction mixture is heated at 85° C. for 17 h, cooled, and partitioned with ethyl acetate (150 mL), water (60 mL), and brine (30 mL). The organic layer is washed with water (5×60 mL) and brine (2×100 mL) and dried ($MgSO_4$). The solvent is evaporated in vacuo and the residue is dissolved in THF, evaporated in vacuo, and dried under high vacuum to give about 1 g of approximately a 2.5:1 mixture of the crude the title compounds which are not separated but used directly as described below; MS: 416, 418 $(M+H)^+$, LC/MS ret. t=2.72 (minor) and 2.83 (major) min.

Example 277

(2S,4R)-4-chloro-1-(4-(5-cyclopropyl-1H-pyrazol-3-ylamino)pyrrolo[1,2-f][1,2,4]triazin-2-yl)-N-(6-fluoropyridin-3-yl)pyrrolidine-2-carboxamide (major isomer) and (2S,4S)-4-chloro-1-(4-(5-cyclopropyl-1H-pyrazol-3-ylamino)pyrrolo[1,2-f][1,2,4]triazin-2-yl)-N-(6-fluoropyridin-3-yl)pyrrolidine-2-carboxamide (minor isomer)

A cold solution of 2-fluoro-5-aminopyridine (1.70 g, 15.1 mmol) in dry THF (45 mL) under nitrogen at 0° C. is treated slowly with stirring with isopropylmagnesium chloride (2.0 M in THF; 7.3 mL, 14.6 mmol). After 10-15 min, this solution is added to all of the crude material of Example 276 (1.32 mmol theoretical) and the mixture is stirred at rt for 75 min. A cold solution of TFA (1.40 mL) in methanol (15 mL) is added and the mixture is then purified by preparative HPLC (using 23% solvent B to 90% solvent B over 11 min). The desired fractions containing the products (ret t=9.34 min, minor isomer; ret t=10.05 min, major isomer) are processed to the title compounds, obtained as their free bases, using Waters Oasis® MCX Extraction Cartridges, following the general method described above, to give 170.2 mg (26.8%, major isomer) and 96.5 mg (15.2%, minor isomer) of the pure title compounds of Example 277 as solids: (Major isomer) MS: 482, 484 $(M+H)^+$, LC/MS ret. t=2.60 min.; HPLC (Method E) ret. t.=14.45 min; 500 MHz $^1$H NMR ($CD_3OD$) δ 8.26 (s, 1H), 8.03 (brs, 1H), 7.40 (s, 1H), 7.00 (dd, 1H, J=2.8, 8.9 Hz), 6.87 (d, 1H, J=4.3 Hz), 6.52-6.50 (m, 1H), 6.32 (brs, 1H), 4.91-4.87 (m, 1H), 4.80-4.74 (m, 1H), 4.13-4.07 (m, 2H), 2.69-2.62 (m, 2H), 1.85-1.78 (m, 1H), 0.95-0.88 (m, 2H), 0.75-0.65 (m, 2H). (Minor isomer); MS: 482, 484 $(M+H)^+$, LC/MS ret. t=2.50 min.; HPLC (Method E) ret. t.=13.55 min; 500 MHz $^1$H NMR ($CD_3OD$) δ 8.33 (s, 1H), 8.05 (m, 1H), 7.44 (s, 1H), 7.01 (dd, 1H, J=2.8, 9.0 Hz), 6.89 (d, 1H, J=4.3 Hz), 6.53-6.51 (m, 1H), 6.29 (brs, 1H), 4.83-4.78 (m, 2H), 4.16-4.11 (m, 1H), 3.97 (d, 1H, J=12.2 Hz), 2.97-2.89 (m, 1H), 2.66 (d, 1H, J=14.4 Hz), 1.83-1.76 (m, 1H), 0.94-0.84 (m, 2H), 0.73-0.67 (m, 1H), 0.62-0.56 (m, 1H).

Example 278

(2S,4S)-1-(4-(5-cyclopropyl-1H-pyrazol-3-ylamino)pyrrolo[1,2-f][1,2,4]triazin-2-yl)-N-(6-fluoropyridin-3-yl)-4-(methylsulfonyl)pyrrolidine-2-carboxamide

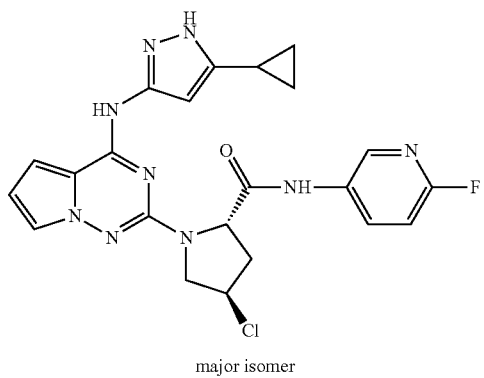

major isomer

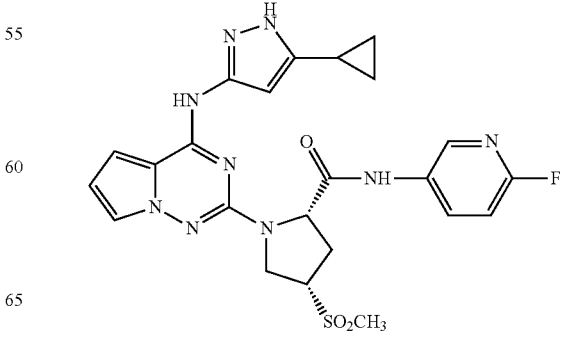

The major product from Example 277 (51.9 mg, 0.108 mmol) and methanesulfinic acid sodium salt (367 mg, 3.6 mmol) is dissolved in dry DMF (1 mL). and placed in a 0.5-2.0 mL microwave vial, flushed with nitrogen and capped. The reaction is heated in a Biotage Initiator Microwave unit for 3-4 h at 130-140° C., and then allowed to stand at rt for 70 h. The reaction mixture is purified by preparative HPLC (using 20% solvent B to 92% solvent B over 11 min). The desired fractions containing the product (ret t=8.07 min) are evaporated to dryness to give 10.1 mg (18%) of the title compound as a solid; MS: 526 (M+H)$^+$, LC/MS ret. t=2.03 min.; HPLC (Method A but with a 30 min rather than a 15 min gradient) ret. t.=14.27 min; 500 MHz $^1$H NMR (CDCl$_3$) δ 8.05 (brs, 1H), 8.02-7.96 (m, 1H), 7.40-7.36 (m, 1H), 6.80 (dd, 1H, J=3.1, 8.9 Hz), 6.73-6.69 (m, 1H), 6.50 (dd, 1H, J=2.4, 4.6 Hz), 6.24 (brs, 1H), 4.78-4.69 (m, 1H), 4.25-4.09 (m, 2H), 3.83-3.75 (m, 1H), 3.01 (s, 3H), 2.94-2.81 (m, 2H), 1.82-1.74 (m, 1H), 0.97-0.84 (m, 2H), 0.78-0.65 (m, 2H).

Example 279

(2S,4R)-1-(4-(5-cyclopropyl-1H-pyrazol-3-ylamino) pyrrolo[1,2-f][1,2,4]triazin-2-yl)-N-(6-fluoropyridin-3-yl)-4-(methylsulfonyl)pyrrolidine-2-carboxamide

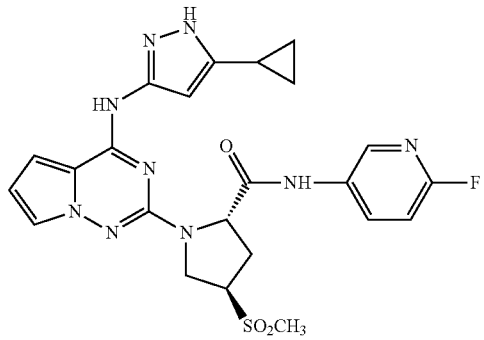 [SMILES: CS(=O)(=O)[C@@H]1C[C@@H](C(=O)Nc2ccc(F)nc2)N(c2nc(Nc3cc(C4CC4)[nH]n3)c3cccn3n2)C1]

The minor product from Example 277 (63.0 mg, 0.131 mmol) and methanesulfinic acid sodium salt (265 mg, 2.6 mmol) is dissolved in dry DMF (1.3 mL) and is converted to 3.3 mg (5%) of the title compound as a solid using the method described in Example 278; MS: 526 (M+H)$^+$, LC/MS ret. t=2.11 min.; HPLC (Method A but with a 30 min rather than a 15 min gradient) ret. t.=14.87 min; 500 MHz $^1$H NMR (CD$_3$OD) δ 8.25 (brs, 1H), 8.08-7.99 (m, 1H), 7.45-7.39 (m, 1H), 7.03-6.95 (m, 1H), 6.91-6.84 (m, 1H), 6.55-6.48 (m, 1H) 6.25 (brs, 1H), 5.00-4.94 (m, 1H), 4.28-4.11 (m, 2H), 4.10-4.00 (m, 1H), 3.07 (s, 3H), 2.84-2.74 (m, 1H), 2.72-2.63 (m, 1H), 1.86-1.77 (m, 1H), 0.95-0.86 (m, 2H), 0.72-0.62 (m, 2H).

Example 280

(2S,4S)-4-hydroxy-N-(pyrazin-2-yl)-1-(4-(5-(1-(trifluoromethyl)cyclopropyl)-1H-pyrazol-3-ylamino) pyrrolo[1,2-f][1,2,4]triazin-2-yl)pyrrolidine-2-carboxamide

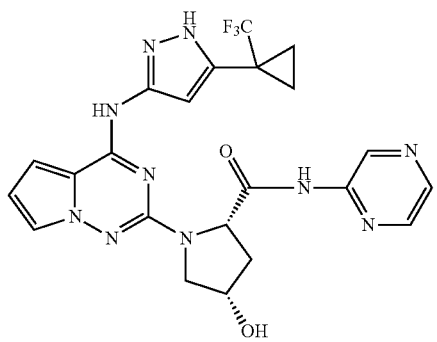 [SMILES: O=C(Nc1cnccn1)[C@@H]1C[C@H](O)CN1c1nc(Nc2cc(C3(C(F)(F)F)CC3)[nH]n2)c2cccn2n1]

Using 5-(1-(trifluoromethyl)cyclopropyl)-1H-pyrazol-3-amine (made using a procedure similar to that described in J. Med. Chem., 2001, 44(26), 4628-4660) and following procedures similar to that described in Example 193A, Examples 257, 258, and 259, the title compound is obtained as a solid; MS: 515 (M+H)$^+$, LC/MS ret. t=2.41 min.; HPLC (Method A but with a 30 min rather than a 15 min gradient) ret. t.=15.08 min; 500 MHz $^1$H NMR (d6-DMSO) δ 12.74 (brs, 1H), 10.46 (brs, 1H), 9.97 (brs, 1H), 9.35 (brs, 1H), 8.34 (s, 2H), 7.44 (brs, 1H), 7.14 (brs, 1H), 6.81 (brs, 1H), 6.44 (brs, 1H), 5.22 (brs, 1H), 4.62 (d, 1H, J=8.9 Hz), 4.42-4.37 (m, 1H), 3.74-3.55 (m, 2H), 2.54-2.46 (m, 1H), 2.13 (d, 1H, J=13.1 Hz), 1.37-1.18 (m, 4H).

Example 281

(2S,4S)-4-hydroxy-N-(1,2,4-thiadiazol-5-yl)-1-(4-(5-(1-(trifluoromethyl)cyclopropyl)-1H-pyrazol-3-ylamino)pyrrolo[1,2-f][1,2,4]triazin-2-yl)pyrrolidine-2-carboxamide

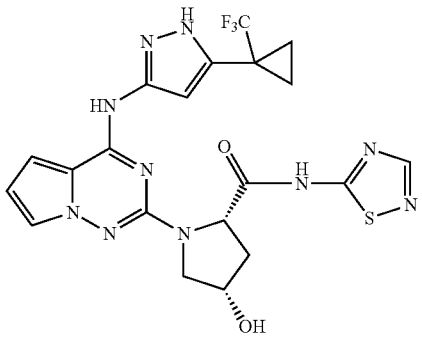 [SMILES: O=C(Nc1ncns1)[C@@H]1C[C@H](O)CN1c1nc(Nc2cc(C3(C(F)(F)F)CC3)[nH]n2)c2cccn2n1]

Using 5-(1-(trifluoromethyl)cyclopropyl)-1H-pyrazol-3-amine (made using a procedure similar to that described in J. Med. Chem., 2001, 44(26), 4628-4660) and following procedures similar to that described in Example 193A, Examples 257, 258, and 256, the title compound is obtained as a solid; MS: 521 (M+H)$^+$, LC/MS ret. t=2.54 min.; HPLC (Method A but with a 30 min rather than a 15 min gradient) ret. t.=15.43 min; 500 MHz $^1$H NMR (CD$_3$OD) δ 8.28 (s, 1H), 7.42 (brs, 1H), 6.93-6.84 (m, 1H), 6.63 (brs, 1H), 6.52 (brs, 1H), 4.96-4.87 (m, 1H), 4.65-4.54 (m, 1H), 3.86-3.74 (m, 2H), 2.66-2.53 (m, 1H), 2.36 (d, 1H, J=13.7 Hz), 1.45-1.32 (m, 2H), 1.31-1.20 (m, 2H).

Example 282

(2S,4R)-4-fluoro-N-(pyrazin-2-yl)-1-(4-(5-(1-(trifluoromethyl)cyclopropyl)-1H-pyrazol-3-ylamino) pyrrolo[1,2-f][1,2,4]triazin-2-yl)pyrrolidine-2-carboxamide

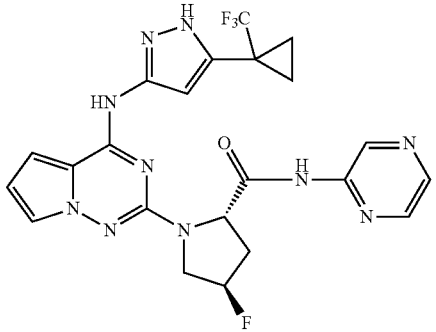 [SMILES: O=C(Nc1cnccn1)[C@@H]1C[C@@H](F)CN1c1nc(Nc2cc(C3(C(F)(F)F)CC3)[nH]n2)c2cccn2n1]

Using 5-(1-(trifluoromethyl)cyclopropyl)-1H-pyrazol-3-amine (made using a procedure similar to that described in J. Med. Chem., 2001, 44(26), 4628-4660) and following procedures similar to that described in Example 193A, Examples 264, 265, and 266, the title compound is obtained as a solid; MS: 517 (M+H)$^+$, LC/MS ret. t=2.71 min.; HPLC (Method A but with a 30 min rather than a 15 min gradient) ret. t.=17.67 min; 500 MHz $^1$H NMR (CD$_3$OD) δ 9.29 (s, 1H), 8.34 (s, 1H), 8.31-8.25 (m, 1H), 7.38 (brs, 1H), 6.90-6.72 (m, 2H), 6.50 (brs, 1H), 5.43 (d, 1H, J=53.1 Hz), 4.89-4.79 (m, 1H), 4.33-4.17 (m, 1H), 4.04-3.87 (m, 1H), 2.85-2.70 (m, 1H), 2.51-2.33 (m, 1H), 1.41-1.14 (m, 4H).

Example 283

(2S,4R)-4-fluoro-1-(4-(1-isopropyl-1H-imidazol-4-ylamino)pyrrolo[1,2-f][1,2,4]triazin-2-yl)-N-(pyrazin-2-yl)pyrrolidine-2-carboxamide

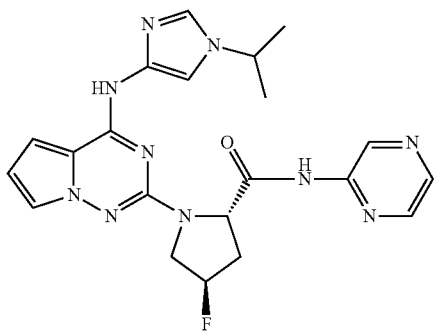 [SMILES: CC(C)n1cnc(Nc2nc(N3C[C@H](F)C[C@H]3C(=O)Nc3cnccn3)nn3cccc23)c1]

Using the compound from Example 228B and following procedures similar to that described in Examples 264, 265, and 266, the title compound is obtained as a solid; MS: 451 (M+H)$^+$, LC/MS ret. t=1.81 min.; HPLC (Method A but with a 30 min rather than a 15 min gradient) ret. t.=15.15 min; 500 MHz $^1$H NMR (CD$_3$OD) δ 9.34 (brs, 1H), 8.34 (brs, 1H), 8.32-8.27 (m, 1H), 7.50 (brs, 1H), 7.45 (brs, 1H), 7.36 (brs, 1H), 6.85 (brs, 1H), 6.50-6.47 (m, 1H), 5.44 (d, 1H, J=53.1 Hz), 4.89-4.84 (m, 1H), 4.47-4.39 (m, 1H), 4.26 (dd, 1H, J=12.8, 23.5 Hz), 3.98 (ddd, 1H, J=3.4, 12.8, 36.3 Hz), 2.86-2.74 (m, 1H), 2.48-2.32 (m, 1H), 1.52 (d, 3H, J=6.7 Hz), 1.49 (d, 3H, J=6.7 Hz).

Example 284

(2S,4S)-N-(6-fluoropyridin-3-yl)-1-(4-(1-isopropyl-1H-imidazol-4-ylamino)pyrrolo[1,2-f][1,2,4]triazin-2-yl)-4-methoxypyrrolidine-2-carboxamide

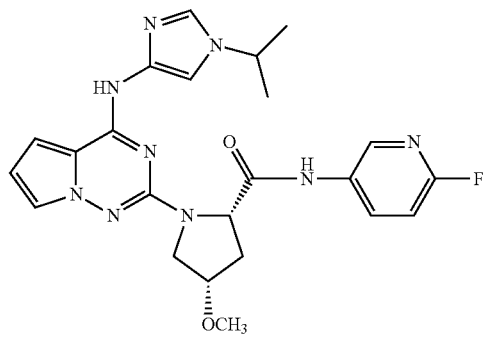 [SMILES: CO[C@H]1C[C@@H](C(=O)Nc2ccc(F)nc2)N(c2nc(Nc3cn(C(C)C)cn3)c3cccn3n2)C1]

Using the compound from Example 228B and following procedures similar to that described in Examples 252, 253, and 254, the title compound is obtained as a solid; MS: 480 (M+H)$^+$, LC/MS ret. t=1.93 min.; HPLC (Method A but with a 30 min rather than a 15 min gradient) ret. t.=15.78 min; 500 MHz $^1$H NMR (CDCl$_3$) δ 8.64 (s, 1H), 8.45 (brs, 1H), 8.24 (s, 1H), 7.98-7.92 (m, 1H), 7.49 (s, 1H), 7.41 (s, 1H), 7.35 (s, 1H), 6.82 (dd, 1H, J=3.4, 8.9 Hz), 6.67-6.64 (m, 1H), 6.52 (dd, 1H, J=2.4, 4.6 Hz), 4.73 (d, 1H, J=9.4 Hz), 4.34-4.27 (m, 1H), 4.14-4.11 (m, 1H), 3.97 (dd, 1H, J=1.8, 11.9 Hz), 3.64 (dd, 1H, J=4.0, 11.9), 3.36 (s, 3H), 2.63-2.57 (m, 1H), 2.42-2.34 (m, 1H), 1.50 (d, 3H, J=6.7 Hz), 1.46 (d, 3H, J=6.7 Hz).

Example 285

(2S,4S)-N-(6-fluoropyridin-3-yl)-4-hydroxy-1-(4-(1-isopropyl-1H-imidazol-4-ylamino)pyrrolo[1,2-f][1,2,4]triazin-2-yl)pyrrolidine-2-carboxamide

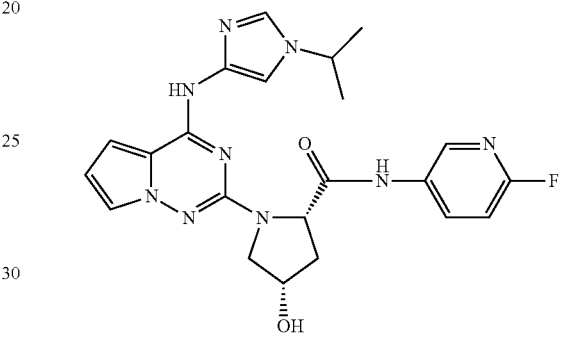

Using the compound from Example 228B and following procedures similar to that described in Examples 257, 258, and 260, the title compound is obtained as a solid; MS: 466 (M+H)$^+$, LC/MS ret. t=1.68 min.; HPLC (Method A but with a 30 min rather than a 15 min gradient) ret. t.=13.34 min; 500 MHz $^1$H NMR (CD$_3$OD) δ 8.34 (s, 1H), 8.05-7.98 (m, 1H), 7.48 (s, 1H), 7.42-7.38 (m, 2H), 6.97 (dd, 1H, J=2.8, 8.9 Hz), 6.85 (brs, 1H), 6.50-6.47 (m, 1H), 4.72 (d, 1H, J=8.6 Hz), 4.57-4.53 (m, 1H), 4.35-4.27 (m, 1H), 3.81-3.72 (m, 2H), 2.60-2.52 (m, 1H), 2.34 (d, 1H, J=13.7 Hz), 1.43 (d, 3H, J=6.7 Hz), 1.40 (d, 3H, J=6.7 Hz).

Example 286

3-(2-((2S,4S)-4-methoxy-2-(thiazol-2-ylcarbamoyl)pyrrolidin-1-yl)pyrrolo[1,2-f][1,2,4]triazin-4-ylamino)-1H-pyrazole-5-carboxamide

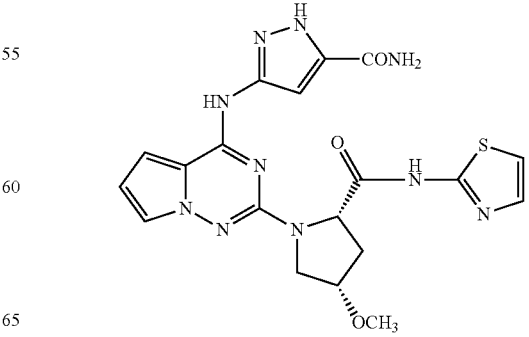

Using the compound from Example 166C and following procedures similar to that described in Examples 252, 253, and 256, the title compound is obtained as a solid; MS: 469 (M+H)+, LC/MS ret. t=2.16 min.; HPLC (Method A but with a 20 min rather than a 15 min gradient) ret. t.=10.47 min; 500 MHz $^1$H NMR (CD$_3$OD) δ 7.45 (s, 1H), 7.36 (s, 1H), 7.16 (brs, 1H). 7.09 (s, 1H), 6.90 (s, 1H), 6.51 (s, 1H), 4.22-4.14 (m, 1H), 4.07-3.99 (m, 1H), 3.73-3.62 (m, 1H), 3.49-3.41 (m, 1H), 3.34 (s, 3H), 2.63-2.53 (m, 1H), 2.49-2.38 (m, 1H).

Example 287

(2S,4S)-1-(4-(5-cyclopropyl-1H-pyrazol-3-ylamino)pyrrolo[1,2-f][1,2,4]triazin-2-yl)-4-hydroxy-N-(1,2,4-thiadiazol-5-yl)pyrrolidine-2-carboxamide

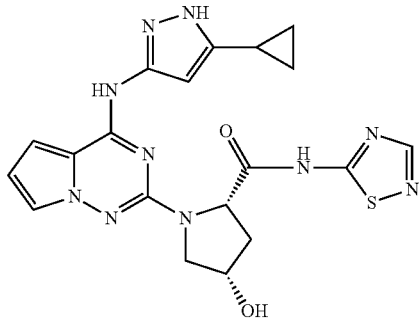 [SMILES: O=C(Nc1ncns1)[C@@H]1C[C@H](O)CN1c1nc(Nc2cc(C3CC3)[nH]n2)c2cccn2n1]

Using the compound from Example 208B and following procedures similar to that described in Example 259, the title compound is obtained as a solid; MS: 453 (M+H)+, LC/MS ret. t=2.02 min.; HPLC (Method A but with a 30 min rather than a 15 min gradient) ret. t.=12.97 min; 500 MHz $^1$H NMR (CD$_3$OD) δ 8.28 (s, 1H), 7.42-7.40 (m, 1H), 6.85 (d, 1H, J=4.6 Hz), 6.52-6.48 (m, 1H), 6.17 (brs, 1H), 4.92 (d, 1H, J=10.1 Hz), 4.59-4.55 (m, 1H), 3.82-3.75 (m, 2H), 2.63-2.55 (m, 1H), 2.35 (d, 1H, J=13.7 Hz), 1.87-1.80 (m, 1H), 0.98-0.92 (m, 2H), 0.77-0.72 (m, 2H).

Example 288

(2S,4S)-4-hydroxy-1-(4-(5-(1-methylcyclopropyl)-1H-pyrazol-3-ylamino)pyrrolo[1,2-f][1,2,4]triazin-2-yl)-N-(1,2,4-thiadiazol-5-yl)pyrrolidine-2-carboxamide

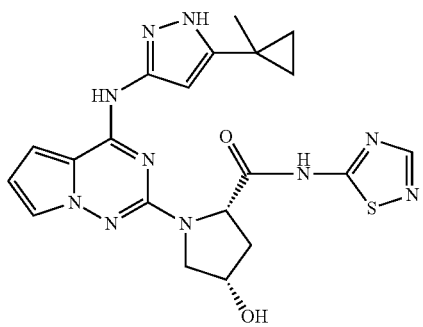 [SMILES: CC1(c2cc(Nc3nc(N4C[C@@H](O)C[C@H]4C(=O)Nc4ncns4)nn4cccc34)n[nH]2)CC1]

Using the compound from Example 258 and following procedures similar to that described in Example 259, the title compound is obtained as a solid; MS: 467 (M+H)+, LC/MS ret. t=2.38 min.; HPLC (Method A but with a 30 min rather than a 15 min gradient) ret. t.=14.13 min; HR/MS, obs 467.1708; calcd 467.1726; 500 MHz $^1$H NMR (CD$_3$OD) δ 8.27 (s, 1H), 7.44-7.37 (m, 1H), 6.89-6.82 (m, 1H), 6.53-6.47 (m, 1H), 6.26 (brs, 1H), 4.94 (d, 1H, J=10.1 Hz), 4.60-4.53 (m, 1H), 3.82-3.75 (m, 2H), 2.62-2.52 (m, 1H), 2.38 (d, 1H, J=13.7 Hz), 1.41 (s, 3H), 0.95-0.90 (m, 2H), 0.78-0.74 (m, 2H).

Example 289

(2S,4S)-N-(6-fluoropyridin-3-yl)-4-methoxy-1-(4-(5-(1-methylcyclopropyl)-1H-pyrazol-3-ylamino)pyrrolo[1,2-f][1,2,4]triazin-2-yl)pyrrolidine-2-carboxamide

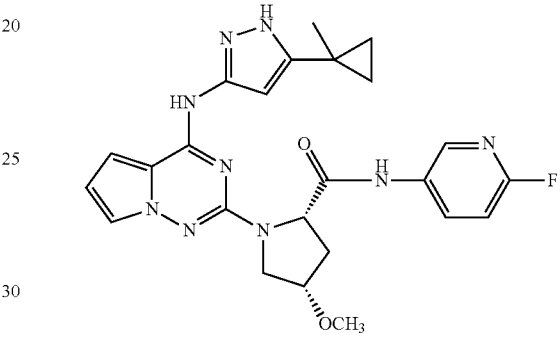

Using the compound from Example 194A and following procedures similar to that described in Examples 252, 253, and 254, the title compound is obtained as a solid; MS: 492 (M+H)+, LC/MS ret. t=2.49 min.; HPLC (Method A but with a 30 min rather than a 15 min gradient) ret. t.=16.77 min; 500 MHz $^1$H NMR (CD$_3$OD) δ 8.30 (s, 1H), 8.00 (brs, 1H), 7.43 (s, 1H), 6.99 (dd, 1H, J=2.9, 8.7 Hz), 6.87 (brs, 1H), 6.50 (brs, 1H), 6.42 (brs, 1H), 4.73 (d, 1H, J=9.8 Hz), 4.17-4.11 (m, 1H), 3.89-3.81 (m, 1H), 3.76-3.69 (m, 1H), 3.35 (s, 3H), 2.63-2.55 (m, 1H), 2.46-2.36 (m, 1H), 1.36 (s, 3H), 0.92-0.82 (m, 2H), 0.75-0.67 (m, 2H).

Example 290

(2S,4S)-4-methoxy-1-(4-(5-(1-methylcyclopropyl)-1H-pyrazol-3-ylamino)pyrrolo[1,2-f][1,2,4]triazin-2-yl)-N-(pyrazin-2-yl)pyrrolidine-2-carboxamide

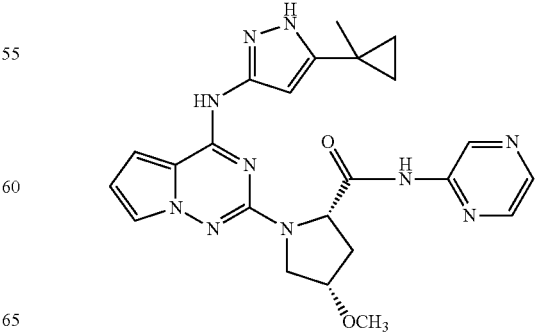

Using the compound from Example 194A and following procedures similar to that described in Examples 252, 253, and 255, the title compound is obtained as a solid; MS: 475 (M+H)+, LC/MS ret. t=2.39 min.; HPLC (Method A but with a 30 min rather than a 15 min gradient) ret. t.=15.83 min; 500 MHz ¹H NMR (CD₃OD) δ 9.45 (s, 1H), 8.29 (s, 2H), 7.43 (s, 1H), 6.88 (brs, 1H), 6.51 (brs, 1H), 6.39 (brs, 1H), 4.76 (d, 1H, J=10.1 Hz), 4.18-4.14 (m, 1H), 3.92-3.86 (m, 1H), 3.71 (dd, 1H, J=3.8, 11.7 Hz), 3.34 (s, 3H), 2.64-2.58 (m, 1H), 2.49-2.41 (m, 1H), 1.38 (s, 3H), 0.92-0.85 (m, 2H), 0.75-0.70 (m, 2H).

Example 291

(2S,4S)-N-(6-fluoropyridin-3-yl)-1-(4-(5-isopropyl-1H-pyrazol-3-ylamino)pyrrolo[1,2-f][1,2,4]triazin-2-yl)-4-methoxypyrrolidine-2-carboxamide

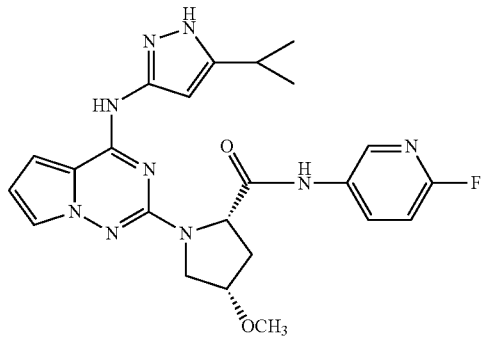 [SMILES: CO[C@H]1C[C@@H](C(=O)Nc2ccc(F)nc2)N(c2nc(Nc3cc(C(C)C)[nH]n3)c3cccn3n2)C1]

Using 5-isopropyl-1H-pyrazol-3-amine (made using a procedure similar to that described in J. Med. Chem., 2001, 44(26), 4628-4660) and following procedures similar to that described in Example 193A, Examples 252, 253, and 254, the title compound is obtained as a solid; MS: 480 (M+H)+, LC/MS ret. t=2.46 min.; HPLC (Method A but with a 30 min rather than a 15 min gradient) ret. t.=16.13 min; 500 MHz ¹H NMR (CD₃OD) δ 8.30 (s, 1H), 8.00 (brs, 1H), 7.44 (s, 1H), 6.99 (dd, 1H, J=2.8, 8.9 Hz), 6.90-6.87 (m, 1H), 6.53-6.50 (m, 2H), 4.75 (d, 1H, J=10.4 Hz), 4.17-4.13 (m, 1H), 3.90-3.84 (m, 1H), 3.76-3.71 (m, 1H), 3.36 (s, 3H), 2.93-2.85 (m, 1H), 2.58 (d, 1H, J=13.4 Hz), 2.49-2.38 (m, 1H), 1.23 (d, 3H, J=6.7 Hz), 1.19 (d, 3H, J=6.7 Hz).

Example 292

(2S,4R)-4-fluoro-N-(6-fluoropyridin-3-yl)-1-(4-(5-(1-methylcyclopropyl)-1H-pyrazol-3-ylamino)pyrrolo[1,2-f][1,2,4]triazin-2-yl)pyrrolidine-2-carboxamide

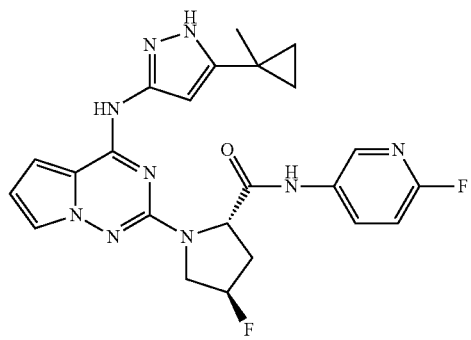 [SMILES: CC1(c2cc(Nc3nc(N4C[C@H](F)C[C@H]4C(=O)Nc4ccc(F)nc4)nn4cccc34)n[nH]2)CC1]

Following the procedures similar to that described in Example 266, the title compound is obtained as a solid; MS: 480 (M+H)+, LC/MS ret. t=2.54 min.; HPLC (Method F) ret. t.=17.64 min; 500 MHz ¹H NMR (CD₃OD) δ 8.25 (s, 1H), 8.02 (brs, 1H), 7.37 (s, 1H), 7.00 (dd, 1H, J=2.8, 8.8 Hz), 6.86 (brs, 1H), 6.49 (brs, 1H), 6.40 (brs, 1H), 5.43 (d, 1H, J=53.1 Hz), 4.83-4.76 (m, 1H), 4.31-4.16 (m, 1H), 3.98-3.80 (m, 1H), 2.80-2.65 (m, 1H), 2.49-2.32 (m, 1H), 1.40 (s, 3H), 0.94-0.89 (m, 2H), 0.78-0.72 (m, 2H).

Example 293

(2S,4R)-1-(4-(5-cyclopropyl-1H-pyrazol-3-ylamino)pyrrolo[1,2-f][1,2,4]triazin-2-yl)-4-fluoro-N-(1,2,4-thiadiazol-5-yl)pyrrolidine-2-carboxamide

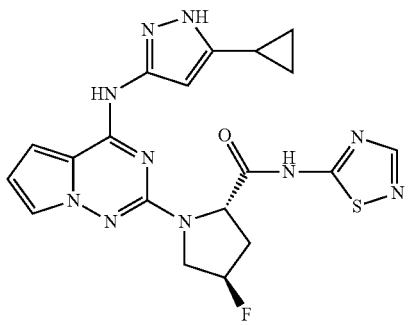 [SMILES: O=C(Nc1ncns1)[C@@H]1C[C@@H](F)CN1c1nc(Nc2cc(C3CC3)[nH]n2)c2cccn2n1]

Using the compound from Example 203A and following procedures similar to that described in Example 256, the title compound is obtained as a solid; MS: 455 (M+H)+, LC/MS ret. t=2.46 min.; HPLC (Method A but with a 30 min rather than a 15 min gradient) ret. t.=16.24 min; 500 MHz ¹H NMR (d6-DMSO) δ 13.15 (brs, 1H), 12.07 (brs, 1H), 10.26 (brs, 1H), 8.46 (s, 1H), 7.34 (brs, 1H), 7.11 (brs, 1H), 6.41 (brs, 1H), 6.31 (brs, 1H), 5.47 (d, 1H, J=53.1 Hz), 4.96-4.81 (m, 1H), 4.15-3.99 (m, 1H), 3.97-3.77 (m, 1H), 2.82-2.66 (m, 1H), 2.39-2.20 (m, 1H), 1.90-1.78 (m, 1H), 0.99-0.83 (m, 2H), 0.80-0.66 (m, 2H).

Example 294

(2S,4R)-4-fluoro-1-(4-(5-(1-methylcyclopropyl)-1H-pyrazol-3-ylamino)pyrrolo[1,2-f][1,2,4]triazin-2-yl)-N-(1,2,4-thiadiazol-5-yl)pyrrolidine-2-carboxamide

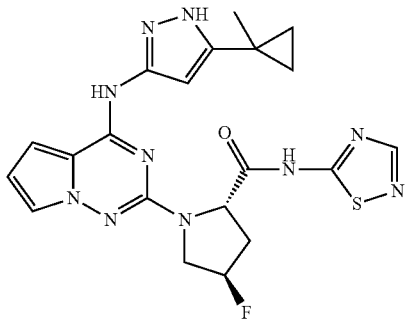 [SMILES: CC1(c2cc(Nc3nc(N4C[C@H](F)C[C@H]4C(=O)Nc4ncns4)nn4cccc34)n[nH]2)CC1]

Using the compound from Example 265 and following procedures similar to that described in Example 256, the title compound is obtained as a solid; MS: 469 (M+H)⁺, LC/MS ret. t=2.44 min.; HPLC (Method A but with a 30 min rather than a 15 min gradient) ret. t=17.69 min; 500 MHz ¹H NMR (CD₃OD) δ 8.30 (s, 1H), 7.33 (brs, 1H), 6.82 (brs, 1H), 6.51-6.44 (m, 1H), 6.25 (brs, 1H), 5.44 (d, 1H, J=53.4 Hz), 4.99-4.91 (m, 1H), 4.24 (dd, 1H, J=12.8, 23.5 Hz), 4.02-3.86 (m, 1H), 2.82-2.72 (m, 1H), 2.47-2.30 (m, 1H), 1.47 (s, 3H), 1.04-0.94 (m, 2H), 0.85-0.76 (m, 2H).

Example 295

(2S,4S)-N-(6-fluoropyridin-3-yl)-4-hydroxy-1-(4-(5-(2,2,2-trifluoroethyl)-1H-pyrazol-3-ylamino)pyrrolo[1,2-f][1,2,4]triazin-2-yl)pyrrolidine-2-carboxamide

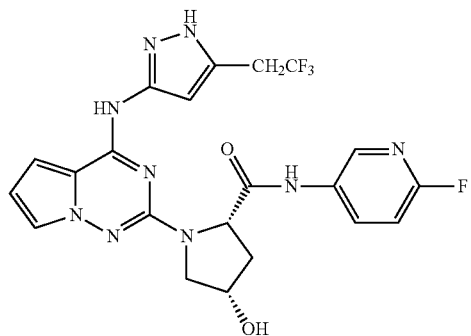

Using 5-(2,2,2-trifluoroethyl)-1H-pyrazol-3-amine (made using a procedure similar to that described in J. Med. Chem., 2001, 44(26), 4628-4660) and following procedures similar to that described in Example 193A, Examples 257, 258, and 260, the title compound is obtained as a solid; MS: 506 (M+H)⁺, LC/MS ret. t=2.34 min.; HPLC (Method A but with a 30 min rather than a 15 min gradient) ret. t=14.65 min; 500 MHz ¹H NMR (CD₃OD) δ 8.31 (s, 1H), 8.12 (brs, 1H), 7.74 (brs, 1H), 7.44 (s, 1H), 6.99 (dd, 1H, J=2.7, 8.9 Hz), 6.92-6.88 (m, 1H), 6.53 (dd, 1H, J=2.5, 4.3 Hz), 4.73-4.69 (m, 1H), 4.62-4.57 (m, 1H), 3.87-3.73 (m, 2H), 3.58-3.48 (m, 2H), 2.64-2.56 (m, 1H), 2.35-2.29 (m, 1H).

Example 296

(2S,4R)-4-cyano-1-(4-(5-cyclopropyl-1H-pyrazol-3-ylamino)pyrrolo[1,2-f][1,2,4]triazin-2-yl)-N-(6-fluoropyridin-3-yl)pyrrolidine-2-carboxamide

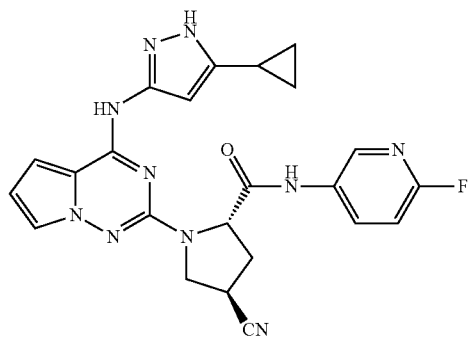 [SMILES: N#C[C@@H]1C[C@@H](C(=O)Nc2ccc(F)nc2)N(c2nc(Nc3cc(C4CC4)[nH]n3)c3cccn3n2)C1]

Using (2S,4R)-4-cyanopyrrolidine-2-carboxylic acid hydrochloride (made from (2S,4R)-1-(tert-butoxycarbonyl)-4-cyanopyrrolidine-2-carboxylic acid, purchased from Anaspec and deprotected using 4 N HCl in dioxane) and the compound from Example 1C, and following procedures related to those described in Example 179 (but at 130° C. instead of 155° C.) and Example 202, the title compound is obtained as a solid; MS: 473 (M+H)⁺, LC/MS ret. t=2.31 min.; HPLC (Method A but with a 30 min rather than a 15 min gradient) ret. t=16.47 min; IR (KBr) 2251 cm⁻¹; 500 MHz ¹H NMR (CD₃OD) δ 8.23 (s, 1H), 7.99 (brs, 1H), 7.43 (s, 1H), 7.00 (dd, 1H, J=3.1, 8.9 Hz), 6.89 (s, 1H), 6.52 (s, 1H), 6.28 (brs, 1H), 4.93-4.83 (m, 1H), 4.11-4.02 (m, 1H), 3.92-3.82 (m, 1H), 3.64-3.54 (m, 1H), 2.75-2.67 (m, 1H), 2.66-2.56 (m, 1H), 1.84-1.76 (m, 1H), 0.93-0.86 (m, 2H), 0.72-0.60 (m, 2H).

Example 297

(2S,4R)-methyl 1-(4-(5-cyclopropyl-1H-pyrazol-3-ylamino)pyrrolo[1,2-f][1,2,4]triazin-2-yl)-4-hydroxypyrrolidine-2-carboxylate

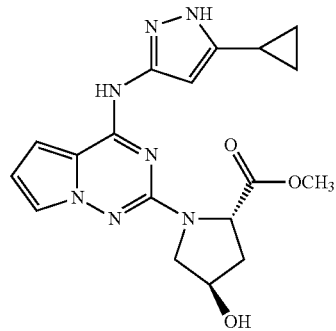 [SMILES: COC(=O)[C@@H]1C[C@@H](O)CN1c1nc(Nc2cc(C3CC3)[nH]n2)c2cccn2n1]

Dry methanol (800 mL) is stirred and cooled to 0° C. and slowly treated with acetyl chloride (15.4 mL, 217 mmol) over 15 min. This solution is stirred at 0 C for 15 min and at rt for 2-3 h. The material from 216A (8.00 g, 21.7 mmol) is then added and the reaction is stirred overnight at room temperature. The crude reaction mixture is evaporated in vacuo and partitioned with ethyl acetate (1500 mL) and saturated aqueous sodium bicarbonate solution (200 mL). The organic layer is washed with water (100 mL) and brine (100 mL), and dried (Na₂SO₄). The solvent is evaporated in vacuo and the residue is treated with methylene chloride (300 mL) and methanol (50 mL). The resulting solid is collected by filtration and dried in vacuo to give 2.40 g (26%) of the title compound. The filtrate is purified by silica gel chromatography using a Biotage instrument (see above for general details) with a Flash 65+M cartridge using a gradient from 100% dichloromethane to 10% methanol in dichloromethane. The desired fractions containing the product were evaporated in vacuo to give 4.77 g (51%) of additional title compound as a solid which is used directly as described below: MS: 384 (M+H)⁺, LC/MS ret. t=1.91 min; HPLC (Method A but with a 30 min rather than a 15 min gradient) ret. t=12.32 min; 500 MHz ¹H NMR (CD₃OD) δ 7.35 (brs, 1H), 6.83 (brs, 1H), 6.51-6.40 (m, 2H), 4.80-4.72 (m, 1H), 4.62-4.52 (m, 1H), 3.85-3.77 (m, 1H), 3.72-3.60 (m, 4H), 2.42-2.34 (m, 1H), 2.26-2.14 (m, 1H), 1.99-1.91 (m, 1H), 1.08-0.71 (m, 4H).

Example 298

(2S,4S)-methyl 1-(4-(5-cyclopropyl-1H-pyrazol-3-ylamino)pyrrolo[1,2-f][1,2,4]triazin-2-yl)-4-(2H-tetrazol-2-yl)pyrrolidine-2-carboxylate (major isomer) and (2S,4S)-methyl 1-(4-(5-cyclopropyl-1H-pyrazol-3-ylamino)pyrrolo[1,2-f][1,2,4]triazin-2-yl)-4-(1H-tetrazol-1-yl)pyrrolidine-2-carboxylate (minor isomer)

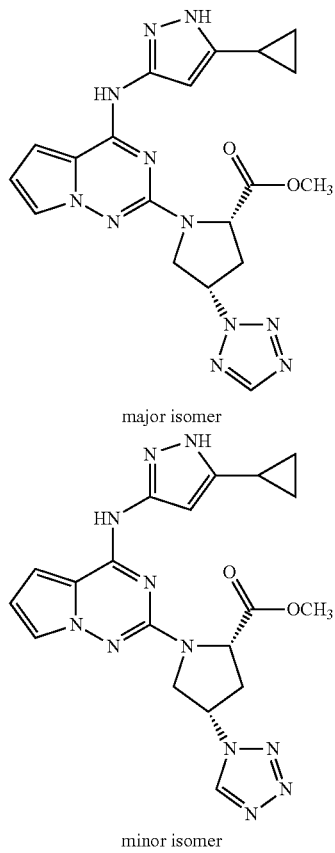

major isomer minor isomer

A suspension of the compound from Example 297 (212.0 mg, 0.553 mmol), triphenylphosphine (662.0 mg, 2.524 mmol), and 1H-tetrazole (196.7 mg, 2.81 mmol) in dry THF (4.5 mL) is stirred under nitrogen at rt and slowly treated over 2-3 min with diisopropyl azodicarboxylate (475 µlit, 2.41 mmol). The mixture is stirred at rt for 3 h, quenched with water (70 µlit) and diluted with methanol (12 mL). The reaction mixture is then purified by preparative HPLC (using 22% solvent B to 85% solvent B over 11 min). The desired fractions containing the major product (ret t=9.02 min) are processed to the title compound (major isomer), obtained as its free base, using a 2 gram (20 cc) Phenomenex Strata-XL-C Extraction Cartridge, following the general method described above, to give 82.6 mg (34%) of the pure title compound (major isomer) of Example 298 as a solid. The minor isomer (ret t=8.15 min) can be obtained similarly. Data for major isomer: MS: 436 (M+H)$^+$, LC/MS ret. t=2.13 min.; (Method A but with a 30 min rather than a 15 min gradient) ret. t.=15.20 min.; 500 MHz $^1$H NMR (CD$_3$OD) δ 8.75 (s, 1H), 7.38 (s, 1H), 6.86-6.82 (m, 1H), 6.48 (s, 1H), 6.31 (brs, 1H), 5.63-5.57 (m, 1H), 4.91 (dd, 1H, J=3.5, 9.3 Hz), 4.48-4.42 (m, 1H), 4.36-4.30 (m, 1H), 3.56 (s, 3H), 3.23-3.17 (m, 1H), 3.16-3.09 (m, 1H), 1.96-1.89 (m, 1H), 1.04-0.96 (m, 2H), 0.84-0.77 (m, 2H).

Example 299

(2S,4S)-1-(4-(5-cyclopropyl-1H-pyrazol-3-ylamino)pyrrolo[1,2-f][1,2,4]triazin-2-yl)-N-(6-fluoropyridin-3-yl)-4-(2H-tetrazol-2-yl)pyrrolidine-2-carboxamide

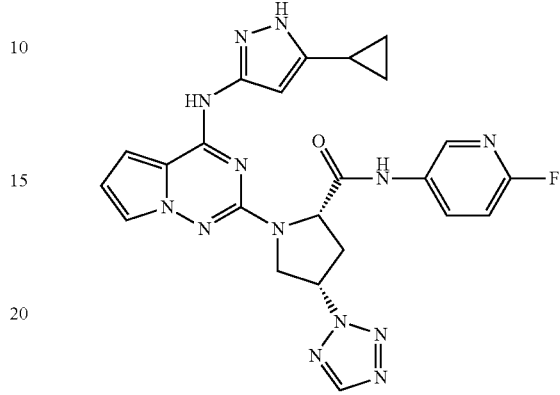

Using a procedure related to that of Example 254, the major isomer from Example 298 (46.4 mg, 0.107 mmol) is converted to the title compound of Example 299 (46.4 mg, 84%), obtained as a solid; MS: 516 (M+H)$^+$, LC/MS ret. t=2.05 min.; HPLC (Method A but with a 30 min rather than a 15 min gradient) ret. t.=15.01 min; 500 MHz $^1$H NMR (CD$_3$OD) δ 8.69 (s, 1H), 8.11 (s, 1H), 7.83 (brs, 1H), 7.46 (s, 1H), 6.93 (dd, 1H, J=2.7, 8.9 Hz), 6.90 (d, 1H, J=4.0 Hz), 6.54 (dd, 1H, J=2.6, 4.4 Hz), 6.28 (brs, 1H), 5.66-5.61 (m, 1H), 4.90 (dd, 1H, J=2.7, 10.1 Hz), 4.62 (d, 1H, J=11.9 Hz), 4.38-4.31 (m, 1H), 3.34-3.30 (m, 1H), 3.20-3.09 (m, 1H), 1.81-1.74 (m, 1H), 0.90-0.83 (m, 2H), 0.71-0.65 (m, 1H), 0.61-0.55 (m, 1H).

Example 300

(2S,4S)-4-(4-cyano-1H-pyrazol-1-yl)-1-(4-(5-cyclopropyl-1H-pyrazol-3-ylamino)pyrrolo[1,2-f][1,2,4]triazin-2-yl)-N-(6-fluoropyridin-3-yl)pyrrolidine-2-carboxamide

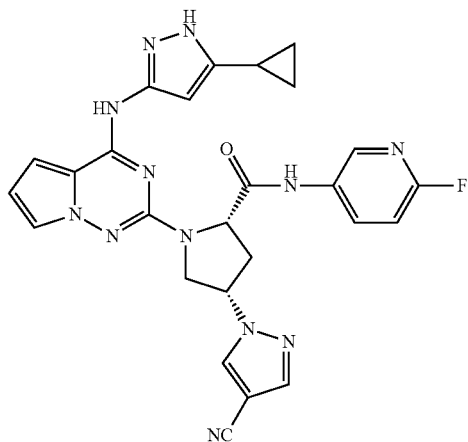 [SMILES: N#Cc1cnn([C@H]2C[C@@H](C(=O)Nc3ccc(F)nc3)N(c3nc(Nc4cc(C5CC5)[nH]n4)c4cccn4n3)C2)c1]

Using a procedure related to that of Example 298, the compound of Example 217 (60.0 mg, 0.129 mmol) and 4-cyanopyrazole (48.2 mg, 0.518 mmol) is converted to the title compound of Example 300 (11.5 mg, 16.5%), obtained as a solid; MS: 539 (M+H)$^+$, LC/MS ret. t=2.22 min.; HPLC (Method A but with a 30 min rather than a 15 min gradient) ret. t.=16.74 min; 500 MHz $^1$H NMR (CD$_3$OD) δ 8.46 (s, 1H), 8.18 (brs, 1H), 7.91 (brs, 1H), 7.88 (s, 1H), 7.44-7.42 (m, 1H), 6.98 (dd, 1H, J=3.0, 8.9 Hz), 6.89 (d, 1H, J=3.4 Hz), 6.52 (dd, 1H, J=2.4, 4.6 Hz), 6.24 (brs, 1H), 5.19-5.13 (m, 1H), 4.83-4.78 (m, 1H), 4.30-4.23 (m, 2H), 3.00-2.95 (m, 2H), 1.81-1.74 (m, 1H), 0.91-0.82 (m, 2H), 0.70-0.64 (m, 1H), 0.61-0.55 (m, 1H).

Example 301

(2S,4S)-1-(4-(5-cyclopropyl-1H-pyrazol-3-ylamino)pyrrolo[1,2-f][1,2,4]triazin-2-yl)-N-(6-fluoropyridin-3-yl)-4-(5-methyl-2H-tetrazol-2-yl)pyrrolidine-2-carboxamide

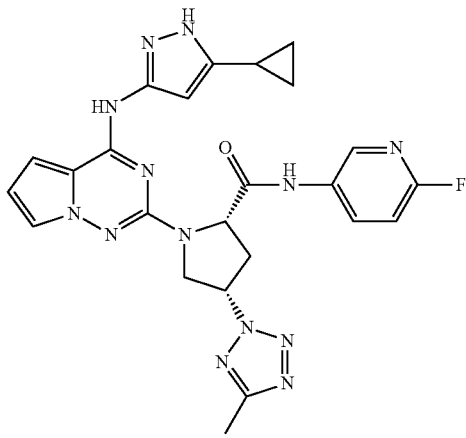 [SMILES: Cc1nnn([C@H]2C[C@@H](C(=O)Nc3ccc(F)nc3)N(c3nc(Nc4cc(C5CC5)[nH]n4)c4cccn4n3)C2)n1]

Using procedures related to those of Example 298 and Example 254, the compound of Example 297 (110.0 mg, 0.287 mmol) and 5-methyl-1H-tetrazole (96.0 mg, 1.15 mmol) is converted to the title compound of Example 301 (8.5 mg, 5.6%), obtained as a solid; MS: 530 (M+H)$^+$, LC/MS ret. t=2.21 min.; HPLC (Method A but with a 30 min rather than a 15 min gradient) ret. t.=15.58 min; 500 MHz $^1$H NMR (CD$_3$OD) δ 8.15 (s, 1H), 7.88 (brs, 1H), 7.45 (s, 1H), 6.97 (dd, 1H, J=2.8, 8.9 Hz), 6.89 (d, 1H, J=4.3 Hz), 6.53 (dd, 1H, J=2.6, 4.4 Hz), 6.25 (brs, 1H), 5.56-5.51 (m, 1H), 4.90-4.87 (m, 1H), 4.58 (d, 1H, J=11.9 Hz), 4.28 (dd, 1H, J=5.6, 12.0 Hz), 3.31-3.25 (m, 1H), 3.13-3.05 (m, 1H), 2.38 (s, 3H), 1.81-1.74 (m, 1H), 0.92-0.82 (m, 2H), 0.72-0.65 (m, 1H), 0.60-0.54 (m, 1H).

Example 302

(2S,4S)-4-(4-chloro-1H-pyrazol-1-yl)-1-(4-(5-cyclopropyl-1H-pyrazol-3-ylamino)pyrrolo[1,2-f][1,2,4]triazin-2-yl)-N-(6-fluoropyridin-3-yl)pyrrolidine-2-carboxamide

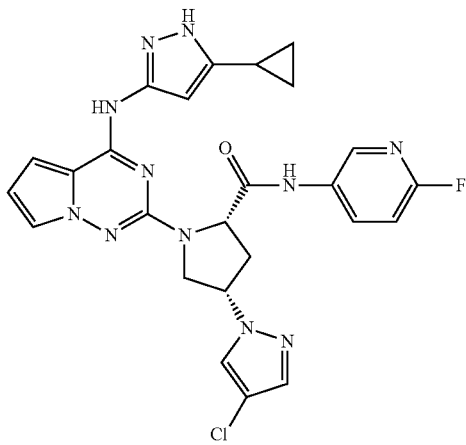 [SMILES: O=C(Nc1ccc(F)nc1)[C@@H]1C[C@H](n2cc(Cl)cn2)CN1c1nc(Nc2cc(C3CC3)[nH]n2)c2cccn2n1]

Using procedures related to those of Example 298 and Example 254, the compound of Example 297 (75.0 mg, 0.196 mmol) and 4-chloropyrazole (68.6 mg, 0.666 mmol) is converted to the title compound of Example 302 (29.0 mg, 27%), obtained as a solid; MS: 548, 550 (M+H)$^+$, LC/MS ret. t=2.421 min.; HPLC (Method A but with a 30 min rather than a 15 min gradient) ret. t.=18.07 min; 500 MHz $^1$H NMR (CD$_3$OD) δ 8.18 (s, 1H), 7.92 (s, 1H), 7.90 (brs, 1H), 7.45-7.39 (m, 2H), 6.99-6.94 (m, 1H), 6.88 (s, 1H), 6.52 (s, 1H), 6.29 (brs, 1H), 5.08-5.01 (m, 1H), 4.80-4.75 (m, 1H), 4.29 (d, 1H, J=11.6 Hz), 4.22-4.16 (m, 1H), 2.98-2.90 (m, 2H), 1.83-1.75 (m, 1H), 0.92-0.82 (m, 2H), 0.72-0.66 (m, 1H), 0.64-0.57 (m, 1H).

Example 303

(2S,4S)-4-(4-bromo-1H-pyrazol-1-yl)-1-(4-(5-cyclopropyl-1H-pyrazol-3-ylamino)pyrrolo[1,2-f][1,2,4]triazin-2-yl)-N-(6-fluoropyridin-3-yl)pyrrolidine-2-carboxamide

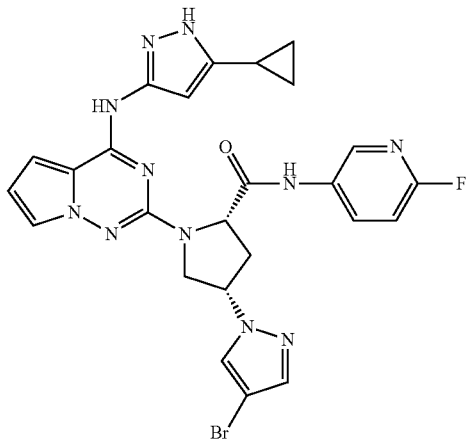

Using procedures related to those of Example 298 and Example 254, the compound of Example 297 (61.9 mg, 0.162 mmol) and 4-bromopyrazole (81.6 mg, 0.555 mmol) is converted to the title compound of Example 303 (29.7 mg, 31%), obtained as a solid; MS: 592, 594 (M+H)$^+$, LC/MS ret. t=2.42 min.; HPLC (Method A but with a 30 min rather than a 15 min gradient) ret. t.=18.16 min; 500 MHz $^1$H NMR (CD$_3$OD) δ 8.18 (s, 1H), 7.94 (s, 1H), 7.89 (brs, 1H), 7.47-7.42 (m, 2H), 6.99-6.95 (m, 1H), 6.88 (s, 1H), 6.52 (s, 1H), 6.28 (brs, 1H), 5.10-5.04 (m, 1H), 4.80-4.75 (m, 1H), 4.34-4.29 (m, 1H), 4.232-4.17 (m, 1H), 2.99-2.92 (m, 2H), 1.83-1.75 (m, 1H), 0.92-0.83 (m, 2H), 0.72-0.66 (m, 1H), 0.63-0.57 (m, 1H).

Example 304

(2S,4S)-4-(2-chloro-1H-imidazol-1-yl)-1-(4-(5-cyclopropyl-1H-pyrazol-3-ylamino)pyrrolo[1,2-f][1,2,4]triazin-2-yl)-N-(6-fluoropyridin-3-yl)pyrrolidine-2-carboxamide

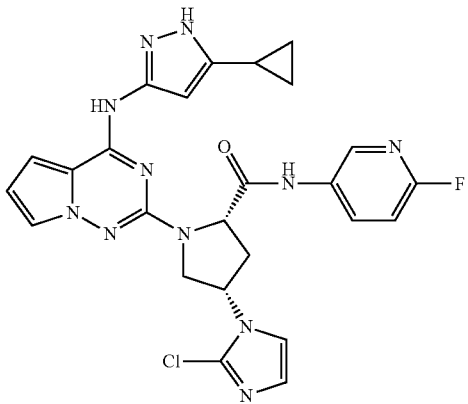 [SMILES: O=C(Nc1ccc(F)nc1)[C@@H]1C[C@H](n2ccnc2Cl)CN1c1nc(Nc2cc(C3CC3)[nH]n2)c2cccn2n1]

Using procedures related to those of Example 298 and Example 254, the compound of Example 297 (61.9 mg, 0.162 mmol) and 2-chloroimidazole (57.0 mg, 0.5515 mmol) is converted to the title compound of Example 304 (14.0 mg, 16%), obtained as a solid; MS: 548, 550 (M+H)$^+$, LC/MS ret. t=2.18 min.; HPLC (Method A but with a 30 min rather than a 15 min gradient) ret. t.=16.16 min.

Example 305

(2S,4S)-1-(4-(5-cyclopropyl-1H-pyrazol-3-ylamino)pyrrolo[1,2-f][1,2,4]triazin-2-yl)-N-(6-fluoropyridin-3-yl)-4-(2H-1,2,3-triazol-2-yl)pyrrolidine-2-carboxamide

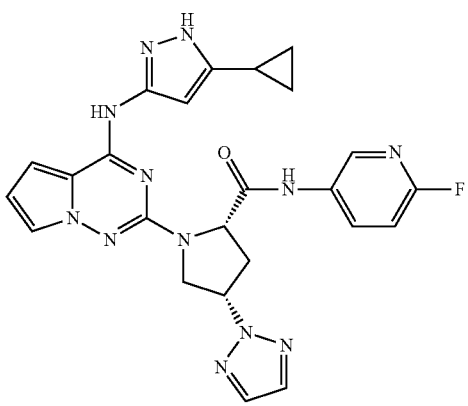 [SMILES: O=C(Nc1ccc(F)nc1)[C@@H]1C[C@H](n2nccn2)CN1c1nc(Nc2cc(C3CC3)[nH]n2)c2cccn2n1]

Using a procedure related to that of Example 298, the compound of Example 297 (59.4 mg, 0.155 mmol) and 1H-1,2,3-triazole (50.4 mg, 0.73 mmol) is converted to a mixture of major [4-(2H-1,2,3-triazol-2-yl); 36.3 mg; 54%] and minor [(4-(1H-1,2,3-triazol-1-yl); 17.3 mg; 26%]triazole methyl ester regioisomers, which are separated by preparative HPLC (using 25% solvent B to 95% solvent B over 11 min). The desired fractions containing the products (ret t=7.59 min, minor isomer; ret t=8.90 min, major isomer) are processed to their corresponding free bases, using Waters Oasis® MCX Extraction Cartridges, following the general method described above. The major isomer (32.0 mg, 0.074 mmol) is then converted to the title compound of Example 305 using a procedure related to Example 254 (29.0 mg, 76%), obtained as a solid; MS: 515 (M+H)$^+$, LC/MS ret. t=2.26 min.; HPLC (Method A) ret. t.=10.22 min.

Example 306

(2S,4S)-1-(4-(5-cyclopropyl-1H-pyrazol-3-ylamino)pyrrolo[1,2-f][1,2,4]triazin-2-yl)-N-(6-fluoropyridin-3-yl)-4-(1H-1,2,4-triazol-1-yl)pyrrolidine-2-carboxamide

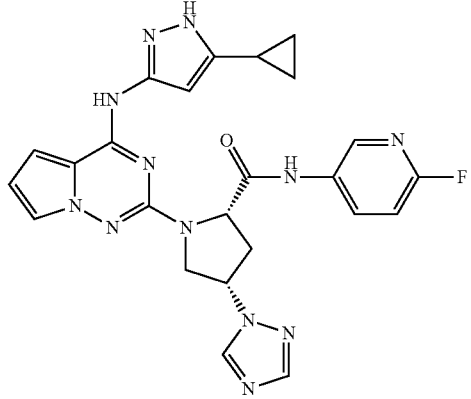 [SMILES: O=C(Nc1ccc(F)nc1)[C@@H]1C[C@H](n2cncn2)CN1c1nc(Nc2cc(C3CC3)[nH]n2)c2cccn2n1]

Using procedures related to those of Example 298 and Example 254, the compound of Example 297 (64.5 mg, 0.168 mmol) and 1,2,4-triazole (53.1 mg, 0.769 mmol) is converted to the title compound of Example 306 (29.7 mg, 44%), obtained as a solid; MS: 515 (M+H)$^+$, LC/MS ret. t=2.12 min.; HPLC (Method) ret. t.=8.85 min.

Example 307

(2S,4S)-1-(4-(5-cyclopropyl-1H-pyrazol-3-ylamino)pyrrolo[1,2-f][1,2,4]triazin-2-yl)-4-(4,5-dichloro-1H-imidazol-1-yl)-N-(6-fluoropyridin-3-yl)pyrrolidine-2-carboxamide

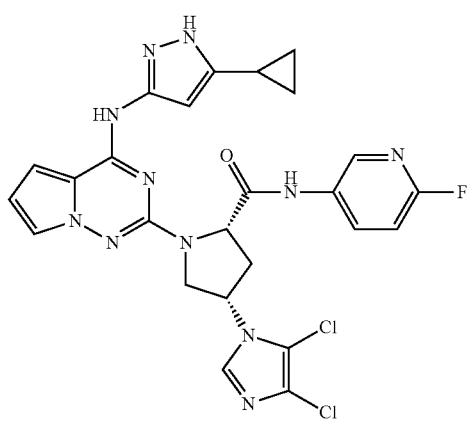 [SMILES: O=C(Nc1ccc(F)nc1)[C@@H]1C[C@H](n2cnc(Cl)c2Cl)CN1c1nc(Nc2cc(C3CC3)[nH]n2)c2cccn2n1]

Using procedures related to those of Example 298 and Example 254, the compound of Example 297 (102.0 mg, 0.266 mmol) and 4,5-dichloroimidazole (184.0 mg, 1.343 mmol) is converted to the title compound of Example 307 (21.9 mg, 14%), obtained as a solid; MS: 582, 584 (M+H)$^+$, LC/MS ret. t=2.58 min.; HPLC (Method C but with a 30 min rather than a 20 min gradient) ret. t.=17.20 min.

Example 308

(2S,4S)-1-(4-(5-cyclopropyl-1H-pyrazol-3-ylamino)pyrrolo[1,2-f][1,2,4]triazin-2-yl)-4-(2,4-difluorophenoxy)-N-(6-fluoropyridin-3-yl)pyrrolidine-2-carboxamide

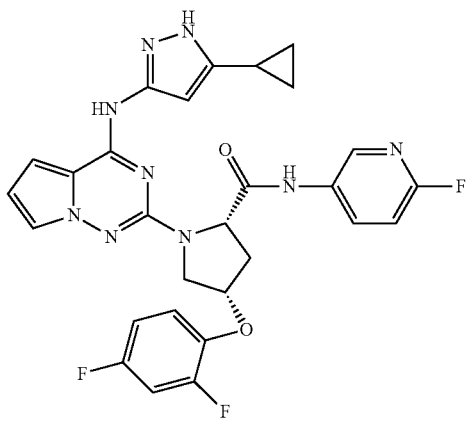 [SMILES: O=C(Nc1ccc(F)nc1)[C@@H]1C[C@H](Oc2ccc(F)cc2F)CN1c1nc(Nc2cc(C3CC3)[nH]n2)c2cccn2n1]

Using procedures related to those of Example 298 and Example 254, the compound of Example 297 (204.0 mg, 0.532 mmol) and 2,4-difluorophenol (150 μlit, 1.57 mmol) is converted to the title compound of Example 307 (38.7 mg, 19%), obtained as a solid; MS: 576 (M+H)$^+$, LC/MS ret. t=2.75 min.; HPLC (Method A but with a 30 min rather than a 15 min gradient) ret. t.=19.94 min.

Example 309

(2S,4S)-4-(4-bromo-2-fluorophenoxy)-1-(4-(5-cyclopropyl-1H-pyrazol-3-ylamino)pyrrolo[1,2-f][1,2,4]triazin-2-yl)-N-(6-fluoropyridin-3-yl)pyrrolidine-2-carboxamide

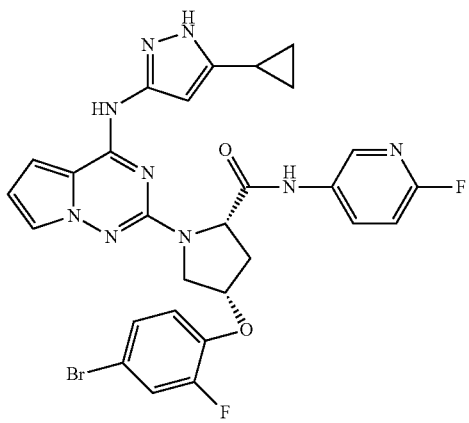 [SMILES: O=C(Nc1ccc(F)nc1)[C@@H]1C[C@H](Oc2ccc(Br)cc2F)CN1c1nc(Nc2cc(C3CC3)[nH]n2)c2cccn2n1]

Using the procedure related to Example 298, the compound of Example 217 (39.8 mg, 0.860 mmol) and 4-bromo-2-fluorophenol (35 μlit, 0.320 mmol) is converted to the title compound of Example 309 (24.0 mg, 44%), obtained as a solid; MS: 636, 638 (M+H)$^+$, LC/MS ret. t=2.85 min.; HPLC (Method A but with a 30 min rather than a 15 min gradient) ret. t.=21.35 min.

Example 310

(2S,4R)-N-(pyrazin-2-yl)-4-(2H-tetrazol-2-yl)-1-(4-(5-(1-(trifluoromethyl)cyclopropyl)-1H-pyrazol-3-ylamino)pyrrolo[1,2-f][1,2,4]-triazin-2-yl)pyrrolidine-2-carboxamide

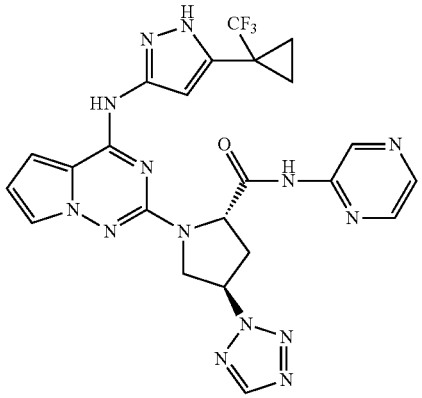 [SMILES: O=C(Nc1cnccn1)[C@@H]1C[C@@H](n2ncnn2)CN1c1nc(Nc2cc(C3(C(F)(F)F)CC3)[nH]n2)c2cccn2n1]

Using the procedure related to Example 298, the compound of Example 280 (48.2 mg, 0.094 mmol) and 1H-tetrazole (46.8 mg, 0.667 mmol) is converted to the title compound of Example 310 (7.3 mg, 13.7%), obtained as a solid; MS: 567 (M+H)$^+$, LC/MS ret. t=2.45 min.; HPLC (Method A but with a 30 min rather than a 15 min gradient) ret. t.=25.18 min.

Example 311

(2S,4R)-1-(4-(5-cyclopropyl-1H-pyrazol-3-ylamino)pyrrolo[1,2-f][1,2,4]triazin-2-yl)-N-(6-fluoropyridin-3-yl)-4-(2H-tetrazol-2-yl)pyrrolidine-2-carboxamide

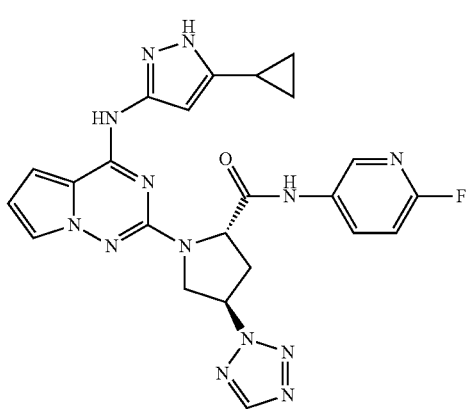 [SMILES: O=C(Nc1ccc(F)nc1)[C@@H]1C[C@@H](n2ncnn2)CN1c1nc(Nc2cc(C3CC3)[nH]n2)c2cccn2n1]

241

Using the procedure related to Example 298, the compound of Example 208 (30.0 mg, 0.065 mmol) and 1H-tetrazole (38.0 mg, 0.542 mmol) is converted to the title compound of Example 311 (15.8 mg, 47.4%), obtained as a solid; MS: 516 (M+H)⁺, LC/MS ret. t=2.20 min.; HPLC (Method A but with a 30 min rather than a 15 min gradient) ret. t.=16.38 min.

Example 312

(2S,4S)-4-cyano-1-(4-(5-cyclopropyl-1H-pyrazol-3-ylamino)pyrrolo[1,2-f][1,2,4]triazin-2-yl)-N-(6-fluoropyridin-3-yl)pyrrolidine-2-carboxamide

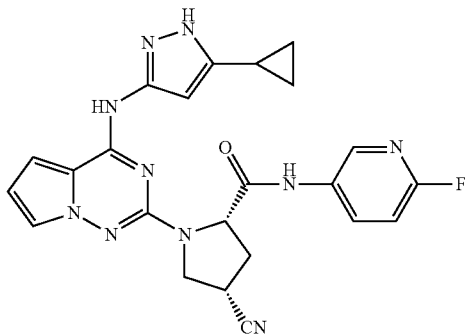 [SMILES: N#C[C@H]1C[C@@H](C(=O)Nc2ccc(F)nc2)N(c2nc(Nc3cc(C4CC4)[nH]n3)c3cccn3n2)C1]

Using (2S,4S)-4-cyanopyrrolidine-2-carboxylic acid, trifluoroacetic acid salt (made by standard hydrolysis of its corresponding methyl ester, see J. Med. Chem., 1988, 31, 875-885) and the compound from Example 1C, and following procedures related to those described in Examples 252 and 271, the title compound is obtained as a solid; MS: 473 (M+H)⁺, LC/MS ret. t=2.00 min.; HPLC (Method A but with a 30 min rather than a 15 min gradient) ret. t.=15.47 min.

Example 313

2-chloropyrrolo[1,2-f][1,2,4]triazin-4-amine

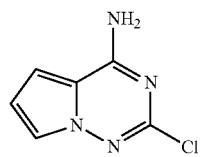 [SMILES: Nc1nc(Cl)nn2cccc12]

To a suspension of the compound from Example 1B, (2.83 g, 15.1 mmol). in isopropyl alcohol (50 mL) is added 1,1,1,3,3,3-hexamethyldisilazane (13.0 mL, 61.6 mmol) followed by N,N-diisopropylethylamine (2.8 mL, 16.1 mmol). The reaction mixture is stirred at rt for 2.5 h, during which time a solid precipitates out. The mixture is cooled to −20 C for 45 min, filtered, and washed with cold isopropyl alcohol (30 mL). After drying in vacuo overnight, 2.43 g (95%) of the pure title compound is obtained as a solid; MS: 169, 171 (M+H)⁺, LC/MS ret. t=1.65 min.; 500 MHz ¹H NMR (CDCl₃) δ 7.58-7.54 (m, 1H), 6.71-6.61 (m, 2H), 5.98-5.71 (brs, 2H).

242

Example 314

(S)-1-(4-aminopyrrolo[1,2-f][1,2,4]triazin-2-yl)-2-methylpyrrolidine-2-carboxylic acid

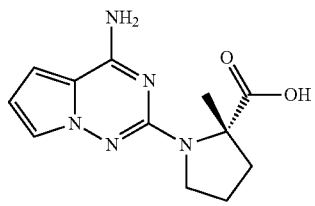 [SMILES: C[C@@]1(C(=O)O)CCCN1c1nc(N)c2cccn2n1]

To a flame dried 100 mL pressure bottle under nitrogen is added (S)-2-methylpyrrolidine-2-carboxylic acid (4.98 g, 38.6 mmol), potassium tert-butoxide (4.28 g, 38.1 mmol), and 11 mL of anhydrous 1-methyl-2-pyrrolidinone (NMP). N,N-diisopropylethylamine (1.60 mL, 9.2 mmol) is then added and the resulting suspension is flushed with nitrogen, magnetically stirred, and sonnicated until almost all solids have dissolved. The compound from Example 313 (900.0 mg, 5.32 mmol) is then added, the resulting solution is flushed with nitrogen, and heated to 155° C. for 63 h. The reaction is cooled to rt, treated with 1 N aqueous HCl (42.0 mL), partially concentrated in vacuo, and then purified by preparative HPLC (using 12% solvent B to 80% solvent B over 10 min). The desired fractions containing the product are concentrated to give 1.05 g (52%) of the title compound as a solid (TFA salt): MS: 262 (M+H)⁺, LC/MS ret. t=1.74 min; 500 MHz ¹H NMR (CD₃OD) δ 7.52-7.49 (m, 1H), 7.19-7.15 (m, 1H), 6.64-6.59 (m, 1H), 3.85-3.79 (m, 1H), 3.75-3.67 (m, 1H), 2.42-2.33 (m, 1H), 2.21 (m, 3H), 1.73 (s, 3H).

Example 315

(S)-1-(4-(5-cyanothiazol-2-ylamino)pyrrolo[1,2-f][1,2,4]triazin-2-yl)-2-methylpyrrolidine-2-carboxylic acid

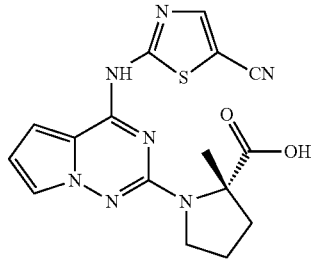 [SMILES: C[C@@]1(C(=O)O)CCCN1c1nc(Nc2ncc(C#N)s2)c2cccn2n1]

The compound from Example 314 (201.7 mg, 0.538 mmol) is dissolved in anhydrous THF (4.0 mL) and treated under nitrogen with stirring with sodium hydride (109.0 mg, 4.54 mmol). The reaction mixture is stirred at rt for 10 min and 2-chloro-5-cyanothiazole (127.0 mg, 0.878 mmol) is added. After 17.5 h at rt, additional sodium hydride (282 mg, 11.8 mmol) and 2-chloro-5-cyanothiazole (165.0 mg, 1.14 mmol) is added and the mixture is stirred at rt for 5 h. The reaction is cooled to rt, treated with a cold solution of trifluoroacetic acid (800 Wit) in methanol (8 mL), and then purified by preparative HPLC (using 15% solvent B to 100% solvent B over 10 min). The desired fractions containing the product are concentrated to give 107 mg (41%) of the title compound as a solid (TFA salt) which is used directly as described below: MS: 370 (M+H)$^+$, LC/MS ret. t=1.86 min.

Example 316

(S)-1-(4-(5-cyanothiazol-2-ylamino)pyrrolo[1,2-f][1,2,4]triazin-2-yl)-N-(6-fluoropyridin-3-yl)-2-methylpyrrolidine-2-carboxamide

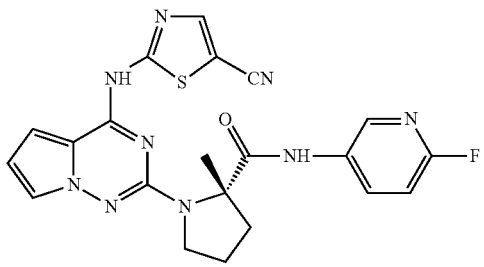 [SMILES: C[C@@]1(C(=O)Nc2ccc(F)nc2)CCCN1c1nc(Nc2ncc(C#N)s2)c2cccn2n1]

The compound from Example 315 (46.6 mg, 0.096 mmol) is converted to the title compound of Example 316 (20 mg, 36%, TFA salt), using a procedure similar to that described in Example 271, except DMSO is used as the solvent instead of NMP and the preparative HPLC fractions are concentrated in vacuo: MS: 464 (M+H)$^+$, LC/MS ret. t=2.84 min.

Example 317

(S)-2-(2-(2-(6-fluoropyridin-3-ylcarbamoyl)-2-methylpyrrolidin-1-yl)pyrrolo[1,2-f][1,2,4]triazin-4-ylamino)thiazole-5-carboxamide

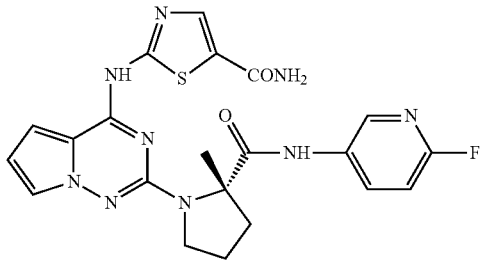 [SMILES: C[C@@]1(C(=O)Nc2ccc(F)nc2)CCCN1c1nc(Nc2ncc(C(N)=O)s2)c2cccn2n1]

A magnetically stirred solution of the compound from Example 316 (20 mg, 0.035 mmol in DMSO (3 mL) is treated sequentially with 10 N aqueous sodium hydroxide (200 μlit), 30% hydrogen peroxide (200 Wit), water (400 Wit), and additional 30% hydrogen peroxide (200 μlit). The mixture is heated at 60° C. for 15 min, cooled, treated with a solution of glacial acetic acid (160 mg) in methanol (5 mL), and then purified by preparative HPLC (using 16% solvent B to 100% solvent B over 10 min). The desired fractions containing the product are concentrated to give 7.7 mg (37%) of the title compound as a solid (TFA salt): MS: 482 (M+H)$^+$, LC/MS ret. t=2.43 min; HPLC (Method F) ret. t.=14.25 min.

Example 318

(2S,4S)-1-(4-(5-Cyclopropyl-1H-pyrazol-3-ylamino)pyrrolo[1,2-f][1,2,4]triazin-2-yl)-4-fluoro-N-(1,2,4-thiadiazol-5-yl)pyrrolidine-2-carboxamide

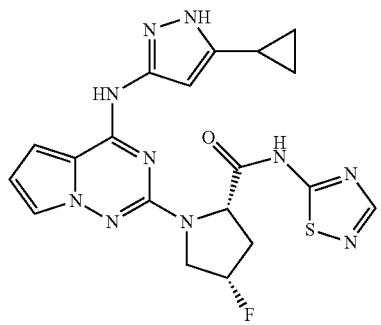 [SMILES: O=C(Nc1ncns1)[C@@H]1C[C@H](F)CN1c1nc(Nc2cc(C3CC3)[nH]n2)c2cccn2n1]

318A. (2S,4S)-1-(4-(5-Cyclopropyl-1H-pyrazol-3-ylamino)pyrrolo[1,2-f][1,2,4]triazin-2-yl)-4-fluoropyrrolidine-2-carboxylic acid

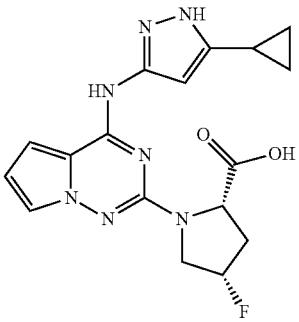 [SMILES: O=C(O)[C@@H]1C[C@H](F)CN1c1nc(Nc2cc(C3CC3)[nH]n2)c2cccn2n1]

(2S,4S)-4-Fluoropyrrolidine-2-carboxylic acid hydrochloride (3.39 g, 20.0 mmol) was suspended in NMP (25 mL) to which was added 5 M NaOH (4.00 mL, 20.0 mmol), followed by DIPEA (1.92 mL, 11.0 mmol) and 2-chloro-N-(5-cyclopropyl-1H-pyrazol-3-yl)pyrrolo[1,2-f][1,2,4]triazin-4-amine (1.37 g, 5.00 mmol). The reaction mixture was heated to 135° C. for 3 d, and then cooled to room temperature. The reaction was diluted with water (500 mL) and washed with EtOAc (2×250 mL). The organic layers were discarded, and the aqueous layer was adjusted to pH 2-3 with 1 N HCl and extracted with EtOAc (2×250 mL). The combined extracts were washed with brine (250 mL), dried (MgSO$_4$), filtered, and concentrated in vacuo. The resulting residue was shaken vigorously with water (500 mL), and a precipitate was removed by vacuum filtration. The solids were again vigorously shaken with water (150 mL) and dried via vacuum filtration to afford slightly impure 318A (974 mg, 52%). 318A had an analytical HPLC retention time=1.73 min (Waters XBridge 4.6×50 mm, 5-95% aqueous acetonitrile over 5 min containing 10 mM ammonium acetate) and a LC/MS M$^+$+1=372.

318B. (2S,4S)-Methyl 1-(4-(5-cyclopropyl-1H-pyrazol-3-ylamino)pyrrolo[1,2-f][1,2,4]triazin-2-yl)-4-fluoropyrrolidine-2-carboxylate

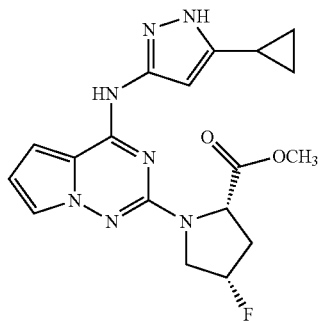 [SMILES: COC(=O)[C@@H]1C[C@H](F)CN1c1nc(Nc2cc(C3CC3)[nH]n2)c2cccn2n1]

Slightly impure (2S,4S)-1-(4-(5-cyclopropyl-1H-pyrazol-3-ylamino)pyrrolo[1,2-f][1,2,4]triazin-2-yl)-4-fluoropyrrolidine-2-carboxylic acid (900 mg, approx. 2.19 mmol) was dissolved in MeOH (22 mL) and cooled to 0° C. Acetyl chloride (1.56 mL, 21.9 mmol) was added, and the reaction was stirred at 0° C. for several minutes before warming to room temperature. After 16 h, the reaction was concentrated in vacuo. The residue was diluted with EtOAc (300 mL) and washed with saturated aqueous NaHCO$_3$ (300 mL), water (300 mL) and brine (150 mL). The organics were dried (MgSO$_4$), filtered, and concentrated in vacuo. The compound was purified by silica gel flash chromatography (0-50% 90:10:1 [CH$_2$Cl$_2$/MeOH/conc NH$_4$OH]/CH$_2$Cl$_2$) to give 318B (564 mg, 66%). 318B had an analytical HPLC retention time=1.93 min (Waters XBridge 4.6×50 mm, 5-95% aqueous acetonitrile over 5 min containing 10 mM ammonium acetate) and a LC/MS M$^+$+1=386.

318C. (2S,4S)-1-(4-(5-Cyclopropyl-1H-pyrazol-3-ylamino)pyrrolo[1,2-f][1,2,4]triazin-2-yl)-4-fluoro-N-(1,2,4-thiadiazol-5-yl)pyrrolidine-2-carboxamide 1,2,4-Thiadiazol-5-amine (656 mg, 6.49 mmol) was dissolved in 1,2-dimethoxyethane (30 mL) and cooled in an ice bath. Methylmagnesium bromide (3.0 M in diethyl ether, 2.16 mL, 6.49 mmol) was slowly added, and the mixture was stirred for 20 min. The reaction was warmed to room temperature, and (2S,4S)-methyl 1-(4-(5-cyclopropyl-1H-pyrazol-3-ylamino)pyrrolo[1,2-f][1,2,4]triazin-2-yl)-4-fluoropyrrolidine-2-carboxylate (250 mg, 0.649 mmol) was added. The reaction mixture was heated to 80° C. for 16 h then cooled to room temperature. Water (200 mL) was added, and the reaction was extracted with EtOAc (2×100 mL). The combined organic layers were washed with brine (200 mL), dried (MgSO$_4$), filtrered, and concentrated in vacuo. Recrystallization from MeOH gave the title compound (90 mg, 30%), which had an analytical HPLC retention time=3.02 min (Phenomenex Luna 4.6×50 mm, 10-90% aqueous MeOH over 5 min containing 0.1% TFA) and a LC/MS M$^+$+1=455.

We claim:
1. A compound selected from the group consisting of
(R)-1-(4-(5-cyclopropyl-1H-pyrazol-3-ylamino)pyrrolo[1,2-f][1,2,4]triazin-2-yl)pyrrolidine-2-carboxylic acid,
(S)-methyl-1-(4-(5-cyclopropyl-1H-pyrazol-3-ylamino)pyrrolo[1,2-f][1,2,4]triazin-2-yl)-2-methylpyrrolidine-2-carboxylate,
(2S,4S)-1-(4-(5-cyclopropyl-1H-pyrazol-3-ylamino)pyrrolo[1,2-f][1,2,4]triazin-2-yl)-4-methoxypyrrolidine-2-carboxylic acid,
(2S,4S)-methyl 1-(4-(5-cyclopropyl-1H-pyrazol-3-ylamino)pyrrolo[1,2-f][1,2,4]triazin-2-yl)-4-methoxypyrrolidine-2-carboxylate,
(2S,4S)-4-hydroxy-1-(4-(5-(1-methylcyclopropyl)-1H-pyrazol-3-ylamino)pyrrolo[1,2-f][1,2,4]triazin-2-yl)pyrrolidine-2-carboxylic acid,
(2S,4R)-methyl 1-(4-(5-cyclopropyl-1H-pyrazol-3-ylamino)pyrrolo[1,2-f][1,2,4]triazin-2-yl)-4-methoxypyrrolidine-2-carboxylate,
(2S,4R)-4-fluoro-1-(4-(5-(1-methylcyclopropyl)-1H-pyrazol-3-ylamino)pyrrolo[1,2-f][1,2,4]triazin-2-yl)pyrrolidine-2-carboxylic acid,
(2S,4R)-methyl 4-fluoro-1-(4-(5-(1-methylcyclopropyl)-1H-pyrazol-3-ylamino)pyrrolo[1,2-f][1,2,4]triazin-2-yl)pyrrolidine-2-carboxylate,
(2S,4R)-4-methoxy-1-(4-(5-(1-methylcyclopropyl)-1H-pyrazol-3-ylamino)pyrrolo[1,2-f][1,2,4]triazin-2-yl)pyrrolidine-2-carboxylic acid,
(2S,4R)-methyl 4-methoxy-1-(4-(5-(1-methylcyclopropyl)-1H-pyrazol-3-ylamino)pyrrolo[1,2-f][1,2,4]triazin-2-yl)pyrrolidine-2-carboxylate,
(2S,4S)-ethyl 1-(4-(5-cyclopropyl-1H-pyrazol-3-ylamino)pyrrolo [1,2-f][1,2,4]triazin-2-yl)-4-hydroxypyrrolidine-2-carboxylate,
((2S,4R)-ethyl 4-chloro-1-(4-(5-cyclopropyl-1H-pyrazol-3-ylamino)pyrrolo [1,2-f][1,2,4]triazin-2-yl)pyrrolidine-2-carboxylate,
(2S,4S)-ethyl 4-chloro-1-(4-(5-cyclopropyl-1H-pyrazol-3-ylamino)pyrrolo [1,2-f][1,2,4]triazin-2-yl)pyrrolidine-2-carboxylate,
(2S,4R)-methyl 1-(4-(5-cyclopropyl-1H-pyrazol-3-ylamino)pyrrolo[1,2-f][1,2,4]triazin-2-yl)-4-hydroxypyrrolidine-2-carboxylate,
(2S,4S)-methyl 1-(4-(5-cyclopropyl-1H-pyrazol-3-ylamino)pyrrolo [1,2-f][1,2,4]triazin-2-yl)-4-(2H-tetrazol-2-yl)pyrrolidine-2-carboxylate,
(2S,4S)-methyl 1-(4-(5-cyclopropyl-1H-pyrazol-3-ylamino)pyrrolo[1,2-f][1,2,4]triazin-2-yl)-4-(1H-tetrazol-1-yl)pyrrolidine-2-carboxylate,
or a pharmaceutically acceptable salt, tautomer or stereoisomer thereof.

* * * * *